United States Patent
Lee et al.

(10) Patent No.: US 11,434,228 B2
(45) Date of Patent: Sep. 6, 2022

(54) HETEROCYCLIC COMPOUND AND ORGANIC LIGHT EMITTING DEVICE COMPRISING SAME

(71) Applicant: LT MATERIALS CO., LTD., Yongin (KR)

(72) Inventors: Gi-Back Lee, Osan-si (KR); Seong-Jong Park, Osan-si (KR); Ji-Young Kim, Yongin-si (KR); Won-Jang Jeong, Hwaseong-si (KR); Jin-Seok Choi, Suwon-si (KR); Dae-Hyuk Choi, Yongin-si (KR); Joo-Dong Lee, Seongnam-si (KR)

(73) Assignee: LT MATERIALS CO., LTD., Yongin (KR)

( * ) Notice: Subject to any disclaimer, the term of this patent is extended or adjusted under 35 U.S.C. 154(b) by 400 days.

(21) Appl. No.: 16/650,732

(22) PCT Filed: Oct. 1, 2018

(86) PCT No.: PCT/KR2018/011624
§ 371 (c)(1),
(2) Date: Mar. 25, 2020

(87) PCT Pub. No.: WO2019/066607
PCT Pub. Date: Apr. 4, 2019

(65) Prior Publication Data
US 2020/0308150 A1  Oct. 1, 2020

(30) Foreign Application Priority Data
Sep. 29, 2017 (KR) .......................... 10-2017-0127755

(51) Int. Cl.
| | | |
|---|---|---|
| *C07D 403/14* | (2006.01) | |
| *C07D 403/04* | (2006.01) | |
| *C07D 407/14* | (2006.01) | |
| *C07D 409/14* | (2006.01) | |
| *H01L 51/00* | (2006.01) | |
| *H01L 51/42* | (2006.01) | |
| *H01L 51/50* | (2006.01) | |

(52) U.S. Cl.
CPC ......... *C07D 403/14* (2013.01); *C07D 403/04* (2013.01); *C07D 407/14* (2013.01); *C07D 409/14* (2013.01); *H01L 51/0054* (2013.01); *H01L 51/0067* (2013.01); *H01L 51/0073* (2013.01); *H01L 51/4273* (2013.01); *H01L 51/5072* (2013.01); *H01L 51/5092* (2013.01)

(58) Field of Classification Search
CPC .............. C07D 403/04; H01L 51/0054; H01L 51/0067; H01L 51/0073; H01L 51/4273; H01L 51/5072; H01L 51/5092; H01L 51/504; H01L 51/0072; H01L 51/50; H01L 51/0071; H01L 51/5096; C09K 11/06

See application file for complete search history.

(56) References Cited

U.S. PATENT DOCUMENTS

| | | | |
|---|---|---|---|
| 4,356,429 A | 10/1982 | Tang | |
| 2011/0049494 A1 | 3/2011 | Kim et al. | |
| 2018/0323379 A1* | 11/2018 | Kim | .................. H01L 51/0072 |

FOREIGN PATENT DOCUMENTS

| | | | | |
|---|---|---|---|---|
| CN | 101870697 A | 10/2010 | | |
| JP | 2010-215759 A | 9/2010 | | |
| KR | 10-2011-0023090 A | 3/2011 | | |
| KR | 10-2014-0093163 A | 7/2014 | | |
| KR | 10-2015-0010548 A | 1/2015 | | |
| KR | 10-2015-0028173 A | 3/2015 | | |
| KR | 10-2017-0053534 A | 5/2017 | | |
| WO | WO-2014112728 A1 * | 7/2014 | ........... | C07D 209/82 |

OTHER PUBLICATIONS

Hao et at al. "Synthesis of H-pyrazolo[5,1-a]isoquinolines via a silver triflate-catalyzed tandem reaction of N'-(2-alkynylbenzylidene) hydrazide with alcohol" Tetrahedron 2013, 69, 9219-9223. (Year: 2013).*

Gong et al. "Synthesis of pyrazolo[5,1-a]isoquinolines via a silver(I)-catalyzed reaction of (1-arylethylidene)-hydrazides with N'-(2-alkynylbenzylidene)-hydrazides" Org. Biomol. Chem. 2015, 13, 11657-11662. (Year: 2015).*

Kim et al. "Pyrazole-Based Compound and Organic Light Emitting Device Using Same" WO 2014112728 A1 (Pub. Jul. 24, 2014) English machine translation (online) (obtained from Dialog on Jun. 16, 2022). (Year: 2014).*

International Search Report (PCT/ISA/210) issued in PCT/KR2018/011624, dated Jan. 10, 2019.

Kuwabara et al., "Thermally Stable Multilayered Organic Electroluminescent Devices Using Novel Starburst Molecules, 4,4',4"-Tri(N-carbazolyl)triphenylamine (TCTA) and 4,4' ,4"-Tris(3-methylphenylphenylamino)triphenylamine (m-MTDATA), as Hole-Transport Materials", Advanced Materials, 1994, vol. 6, No. 9, pp. 677-679.

* cited by examiner

*Primary Examiner* — Amanda L. Aguirre
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

14 Claims, 3 Drawing Sheets

【FIG. 1】
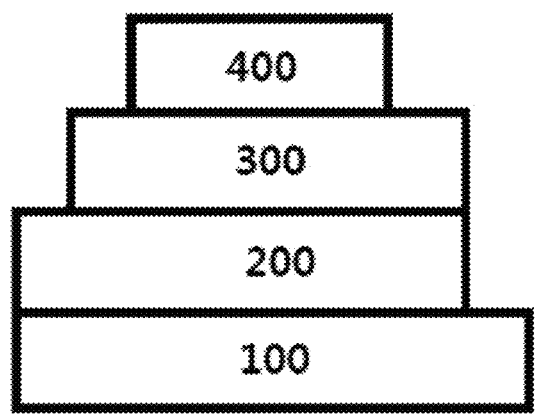
【FIG. 2】
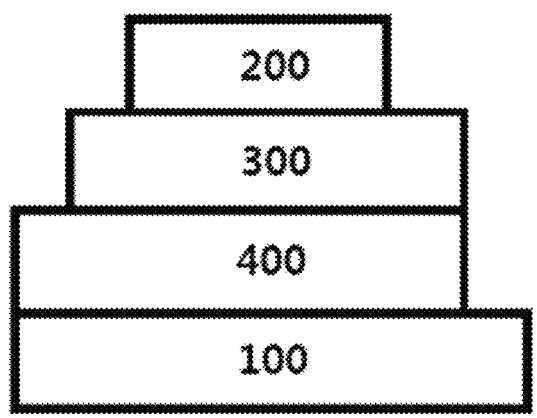

[FIG. 3]
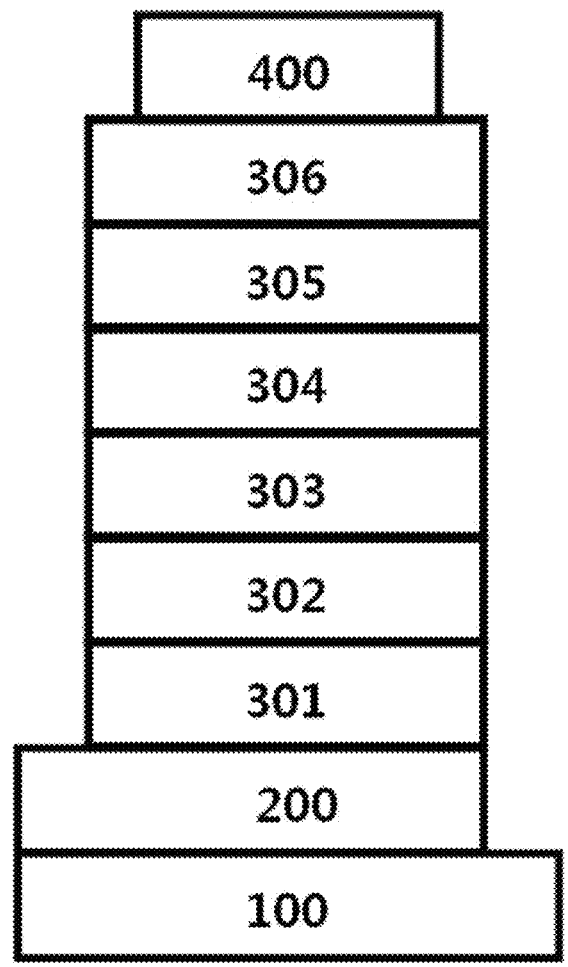

[FIG. 4]

| CATHODE |
|---|
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT EMITTING DEVICE COMPRISING SAME

TECHNICAL FIELD

This application claims priority to and the benefits of Korean Patent Application No. 10-2017-0127755, filed with the Korean Intellectual Property Office on Sep. 29, 2017, the entire contents of which are incorporated herein by reference.

The present specification relates to a heterocyclic compound and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present disclosure is directed to providing a heterocyclic compound and an organic light emitting device comprising the same.

Technical Solution

One embodiment of the present application provides a heterocyclic compound represented by the following Chemical Formula 1.

[Chemical Formula 1]

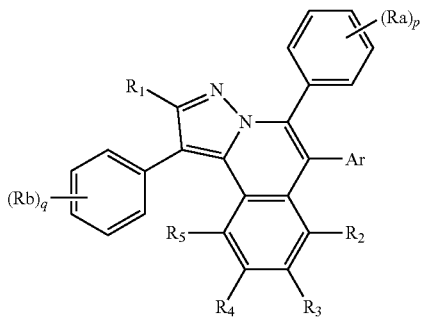

In Chemical Formula 1, $R_1$ is hydrogen; a C1 to C60 alkyl group; a C6 to C60 aryl group; a C2 to C60 heteroaryl group; P(=O)RR'; or SiRR'R", Ar is deuterium; a halogen group; —CN; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, $R_2$ to $R_5$, $R_a$ and $R_b$ are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aliphatic or aromatic hydrocarbon ring, wherein R, R' and R" are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group, and p and q are an integer of 0 to 5.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to one embodiment of the present application.

Advantageous Effects

The compound described in the present specification can be used as an organic material layer material of an organic light emitting device. The compound is capable of performing a role of a hole injection material, a hole transfer material, a light emitting material, an electron transfer material, an electron injection material and the like in the organic light emitting device. Particularly, the compound can be used as an electron transfer layer material or a hole blocking layer material of the organic light emitting device.

When using the compound represented by Chemical Formula 1 in the organic material layer, a driving voltage is lowered and light efficiency is enhanced in the device, and device lifetime properties can be enhanced by thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode [MODE FOR DISCLOSURE]

Hereinafter, the present application will be described in detail.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenzyloxy and the like, but are not limited thereto.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent comprising Si, having the Si atom directly linked as a radical, and is represented by —$SiR_{104}R_{105}R_{106}$. $R_{104}$ to $R_{106}$ are the same as or different from each other, and may be each independently a substituent formed with at least one of hydrogen; deuterium; a halogen group; an alkyl group; an alkenyl group; an alkoxy group; cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

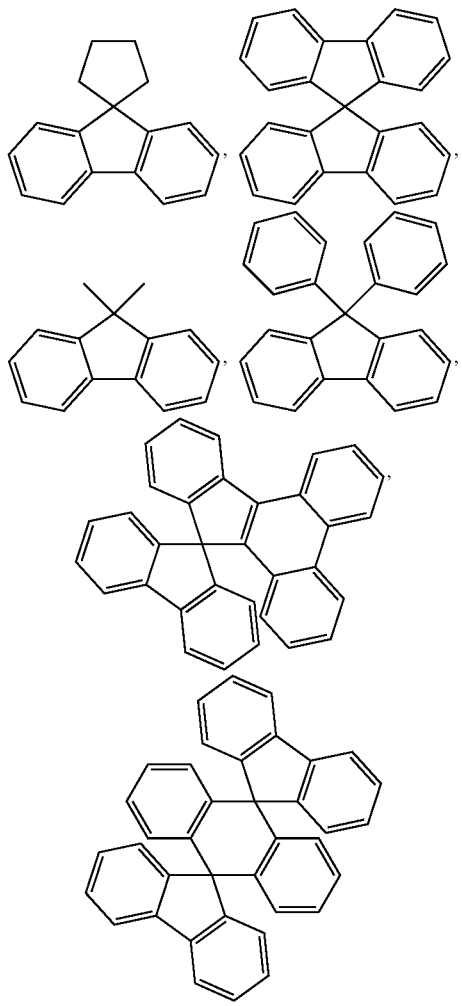

and the like may be included. However, the structure is not limited thereto.

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

In the present specification, specific examples of the phosphine oxide group may comprise a diphenylphosphine oxide group, a dinaphthylphosphine oxide group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

In one embodiment of the present application, when p is 2 or greater, two or more Ras may be the same as or different from each other, and when q is 2 or greater, two or more Rbs may be the same as or different from each other.

One embodiment of the present application provides a compound represented by Chemical Formula 1.

In one embodiment of the present application, $R_1$ of Chemical Formula 1 may be hydrogen; a C1 to C60 alkyl group; a C6 to C60 aryl group; a C2 to C60 heteroaryl group; P(=O) RR'; or SiRR'R".

In another embodiment, $R_1$ of Chemical Formula 1 may be hydrogen; a C1 to C40 alkyl group; a C6 to C40 aryl group; a C2 to C40 heteroaryl group; P(=O) RR'; or SiRR'R".

In another embodiment, $R_1$ of Chemical Formula 1 may be hydrogen; or a C6 to C40 aryl group.

In another embodiment, $R_1$ of Chemical Formula 1 may be hydrogen; a phenyl group; a biphenyl group; a naphthyl group; a phenanthrenyl group; or a triphenylenyl group.

In one embodiment of the present application, $R_2$ to $R_5$, $R_a$ and $R_b$ of Chemical Formula 1 are the same as or different from each other, and may be each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other may bond to each other to form a substituted or unsubstituted aliphatic or aromatic hydrocarbon ring.

In another embodiment, $R_2$ to $R_5$, $R_a$ and $R_b$ of Chemical Formula 1 are the same as or different from each other, and may be each independently hydrogen; a substituted or unsubstituted aryl group; or a substituted or unsubstituted heteroaryl group.

In another embodiment, $R_2$ to $R_5$, $R_a$ and $R_b$ of Chemical Formula 1 are the same as or different from each other, and may be each independently hydrogen; a substituted or unsubstituted C6 to C60 aryl group; or a substituted or unsubstituted C2 to C60 heteroaryl group.

In another embodiment, $R_2$ to $R_5$, $R_a$ and $R_b$ of Chemical Formula 1 are the same as or different from each other, and may be each independently hydrogen; a C6 to C60 aryl group; or a C2 to C60 heteroaryl group.

In another embodiment, $R_2$ to $R_5$, $R_a$ and $R_b$ of Chemical Formula 1 may be hydrogen.

In one embodiment of the present application, Ar of Chemical Formula 1 may be selected from the group consisting of deuterium; a halogen group; —CN; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group.

In one embodiment of the present application, Ar of Chemical Formula 1 may be represented by -(L)m-(Z)n, L is a direct bond; a substituted or unsubstituted arylene group; or a substituted or unsubstituted heteroarylene group, Z is deuterium; a substituted or unsubstituted alkyl group; a halogen group; —CN; a substituted or unsubstituted alkyl group; a substituted or unsubstituted aryl group; a substituted or unsubstituted heteroaryl group; —SiRR'R"; or —P(=O) RR', m is an integer of 0 to 4, and n is an integer of 1 to 5.

In one embodiment of the present application, when m is 2 or greater, two or more Ls may be the same as or different from each other, and when n is 2 or greater, two or more Zs may be the same as or different from each other.

In one embodiment of the present application, L may be a direct bond; a substituted or unsubstituted arylene group; or a substituted or unsubstituted heteroarylene group.

In another embodiment, L may be a direct bond; a substituted or unsubstituted C6 to C60 arylene group; or a substituted or unsubstituted C2 to C60 heteroarylene group.

In another embodiment, L may be a direct bond; a substituted or unsubstituted C6 to C40 arylene group; or a substituted or unsubstituted C2 to C40 heteroarylene group.

In another embodiment, L may be a direct bond; a C6 to C40 arylene group; or a C2 to C40 heteroarylene group.

In another embodiment, L may be a direct bond; a C6 to C40 monocyclic or polycyclic arylene group; or a C2 to C40 N-containing heteroarylene group.

In another embodiment, L may be a direct bond; a phenylene group; a biphenylene group; an anthracenylene group; a divalent phenanthroline group; a divalent triazine group; a divalent pyrimidine group; a divalent pyridine group; or a divalent quinazoline group.

In one embodiment of the present application, Z may be deuterium; a substituted or unsubstituted alkyl group; a halogen group; —CN; a substituted or unsubstituted alkyl group; a substituted or unsubstituted aryl group; a substituted or unsubstituted heteroaryl group; —SiRR'R"; or —P(=O) RR'.

In another embodiment, Z may be a substituted or unsubstituted alkyl group; a substituted or unsubstituted aryl group; a substituted or unsubstituted heteroaryl group; —SiRR'R"; or —P(=O) RR'.

In another embodiment, Z may be a substituted or unsubstituted aryl group; a substituted or unsubstituted heteroaryl group; or —P(=O)RR'.

In another embodiment, Z may be a substituted or unsubstituted C6 to C60 aryl group; a substituted or unsubstituted C2 to C60 heteroaryl group; or —P(=O)RR'.

In another embodiment, Z may be a substituted or unsubstituted C6 to C40 aryl group; a substituted or unsubstituted C2 to C40 heteroaryl group; or —P(=O)RR'.

In another embodiment, Z may be a C6 to C40 aryl group unsubstituted or substituted with a C6 to C40 aryl group and a C2 to C40 heteroaryl group; a C2 to C40 heteroaryl group unsubstituted or substituted with a C6 to C40 aryl group and a C2 to C40 heteroaryl group; or —P(=O)RR'.

In another embodiment, Z may be a C6 to C40 aryl group unsubstituted or substituted with a C6 to C40 monocyclic or polycyclic aryl group and a C2 to C40 monocyclic or polycyclic heteroaryl group; a C2 to C40 heteroaryl group unsubstituted or substituted with a C6 to C40 monocyclic or polycyclic aryl group and a C2 to C40 monocyclic or polycyclic heteroaryl group; or —P(=O)RR'.

In another embodiment, Z may be a phenyl group unsubstituted or substituted with one or more substituents selected from the group consisting of a pyridine group, a carbazole group, a dibenzofuran group and a dibenzothiophene group; a biphenyl group unsubstituted or substituted with a phenyl group; a phenanthrene group; a spirobifluorene group; a triphenylene group; a fluorene group unsubstituted or substituted with a phenyl group, a xanthene group or an acridine group; or an anthracenyl group unsubstituted or substituted with a phenyl group.

In another embodiment, Z may be a pyridine group unsubstituted or substituted with a phenyl group; a pyrimidine group unsubstituted or substituted with one or more substituents selected from the group consisting of a phenyl group, a terphenyl group, a biphenyl group, a spirobifluorenyl group, a dimethylfluorenyl group, a triphenylenyl group, a dibenzofuran group and a carbazole group; a triazine group unsubstituted or substituted with one or more substituents selected from the group consisting of a phenyl group, a terphenyl group, a biphenyl group, a spirobifluorenyl group, a dimethylfluorenyl group, a triphenylenyl group, a dibenzofuran group and a carbazole group; a quinazoline group unsubstituted or substituted with a phenyl group, a biphenyl group or a terphenyl group; a phenanthroline group unsubstituted or substituted with a phenyl group; a carbazole group; a dibenzofuran group; a dibenzothiophene group; a benzimidazole group unsubstituted or substituted with a phenyl group; or a benzothiazole group.

In another embodiment, Z may be P(=O)RR'.

In one embodiment of the present application, R, R' and R" are the same as or different from each other, and may be each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group.

In another embodiment, R, R' and R" are the same as or different from each other, and may be each independently a substituted or unsubstituted alkyl group; a substituted or unsubstituted aryl group; or a substituted or unsubstituted heteroaryl group.

In another embodiment, R, R' and R" are the same as or different from each other, and may be each independently a substituted or unsubstituted aryl group.

In another embodiment, R, R' and R" are the same as or different from each other, and may be each independently a substituted or unsubstituted C6 to C60 aryl group.

In another embodiment, R, R' and R" are the same as or different from each other, and may be each independently a C6 to C60 aryl group.

In another embodiment, R, R' and R" are the same as or different from each other, and may be each independently a C6 to C40 aryl group.

In another embodiment, R, R' and R" are the same as or different from each other, and may be each independently a phenyl group.

In the heterocyclic compound provided in one embodiment of the present application, Chemical Formula 1 is represented by any one of the following compounds.

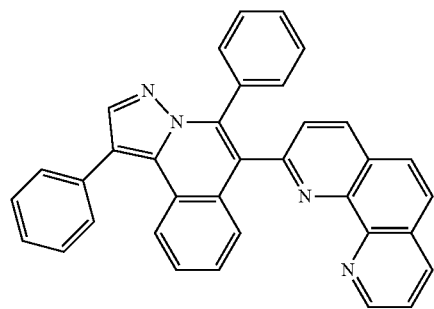

1

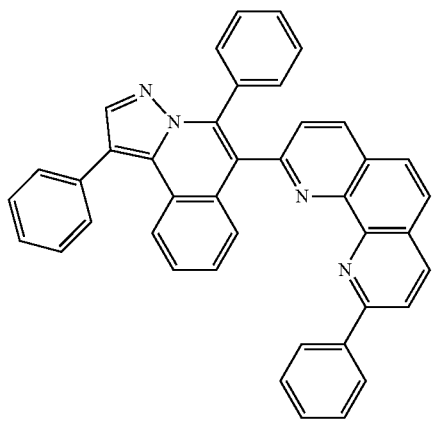

2

-continued
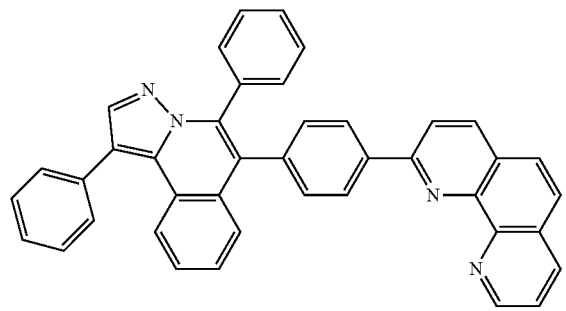
3
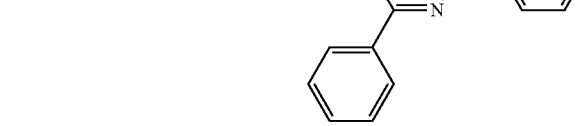
4
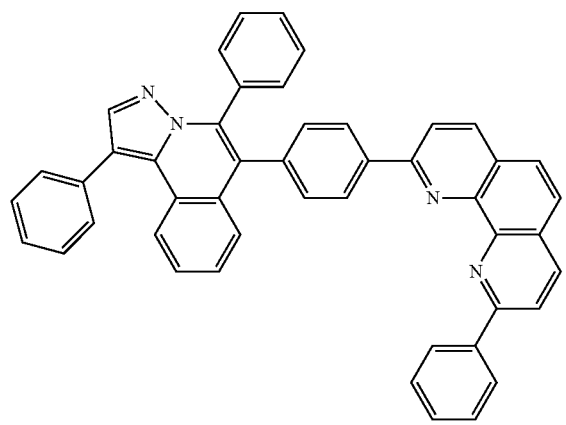 [SMILES: c1ccc(-c2ccc3ccc4ccc(-c5ccc(-c6c(-c7ccccc7)n7ncc(-c8ccccc8)c7c7ccccc67)cc5)nc4c3n2)cc1]
5
6
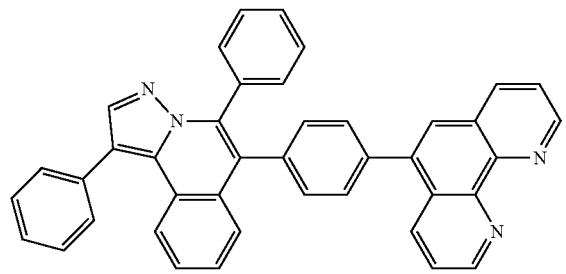
7
8
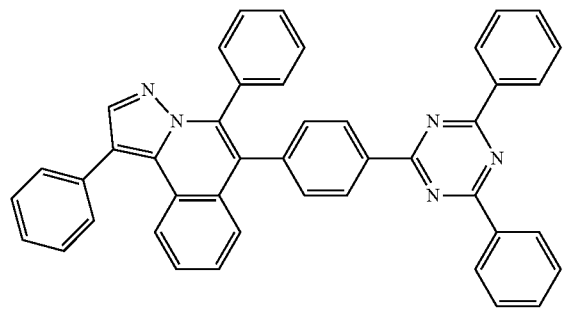
9
10

-continued
11
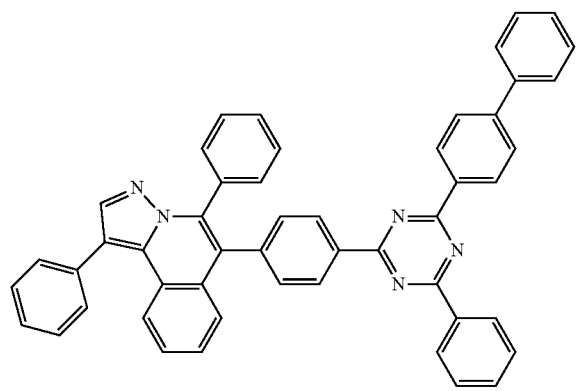
12
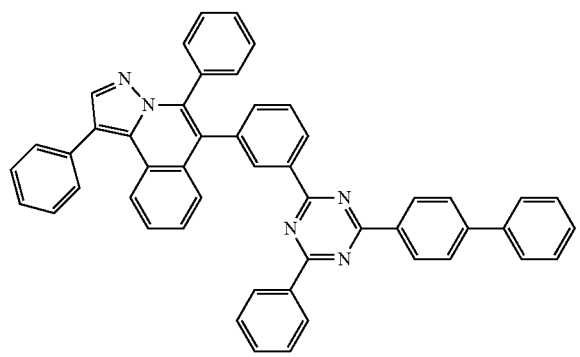
13
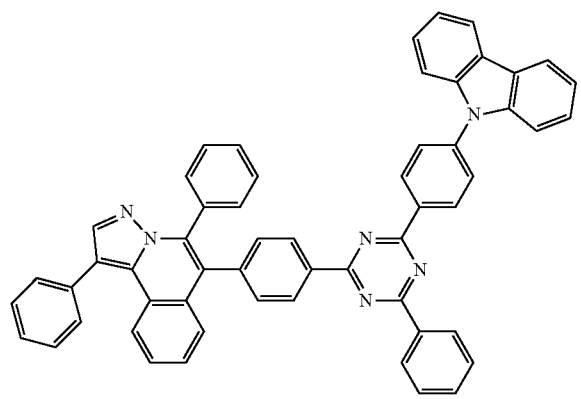
14
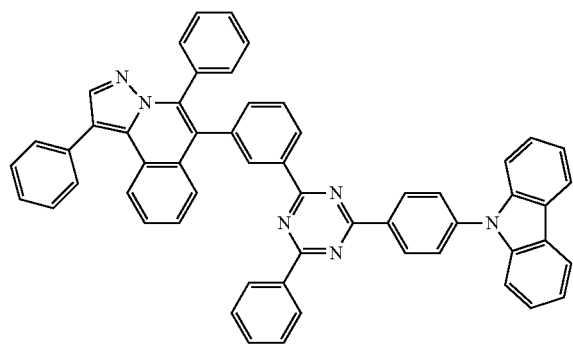
15
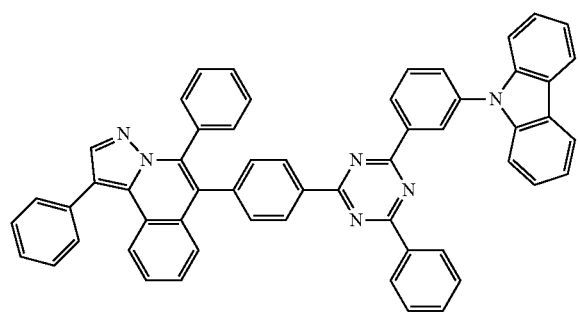
16
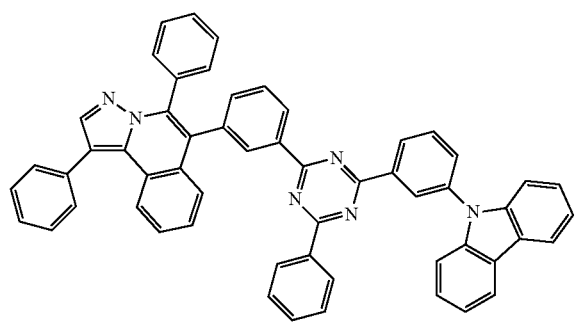
17
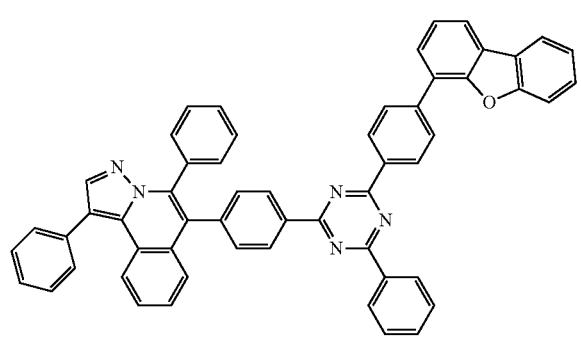
18
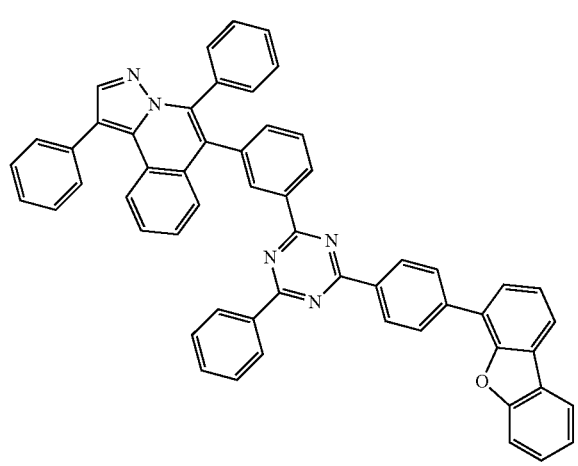

-continued
19
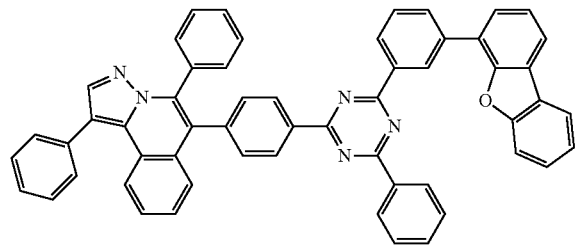
20
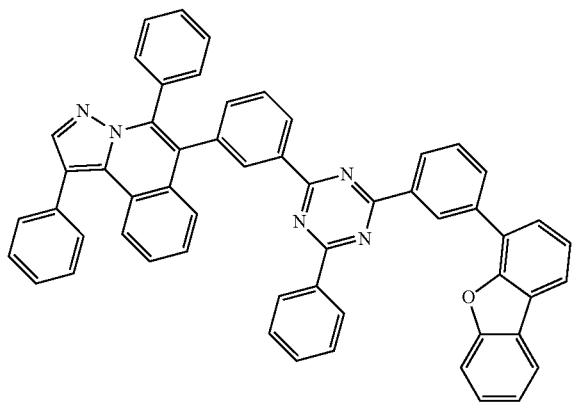
21
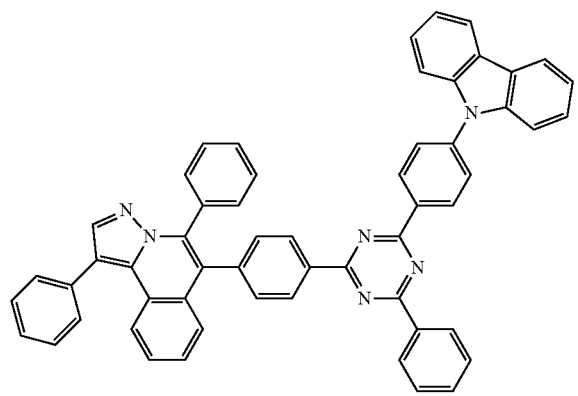
22
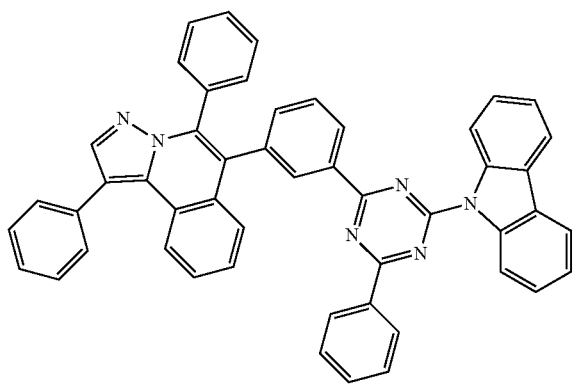
23
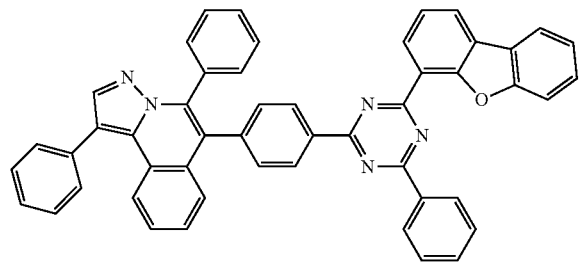
24
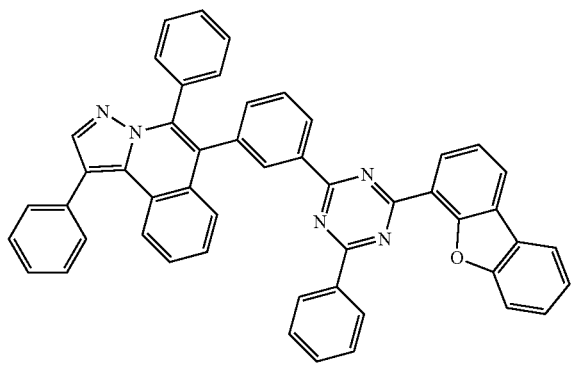
25
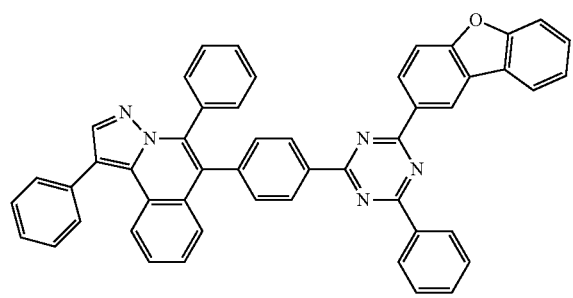
26
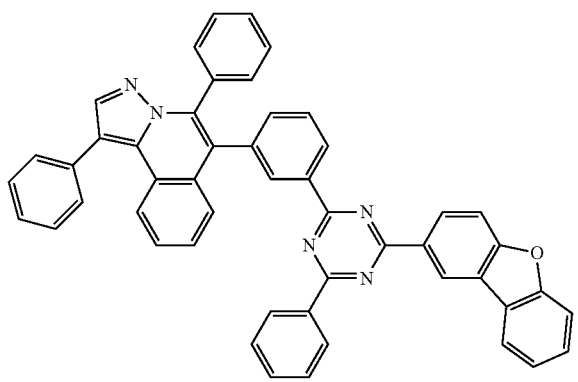

-continued
27
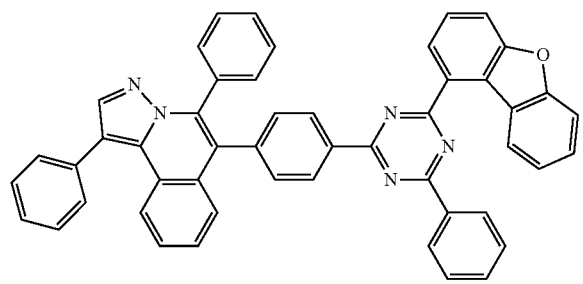
28
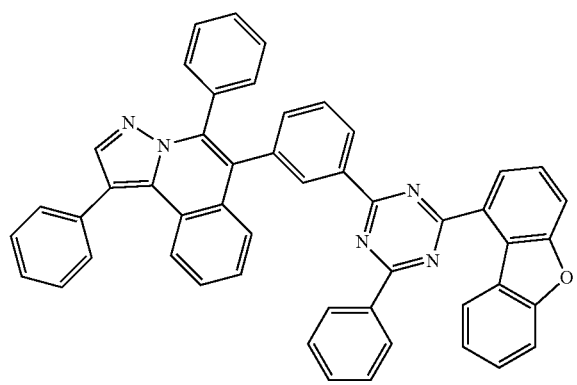
29
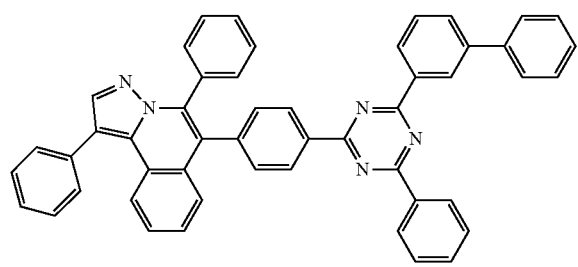
30
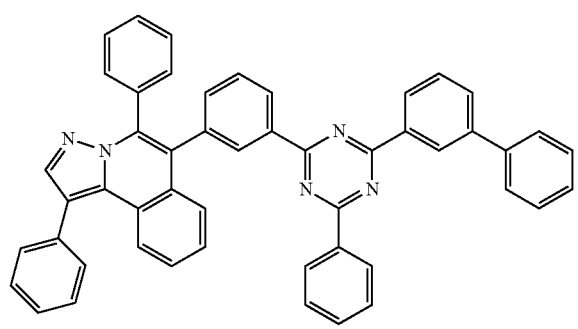
31
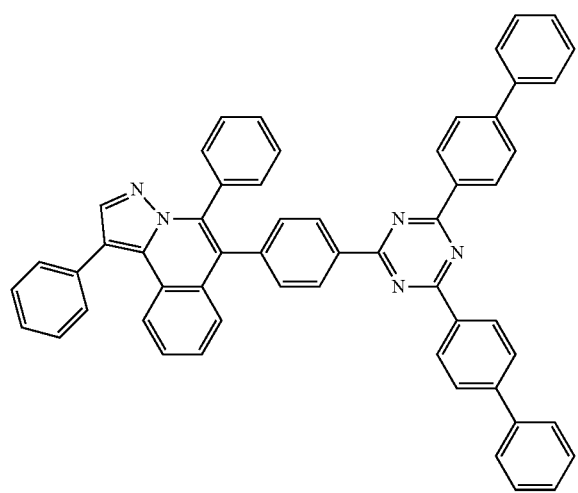
32
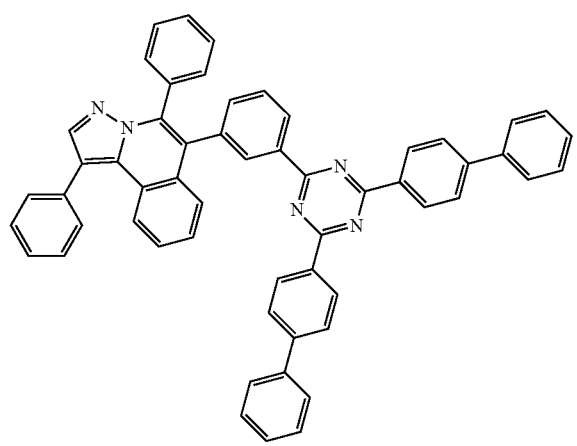

-continued
33
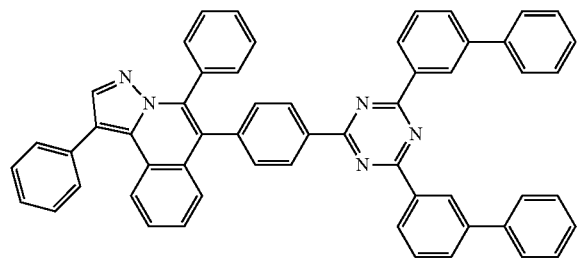
34
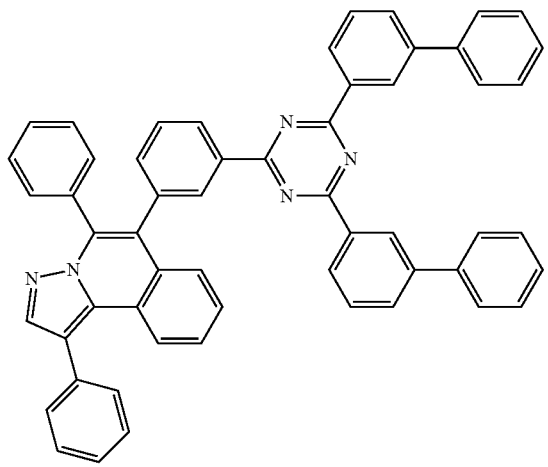
35
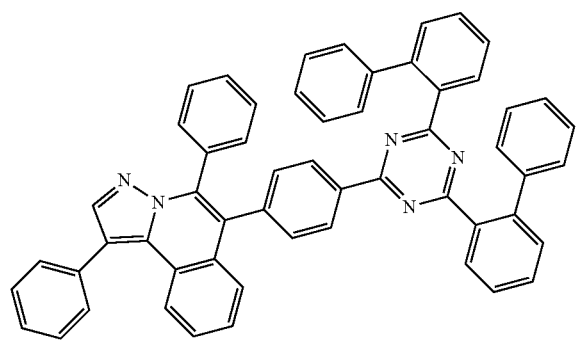
36
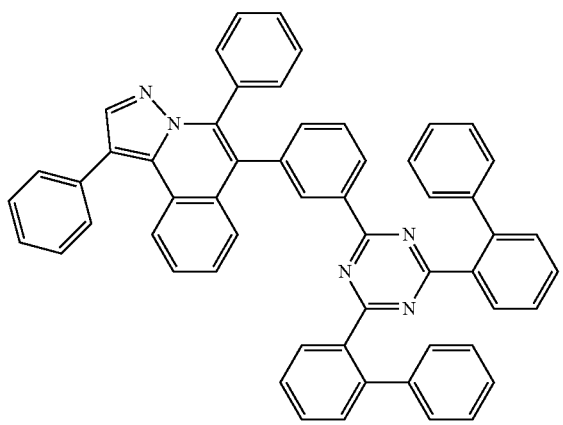
37
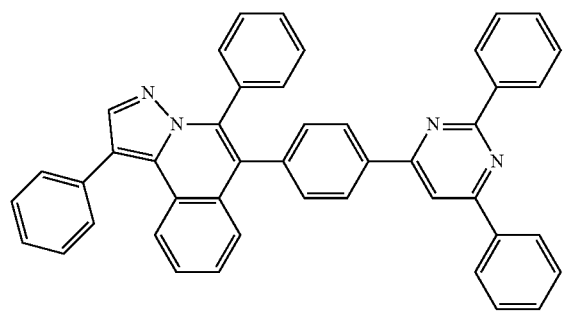
38
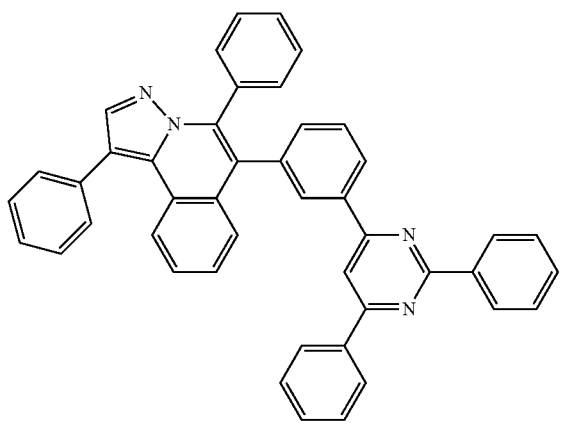

-continued
39
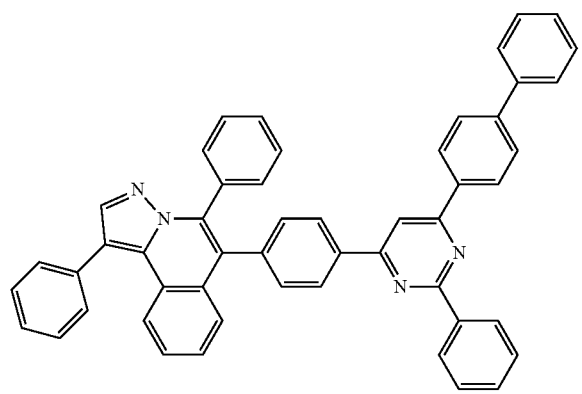
40
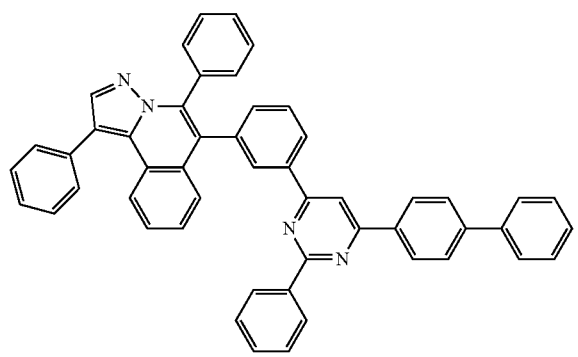
41
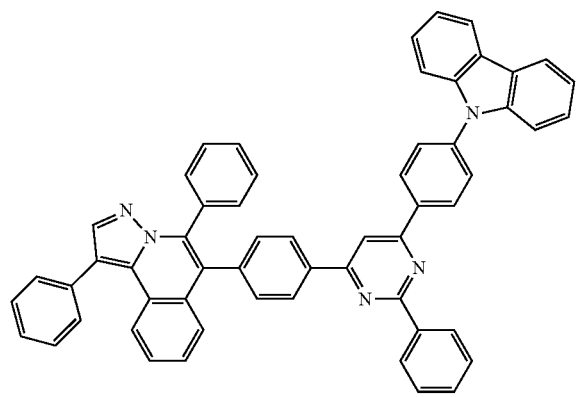
42
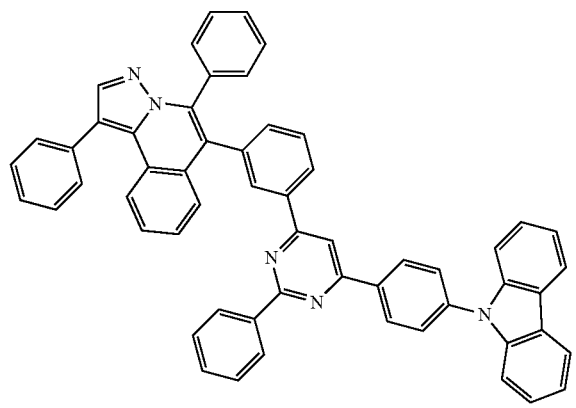
43
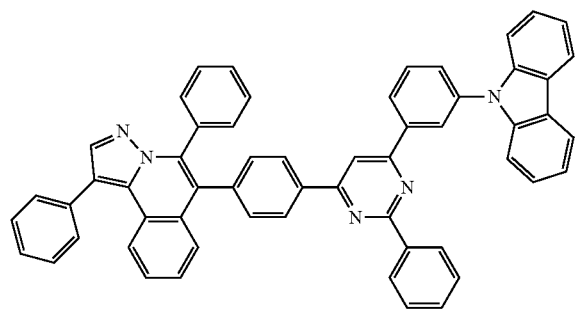
44
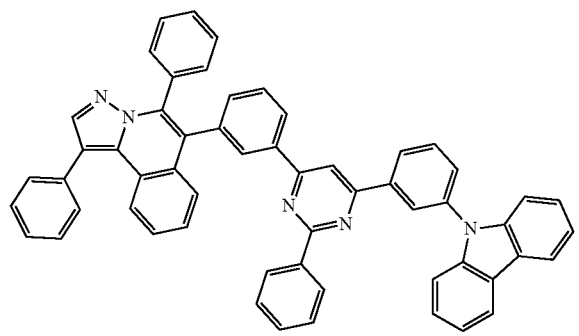
45
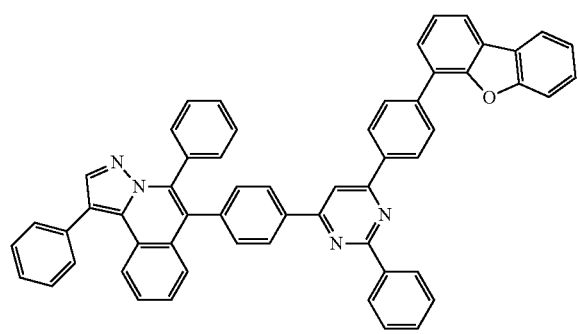
46
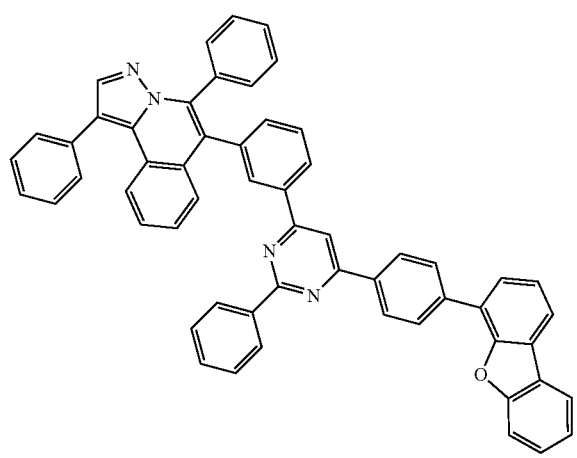

47
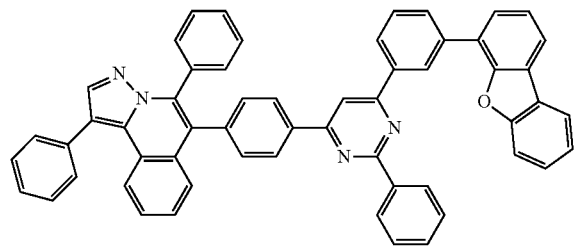
48
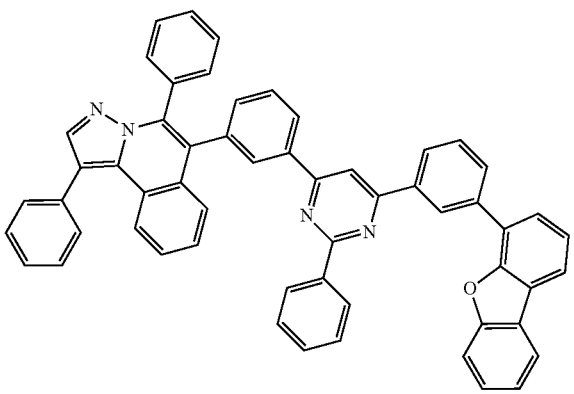
49
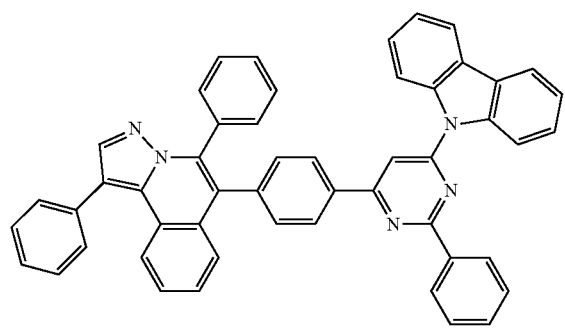
50
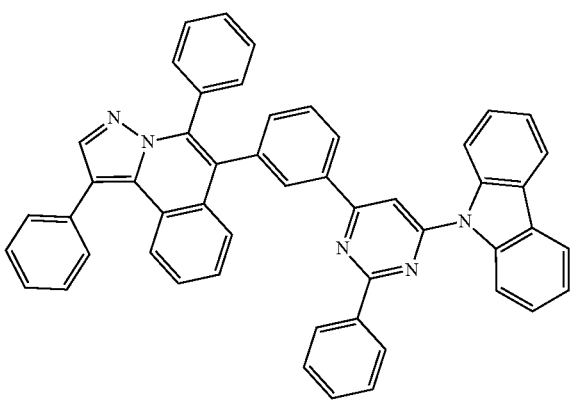
51
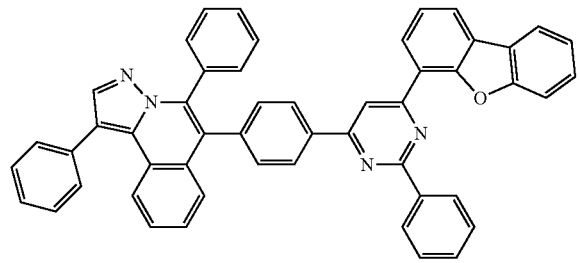
52
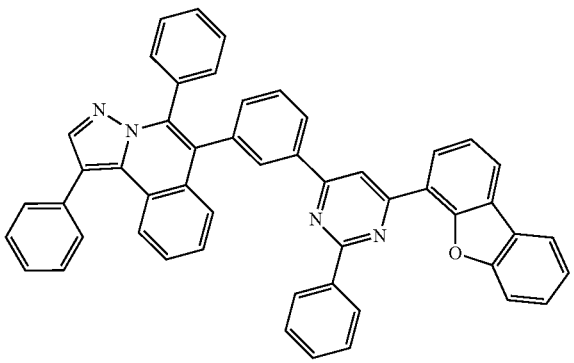
53
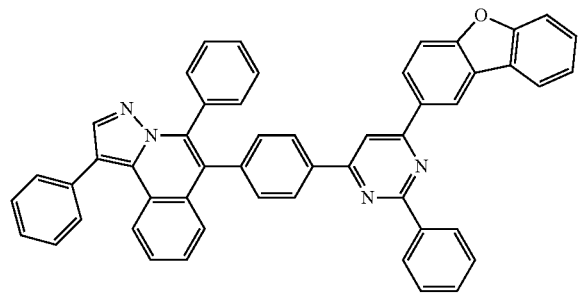
54
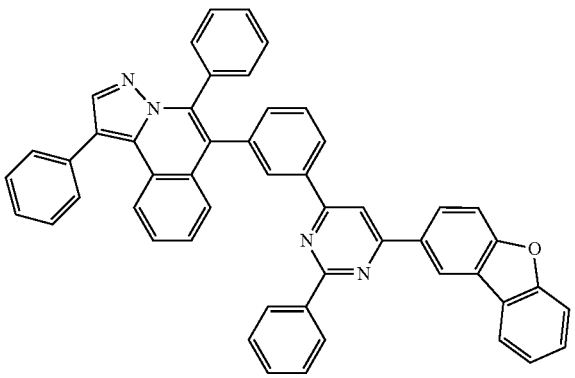

-continued
55
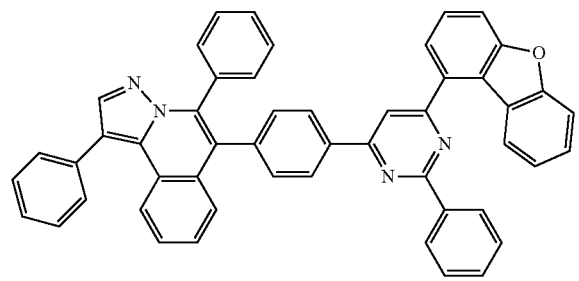
56
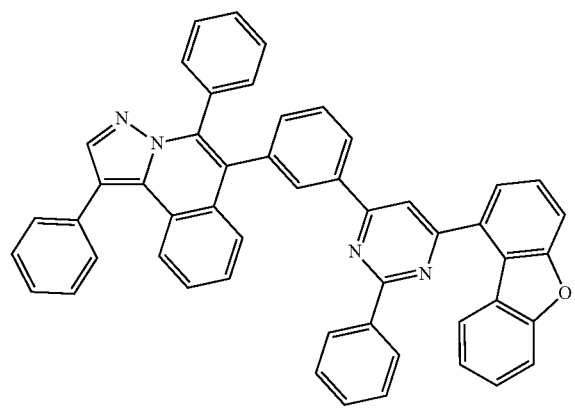
57
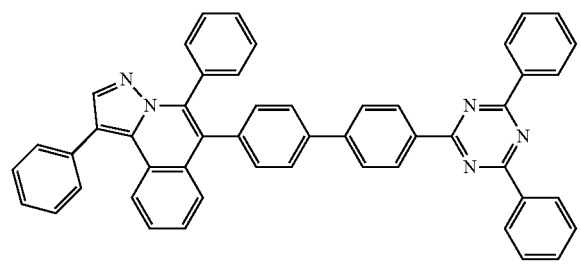
58
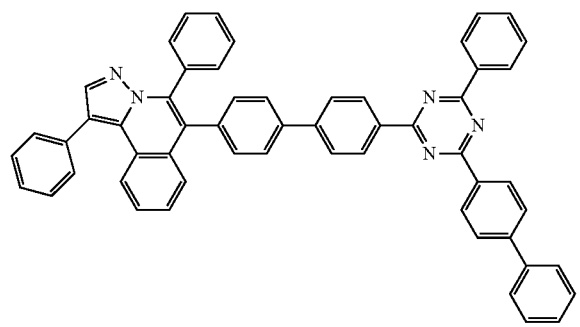
59
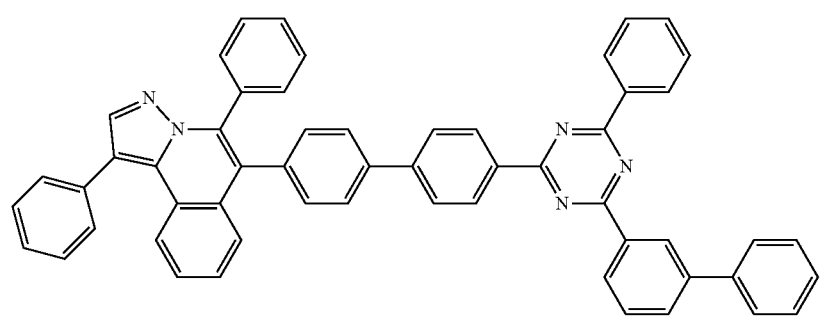
60
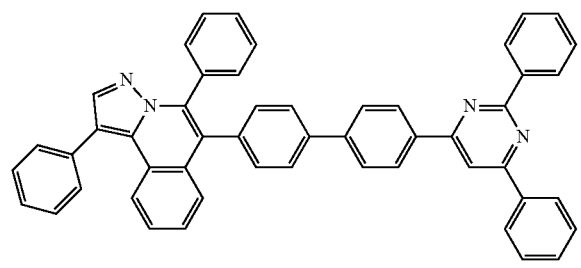
61
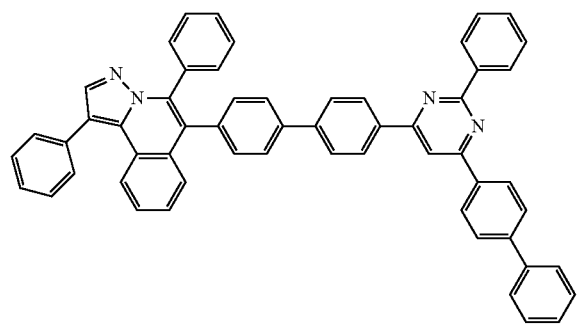

62
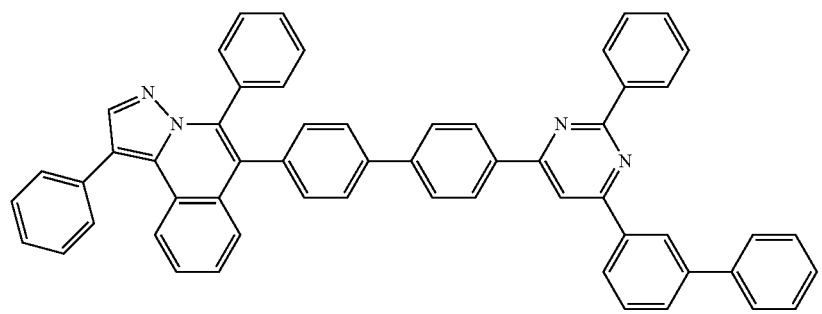
63
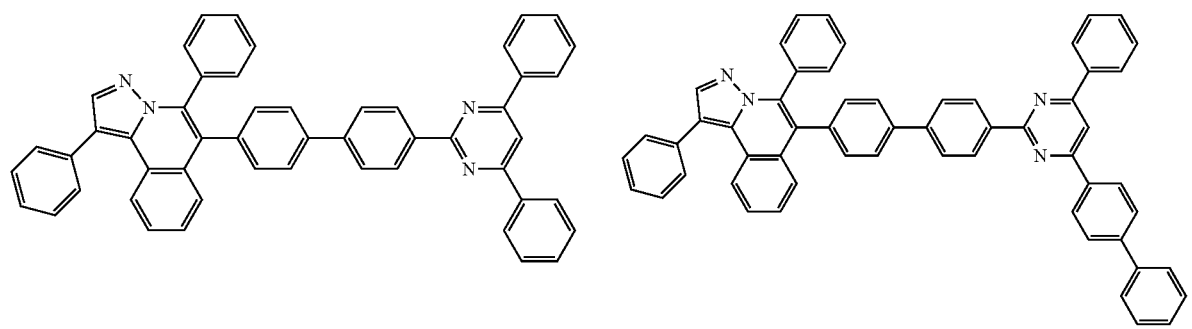
64
65
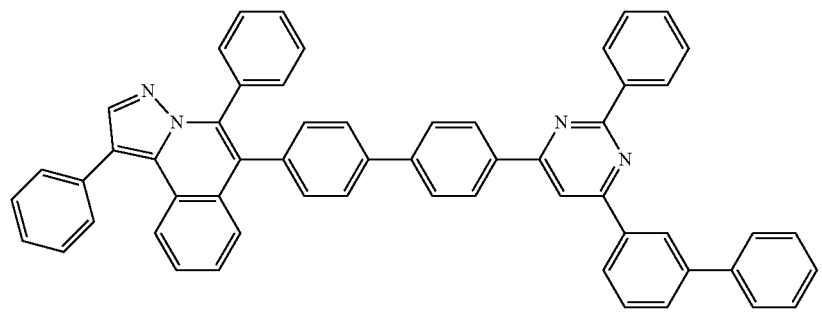
66
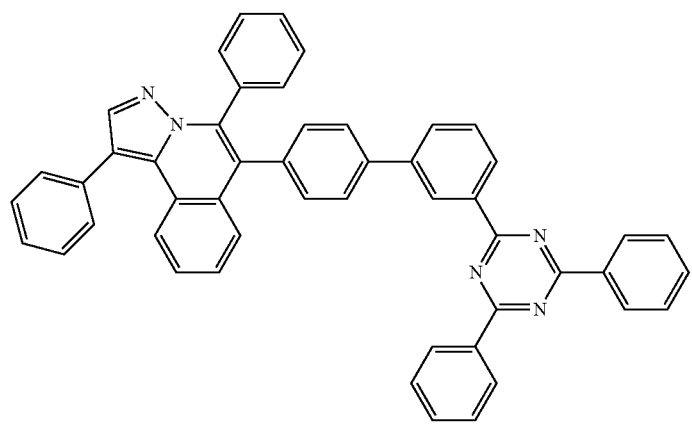

67
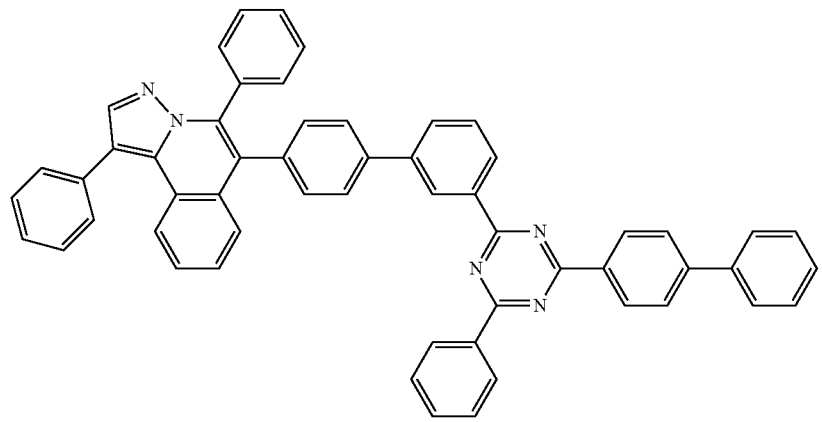
68
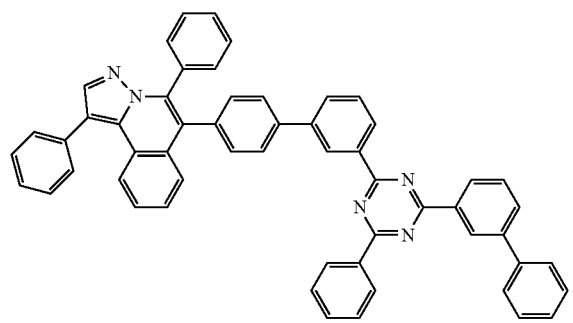
69
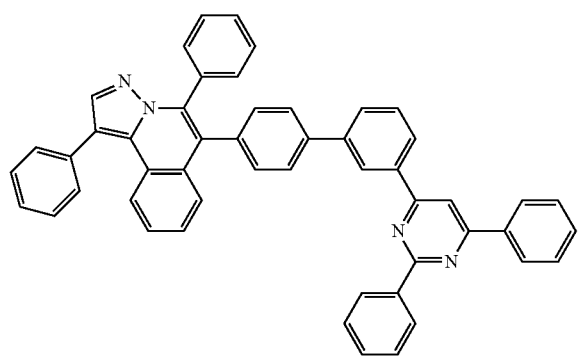
70
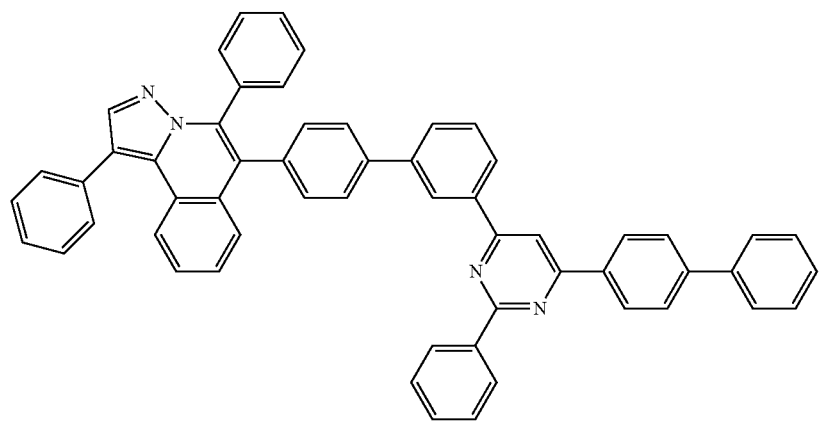
71
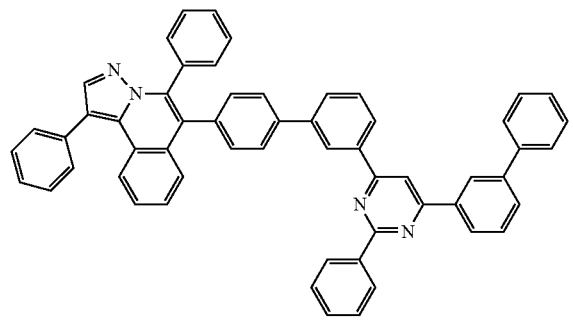
72
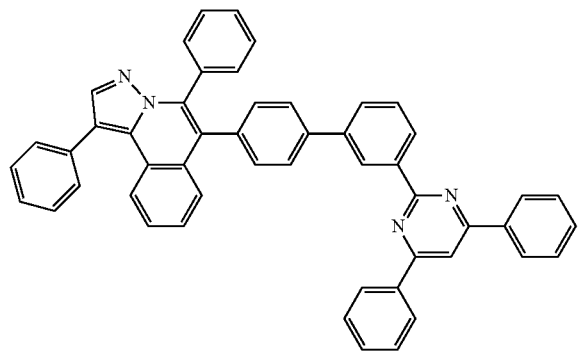

73
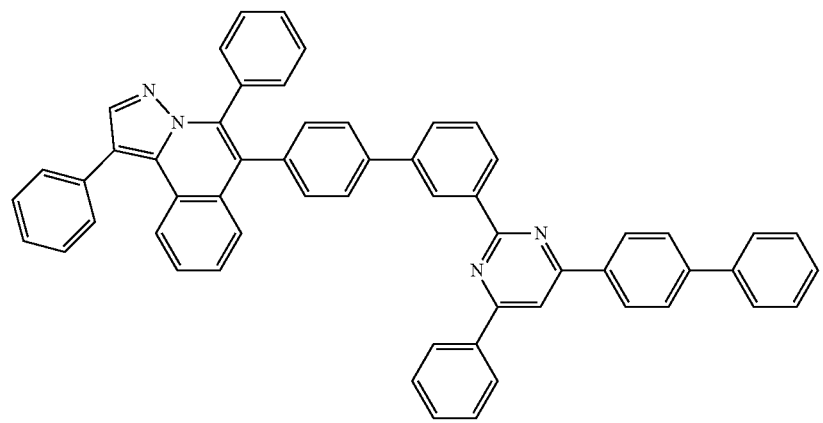
74
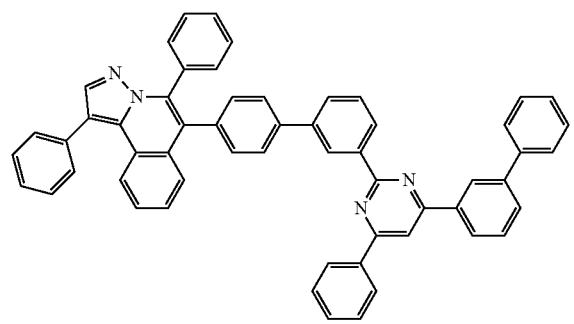
75
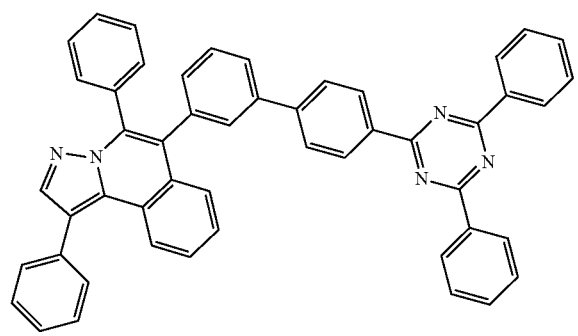
76
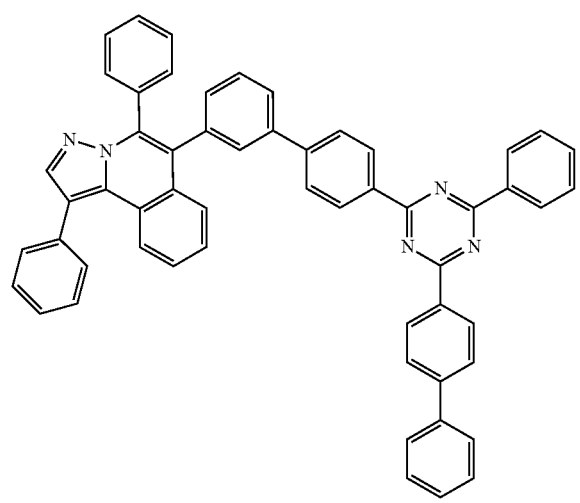
77
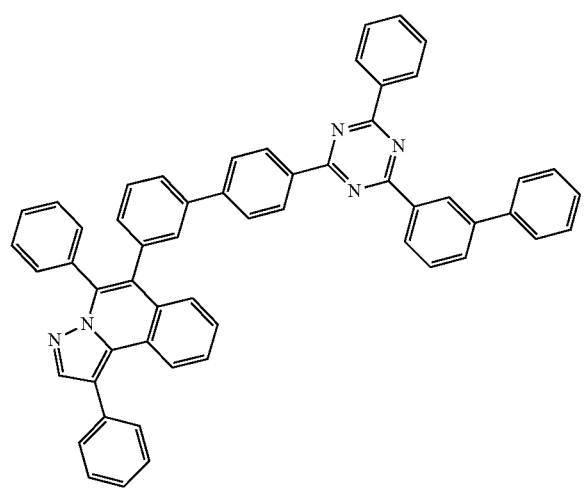

78
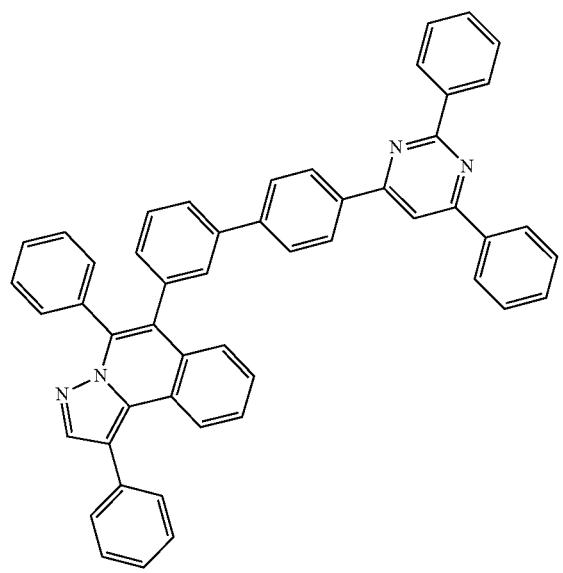
79
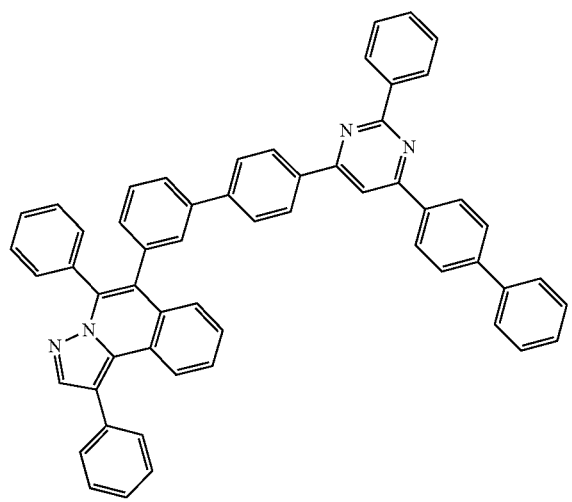
80
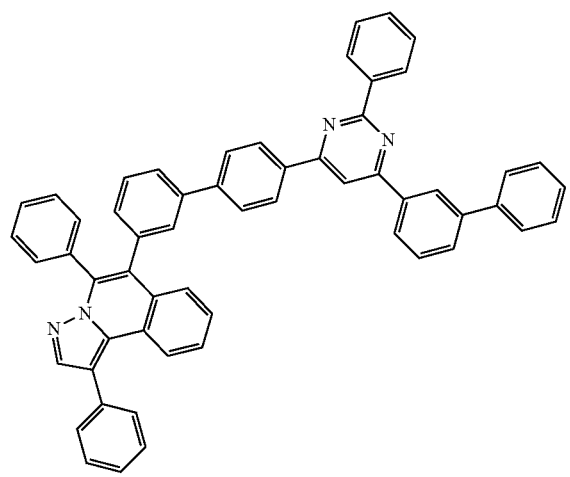
81
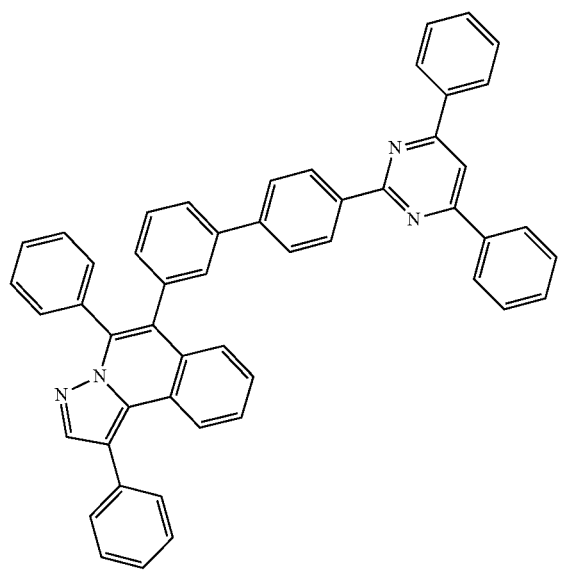

-continued
82
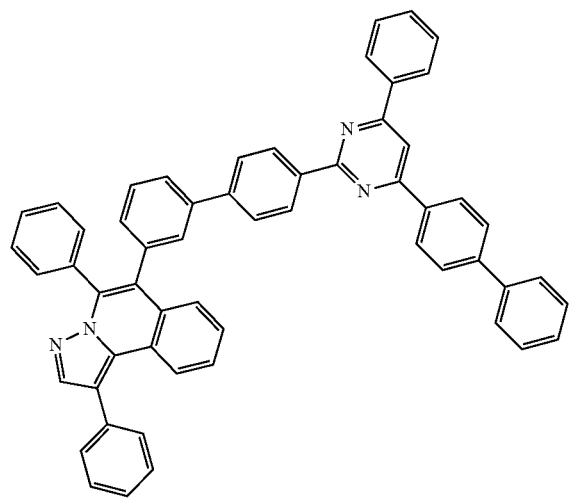
83
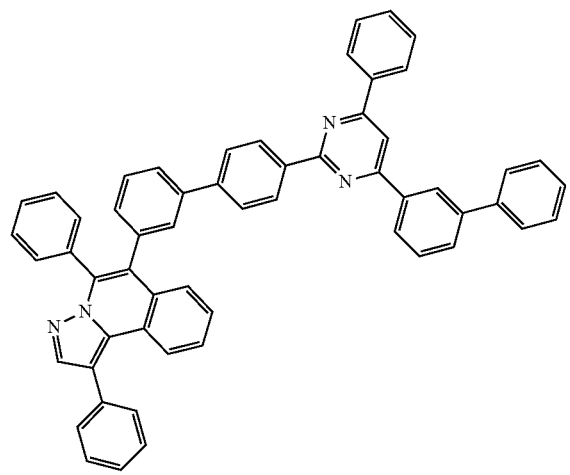
84
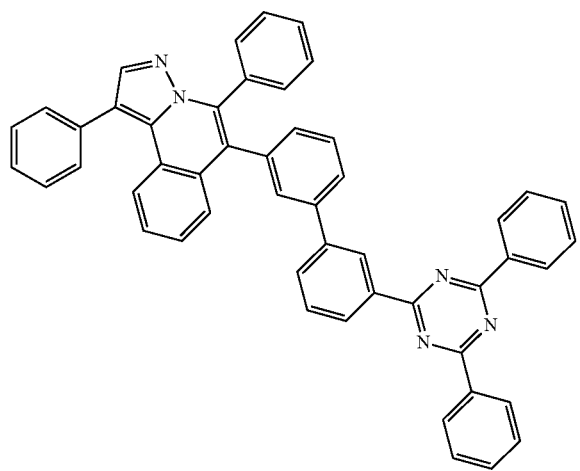
85
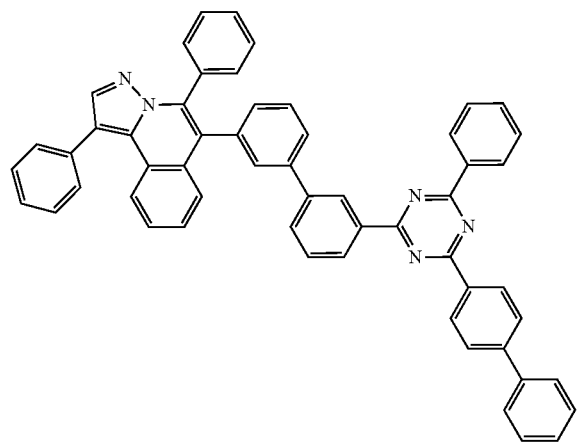
86
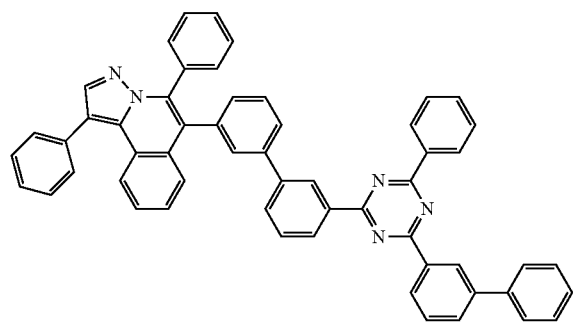
87
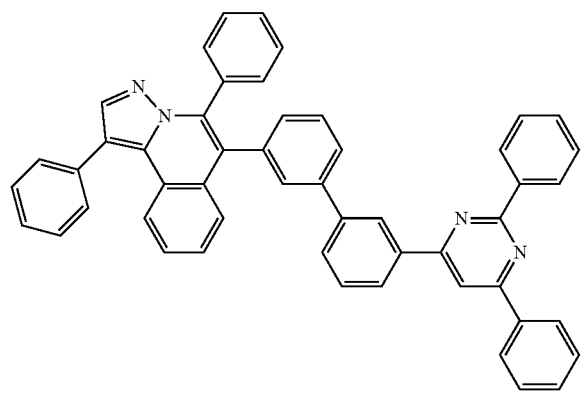

-continued
88
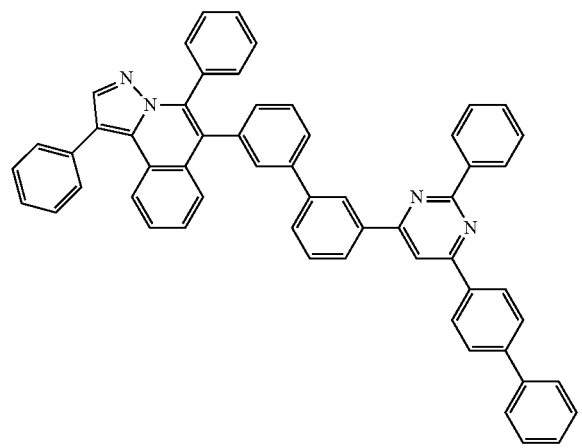
89
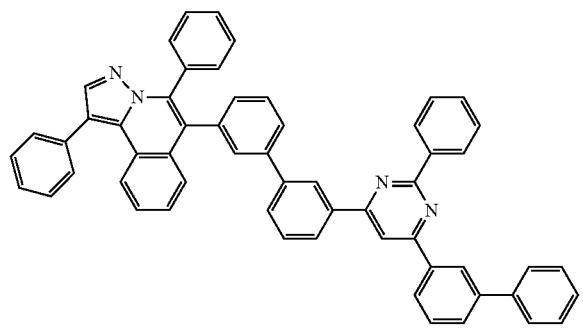
90
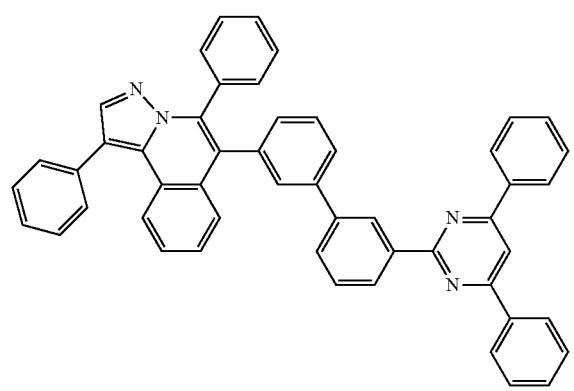
91
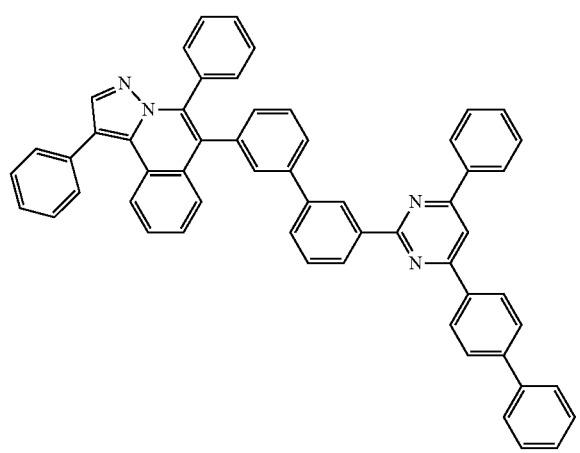
92
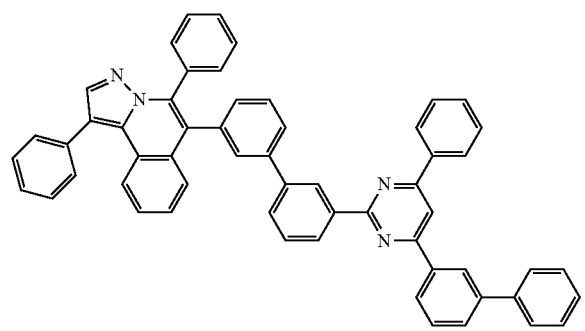
93
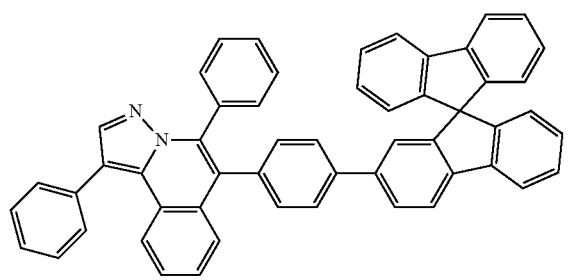
94
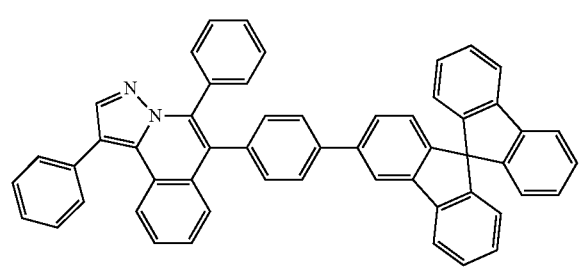
95
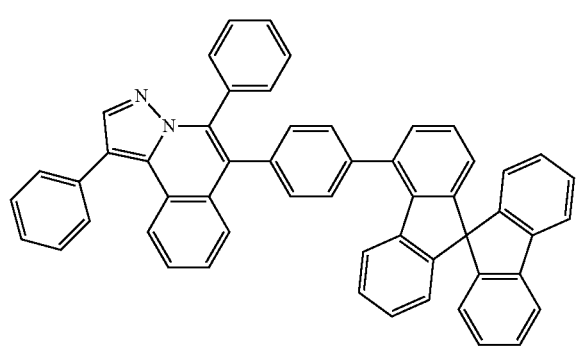

-continued
96
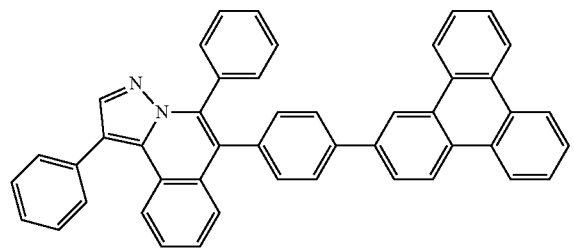
97
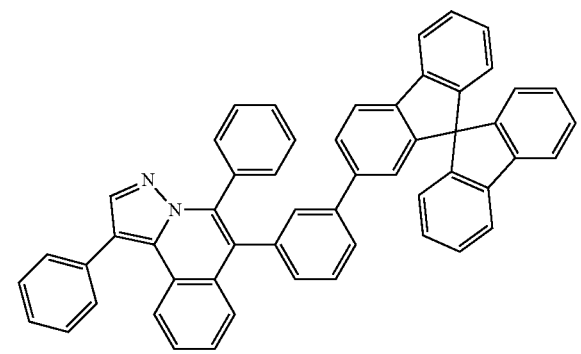
98
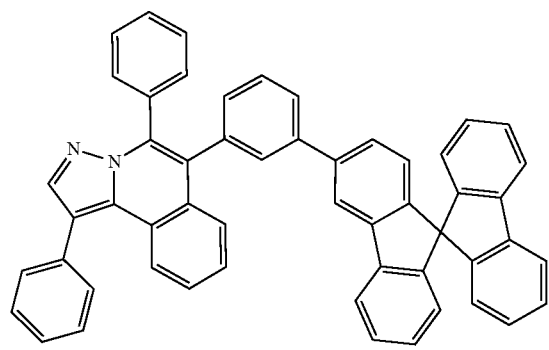
99
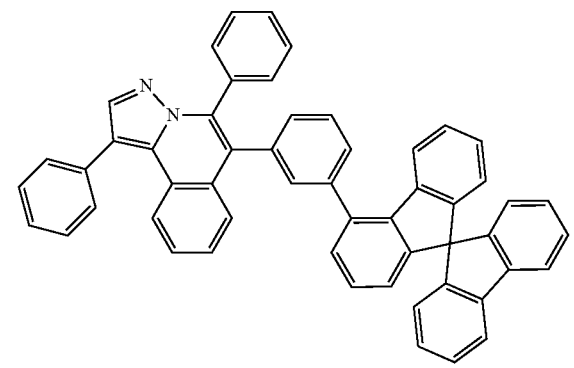
100
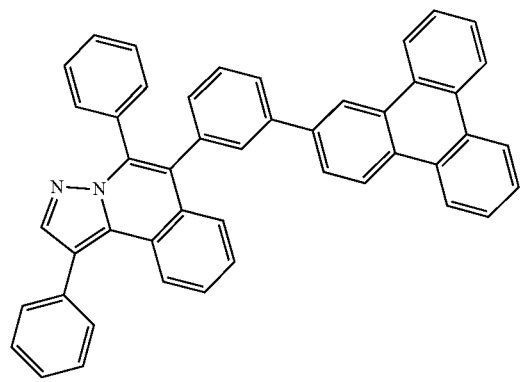
101
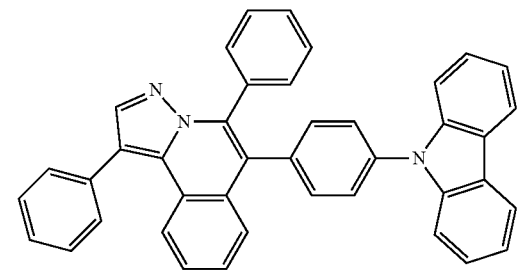
102
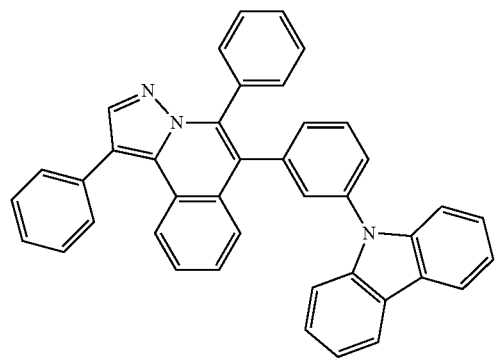
103
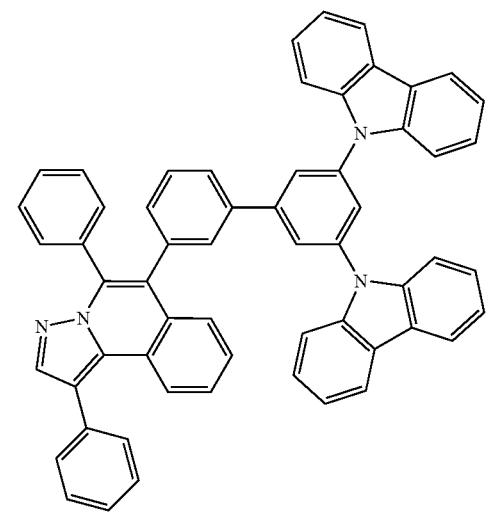

104
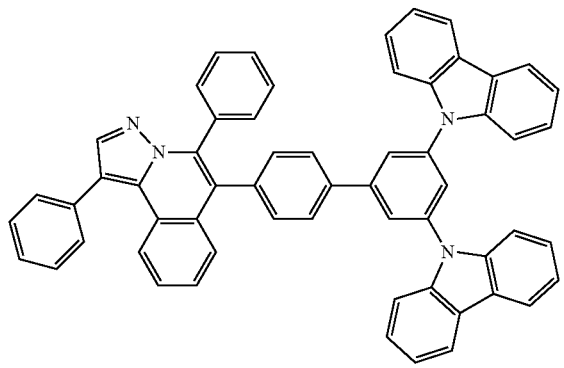
105
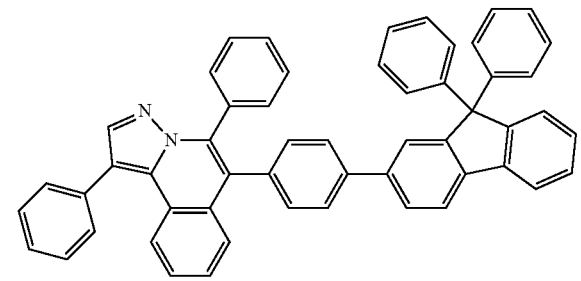
106
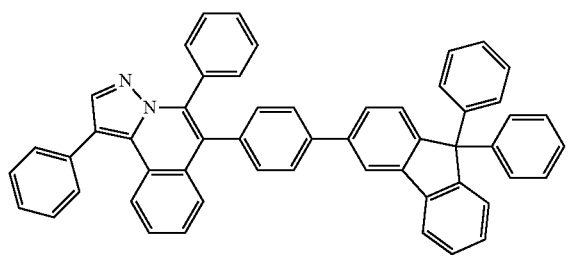
107
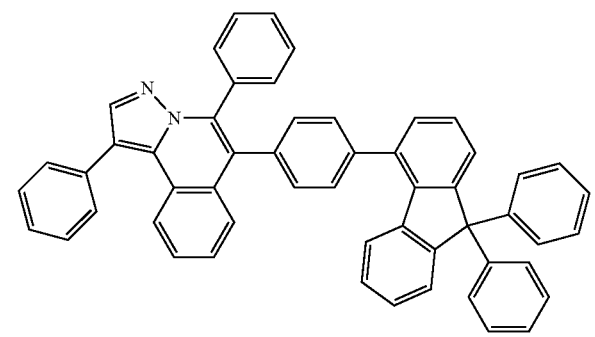
108
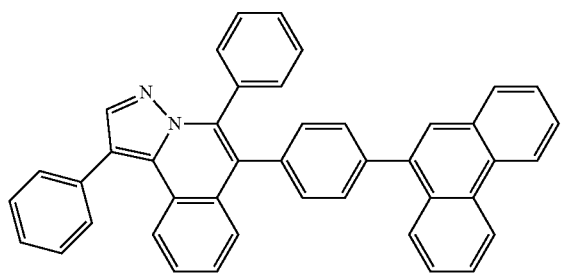
109
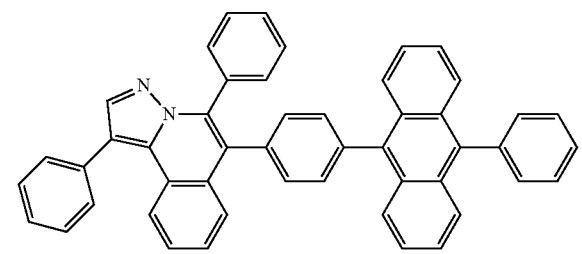
110
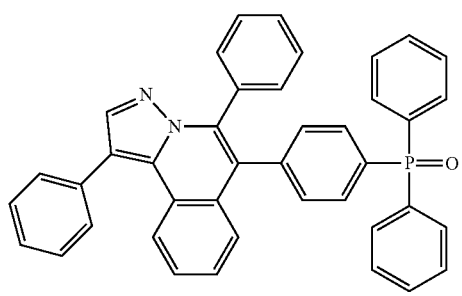
111
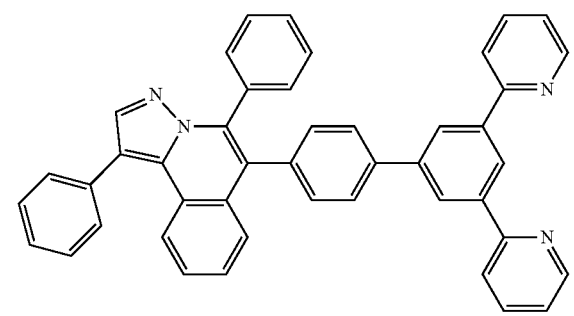

112 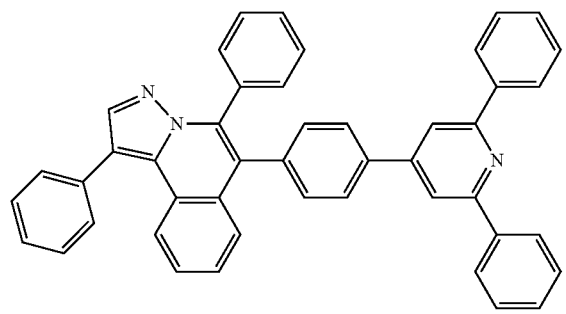
113 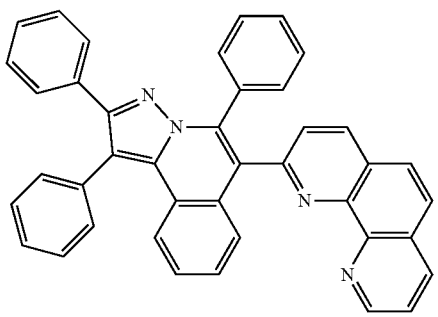
114 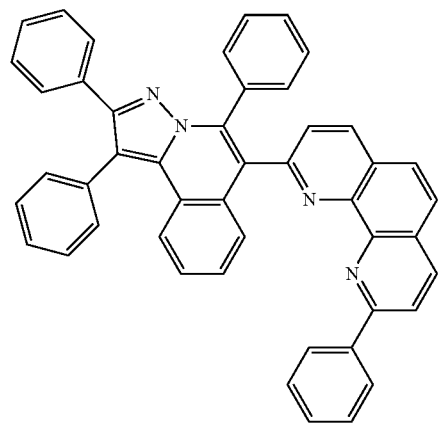
115 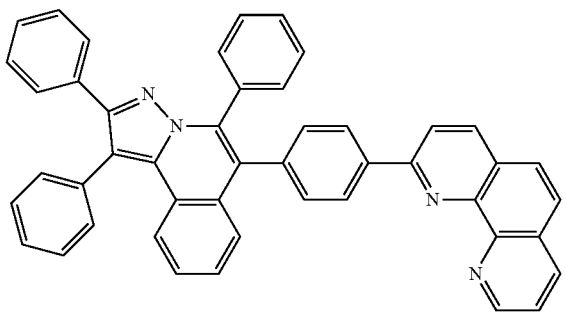
116 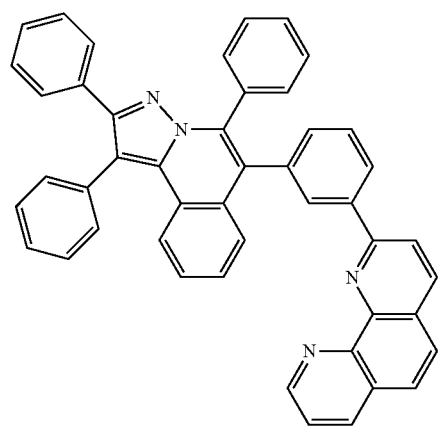
117 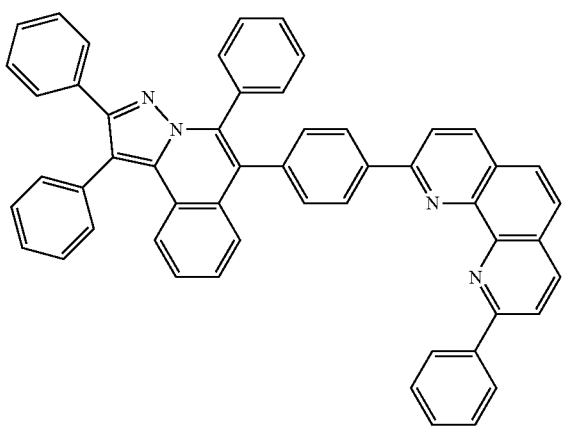

-continued
118
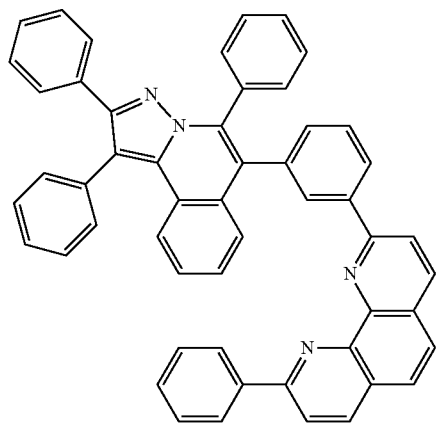
119
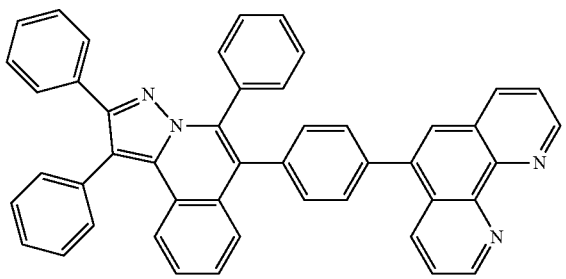
120
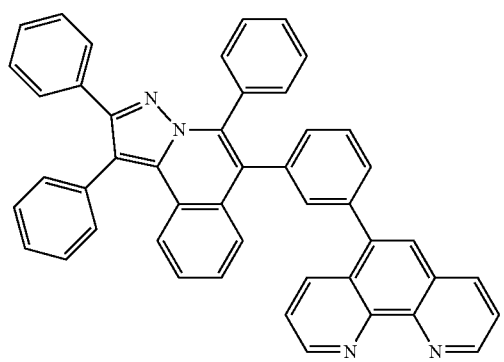
121
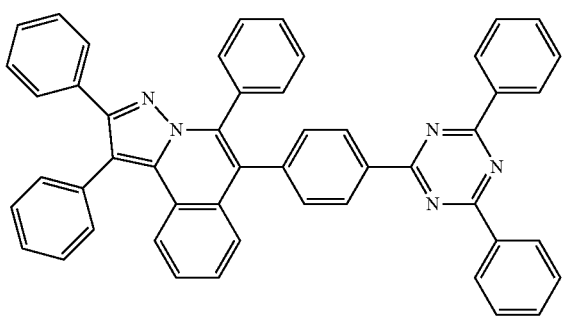
122
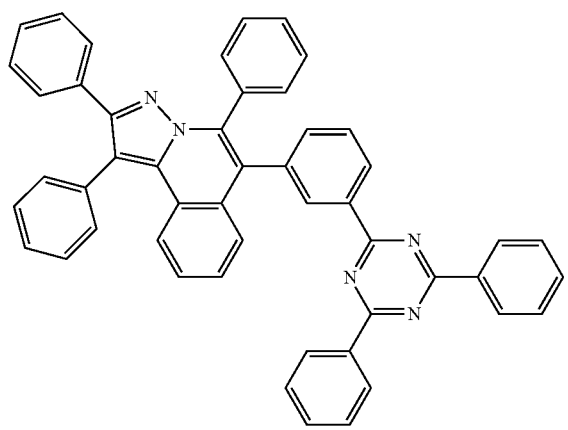
123
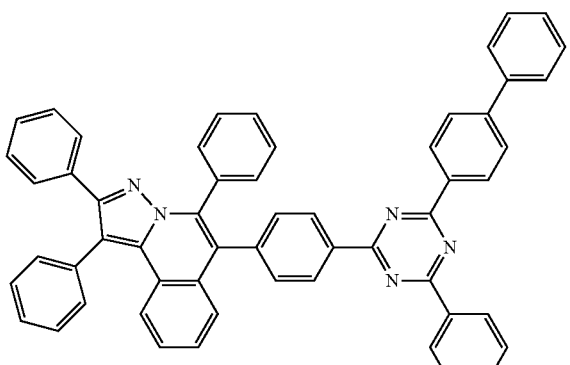

-continued
124
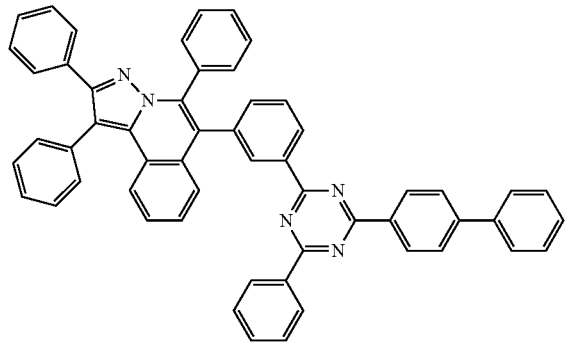
125
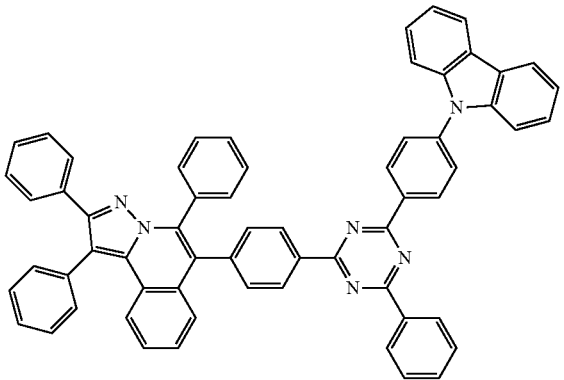
126
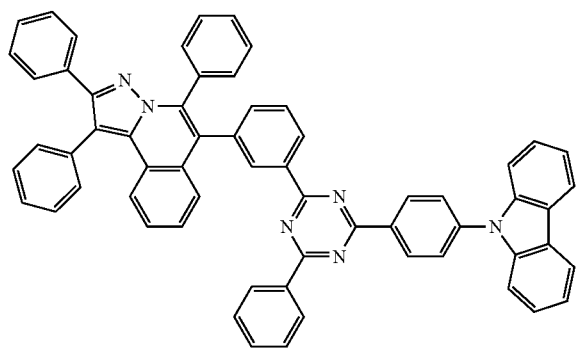
127
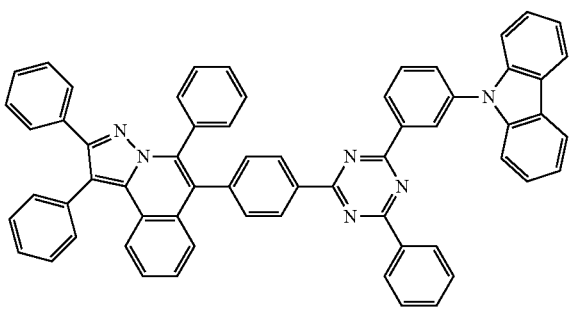
128
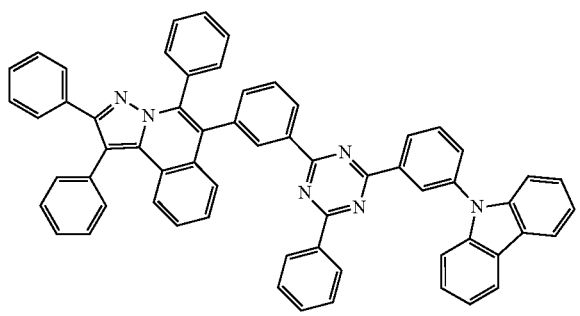
129
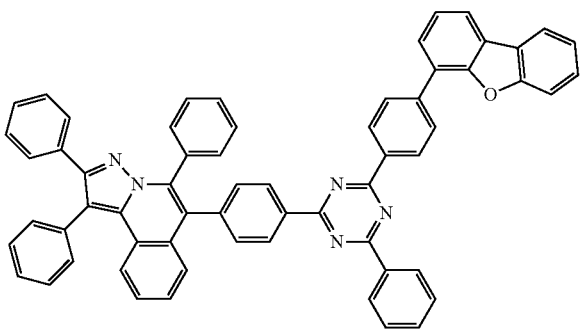
130
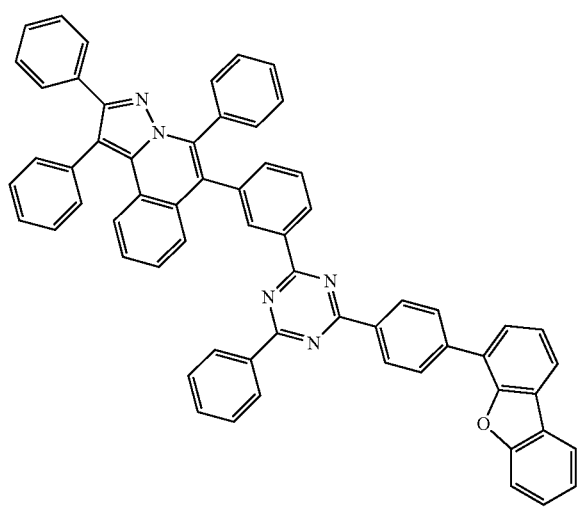
131
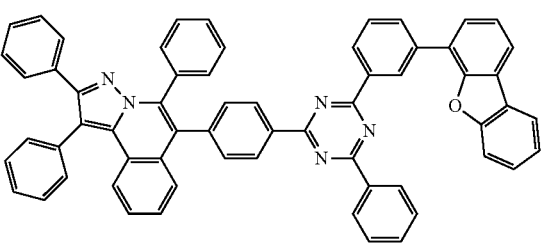

-continued
132
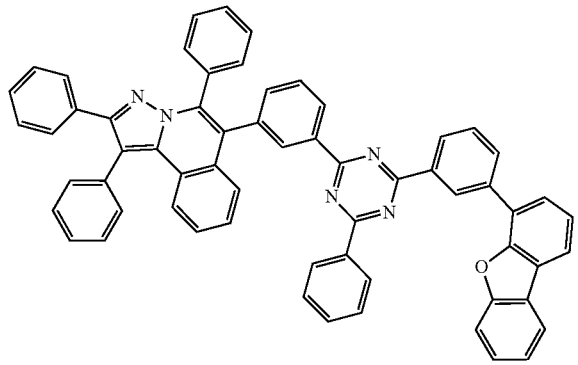
133
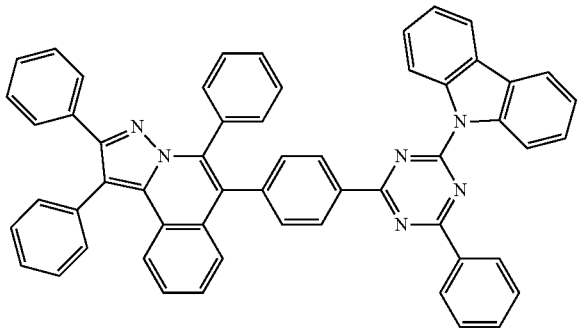
134
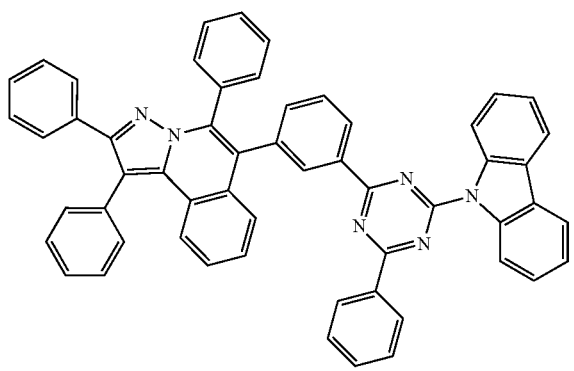
135
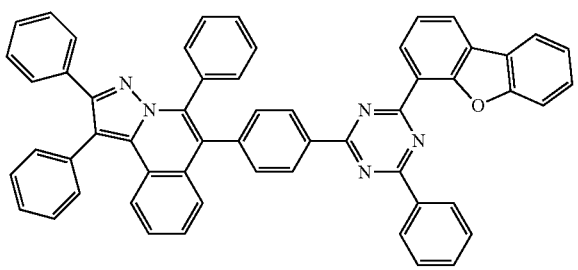
136
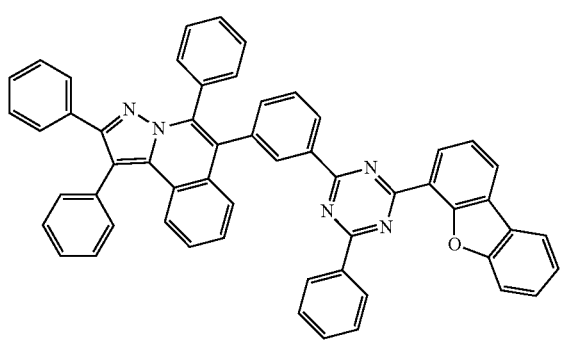
137
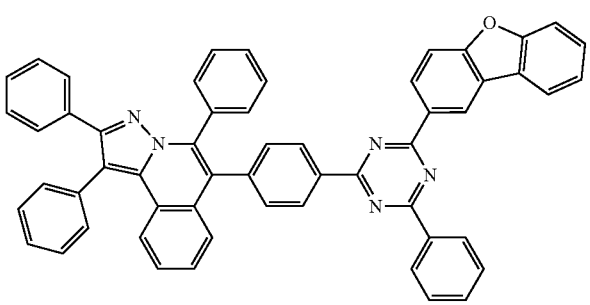
138
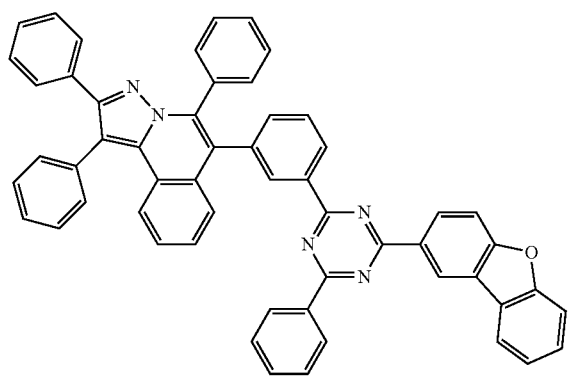
139
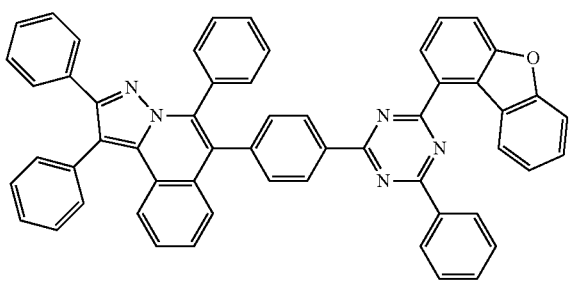

-continued
140
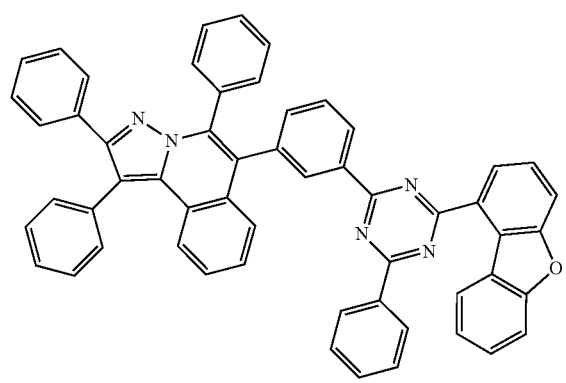
141
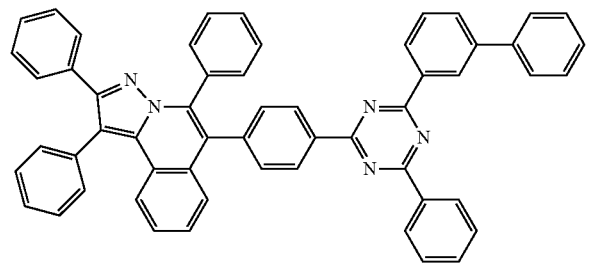
142
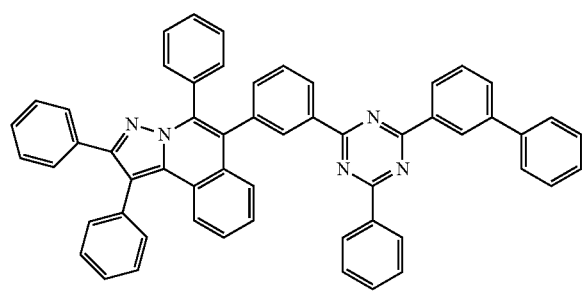
143
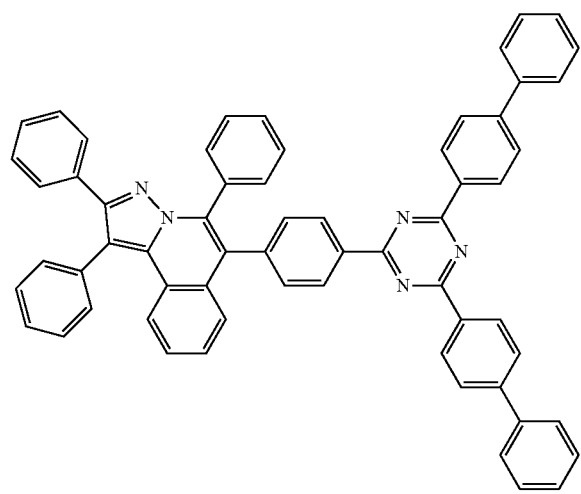
144
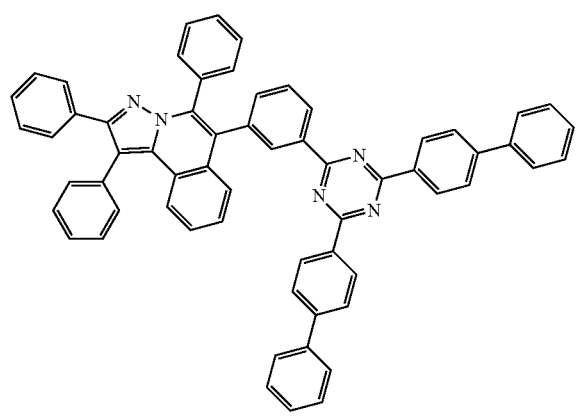
145
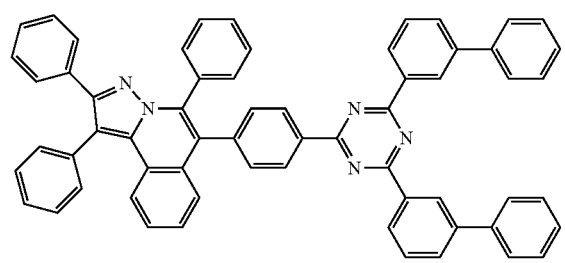

-continued
146
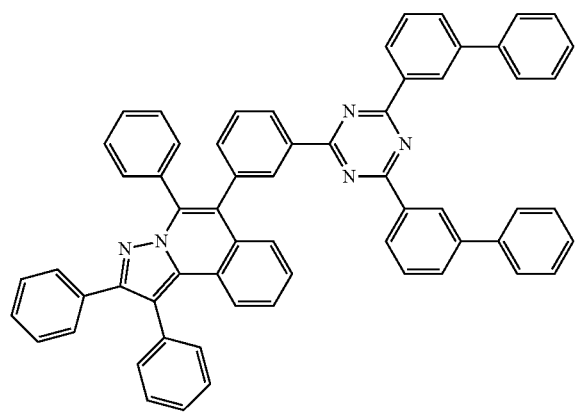
147
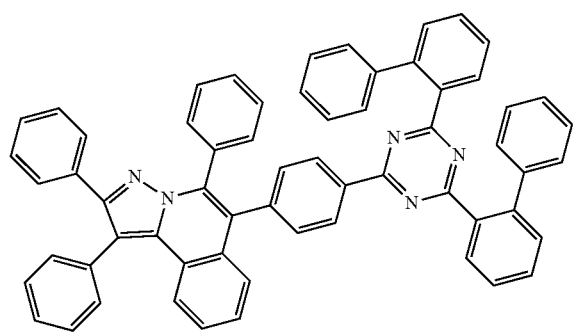
148
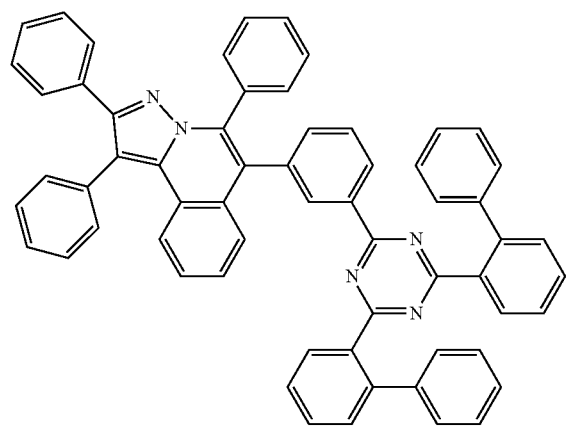
149
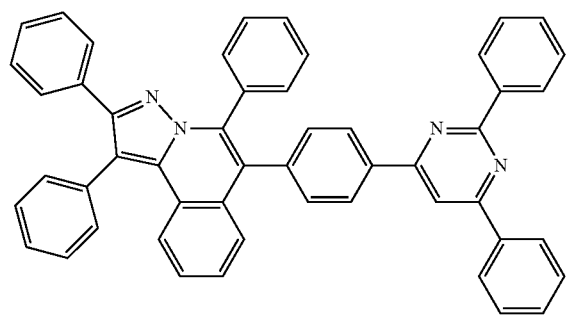
150
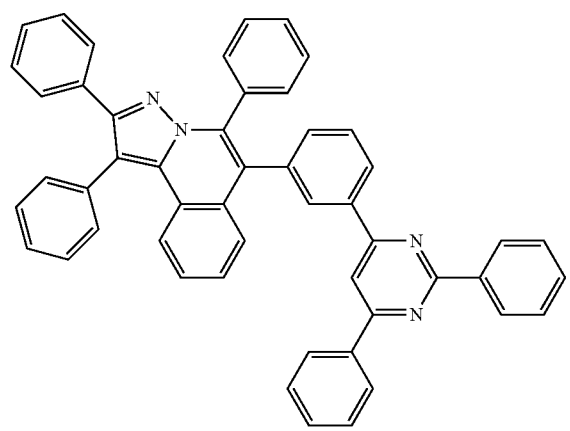
151
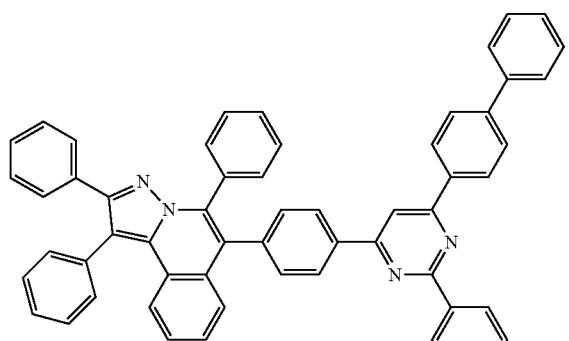

-continued
152
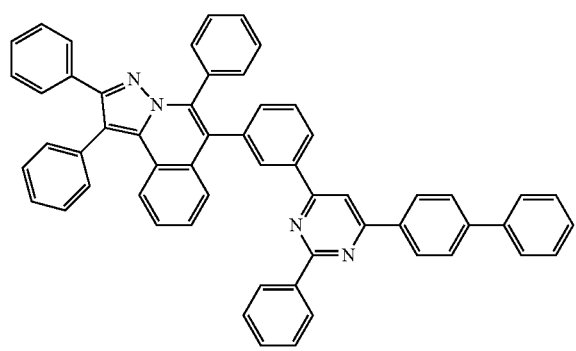
153
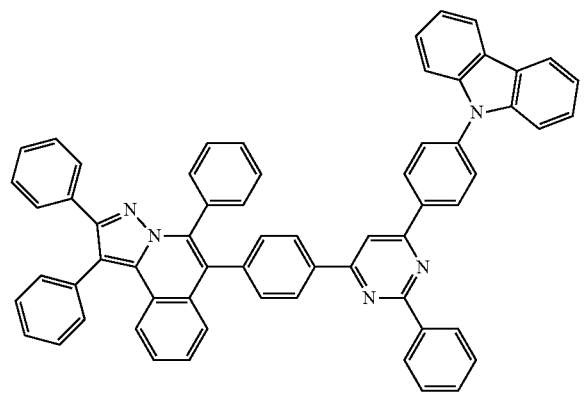
154
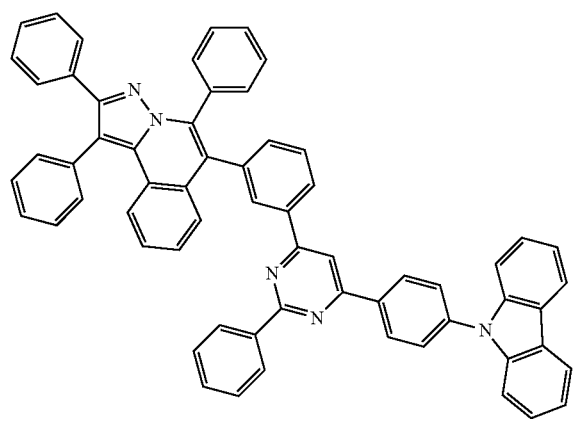
155
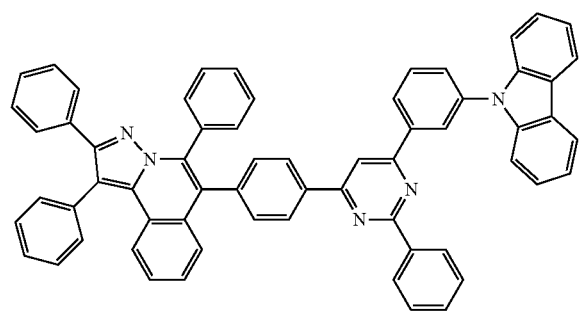
156
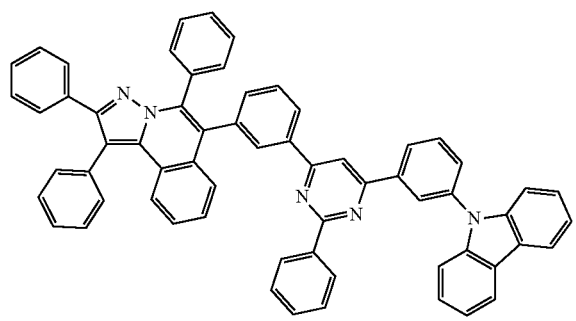
157
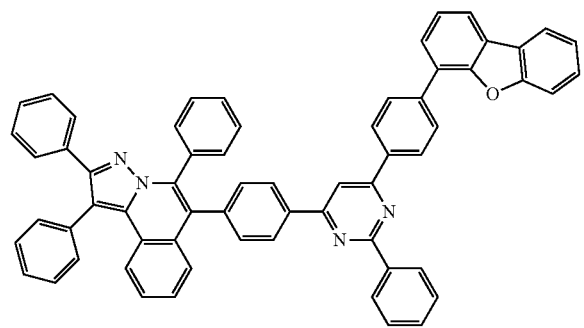

-continued
158
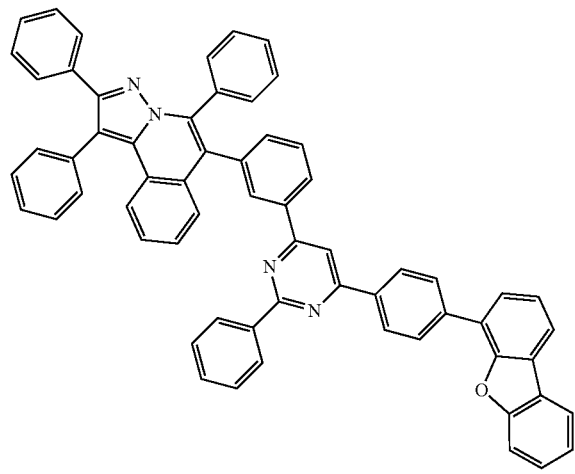
159
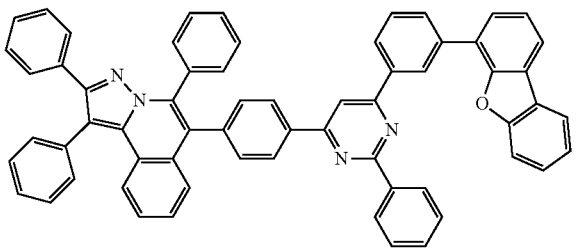
160
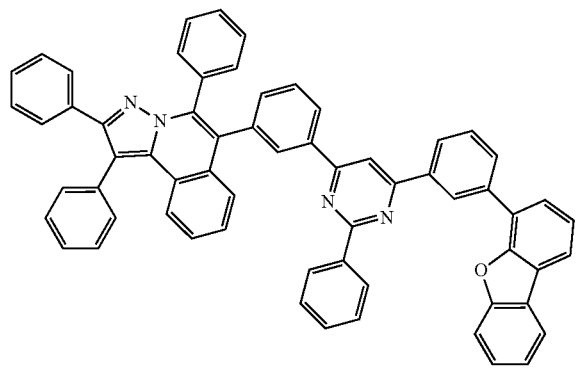
161
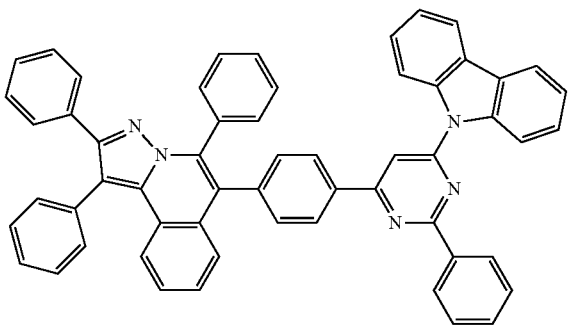
162
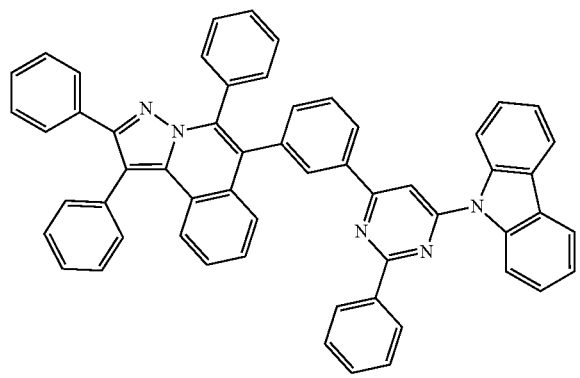
163
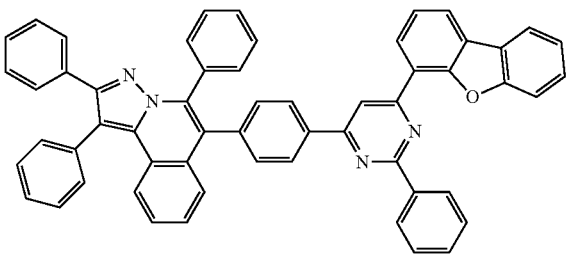
164
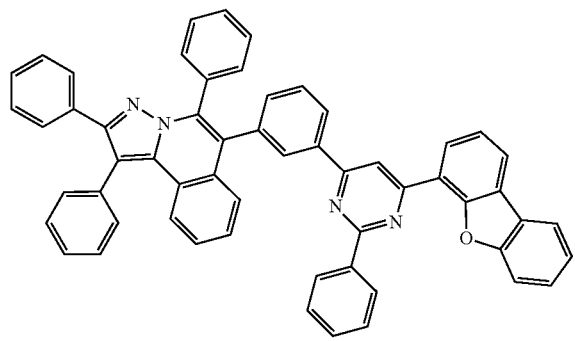
165
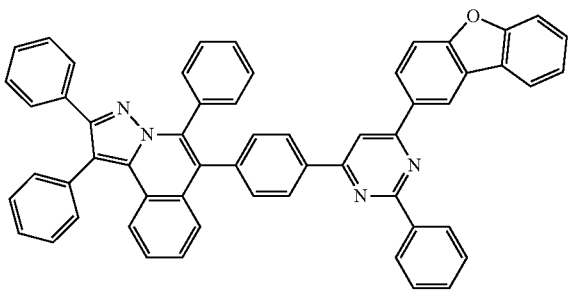

-continued
166
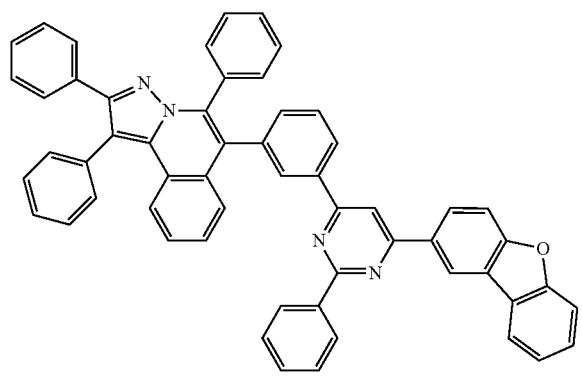
167
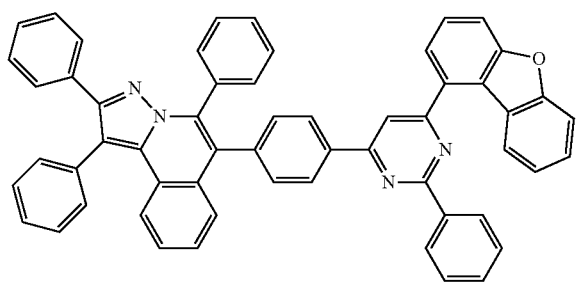
168
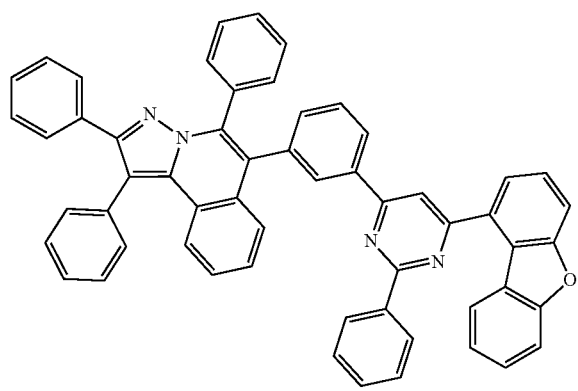
169
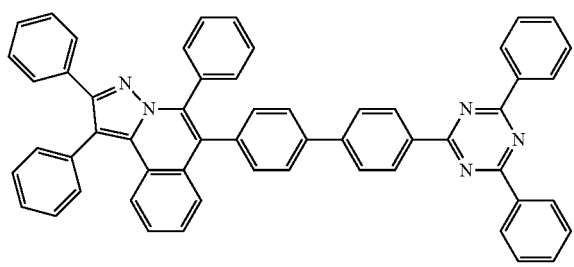
170
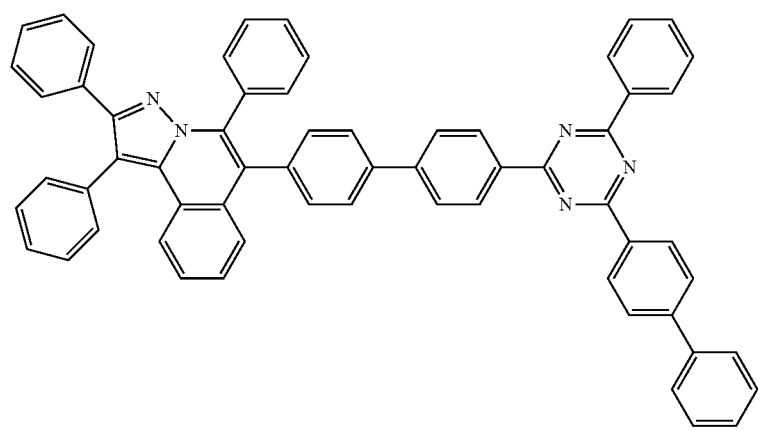
171
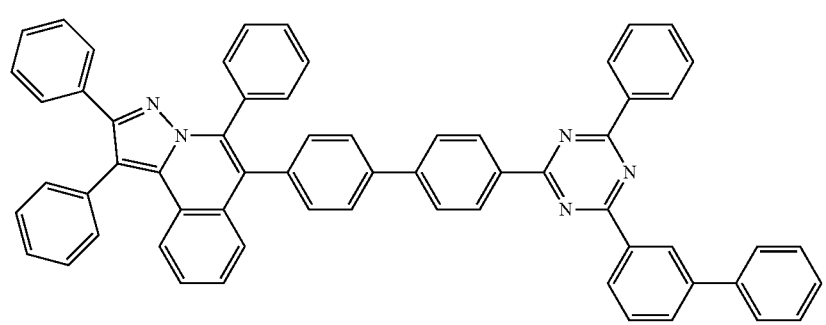

-continued
172
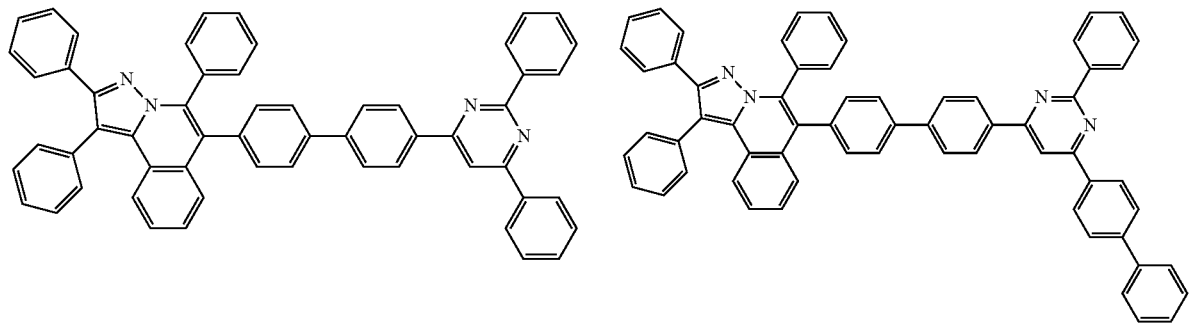
173
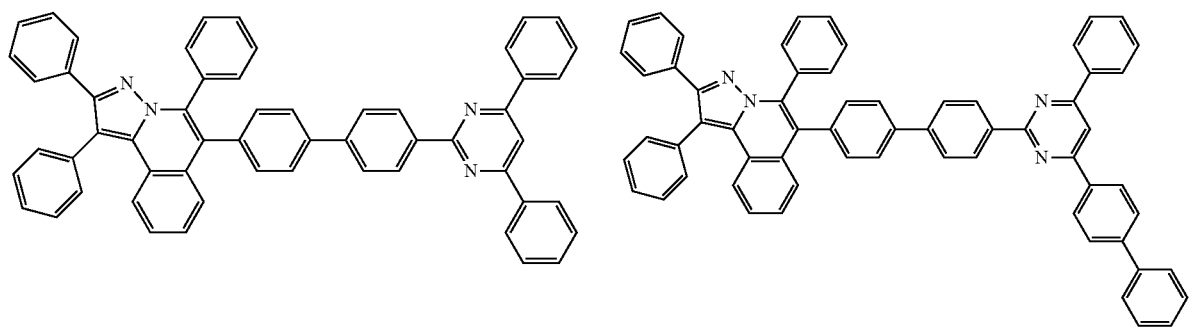
174
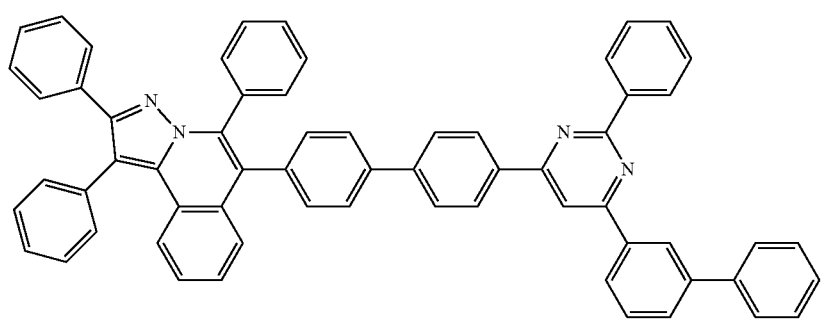
175 176
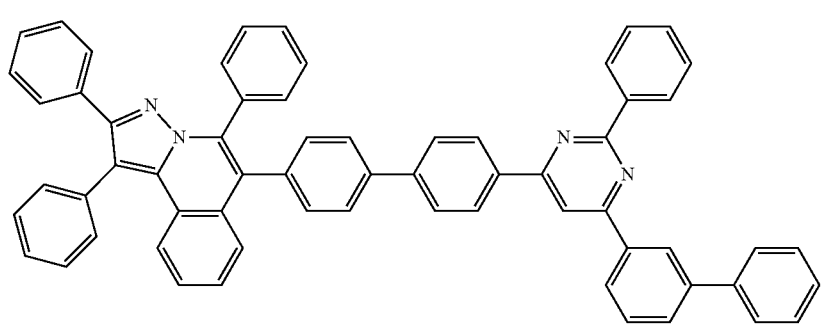
177

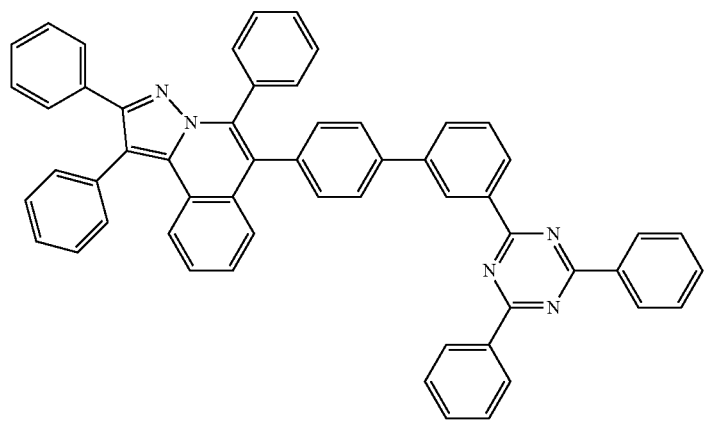
178
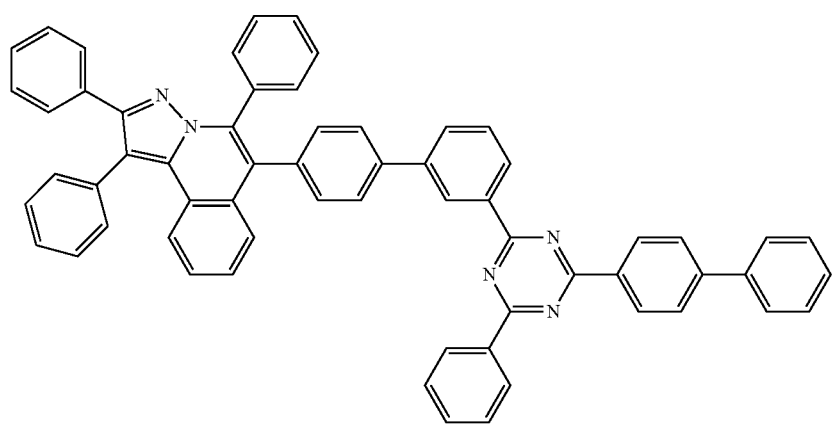
179
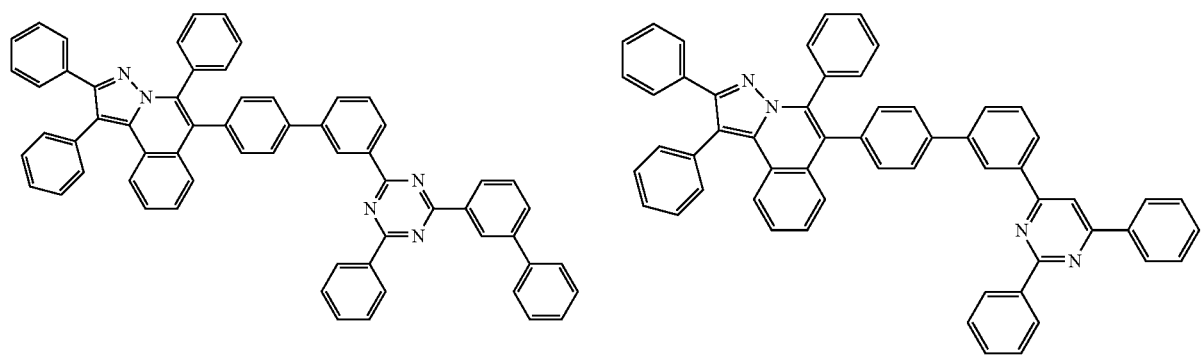
180        181
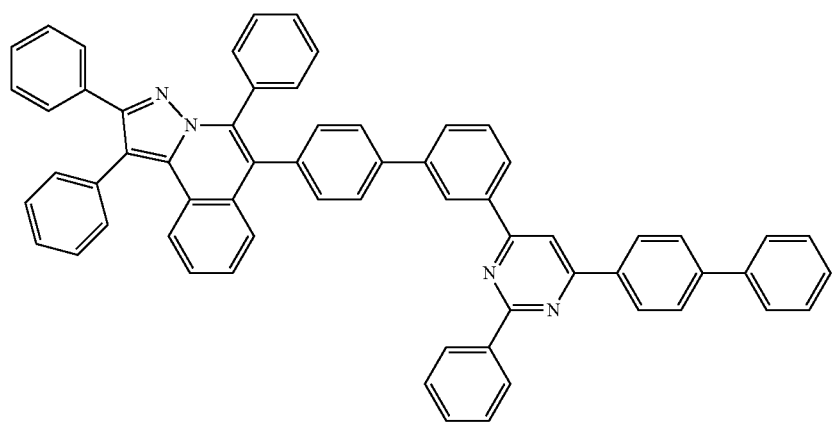
182

-continued
183
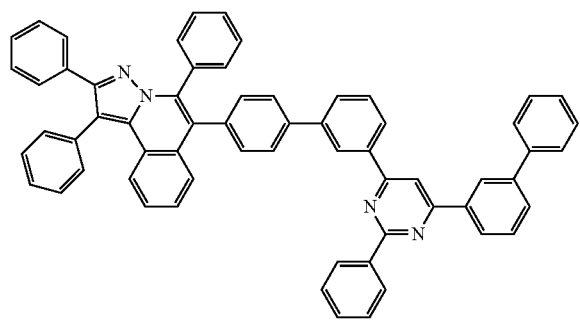
184
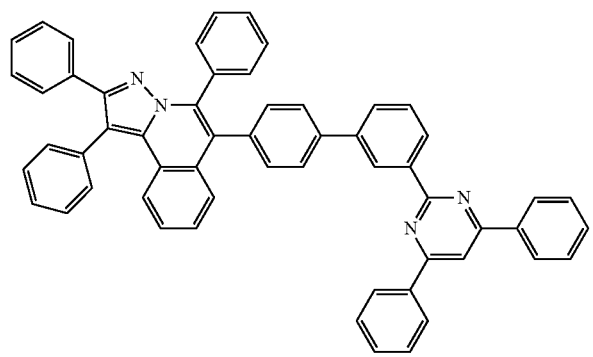
185
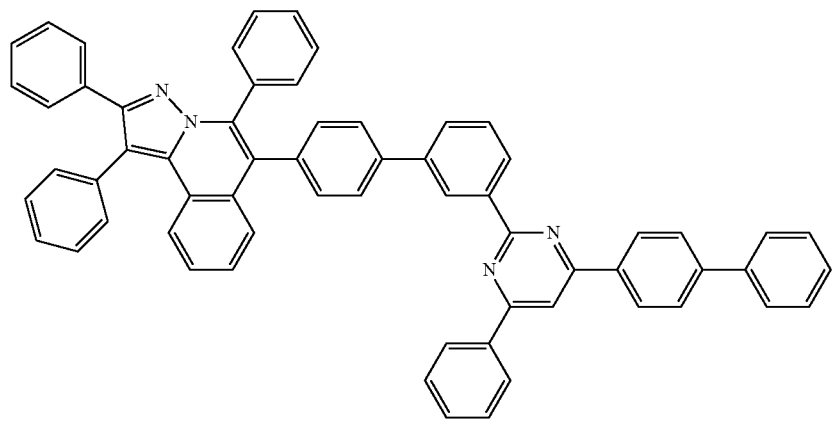
186
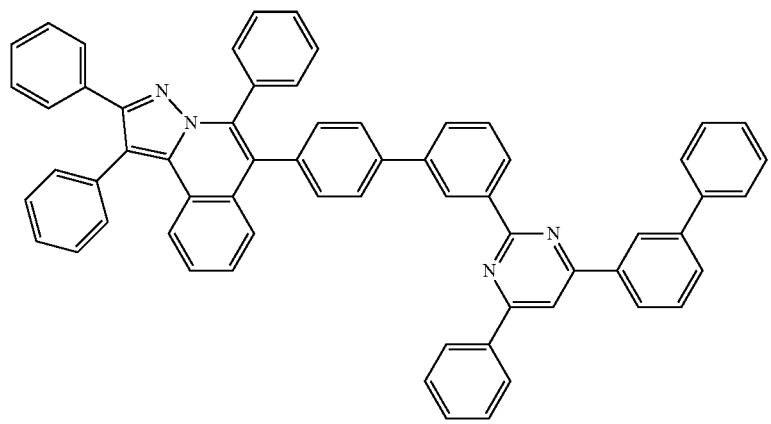

-continued
187
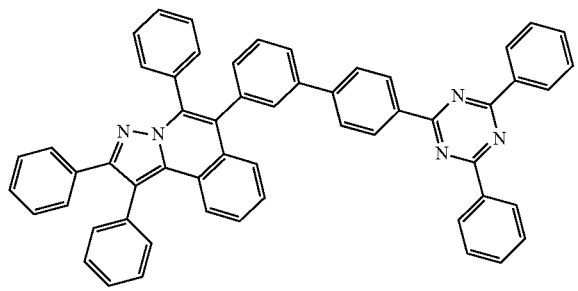
188
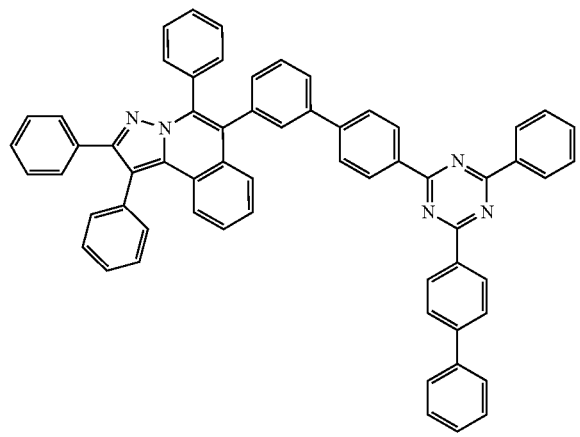
189
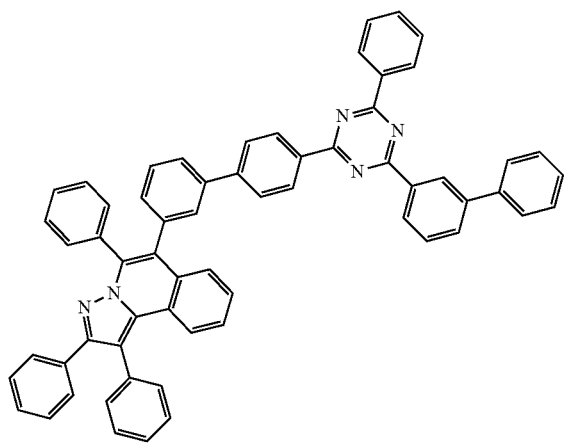
190
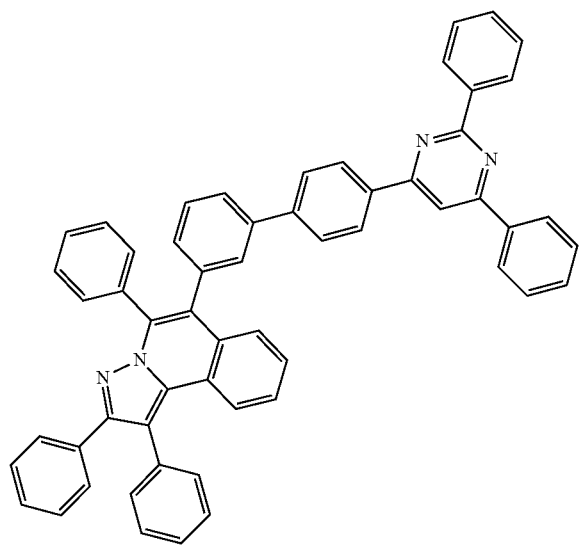
191
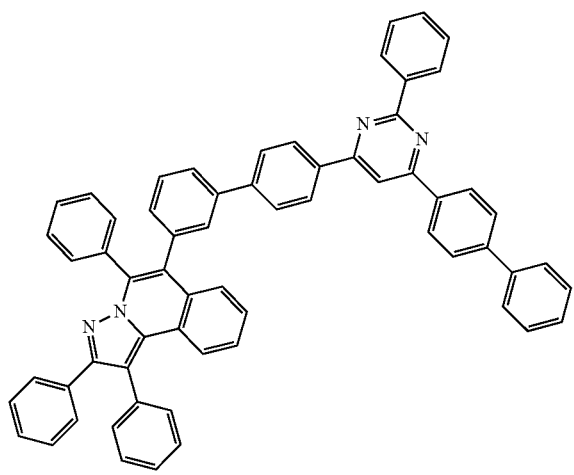
192
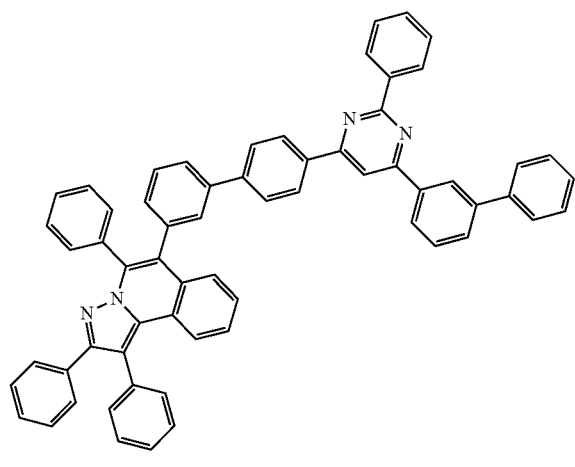

-continued
193
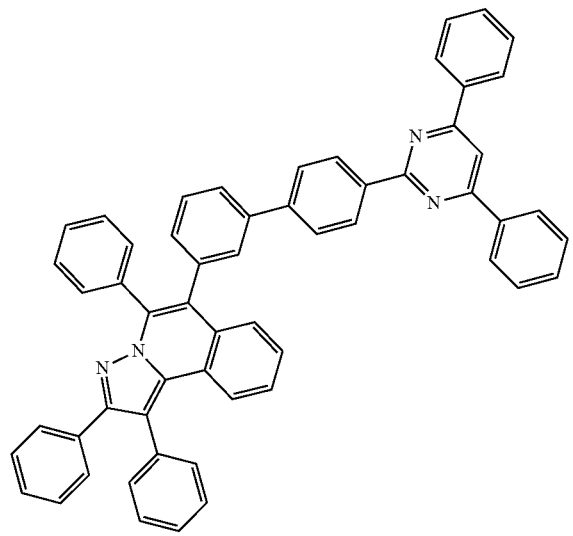
194
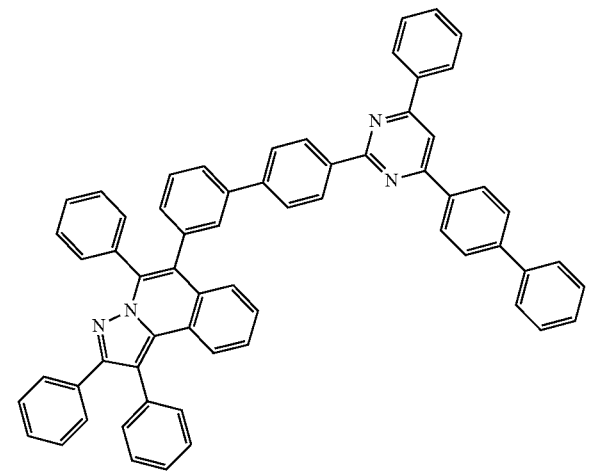
195
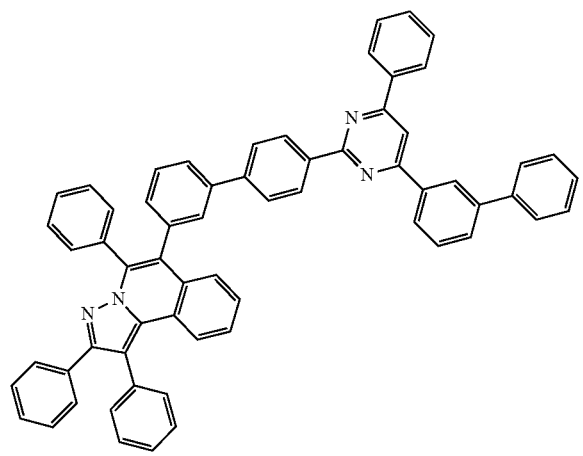
196
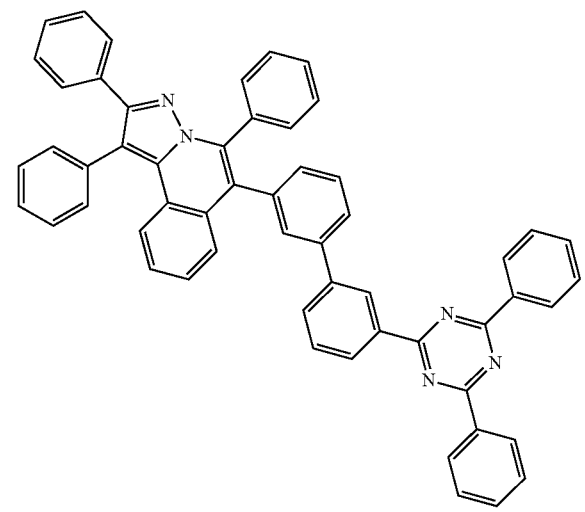
197
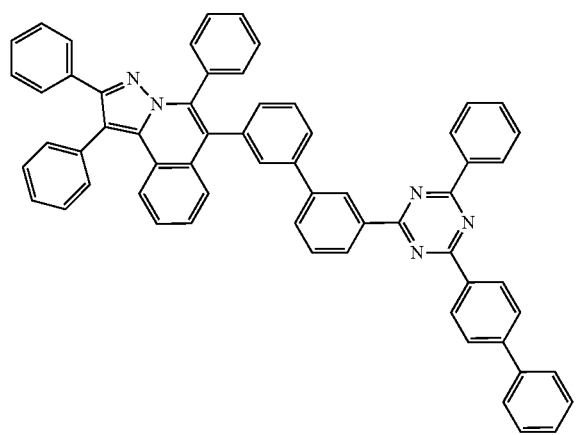
198
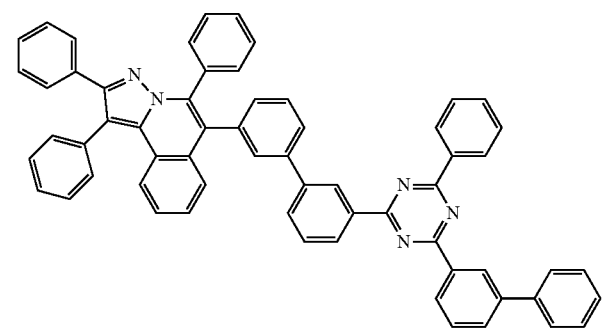

-continued
199
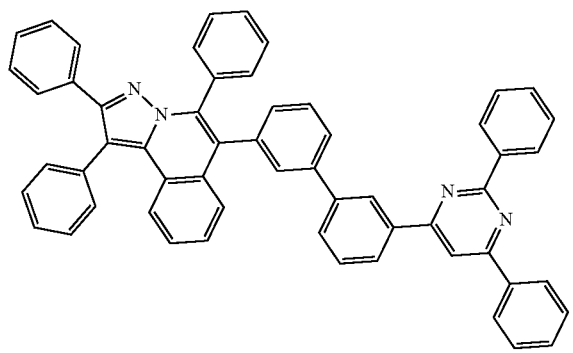
200
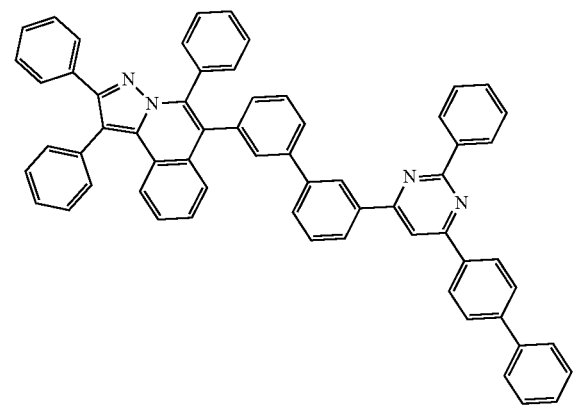
201
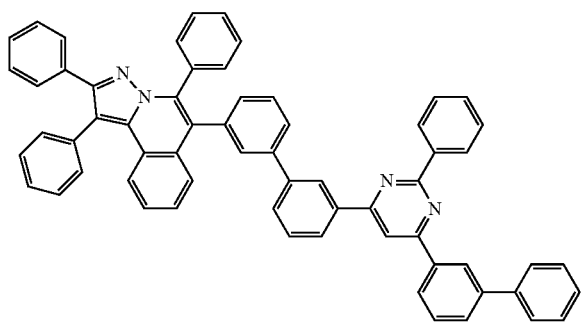
202
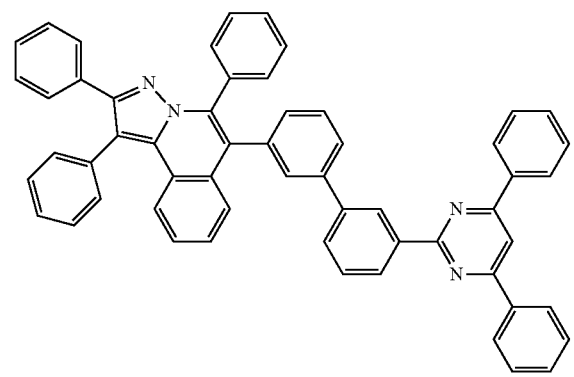
203
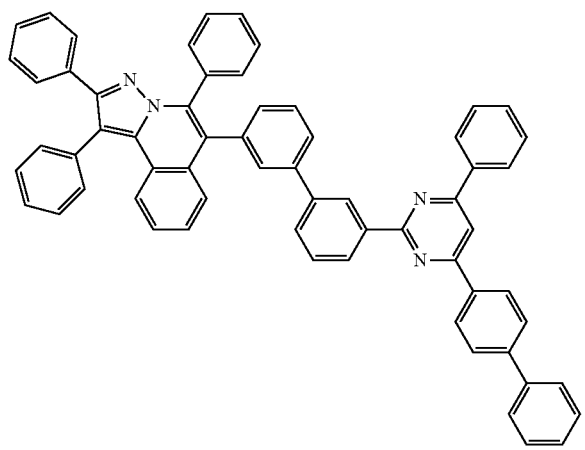
204
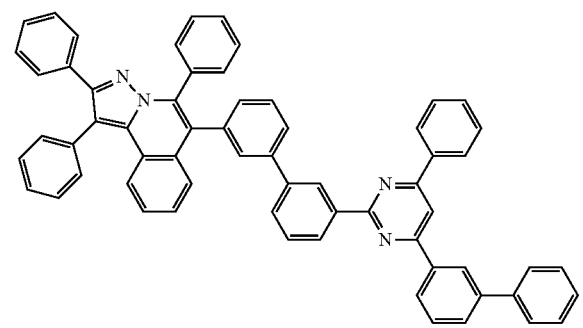
205
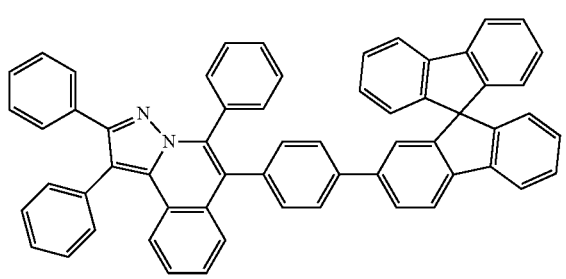
206
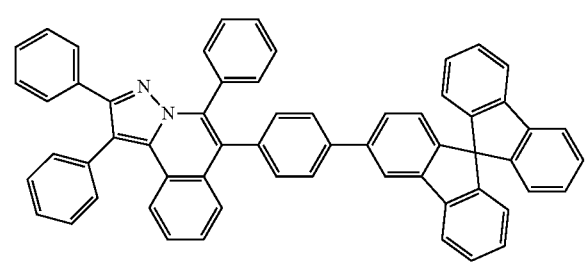

-continued
207
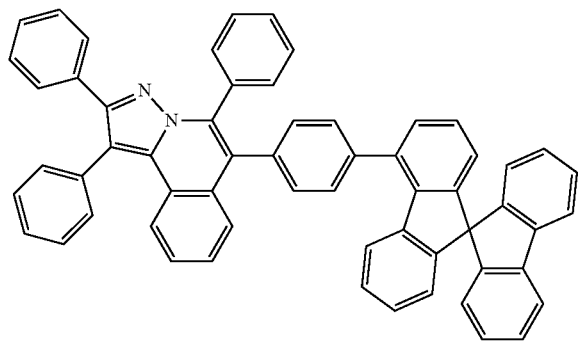
208
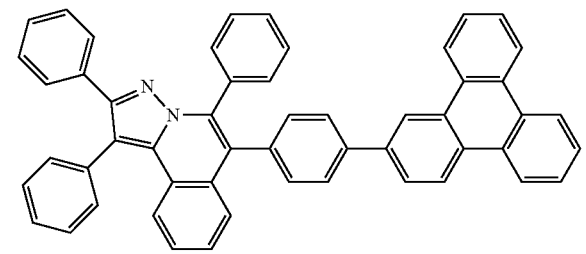
209
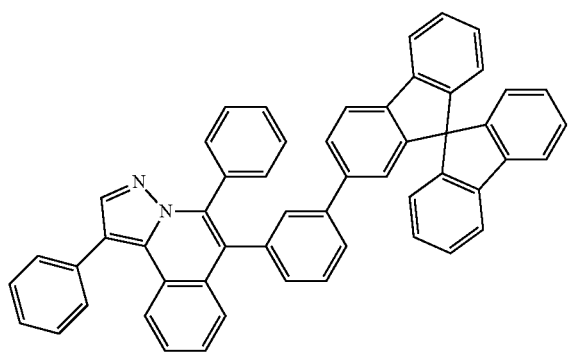
210
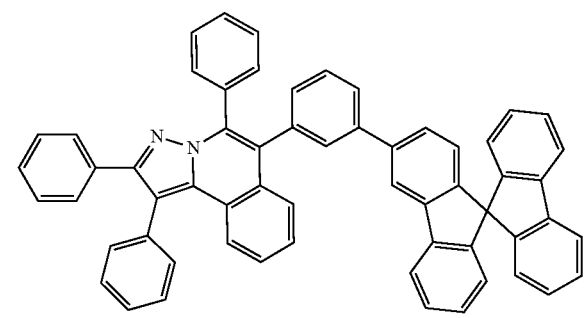
211
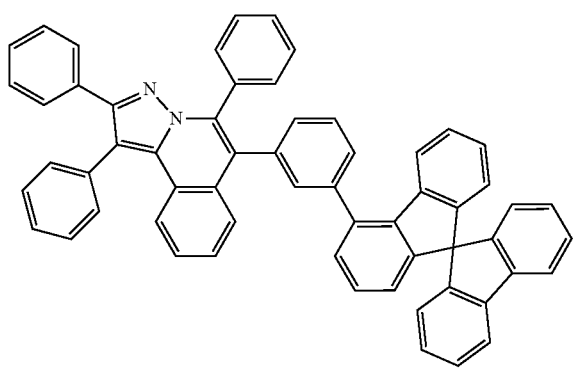
212
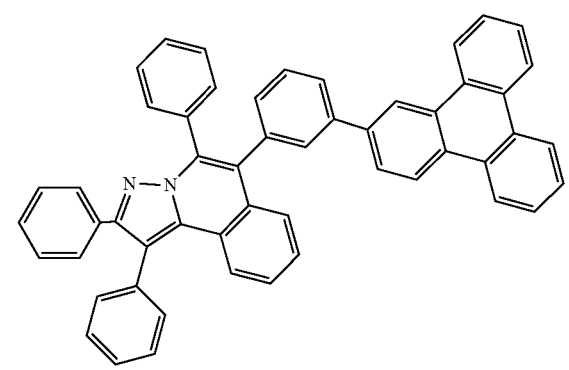
213
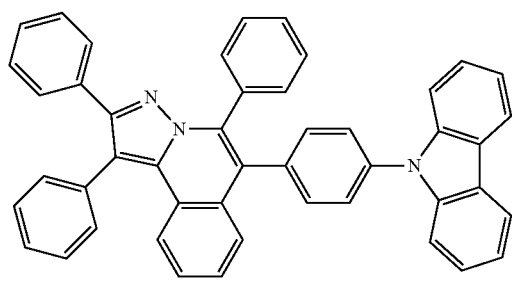
214
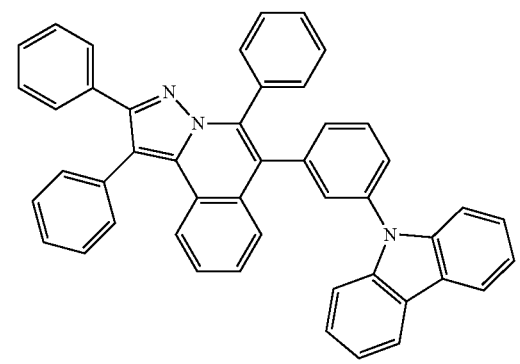

-continued
215 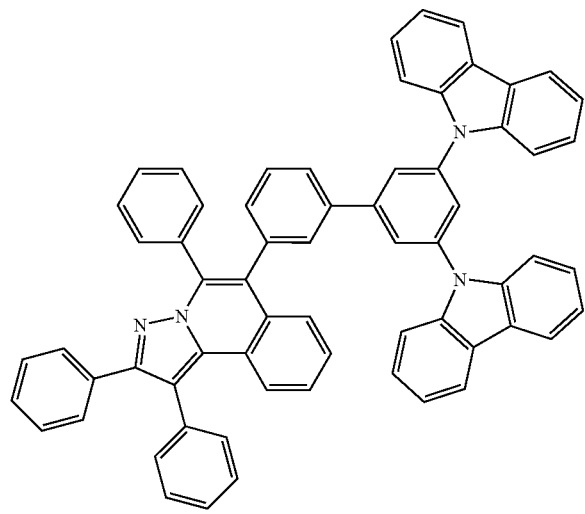
216 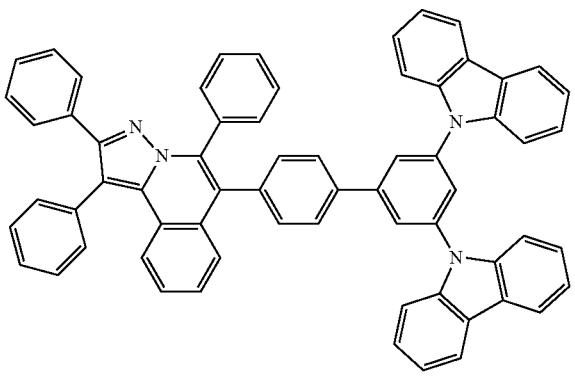
217 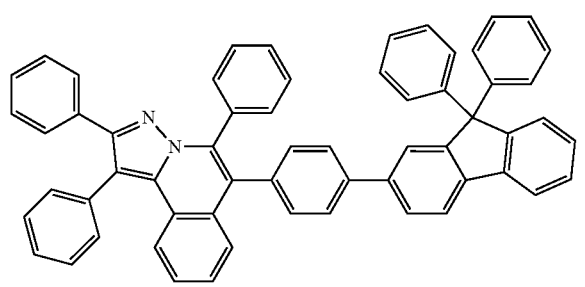
218 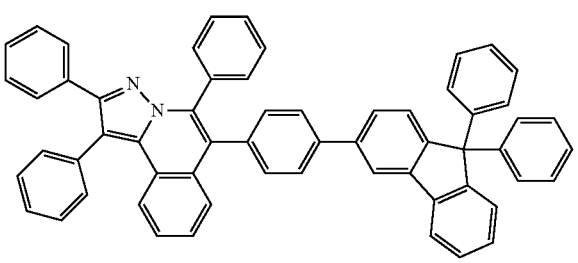
219 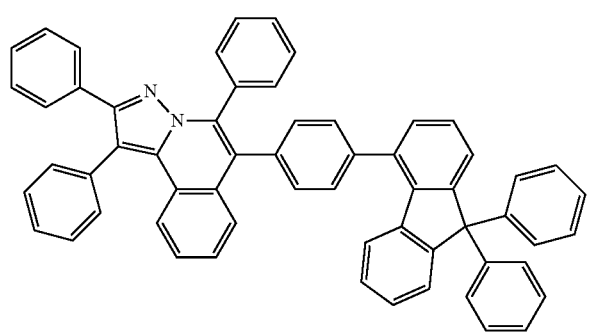
220 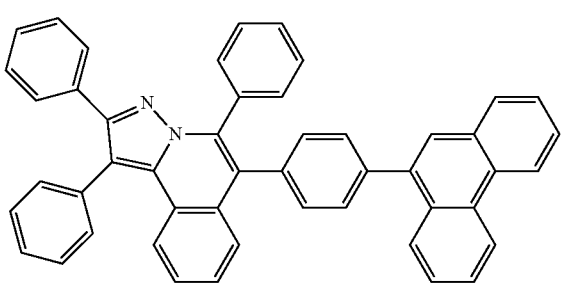
221 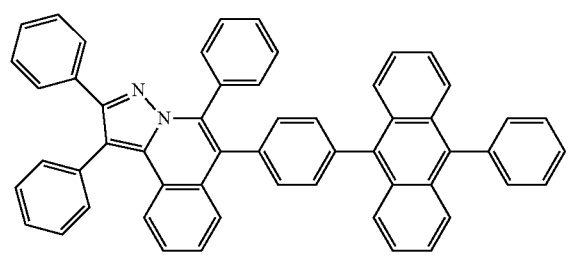
222 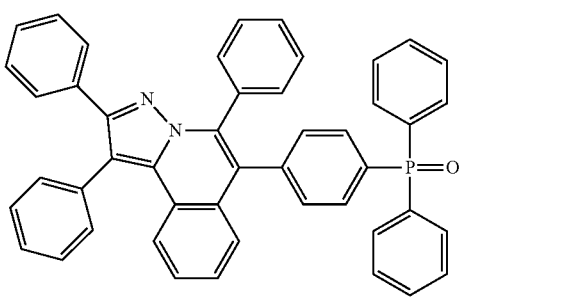

-continued
223
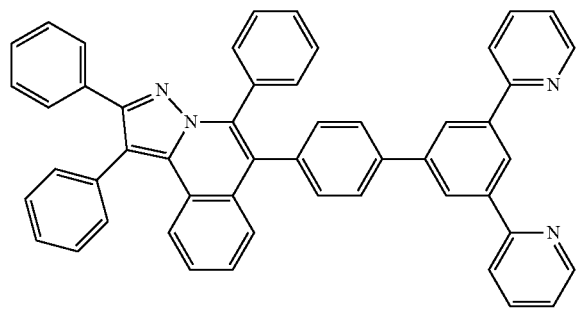
224
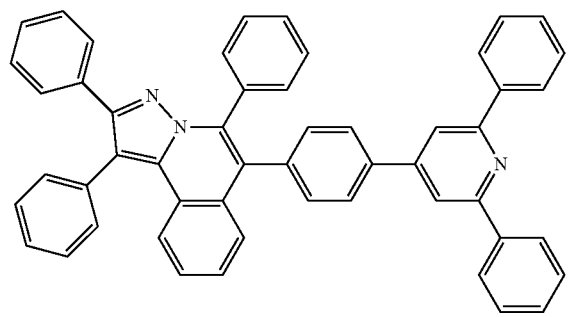
225
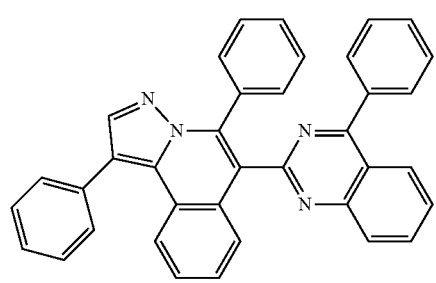
226
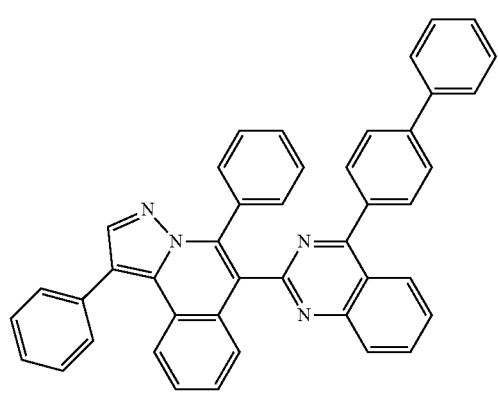
227
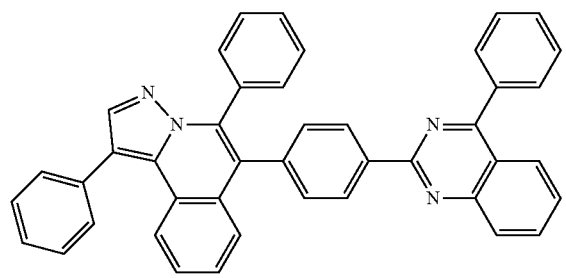
228
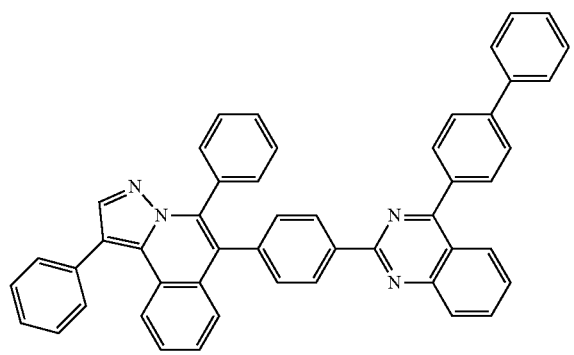
229
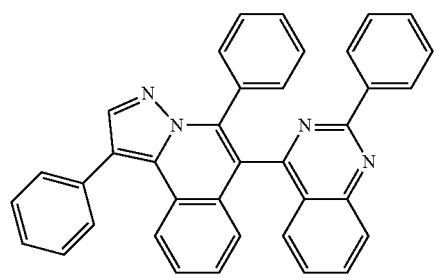
230
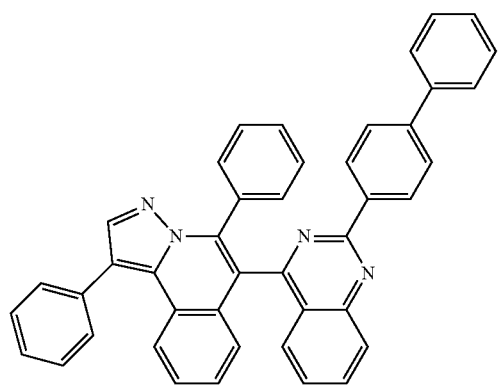

-continued
231
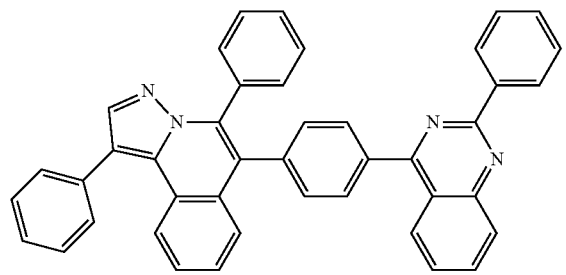
232
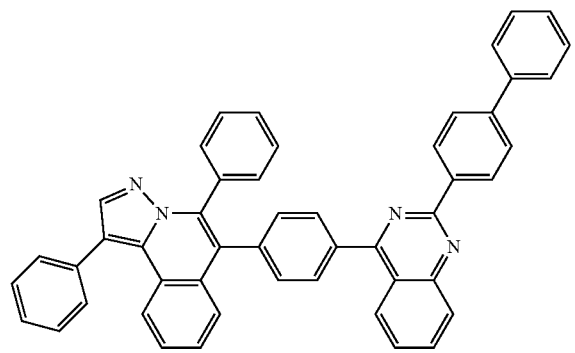
233
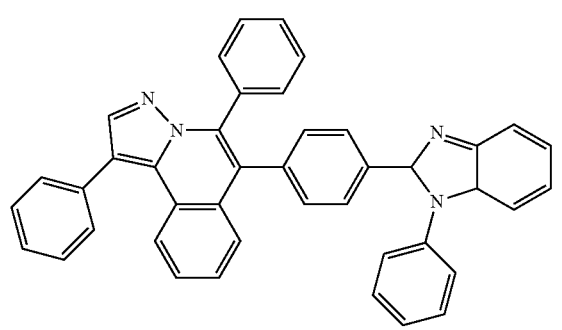
234
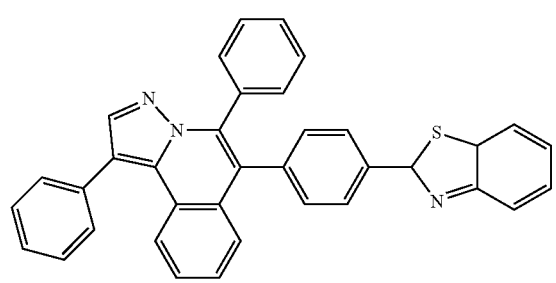
235
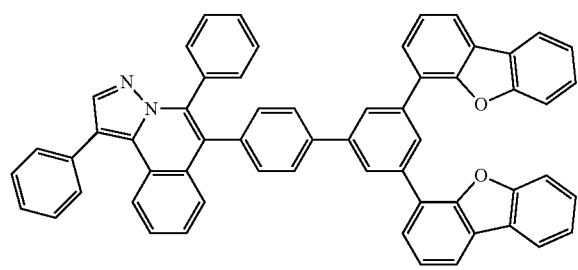
236
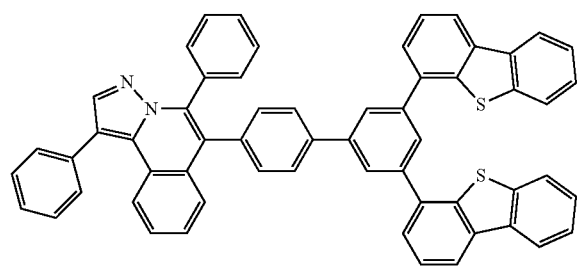
237
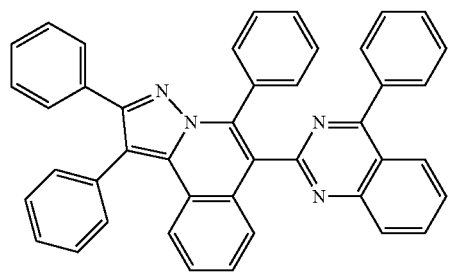
238
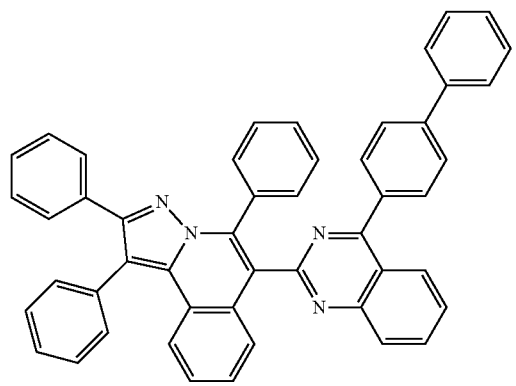

-continued
239
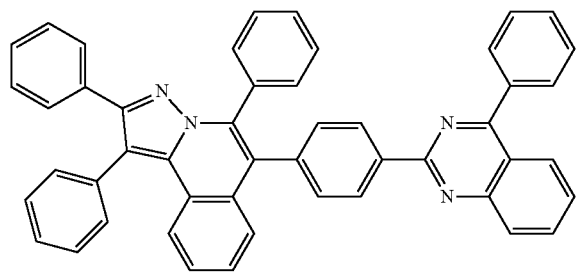
240
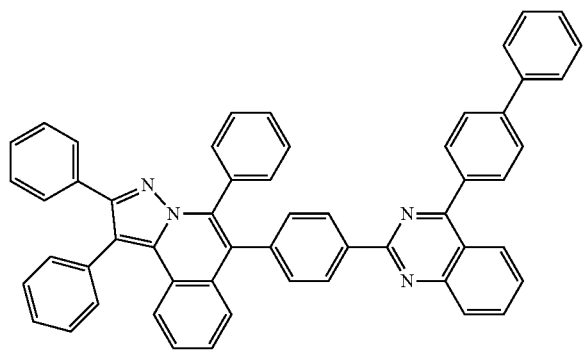
241
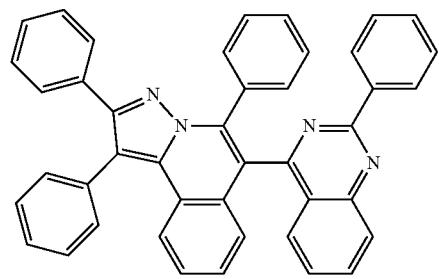
242
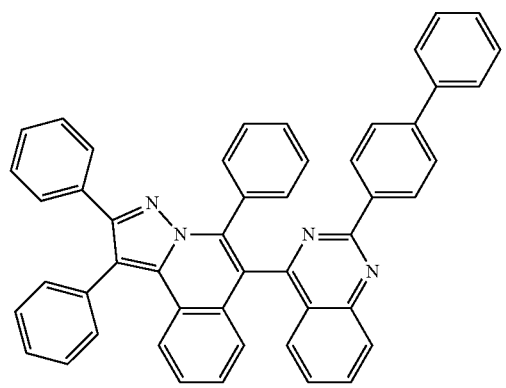
243
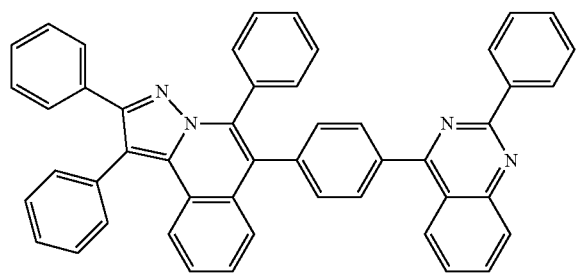
244
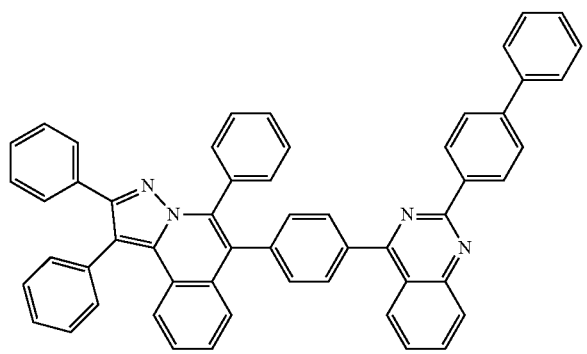
245
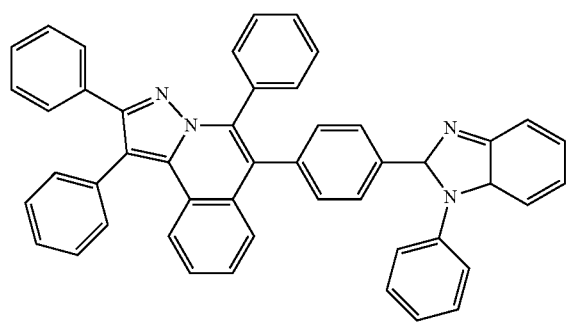
246
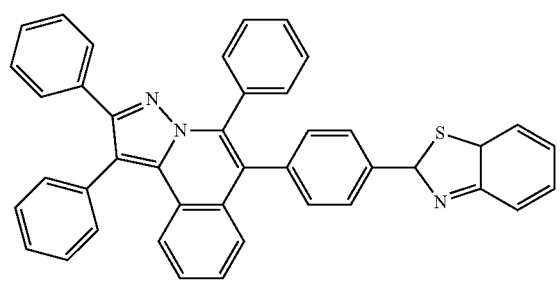

-continued
247 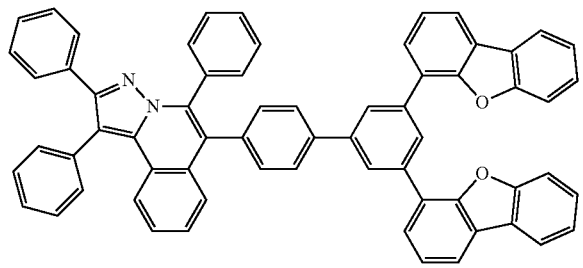
248 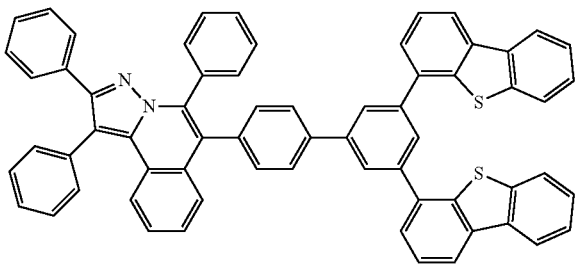
249 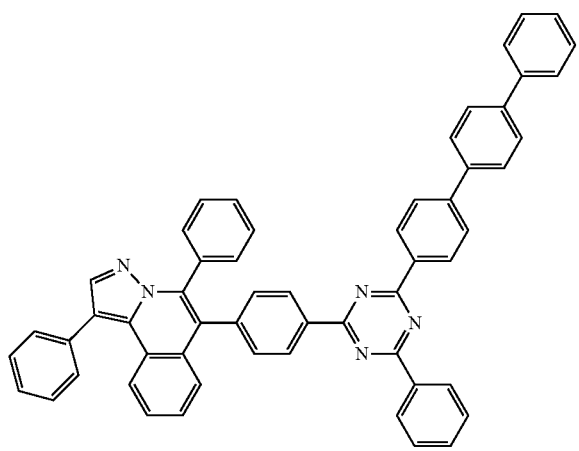
250 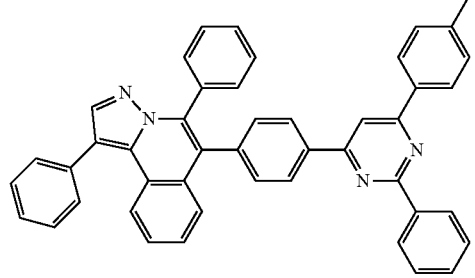
251 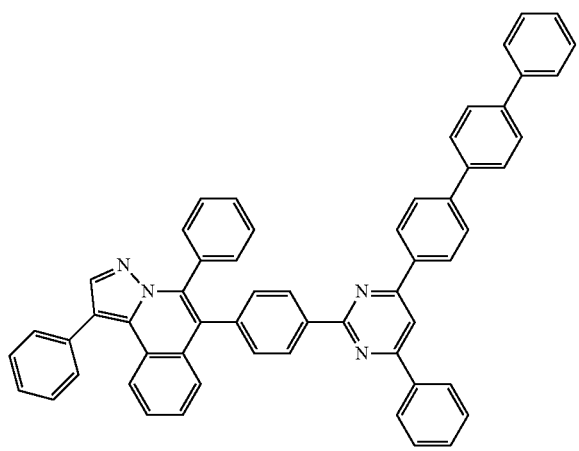
252 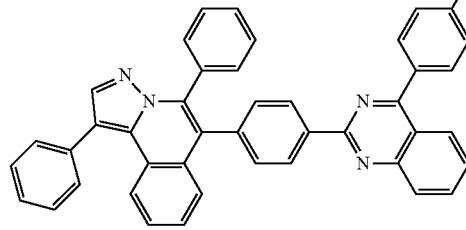
253 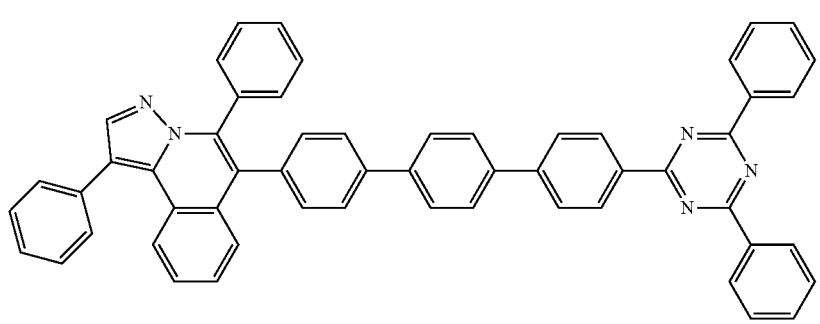

254
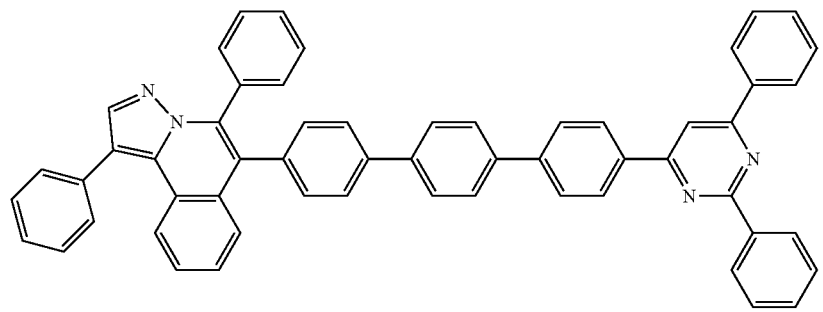
255
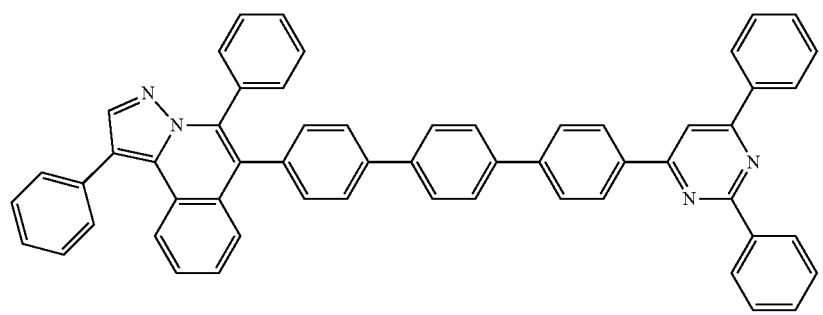
256
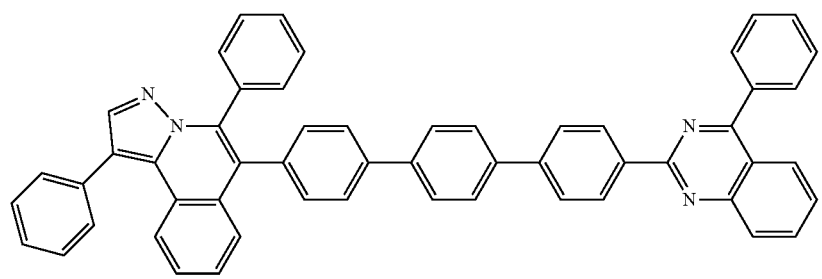
257 258
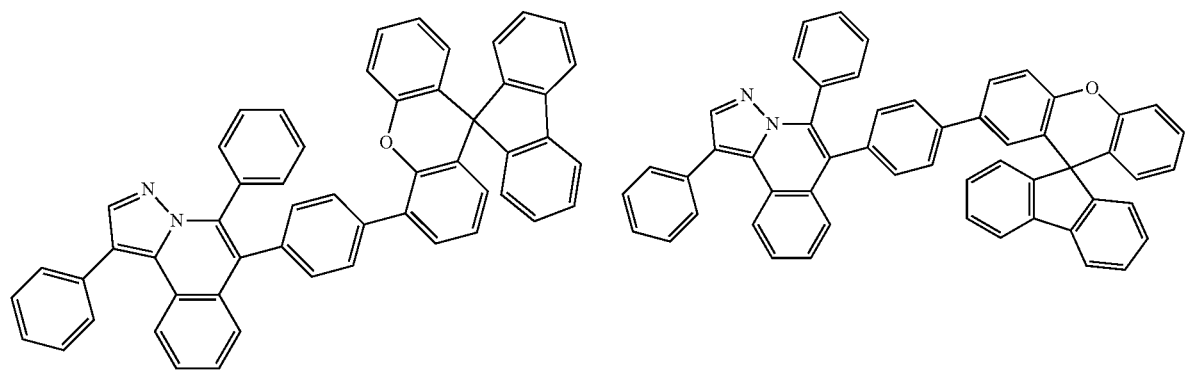
259 260
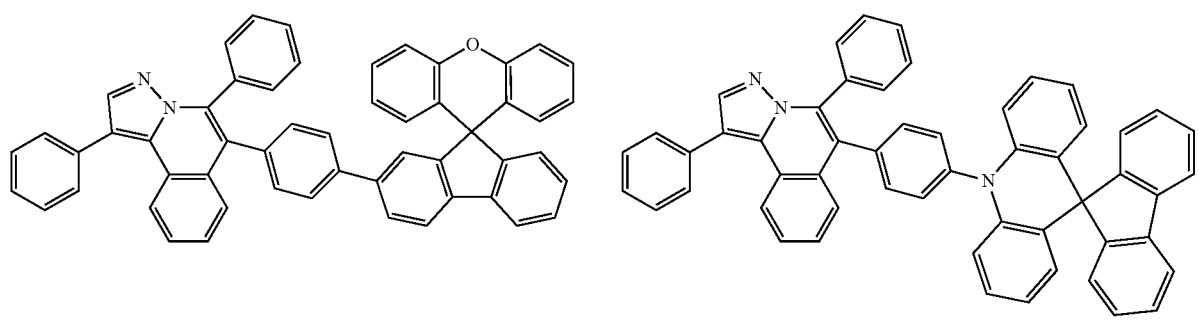

-continued
261
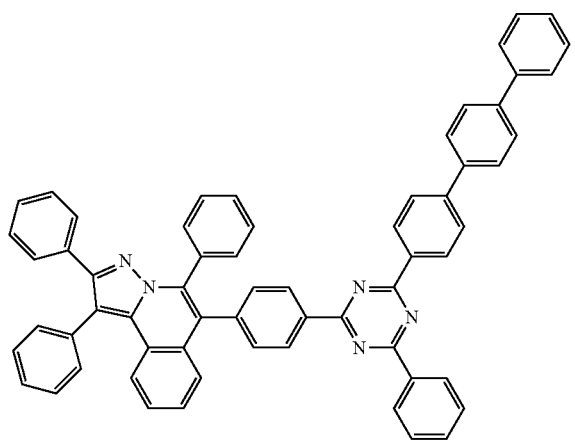
262
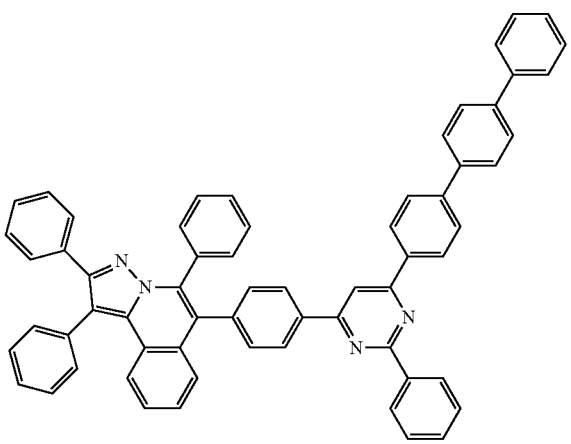
263
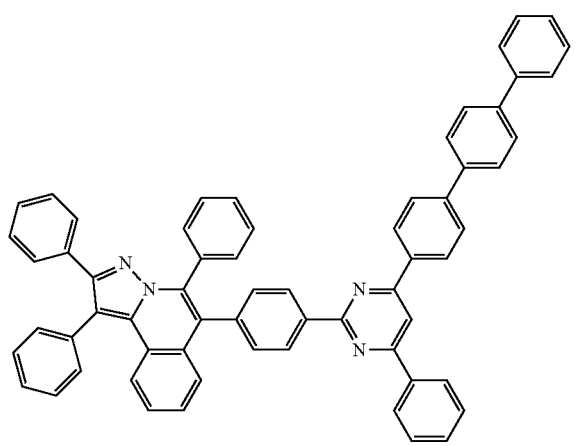
264
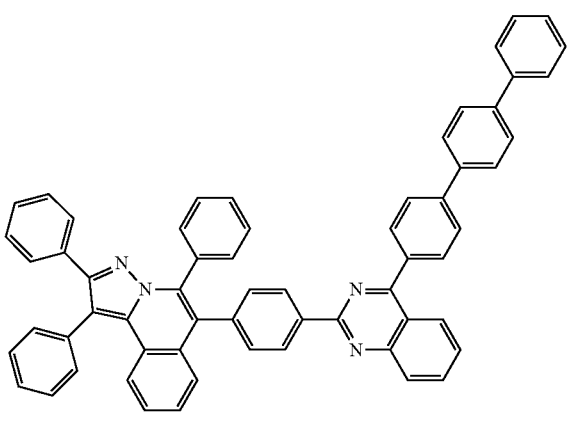
265
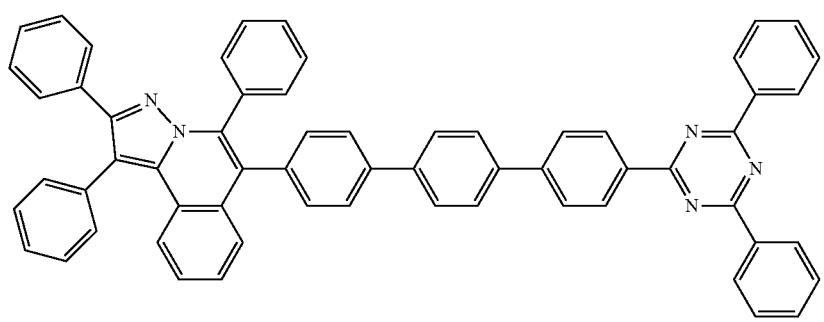
266
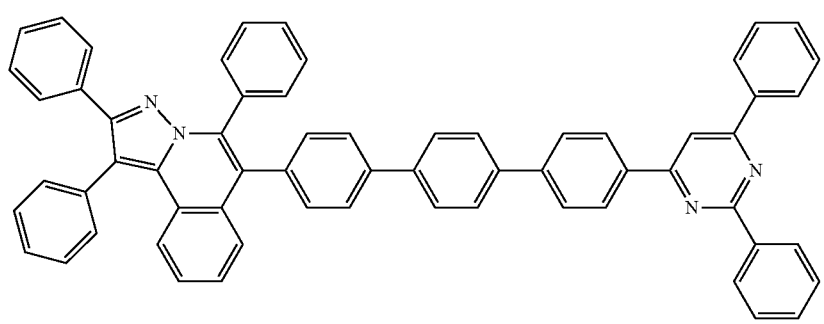

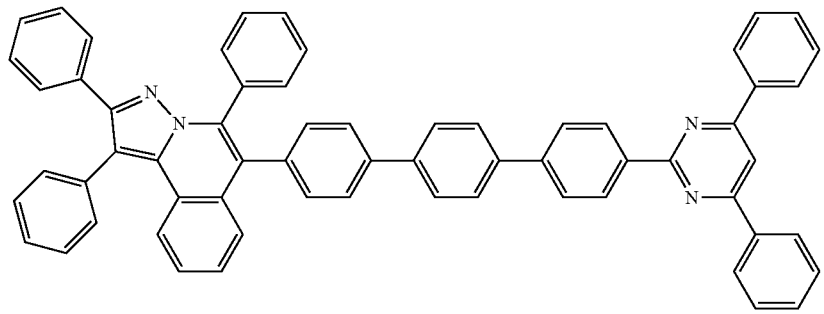
267
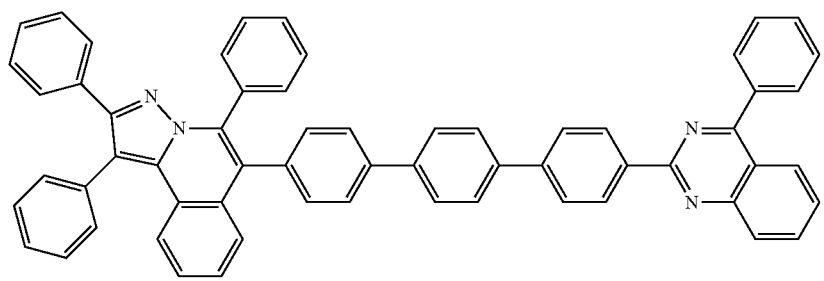
268
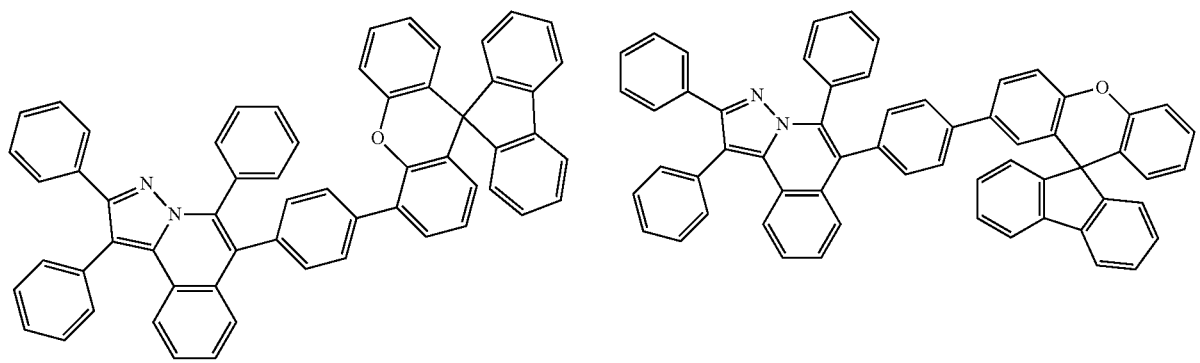
269
270
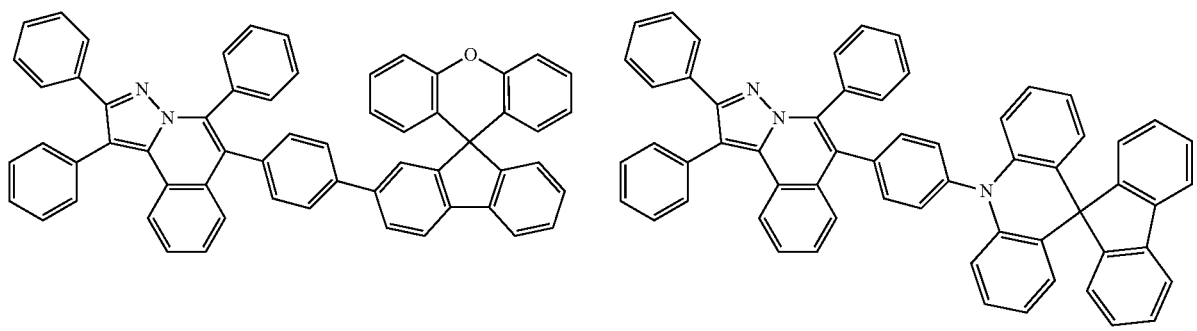
271
272

273
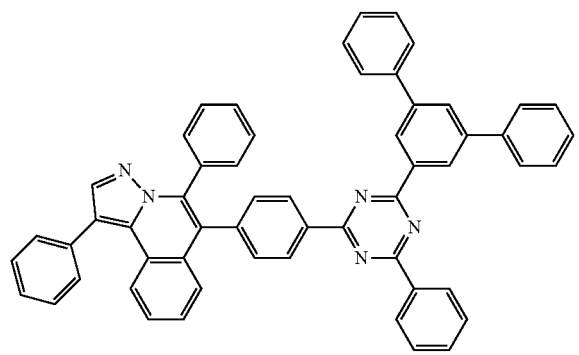
274
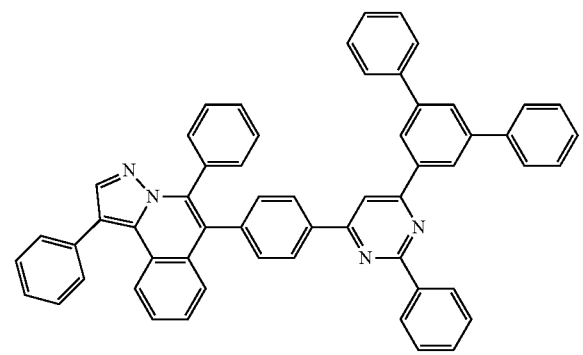
275
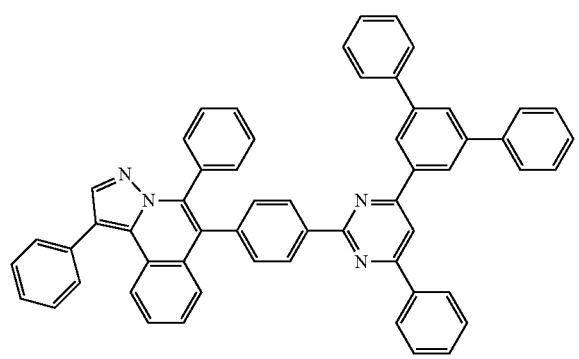
276
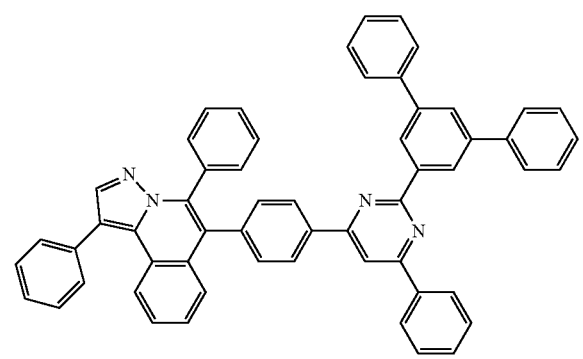
277
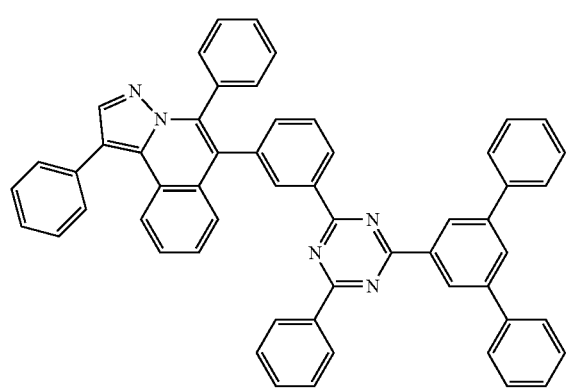
278
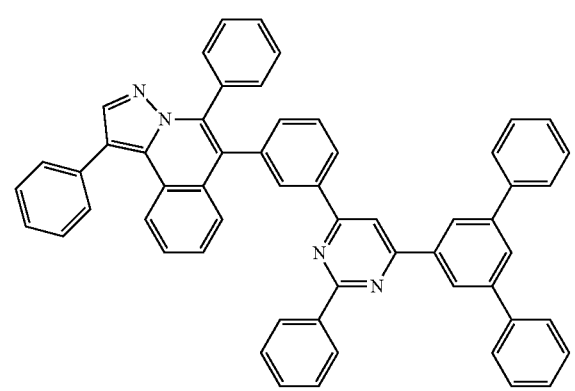
279
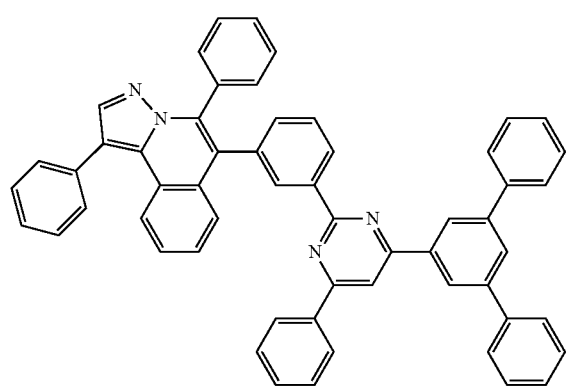
280
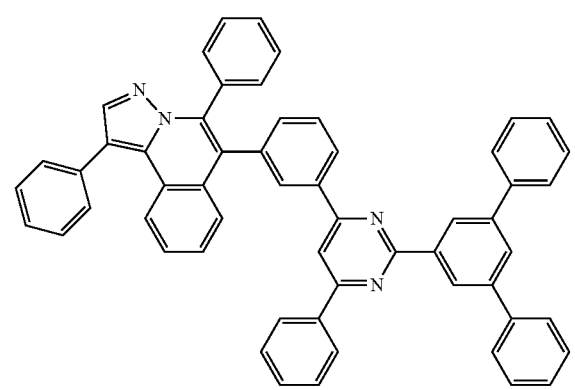

281
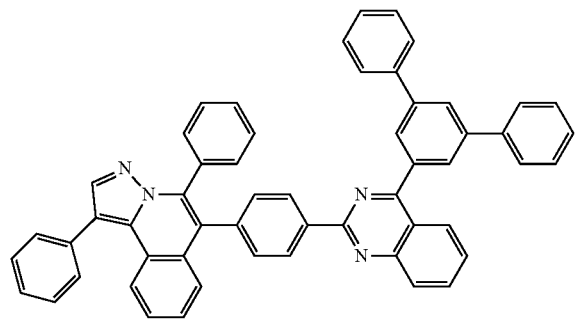
282
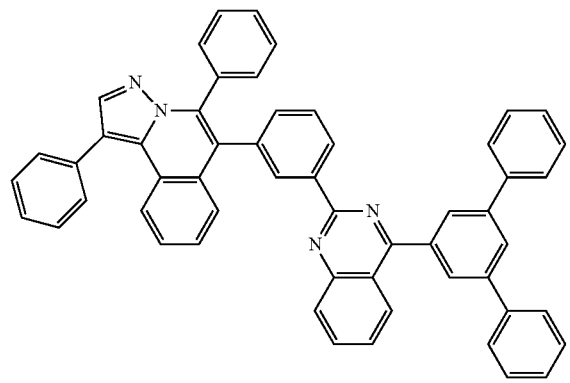
283
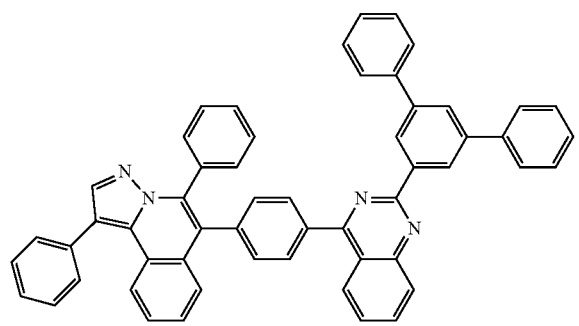
284
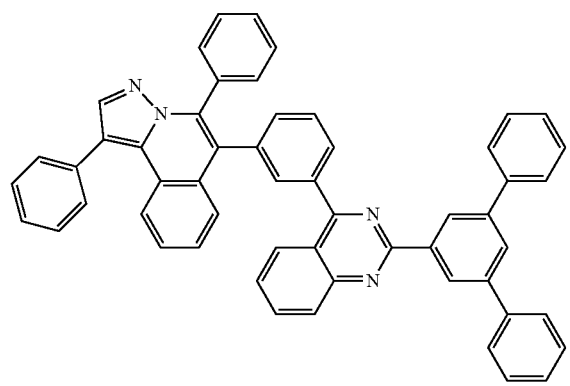
285
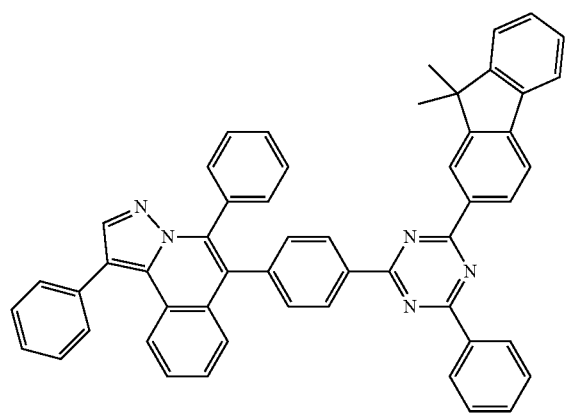
286
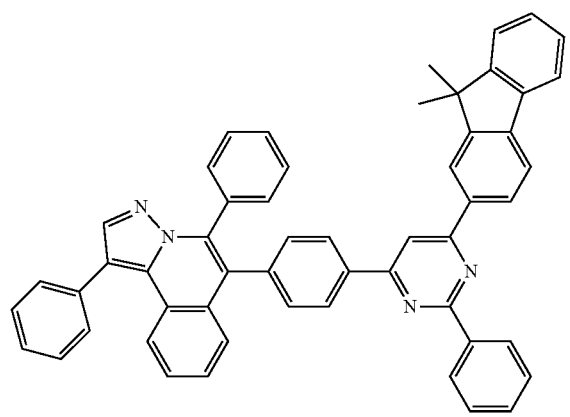

-continued
287
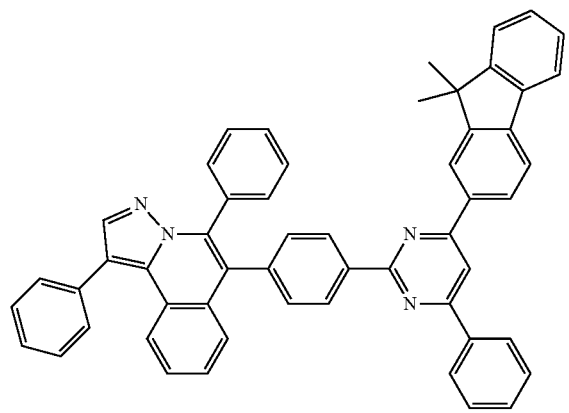
288
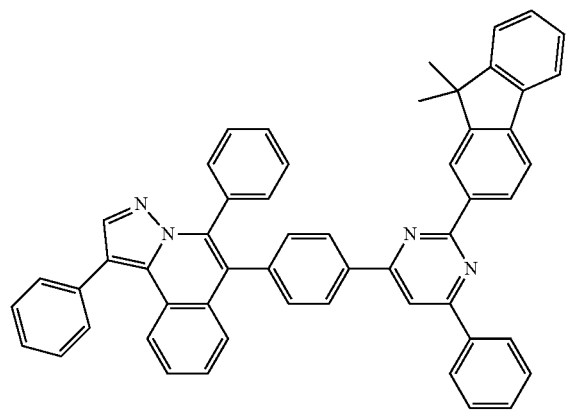
289
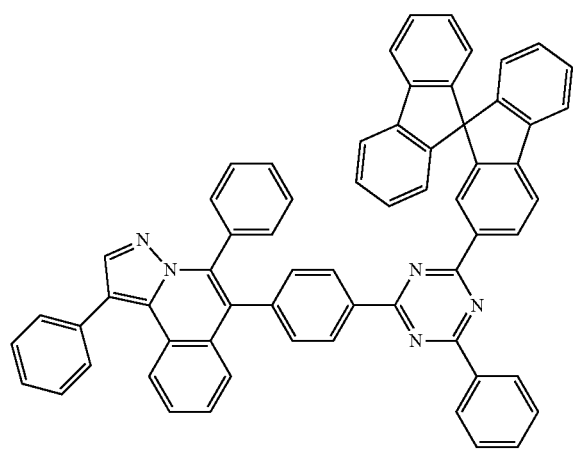
290
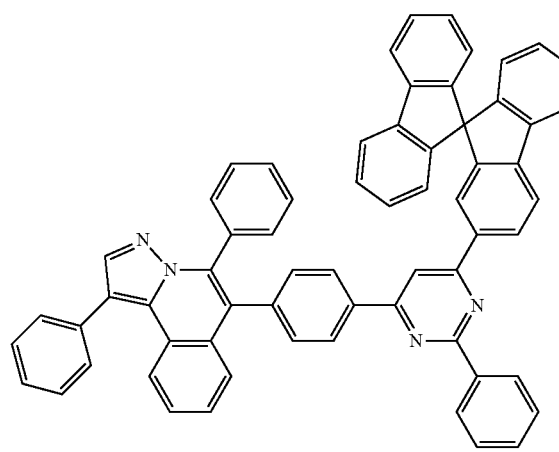
291
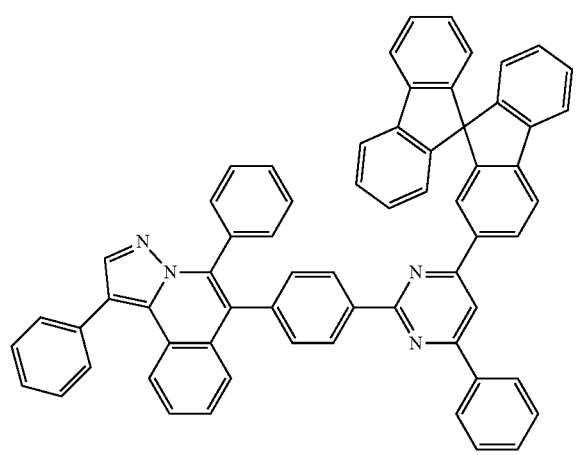
292
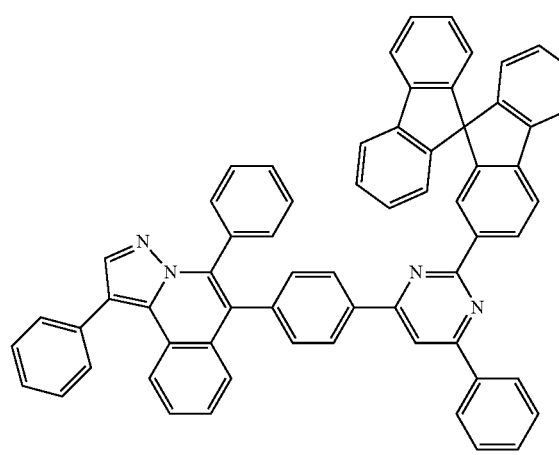

-continued
293
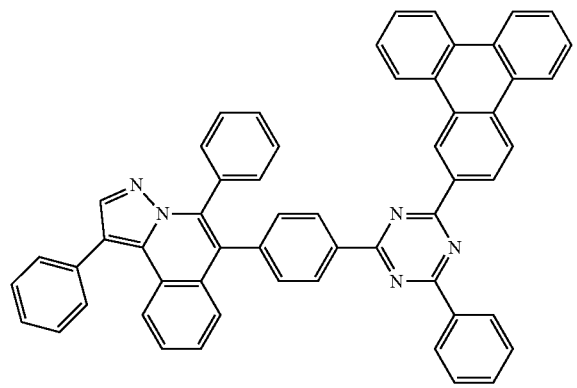
294
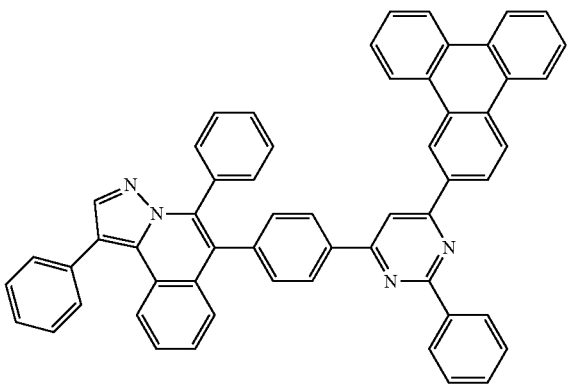
295
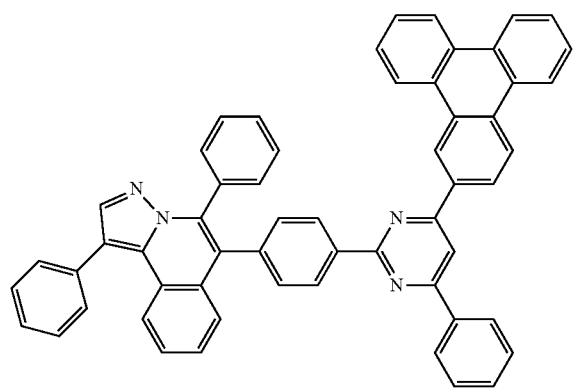
296
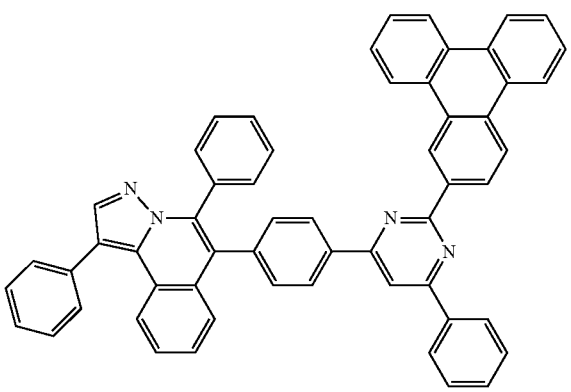
297
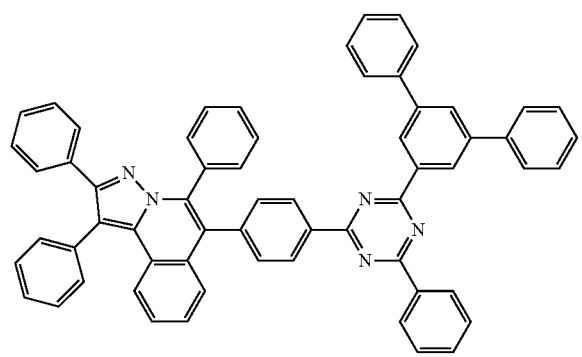
298
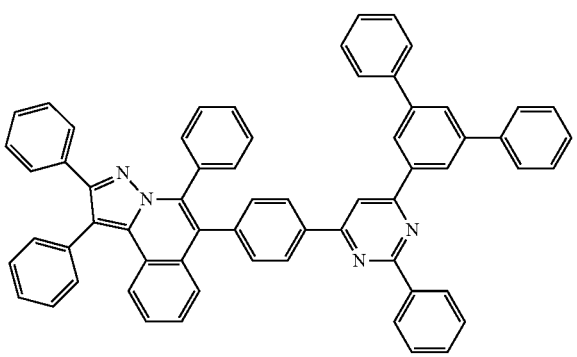
299
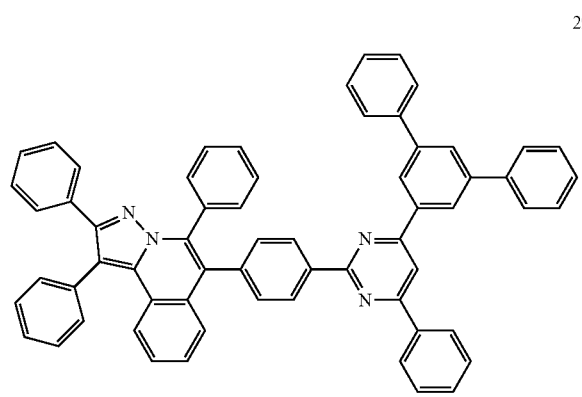
300
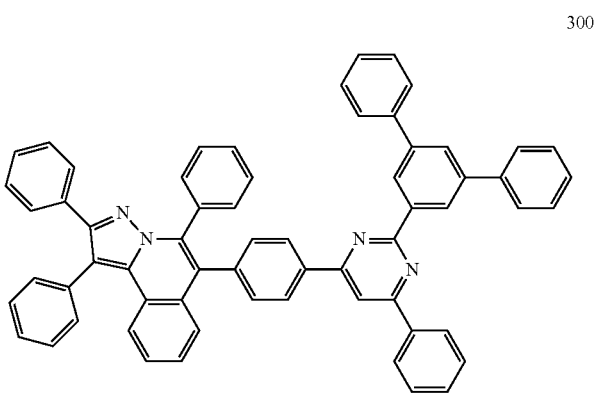

-continued
301
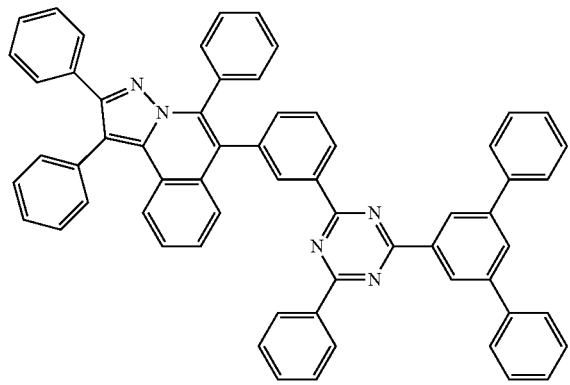
302
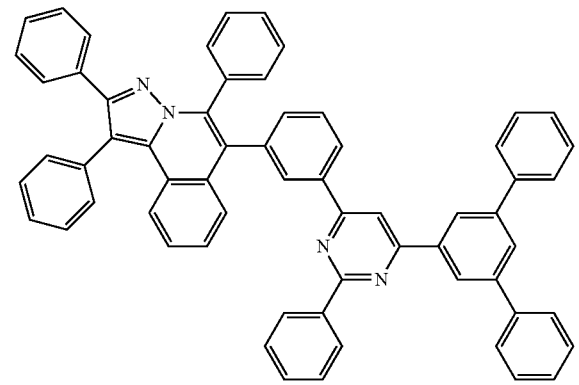
303
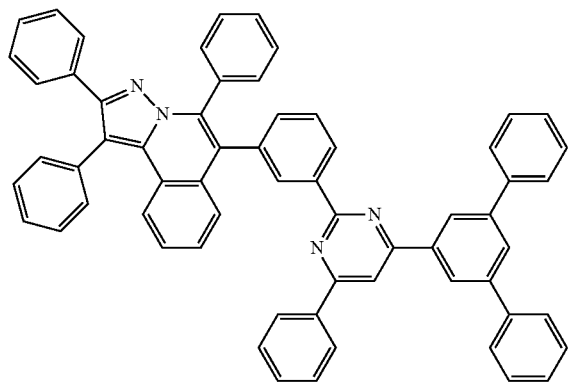
304
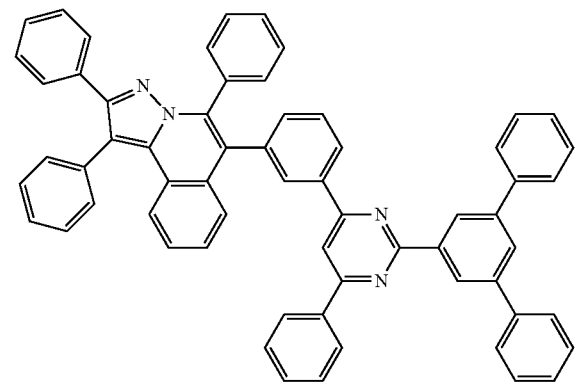
305
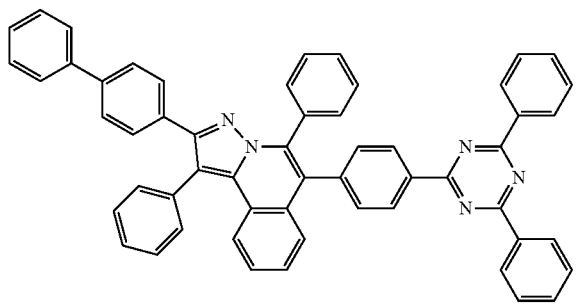
306
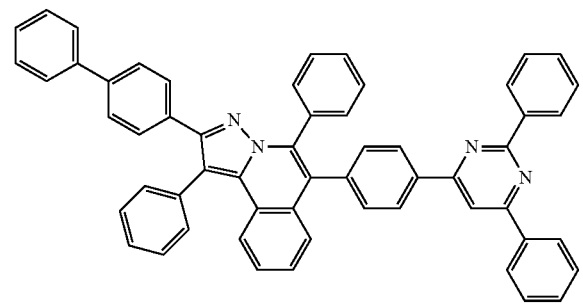
307
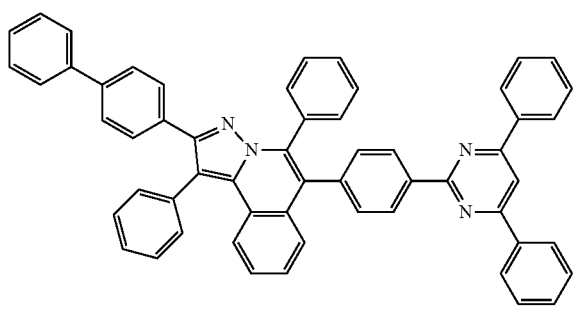
308
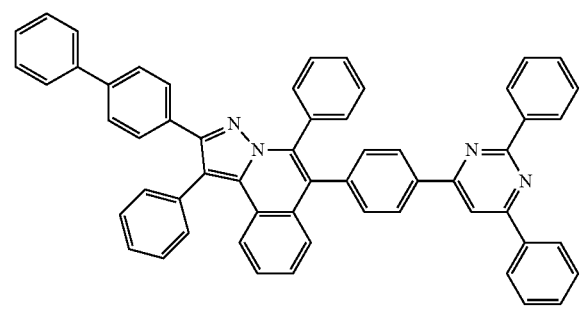

-continued
309
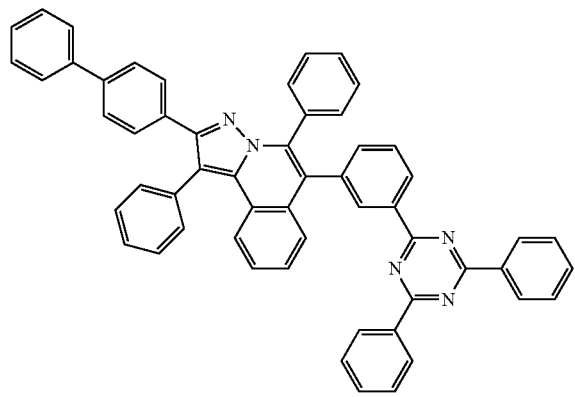
310
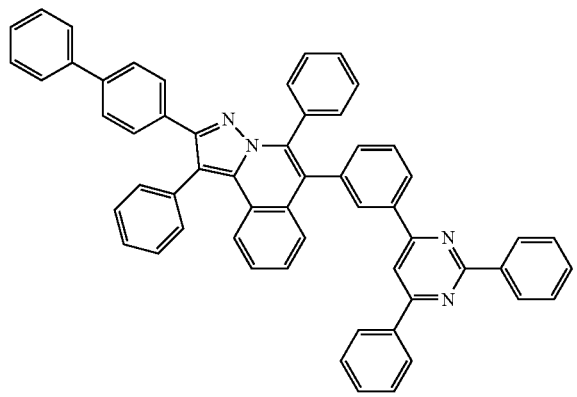
311
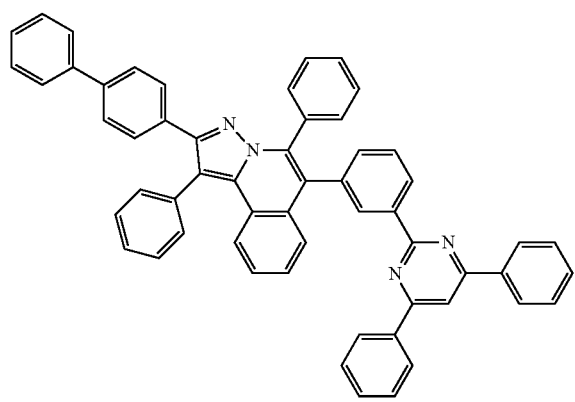
312
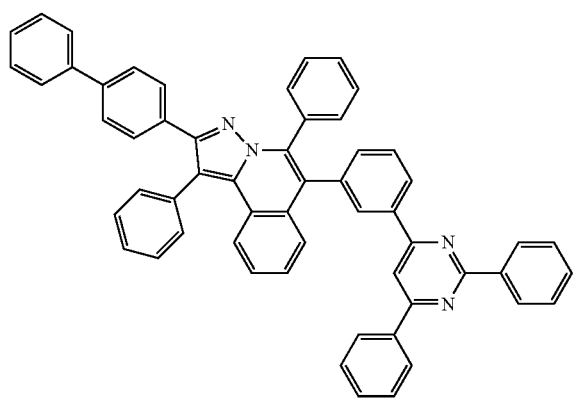
313
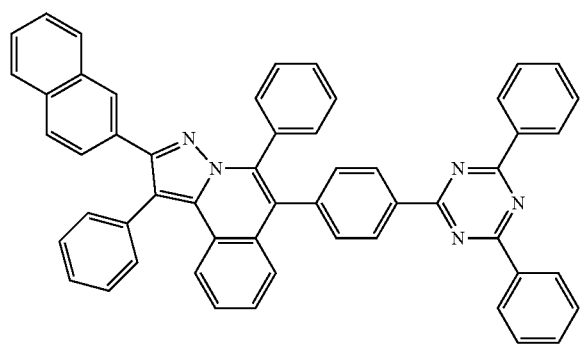
314
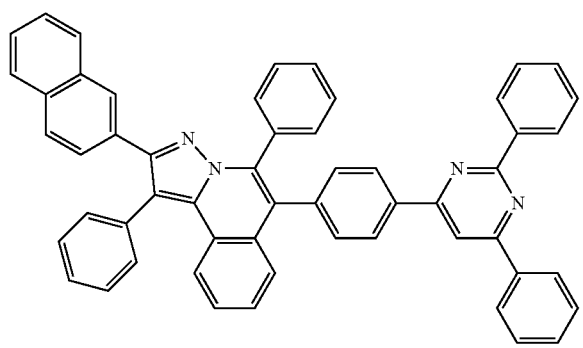
315
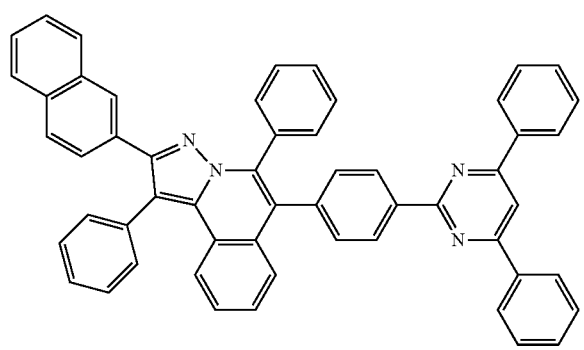
316
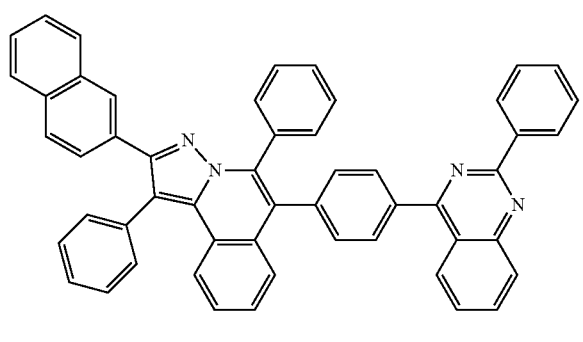

-continued
317
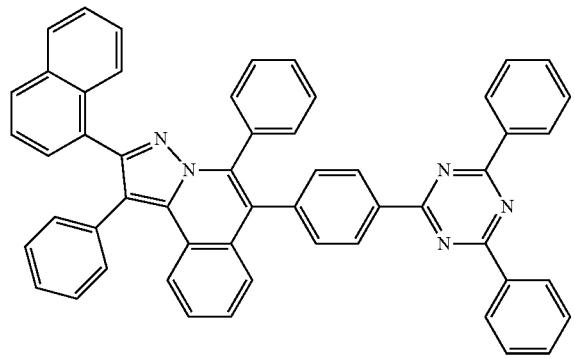
318
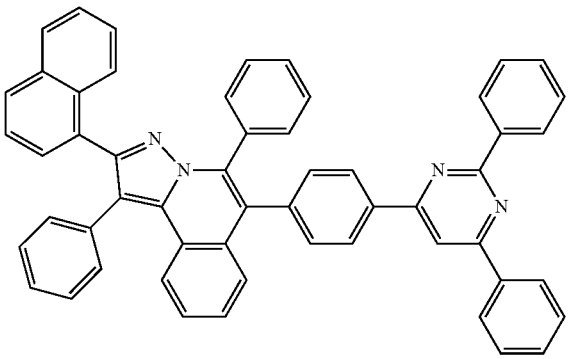
319
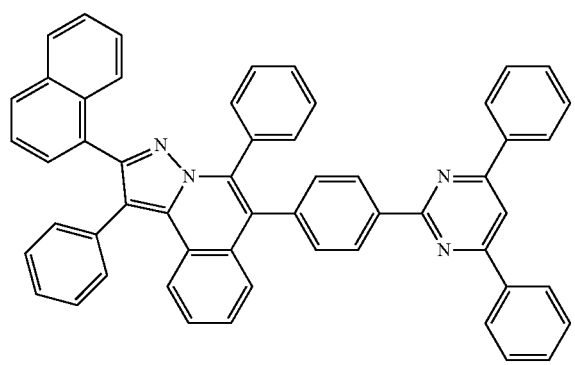
320
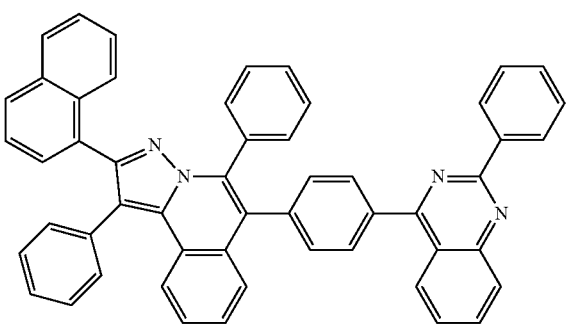
321
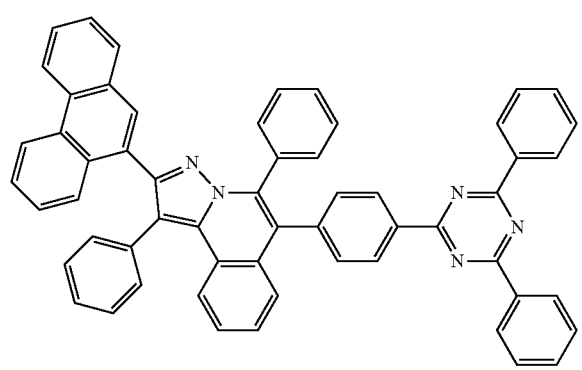
322
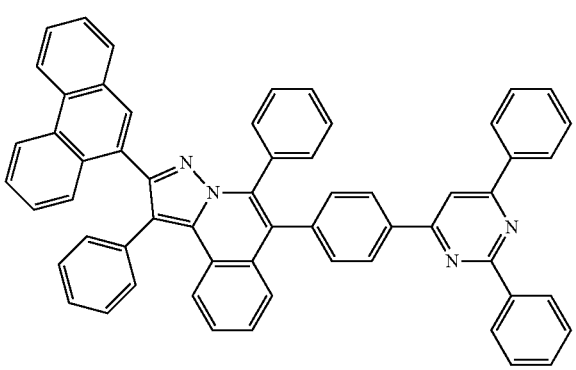
323
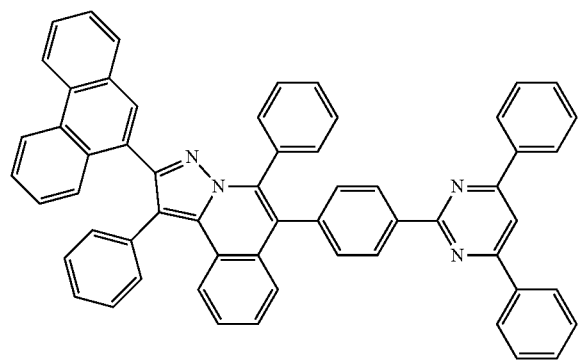
324
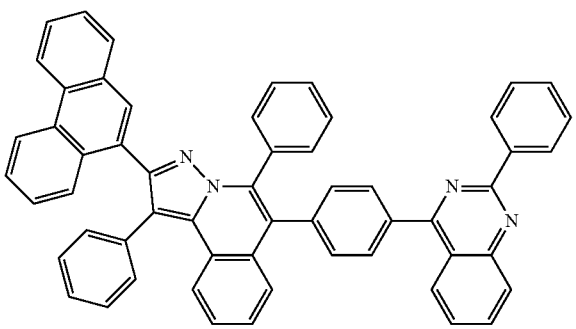

-continued

325
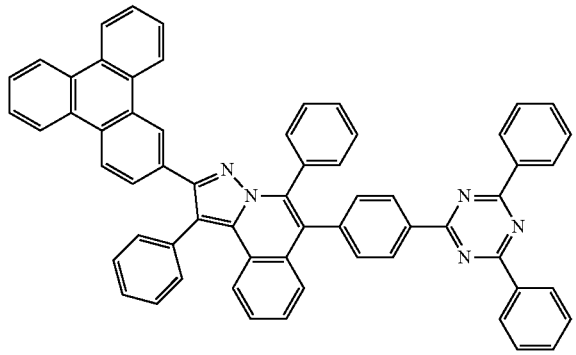

326
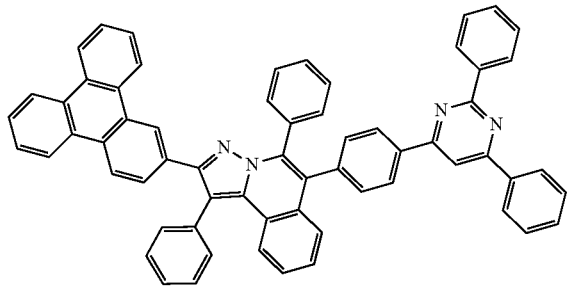

327
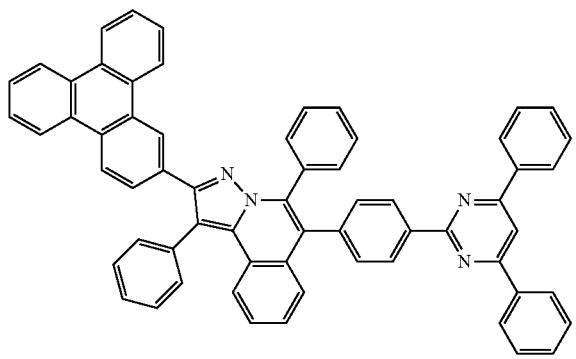

328
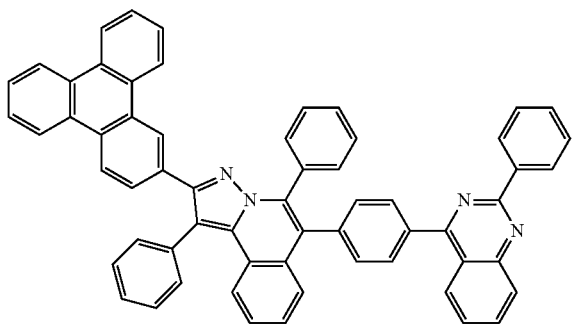

The compound according to one embodiment of the present application may be synthesized through preparation examples to describe later.

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

The heterocyclic compound according to one embodiment of the present application may be prepared through a multistep chemical reaction. Some intermediate compounds are prepared first, and the compound of Chemical Formula 1 may be prepared from the intermediate compounds. More specifically, the heterocyclic compound according to one embodiment of the present application may be prepared based on preparation examples to describe later.

Another embodiment of the present application provides an organic light emitting device comprising the heterocyclic compound represented by Chemical Formula 1.

In addition, in one embodiment of the present application, there is provided an organic light emitting device comprising a first electrode; a second electrode provided opposite to the first electrode; and one or more organic material layers provided between the first electrode and the second electrode, wherein one or more layers of the organic material layers comprise the heterocyclic compound according to Chemical Formula 1.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

Specific descriptions on the heterocyclic compound represented by Chemical Formula 1 are the same as the descriptions provided above.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise less numbers of organic material layers.

In the organic light emitting device of the present disclosure, the organic material layer may comprise a light emitting layer, and the light emitting layer may comprise the heterocyclic compound.

In the organic light emitting device of the present disclosure, the organic material layer comprises an electron injection layer or an electron transfer layer, and the electron injection layer or the electron transfer layer may comprise the heterocyclic compound.

In the organic light emitting device of the present disclosure, the organic material layer comprises an electron transfer layer, and the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

In addition, the organic light emitting device according to one embodiment of the present application comprises an anode, a cathode, and two or more stacks provided between the anode and the cathode, wherein the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present application may comprise a first electrode, a first stack provided on the first electrode and comprising a first light emitting layer, a charge generation layer provided on the first stack, a second stack provided on the charge generation layer and comprising a second light emitting layer, and a second electrode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer described above and the like.

The charge generation layer may be an N-type charge generation layer, and the charge generation layer may further comprise a dopant known in the art in addition to the heterocyclic compound represented by Chemical Formula 1. As the organic light emitting device according to one embodiment of the present application, an organic light emitting device having a 2-stack tandem structure is schematically illustrated in FIG. 4.

Herein, the first electron blocking layer, the first hole blocking layer and the second hole blocking layer and the like described in FIG. 4 may not be included in some cases.

The organic light emitting device according to the present specification may be manufactured using materials and methods known in the art except that one or more layers of the organic material layers comprise the heterocyclic compound represented by Chemical Formula 1.

The organic material layer comprising Chemical Formula 1 may further comprise other materials as necessary.

The heterocyclic compound represented by Chemical Formula 1 may be used as a material of a charge generation layer in an organic light emitting device.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involved in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

<Preparation Example 1> Preparation of Compound 3

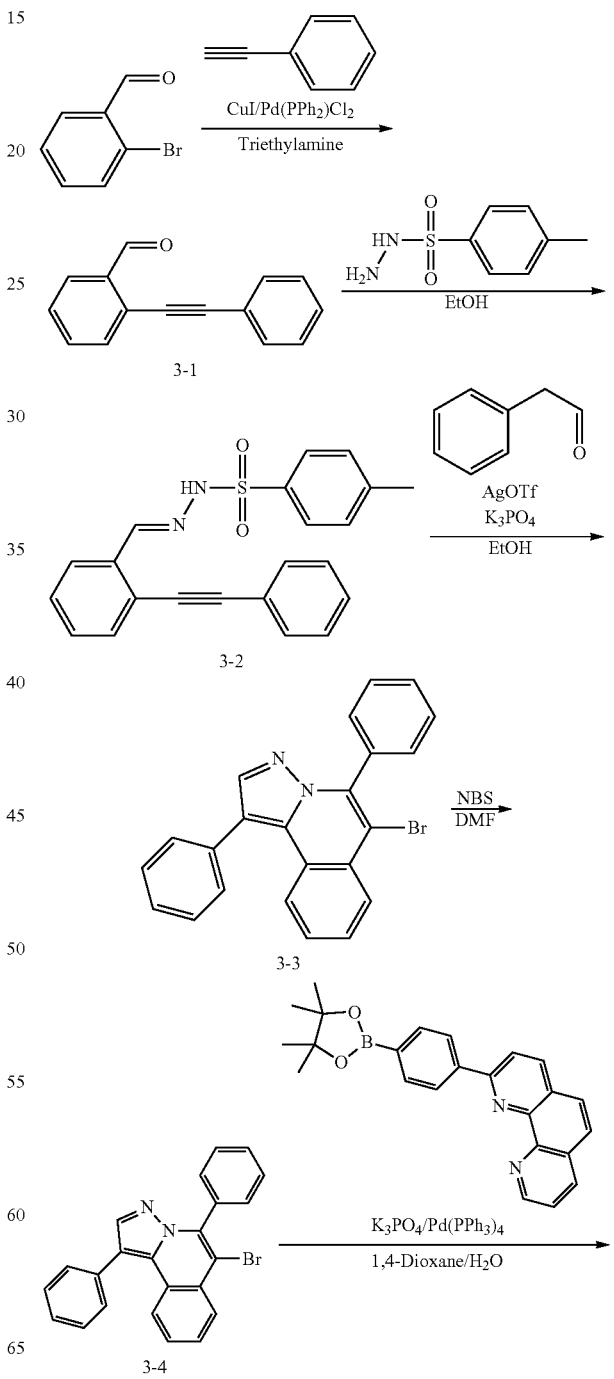

-continued

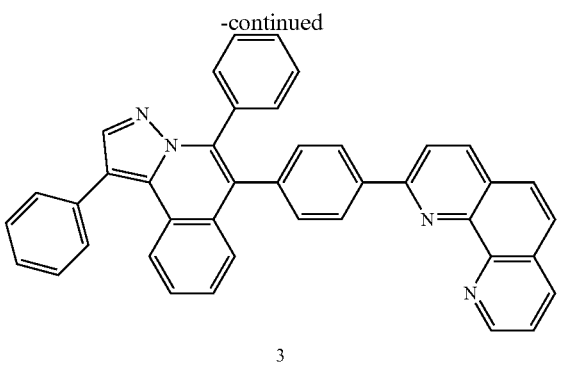

3

(1) Preparation of Compound 3-1

After introducing triethylamine (1500 ml) to 2-bromobenzaldehyde (150 g, 0.81 mol, 1 eq.), ethynylbenzene (99 g, 0.97 mol, 1.2 eq.), Pd(PPh$_3$)$_2$Cl$_2$ (11.8 g, 0.016 mol, 0.02 eq.) and CuI (1.54 g, 0.008 mol, 0.01 eq.), the result was stirred for 4 hours at 60° C. Water was added thereto to terminate the reaction, and the result was extracted using MC and water. After that, water was removed using anhydrous Na$_2$CO$_3$. The result was separated using a silica gel column to obtain Compound 3-1 (150 g) in a 90% yield.

(2) Preparation of Compound 3-2

Compound 3-1 (155 g, 0.75 mol, 1 eq.) and TsNHNH$_2$ (168 g, 0.90 mol, 1.2 eq.) were introduced to EtOH (3100 ml), and the result was stirred for 1 hour at room temperature (R.T). Produced solids were filtered and dried to obtain Compound 3-2 (150 g) in a 53% yield.

(3) Preparation of Compound 3-3

Compound 3-2 (30 g, 0.08 mol, 1 eq.) and AgOTf (3 g, 0.012 mol, 0.15 eq.) were introduced to EtOH (450 ml), and the result was stirred for 2 hours at 70° C. 2-Phenylacetaldehyde (11.55 g, 0.09 mol, 1.2 eq.) and K$_3$PO$_4$ (68 g, 0.32 mol) were introduced thereto, and the result was stirred for 6 hours at 70° C. Water was added thereto to terminate the reaction, and the result was extracted using MC and water. After that, water was removed using anhydrous Na$_2$CO$_3$. The result was separated using a silica gel column to obtain Compound 3-3 (19 g) in a 74% yield.

(4) Preparation of Compound 3-4

Compound 3-3 (19 g, 0.059 mol, 1 eq.) and NBS (11 g, 0.062 mol, 1.05 eq.) were introduced to DMF (190 ml), and the result was stirred for 24 hours at R.T. Water was added thereto to terminate the reaction, and the result was extracted using MC and water. After that, water was removed using anhydrous Na$_2$CO$_3$. The result was separated using a silica gel column to obtain Compound 3-4 (16 g) in a 67% yield.

(5) Preparation of Compound 3

Compound 3-4 (8 g, 0.020 mol, 1 eq.), 2-(4-(4,4,5,5-tetramethyl-1,3,2-dioxaborolan-2-yl)phenyl)-1,10-phenanthroline (8 g, 0.021 mol, 1.05 eq.), K$_3$PO$_4$ (8.5 g, 0.040 mol, 2 eq.) and Pd(PPh$_3$)$_4$ (1.1 g, 0.001 mol, 0.05 eq.) were introduced to 1,4-dioxane (160 ml) and H$_2$O (40 ml), and the result was stirred for 6 hours at 70° C. Produced solids were filtered and dried to obtain Compound 3 (8 g) in a 70% yield.

Target Compound A was synthesized in the same manner as in Preparation Example 1 except that Intermediate A of the following Table 1 was used instead of 2-(4-(4,4,5,5-tetramethyl-1,3,2-dioxaborolan-2-yl)phenyl)-1,10-phenanthroline.

TABLE 1

| Compound Number | Intermediate A | Target Compound A | Yield |
|---|---|---|---|
| 5 | | | 80% |
| 9 | | | 77% |

TABLE 1-continued
| Compound Number | Intermediate A | Target Compound A | Yield |
|---|---|---|---|
| 13 | 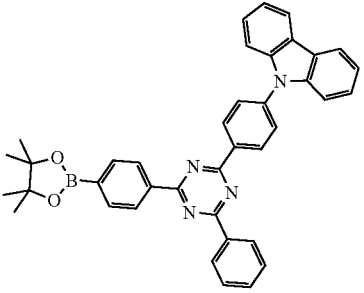 [SMILES: CC1(C)OB(c2ccc(-c3nc(-c4ccccc4)nc(-c4ccc(-n5c6ccccc6c6ccccc65)cc4)n3)cc2)OC1(C)C] | 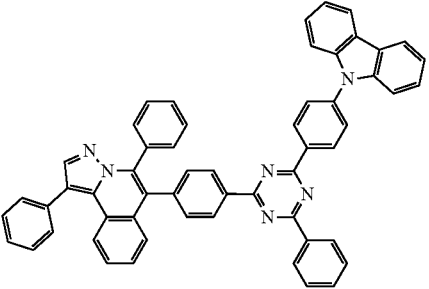 [SMILES: c1ccc(-c2nc(-c3ccc(-c4c(-c5ccccc5)n5ncc(-c6ccccc6)c5c5ccccc45)cc3)nc(-c3ccc(-n4c5ccccc5c5ccccc54)cc3)n2)cc1] | 69% |
| 17 | 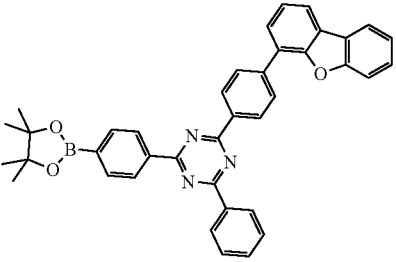 [SMILES: CC1(C)OB(c2ccc(-c3nc(-c4ccccc4)nc(-c4ccc(-c5cccc6c5oc5ccccc56)cc4)n3)cc2)OC1(C)C] | 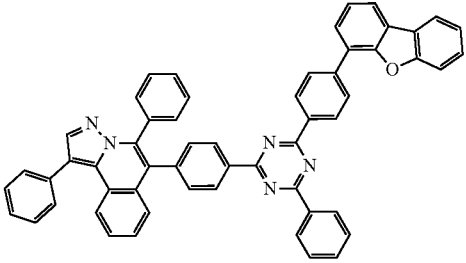 [SMILES: c1ccc(-c2nc(-c3ccc(-c4c(-c5ccccc5)n5ncc(-c6ccccc6)c5c5ccccc45)cc3)nc(-c3ccc(-c4cccc5c4oc4ccccc45)cc3)n2)cc1] | 71% |
| 37 | 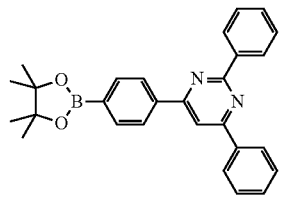 [SMILES: CC1(C)OB(c2ccc(-c3cc(-c4ccccc4)nc(-c4ccccc4)n3)cc2)OC1(C)C] | 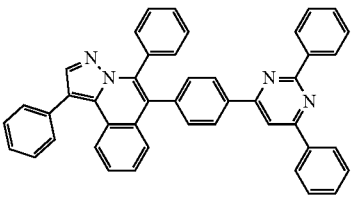 [SMILES: c1ccc(-c2cc(-c3ccc(-c4c(-c5ccccc5)n5ncc(-c6ccccc6)c5c5ccccc45)cc3)nc(-c3ccccc3)n2)cc1] | 72% |
| 41 | 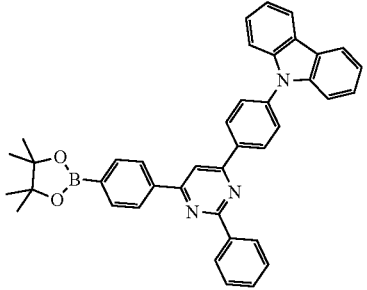 [SMILES: CC1(C)OB(c2ccc(-c3cc(-c4ccc(-n5c6ccccc6c6ccccc65)cc4)nc(-c4ccccc4)n3)cc2)OC1(C)C] | 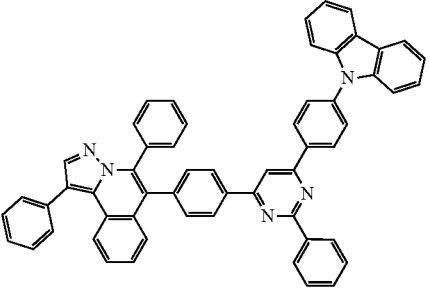 [SMILES: c1ccc(-c2nc(-c3ccc(-c4c(-c5ccccc5)n5ncc(-c6ccccc6)c5c5ccccc45)cc3)cc(-c3ccc(-n4c5ccccc5c5ccccc54)cc3)n2)cc1] | 70% |
| 45 | 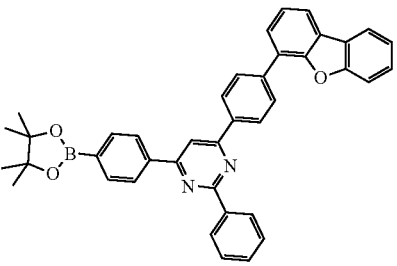 [SMILES: CC1(C)OB(c2ccc(-c3cc(-c4ccc(-c5cccc6c5oc5ccccc56)cc4)nc(-c4ccccc4)n3)cc2)OC1(C)C] | 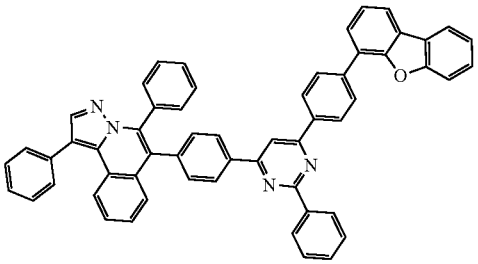 [SMILES: c1ccc(-c2nc(-c3ccc(-c4c(-c5ccccc5)n5ncc(-c6ccccc6)c5c5ccccc45)cc3)cc(-c3ccc(-c4cccc5c4oc4ccccc45)cc3)n2)cc1] | 65% |
| 96 | 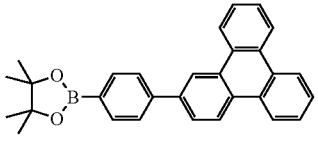 [SMILES: CC1(C)OB(c2ccc(-c3ccc4c5ccccc5c5ccccc5c4c3)cc2)OC1(C)C] | 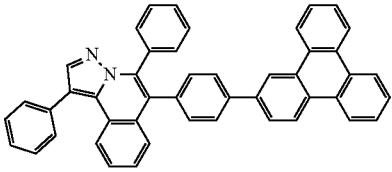 [SMILES: c1ccc(-c2cnn3c(-c4ccccc4)c(-c4ccc(-c5ccc6c7ccccc7c7ccccc7c6c5)cc4)c4ccccc4c23)cc1] | 85% |

TABLE 1-continued

| Compound Number | Intermediate A | Target Compound A | Yield |
|---|---|---|---|
| 110 | | | 81% |
| 112 | | | 88% |
| 227 | | | 80% |
| 233 | | | 76% |
| 273 | | | 70% |
| 274 | | | 72% |

TABLE 1-continued
| Compound Number | Intermediate A | Target Compound A | Yield |
|---|---|---|---|
| 285 | 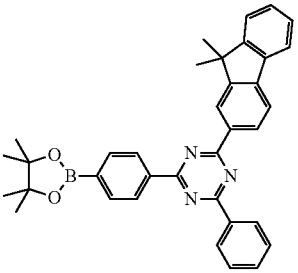 [SMILES: CC1(C)c2ccccc2-c2ccc(-c3nc(-c4ccccc4)nc(-c4ccc(B5OC(C)(C)C(C)(C)O5)cc4)n3)cc21] | 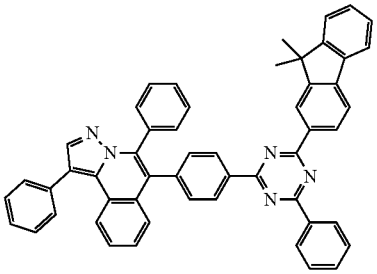 [SMILES: CC1(C)c2ccccc2-c2ccc(-c3nc(-c4ccccc4)nc(-c4ccc(-c5c(-c6ccccc6)n6ncc(-c7ccccc7)c6c6ccccc56)cc4)n3)cc21] | 66% |
| 286 | 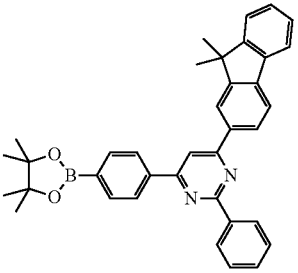 [SMILES: CC1(C)c2ccccc2-c2ccc(-c3cc(-c4ccc(B5OC(C)(C)C(C)(C)O5)cc4)nc(-c4ccccc4)n3)cc21] | 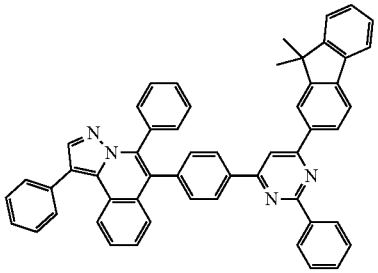 [SMILES: CC1(C)c2ccccc2-c2ccc(-c3cc(-c4ccc(-c5c(-c6ccccc6)n6ncc(-c7ccccc7)c6c6ccccc56)cc4)nc(-c4ccccc4)n3)cc21] | 65% |
| 293 | 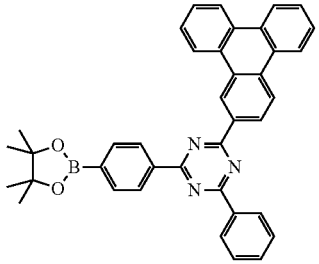 [SMILES: CC1(C)OB(c2ccc(-c3nc(-c4ccccc4)nc(-c4ccc5c6ccccc6c6ccccc6c5c4)n3)cc2)OC1(C)C] | 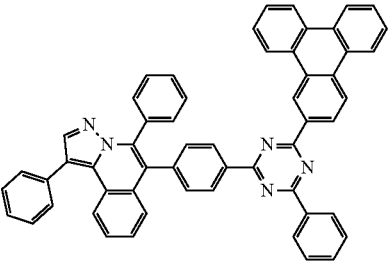 [SMILES: c1ccc(-c2nc(-c3ccc(-c4c(-c5ccccc5)n5ncc(-c6ccccc6)c5c5ccccc45)cc3)nc(-c3ccc4c5ccccc5c5ccccc5c4c3)n2)cc1] | 71% |
| 294 | 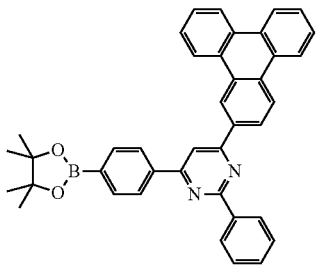 [SMILES: CC1(C)OB(c2ccc(-c3cc(-c4ccc5c6ccccc6c6ccccc6c5c4)nc(-c4ccccc4)n3)cc2)OC1(C)C] | 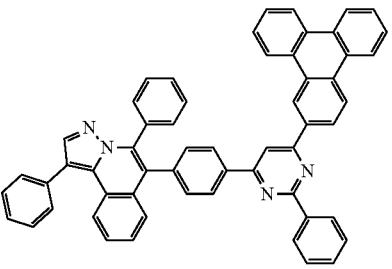 [SMILES: c1ccc(-c2nc(-c3ccc(-c4c(-c5ccccc5)n5ncc(-c6ccccc6)c5c5ccccc45)cc3)cc(-c3ccc4c5ccccc5c5ccccc5c4c3)n2)cc1] | 77% |

<Preparation Example 2> Preparation of Compound 115

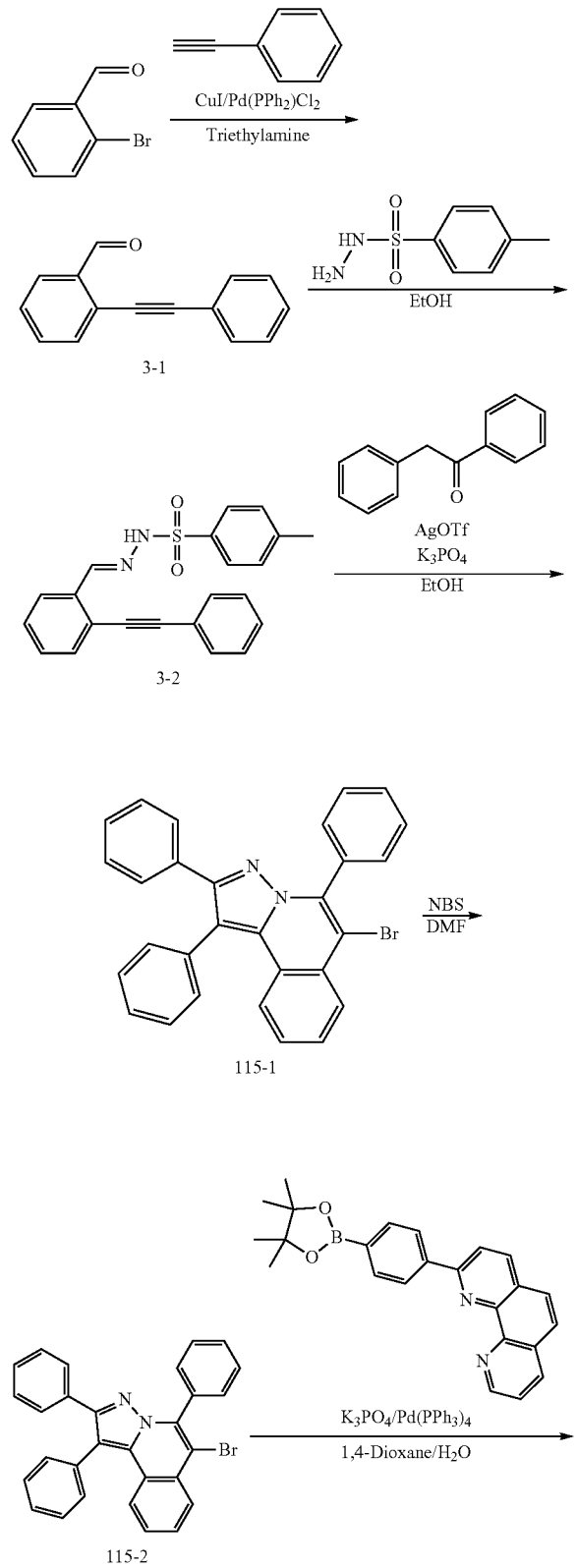

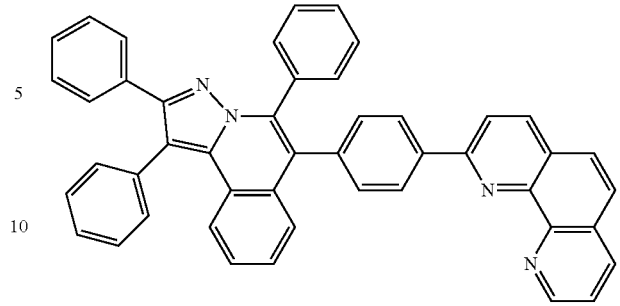

115

(1) Preparation of Compound 115-1

Compound 3-2 (30 g, 0.08 mol, 1 eq.) of Preparation Example 1 and AgOTf (3 g, 0.012 mol, 0.15 eq.) were introduced to EtOH (450 ml), and the result was stirred for 2 hours at 70° C. 1,2-Diphenylethanone (18.8 g, 0.09 mol, 1.2 eq.) and $K_3PO_4$ (68 g, 0.32 mol) were introduced thereto, and the result was stirred for 6 hours at 70° C. Water was added thereto to terminate the reaction, and the result was extracted using MC and water. After that, water was removed using anhydrous $Na_2CO_3$. The result was separated using a silica gel column to obtain Compound 115-1 (18 g) in a 56% yield.

(2) Preparation of Compound 115-2

Compound 115-1 (18 g, 0.045 mol, 1 eq.) and NBS (8.5 g, 0.047 mol, 1.05 eq.) were introduced to DMF (180 ml), and the result was stirred for 24 hours at R.T. Water was added thereto to terminate the reaction, and the result was extracted using MC and water. After that, water was removed using anhydrous $Na_2CO_3$. The result was separated using a silica gel column to obtain Compound 115-2 (18 g) in a 83% yield.

(3) Preparation of Compound 115

Compound 115-2 (8 g, 0.016 mol, 1 eq.), 2-(4-(4,4,5,5-tetramethyl-1,3,2-dioxaborolan-2-yl)phenyl)-1,10-phenanthroline (6.7 g, 0.017 mol, 1.05 eq.), $K_3PO_4$ (7.1 g, 0.033 mol, 2 eq.) and $Pd(PPh_3)_4$ (1.0 g, 0.0008 mol, 0.05 eq.) were introduced to 1,4-dioxane (160 ml) and $H_2O$ (40 ml), and the result was stirred for 6 hours at 70° C. Produced solids were filtered and dried to obtain Compound 115 (7 g) in a 64% yield.

Target Compound B was synthesized in the same manner as in Preparation Example 2 except that Intermediate B of the following Table 2 was used instead of 2-(4-(4,4,5,5-tetramethyl-1,3,2-dioxaborolan-2-yl)phenyl)-1,10-phenanthroline.

TABLE 2
| Compound Number | Intermediate B | Target Compound B | Yield |
|---|---|---|---|
| 117 | 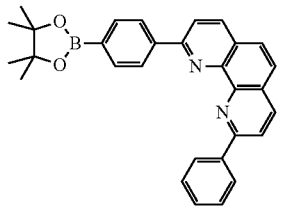 [SMILES: CC1(C)OB(c2ccc(-c3ccc4ccc5ccc(-c6ccccc6)nc5c4n3)cc2)OC1(C)C] | 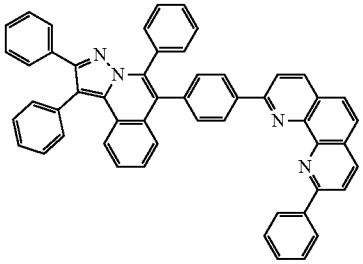 [SMILES: c1ccc(-c2ccc3ccc4ccc(-c5ccc(-c6c(-c7ccccc7)n7nc(-c8ccccc8)c(-c8ccccc8)c7c7ccccc67)cc5)nc4c3n2)cc1] | 77% |
| 121 | 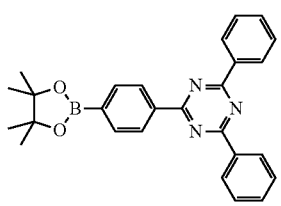 [SMILES: CC1(C)OB(c2ccc(-c3nc(-c4ccccc4)nc(-c4ccccc4)n3)cc2)OC1(C)C] | 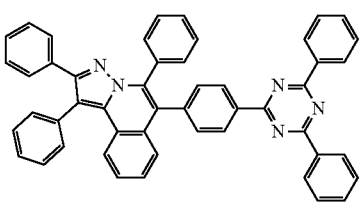 | 71% |
| 125 | 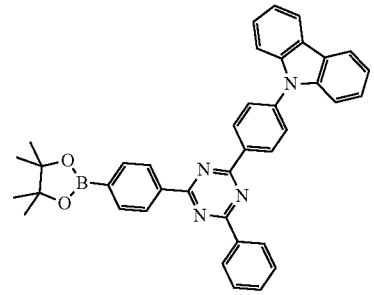 [SMILES: CC1(C)OB(c2ccc(-c3nc(-c4ccccc4)nc(-c4ccc(-n5c6ccccc6c6ccccc65)cc4)n3)cc2)OC1(C)C] | 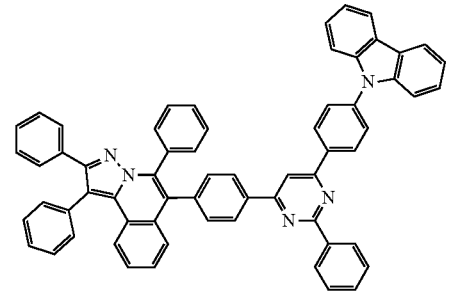 [SMILES: c1ccc(-c2nc(-c3ccc(-c4c(-c5ccccc5)n5nc(-c6ccccc6)c(-c6ccccc6)c5c5ccccc45)cc3)cc(-c3ccc(-n4c5ccccc5c5ccccc54)cc3)n2)cc1] | 76% |
| 129 | 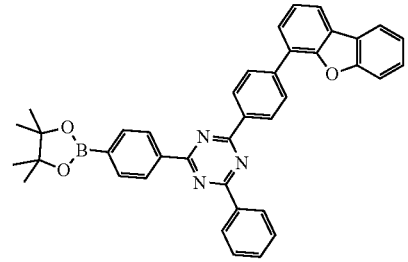 [SMILES: CC1(C)OB(c2ccc(-c3nc(-c4ccccc4)nc(-c4ccc(-c5cccc6c5oc5ccccc56)cc4)n3)cc2)OC1(C)C] | 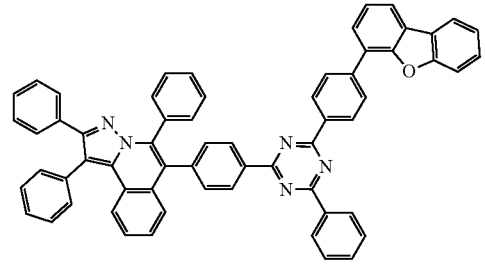 [SMILES: c1ccc(-c2nc(-c3ccc(-c4c(-c5ccccc5)n5nc(-c6ccccc6)c(-c6ccccc6)c5c5ccccc45)cc3)nc(-c3ccc(-c4cccc5c4oc4ccccc45)cc3)n2)cc1] | 73% |
| 149 | 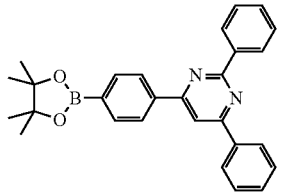 [SMILES: CC1(C)OB(c2ccc(-c3cc(-c4ccccc4)nc(-c4ccccc4)n3)cc2)OC1(C)C] | 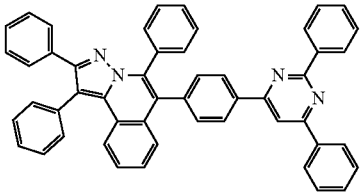 [SMILES: c1ccc(-c2cc(-c3ccc(-c4c(-c5ccccc5)n5nc(-c6ccccc6)c(-c6ccccc6)c5c5ccccc45)cc3)nc(-c3ccccc3)n2)cc1] | 80% |
| 153 | 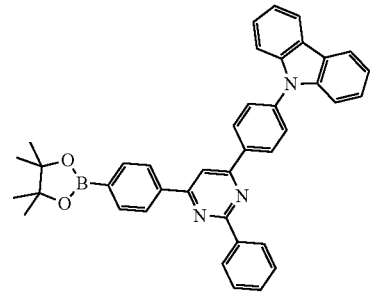 [SMILES: CC1(C)OB(c2ccc(-c3cc(-c4ccc(-n5c6ccccc6c6ccccc65)cc4)nc(-c4ccccc4)n3)cc2)OC1(C)C] | 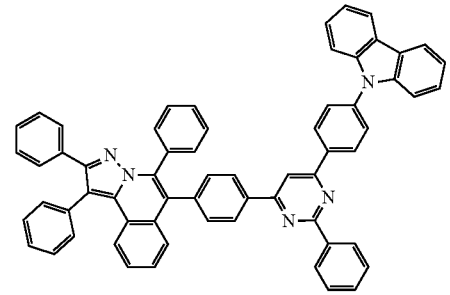 [SMILES: c1ccc(-c2nc(-c3ccc(-c4c(-c5ccccc5)n5nc(-c6ccccc6)c(-c6ccccc6)c5c5ccccc45)cc3)cc(-c3ccc(-n4c5ccccc5c5ccccc54)cc3)n2)cc1] | 71% |

TABLE 2-continued

| Compound Number | Intermediate B | Target Compound B | Yield |
|---|---|---|---|
| 157 | | | 72% |
| 208 | | | 82% |
| 222 | | | 80% |
| 224 | | | 78% |
| 239 | | | 83% |
| 245 | | | 85% |

Compounds were prepared in the same manner as in the preparation examples, and the synthesis identification results are shown in Table 3 and Table 4. Table 3 shows 1H NMR (CDCl$_3$, 200 Mz) measurement values, and Table 4 shows field desorption mass spectrometry (FD-MS) measurement values.

TABLE 3

| Compound | $^1$H NMR (CDCl$_3$, 200 Mz) |
|---|---|
| 3 | δ = 8.81(3H, m), 8.65(1H, s), 8.30(3H, m), 8.06(2H, m), 7.76(3H, m), 7.58~7.28(14H, m) |
| 5 | δ = 8.81(2H, dd), 8.65(1H, s), 8.30(4H, m), 8.06(3H, m), 7.76(3H, m), 7.58~7.28(17H, m) |
| 9 | δ = 8.65(1H, s), 8.30(6H, m), 7.85(4H, m), 7.54~7.41(16H, m), 7.25(2H, dd) |
| 13 | δ = 8.65(1H, s), 8.55(1H, d), 8.30(4H, m), 8.12(1H, d), 7.94~7.76(7H, m), 7.68(3H, m), 7.54~7.33(19H, m) |
| 17 | δ = 8.65(1H, s), 8.30(4H, m), 7.89~7.76(9H, m), 7.66(1H, d), 7.52~7.25(20H, m) |
| 37 | δ = 8.65(1H, s), 8.28(7H, m), 7.92(1H, d), 7.76(3H, m), 7.51~7.41(16H, m), 7.25(2H, d) |
| 41 | δ = 8.65(1H, s), 8.55(1H, d), 8.30(7H, m), 8.12(1H, d), 7.94(2H, m), 7.79(3H, m), 7.68(3H, m), 7.51~7.25(19H, m) |
| 45 | δ = 8.65(1H, s), 8.30(9H, m), 7.76(5H, m), 7.66(1H, d), 7.54~7.25(20H, m) |
| 96 | δ = 9.15(1H, s), 8.93(2H, d), 8.65(1H, s), 8.30(2H, d), 8.12(3H, m), 8.04(1H, d), 7.76(6H, m), 7.54~7.47(10H, m), 7.25(4H, s) |
| 110 | δ = 8.65(1H, s), 8.30(2H, m), 7.92(1H, d), 7.77(9H, m), 7.54~7.41(16H, m) |
| 112 | δ = 8.65(1H, s), 8.30(6H, m), 8.20(2H, s), 7.92(1H, d), 7.76(1H, d), 7.54~7.41(16H, m), 7.25(4H, s) |
| 115 | δ = 8.81(3H, s), 8.38(1H, d), 8.30(2H, d), 8.06(2H, d), 7.92(1H, d) 8.81(4H, m), 7.58~7.35(17H, d) |
| 117 | δ = 8.81(2H, d), 8.30(4H, d), 8.10(3H, m), 7.92(1H, d) 7.76(4H, m), 7.54~7.28(20H, m) |
| 121 | δ = 8.30(6H, m), 7.79(6H, m), 7.54~7.41(19H, m) 7.25(2H, d) |
| 125 | δ = 8.55(1H, d), 8.30(4H, m), 8.12(1H, d), 7.94~7.76(9H, m), 7.68(3H, m), 7.51~7.29(22H, m) |
| 129 | δ = 8.30(4H, m), 7.79(11H, m), 7.66(1H, d), 7.54~7.25(23H, m) |
| 149 | δ = 8.30(7H, m), 7.92(1H, d), 7.76(5H, m), 7.54~7.41(19H, m) 7.25(2H, d) |
| 153 | δ = 8.55(1H, d), 8.27(7H, m), 8.12(1H, d), 7.94(2H, m) 7.79(5H, m), 7.68(3H, m), 7.54~7.29(22H, m) |
| 157 | δ = 8.30(9H, m), 7.89(7H, m), 7.66(1H, d) 7.54~7.25(23H, m) |
| 208 | δ = 9.15(1H, s), 8.93(2H, d), 8.30(2H, d), 8.18(3H, m), 8.04(1H, d), 7.76(8H, d) 7.54~7.47(13H, m), 7.25(4H, s) |
| 222 | δ = 8.30(2H, m), 7.92(1H, d), 7.77(11H, m), 7.51~7.42(19H, m) |
| 224 | δ = 8.30(6H, m), 8.20(2H, s), 7.92(1H, d), 7.79(3H, m), 7.54~7.41(19H, m), 7.25(4H, s) |
| 227 | δ = 8.65(1H, s), 8.30(2H, m), 8.16(1H, d), 7.79(8H, m), 7.54~7.41(14H, m), 7.25(2H, d) |
| 233 | δ = 8.65(1H, s), 8.56(1H, d), 8.30(2H, d), 7.92(3H, m), 1.76(1H, d), 7.59~7.41(16H, m), 7.22(4H, m) |
| 239 | δ = 8.30(2H, m), 8.16(1H, d), 7.79(10H, m), 7.58~7.41(17H, m), 7.25(2H, d) |
| 245 | δ = 8.56(1H, d), 8.30(2H, d), 7.79(6H, m), 7.59~7.41(19H, m), 7.25(4H, m) |
| 273 | δ = 8.65(1H, s), 8.30(4H, m), 7.92(1H, d), 7.85(2H, d), 7.76(1H, d), 7.66(3H, s) 7.52~7.41(23H, m), 7.25(2H, d) |
| 274 | δ = 8.65(1H, s), 8.28(7H, m), 7.92(1H, d), 7.76(1H, d), 7.66(3H, s) 7.52~7.41(23H, m), 7.25(2H, d) |
| 285 | δ = 8.65(1H, s), 8.28(4H, d), 7.85(5H, m), 7.76(2H, d), 7.63(1H, d) 7.55~7.38(15H, m), 7.28(3H, m), 1.72(6H, s) |
| 286 | δ = 8.65(1H, s), 8.30(7H, m), 7.93(3H, m), 7.76(2H, m), 7.63(1H, d), 7.55~7.38(15H, m), 7.28(3H, m), 1.72(6H, s) |
| 293 | δ = 9.15(1H, s), 8.93(2H, d), 8.65(1H, s), 8.28(4H, m), 8.18(3H, m), 8.04(1H, d), 7.76(8H, m), 7.54~7.47(13H, m), 7.25(2H, d) |
| 294 | δ = 9.15(1H, s), 8.93(2H, d), 8.65(1H, s), 8.30(10H, m), 8.04(1H, d), 7.76(6H, m), 7.54~7.47(13H, m), 7.25(2H, d) |

TABLE 4

| Compound | FD-MS | Compound | FD-MS |
|---|---|---|---|
| 1 | m/z = 498.58 (C35H22N4 = 498.18) | 2 | m/z = 574.67 (C41H26N4 = 574.22) |
| 3 | m/z = 574.67 (C41H26N4 = 574.22) | 4 | m/z = 574.67 (C41H26N4 = 574.22) |
| 5 | m/z = 650.77 (C47H30N4 = 650.25) | 6 | m/z = 650.77 (C47H30N4 = 650.25) |
| 7 | m/z = 574.67 (C41H26N4 = 574.22) | 8 | m/z = 574.67 (C41H26N4 = 574.22) |
| 9 | m/z = 627.73 (C44H29N5 = 627.24) | 10 | m/z = 627.73 (C44H29N5 = 627.24) |
| 11 | m/z = 703.83 (C50H33N5 = 703.27) | 12 | m/z = 703.83 (C50H33N5 = 703.27) |
| 13 | m/z = 792.93 (C56H36N6 = 792.30) | 14 | m/z = 792.93 (C56H36N6 = 792.30) |
| 15 | m/z = 792.93 (C56H36N6 = 792.30) | 16 | m/z = 792.93 (C56H36N6 = 792.30) |
| 17 | m/z = 793.91 (C56H35N5O = 793.28) | 18 | m/z = 793.91 (C56H35N5O = 793.28) |
| 19 | m/z = 793.91 (C56H35N5O = 793.28) | 20 | m/z = 793.91 (C56H35N5O = 793.28) |
| 21 | m/z = 716.83 (C50H32N6 = 716.27) | 22 | m/z = 716.83 (C50H32N6 = 716.27) |
| 23 | m/z = 717.81 (C50H31N5O = 717.25) | 24 | m/z = 717.81 (C50H31N5O = 717.25) |
| 25 | m/z = 717.81 (C50H31N5O = 717.25) | 26 | m/z = 717.81 (C50H31N5O = 717.25) |
| 27 | m/z = 717.81 (C50H31N5O = 717.25) | 28 | m/z = 717.81 (C50H31N5O = 717.25) |
| 29 | m/z = 703.83 (C50H33N5 = 703.27) | 30 | m/z = 703.83 (C50H33N5 = 703.27) |
| 31 | m/z = 779.93 (C50H33N5 = 779.30) | 32 | m/z = 779.93 (C50H33N5 = 779.30) |
| 33 | m/z = 779.93 (C50H33N5 = 779.30) | 34 | m/z = 779.93 (C50H33N5 = 779.30) |
| 35 | m/z = 779.93 (C50H33N5 = 779.30) | 36 | m/z = 779.93 (C50H33N5 = 779.30) |
| 37 | m/z = 626.75 (C45H30N4 = 626.25) | 38 | m/z = 626.75 (C45H30N4 = 626.25) |
| 39 | m/z = 702.84 (C51H34N4 = 702.28) | 40 | m/z = 702.84 (C51H34N4 = 702.28) |
| 41 | m/z = 791.94 (C57H37N5 = 791.30) | 42 | m/z = 791.94 (C57H37N5 = 791.30) |
| 43 | m/z = 791.94 (C57H37N5 = 791.30) | 44 | m/z = 791.94 (C57H37N5 = 791.30) |
| 45 | m/z = 792.92 (C57H36N4O = 792.29) | 46 | m/z = 792.92 (C57H36N4O = 792.29) |
| 47 | m/z = 792.92 (C57H36N4O = 792.29) | 48 | m/z = 792.92 (C57H36N4O = 792.29) |
| 49 | m/z = 715.84 (C51H33N5 = 715.27) | 50 | m/z = 715.84 (C51H33N5 = 715.27) |
| 51 | m/z = 716.83 (C51H32N4O = 716.26) | 52 | m/z = 716.83 (C51H32N4O = 716.26) |
| 53 | m/z = 716.83 (C51H32N4O = 716.26) | 54 | m/z = 716.83 (C51H32N4O = 716.26) |
| 55 | m/z = 716.83 (C51H32N4O = 716.26) | 56 | m/z = 716.83 (C51H32N4O = 716.26) |
| 57 | m/z = 703.83 (C50H33N5 = 703.27) | 58 | m/z = 779.93 (C56H37N5 = 779.30) |
| 59 | m/z = 779.93 (C56H37N5 = 779.30) | 60 | m/z = 702.84 (C51H34N4 = 702.28) |
| 61 | m/z = 778.94 (C57H38N4 = 778.31) | 62 | m/z = 778.94 (C57H38N4 = 778.31) |
| 63 | m/z = 702.84 (C51H34N4 = 702.28) | 64 | m/z = 778.94 (C57H38N4 = 778.31) |
| 65 | m/z = 778.94 (C57H38N4 = 778.31) | 66 | m/z = 703.83 (C50H33N5 = 703.27) |
| 67 | m/z = 779.93 (C56H37N5 = 779.30) | 68 | m/z = 779.93 (C56H37N5 = 779.30) |
| 69 | m/z = 702.84 (C51H34N4 = 702.28) | 70 | m/z = 778.94 (C57H38N4 = 778.31) |
| 71 | m/z = 778.94 (C57H38N4 = 778.31) | 72 | m/z = 702.84 (C51H34N4 = 702.28) |
| 73 | m/z = 778.94 (C57H38N4 = 778.31) | 74 | m/z = 778.94 (C57H38N4 = 778.31) |
| 75 | m/z = 703.83 (C50H33N5 = 703.27) | 76 | m/z = 779.93 (C56H37N5 = 779.30) |

TABLE 4-continued

| Compound | FD-MS | Compound | FD-MS |
|---|---|---|---|
| 77 | m/z = 779.93 (C56H37N5 = 779.30) | 78 | m/z = 702.84 (C51H34N4 = 702.28) |
| 79 | m/z = 778.94 (C57H38N4 = 778.31) | 80 | m/z = 778.94 (C57H38N4 = 778.31) |
| 81 | m/z = 702.84 (C51H34N4 = 702.28) | 82 | m/z = 778.94 (C57H38N4 = 778.31) |
| 83 | m/z = 778.94 (C57H38N4 = 778.31) | 84 | m/z = 703.83 (C50H33N5 = 703.27) |
| 85 | m/z = 779.93 (C56H37N5 = 779.30) | 86 | m/z = 779.93 (C56H37N5 = 779.30) |
| 87 | m/z = 702.84 (C51H34N4 = 702.28) | 88 | m/z = 778.94 (C57H38N4 = 778.31) |
| 89 | m/z = 778.94 (C57H38N4 = 778.31) | 90 | m/z = 702.84 (C51H34N4 = 702.28) |
| 91 | m/z = 778.94 (C57H38N4 = 778.31) | 92 | m/z = 778.94 (C57H38N4 = 778.31) |
| 93 | m/z = 710.86 (C54H34N2 = 710.27) | 94 | m/z = 710.86 (C54H34N2 = 710.27) |
| 95 | m/z = 710.86 (C54H34N2 = 710.27) | 96 | m/z = 622.75 (C47H30N2 = 622.24) |
| 97 | m/z = 710.86 (C54H34N2 = 710.27) | 98 | m/z = 710.86 (C54H34N2 = 710.27) |
| 99 | m/z = 710.86 (C54H34N2 = 710.27) | 100 | m/z = 622.75 (C47H30N2 = 622.24) |
| 101 | m/z = 561.67 (C41H27N3 = 561.22) | 102 | m/z = 561.67 (C41H27N3 = 561.22) |
| 103 | m/z = 802.96 (C59H38N4 = 802.31) | 104 | m/z = 802.96 (C59H38N4 = 802.31) |
| 105 | m/z = 712.88 (C54H36N2 = 712.29) | 106 | m/z = 712.88 (C54H36N2 = 712.29) |
| 107 | m/z = 712.88 (C54H36N2 = 712.29) | 108 | m/z = 572.70 (C43H28N2 = 572.23) |
| 109 | m/z = 648.79 (C49H32N2 = 648.26) | 110 | m/z = 596.66 (C41H29N2OP = 596.20) |
| 111 | m/z = 626.75 (C45H30N4 = 626.25) | 112 | m/z = 625.76 (C46H31N3 = 625.25) |
| 113 | m/z = 574.67 (C41H26N4 = 574.22) | 114 | m/z = 650.77 (C47H30N4 = 650.25) |
| 115 | m/z = 650.77 (C47H30N4 = 650.25) | 116 | m/z = 650.77 (C47H30N4 = 650.25) |
| 117 | m/z = 726.86 (C53H34N4 = 726.28) | 118 | m/z = 726.86 (C53H34N4 = 726.28) |
| 119 | m/z = 650.77 (C47H30N4 = 650.25) | 120 | m/z = 650.77 (C47H30N4 = 650.25) |
| 121 | m/z = 703.83 (C50H33N5 = 703.27) | 122 | m/z = 703.83 (C50H33N5 = 703.27) |
| 123 | m/z = 779.93 (C56H37N5 = 779.30) | 124 | m/z = 779.93 (C56H37N5 = 779.30) |
| 125 | m/z = 869.02 (C62H40N6 = 868.33) | 126 | m/z = 869.02 (C62H40N6 = 868.33) |
| 127 | m/z = 869.02 (C62H40N6 = 868.33) | 128 | m/z = 869.02 (C62H40N6 = 868.33) |
| 129 | m/z = 870.01 (C62H39N5O = 869.32) | 130 | m/z = 870.01 (C62H39N5O = 869.32) |
| 131 | m/z = 870.01 (C62H39N5O = 869.32) | 132 | m/z = 870.01 (C62H39N5O = 869.32) |
| 133 | m/z = 792.93 (C56H36N6 = 792.30) | 134 | m/z = 792.93 (C56H36N6 = 792.30) |
| 135 | m/z = 793.91 (C56H35N5O = 793.28) | 136 | m/z = 793.91 (C56H35N5O = 793.28) |
| 137 | m/z = 793.91 (C56H35N5O = 793.28) | 138 | m/z = 793.91 (C56H35N5O = 793.28) |
| 139 | m/z = 793.91 (C56H35N5O = 793.28) | 140 | m/z = 793.91 (C56H35N5O = 793.28) |
| 141 | m/z = 779.93 (C56H37N5 = 779.30) | 142 | m/z = 793.91 (C56H35N5O = 793.28) |
| 143 | m/z = 856.02 (C62H41N5 = 855.34) | 144 | m/z = 856.02 (C62H41N5 = 855.34) |
| 145 | m/z = 856.02 (C62H41N5 = 855.34) | 146 | m/z = 856.02 (C62H41N5 = 855.34) |
| 147 | m/z = 856.02 (C62H41N5 = 855.34) | 148 | m/z = 856.02 (C62H41N5 = 855.34) |
| 149 | m/z = 702.84 (C51H34N4 = 702.28) | 150 | m/z = 702.84 (C51H34N4 = 702.28) |
| 151 | m/z = 778.94 (C57H38N4 = 778.31) | 152 | m/z = 778.94 (C57H38N4 = 778.31) |
| 153 | m/z = 868.03 (C63H41N5 = 867.34) | 154 | m/z = 868.03 (C63H41N5 = 867.34) |
| 155 | m/z = 868.03 (C63H41N5 = 867.34) | 156 | m/z = 868.03 (C63H41N5 = 867.34) |
| 157 | m/z = 869.02 (C63H40N4O = 868.32) | 158 | m/z = 869.02 (C63H40N4O = 868.32) |
| 159 | m/z = 869.02 (C63H40N4O = 868.32) | 160 | m/z = 869.02 (C63H40N4O = 868.32) |
| 161 | m/z = 791.94 (C57H37N5 = 791.30) | 162 | m/z = 791.94 (C57H37N5 = 791.30) |
| 163 | m/z = 792.92 (C57H36N4O = 792.29) | 164 | m/z = 792.92 (C57H36N4O = 792.29) |
| 165 | m/z = 792.92 (C57H36N4O = 792.29) | 166 | m/z = 792.92 (C57H36N4O = 792.29) |
| 167 | m/z = 792.92 (C57H36N4O = 792.29) | 168 | m/z = 792.92 (C57H36N4O = 792.29) |
| 169 | m/z = 779.93 (C56H37N5 = 779.30) | 170 | m/z = 856.02 (C62H41N5 = 855.34) |
| 171 | m/z = 856.02 (C62H41N5 = 855.34) | 172 | m/z = 778.94 (C57H38N4 = 778.31) |
| 173 | m/z = 855.03 (C63H42N4 = 854.34) | 174 | m/z = 855.03 (C63H42N4 = 854.34) |
| 175 | m/z = 778.94 (C57H38N4 = 778.31) | 176 | m/z = 855.03 (C63H42N4 = 854.34) |
| 177 | m/z = 855.03 (C63H42N4 = 854.34) | 178 | m/z = 779.93 (C56H37N5 = 779.30) |
| 179 | m/z = 856.02 (C62H41N5 = 855.34) | 180 | m/z = 856.02 (C62H41N5 = 855.34) |
| 181 | m/z = 778.94 (C57H38N4 = 778.31) | 182 | m/z = 855.03 (C63H42N4 = 854.34) |
| 183 | m/z = 855.03 (C63H42N4 = 854.34) | 184 | m/z = 778.94 (C57H38N4 = 778.31) |
| 185 | m/z = 855.03 (C63H42N4 = 854.34) | 186 | m/z = 855.03 (C63H42N4 = 854.34) |
| 187 | m/z = 779.93 (C56H37N5 = 779.30) | 188 | m/z = 856.02 (C62H41N5 = 855.34) |
| 189 | m/z = 856.02 (C62H41N5 = 855.34) | 190 | m/z = 778.94 (C57H38N4 = 778.31) |
| 191 | m/z = 855.03 (C63H42N4 = 854.34) | 192 | m/z = 855.03 (C63H42N4 = 854.34) |
| 193 | m/z = 778.94 (C57H38N4 = 778.31) | 194 | m/z = 855.03 (C63H42N4 = 854.34) |
| 195 | m/z = 855.03 (C63H42N4 = 854.34) | 196 | m/z = 779.93 (C56H37N5 = 779.30) |
| 197 | m/z = 856.02 (C62H41N5 = 855.34) | 198 | m/z = 856.02 (C62H41N5 = 855.34) |
| 199 | m/z = 778.94 (C57H38N4 = 778.31) | 200 | m/z = 855.03 (C63H42N4 = 854.34) |
| 201 | m/z = 855.03 (C63H42N4 = 854.34) | 202 | m/z = 778.94 (C57H38N4 = 778.31) |
| 203 | m/z = 855.03 (C63H42N4 = 854.34) | 204 | m/z = 855.03 (C63H42N4 = 854.34) |
| 205 | m/z = 786.96 (C60H38N2 = 786.30) | 206 | m/z = 786.96 (C60H38N2 = 786.30) |
| 207 | m/z = 786.96 (C60H38N2 = 786.30) | 208 | m/z = 698.85 (C53H34N2 = 698.27) |
| 209 | m/z = 786.96 (C60H38N2 = 786.30) | 210 | m/z = 786.96 (C60H38N2 = 786.30) |
| 211 | m/z = 786.96 (C60H38N2 = 786.30) | 212 | m/z = 698.85 (C53H34N2 = 698.27) |
| 213 | m/z = 637.77 (C47H31N3 = 637.25) | 214 | m/z = 637.77 (C47H31N3 = 637.25) |
| 215 | m/z = 879.06 (C65H42N4 = 878.34) | 216 | m/z = 879.06 (C65H42N4 = 878.34) |
| 217 | m/z = 788.97 (C60H40N2 = 788.32) | 218 | m/z = 788.97 (C60H40N2 = 788.32) |
| 219 | m/z = 788.97 (C60H40N2 = 788.32) | 220 | m/z = 648.79 (C49H32N2 = 648.26) |
| 221 | m/z = 724.89 (C55H36N2 = 724.29) | 222 | m/z = 672.75 (C47H33N2OP = 672.23) |
| 223 | m/z = 702.84 (C51H34N4 = 702.28) | 224 | m/z = 701.85 (C52H35N3 = 701.28) |
| 225 | m/z = 524.61 (C37H24N4 = 524.20) | 226 | m/z = 600.71 (C43H28N4 = 600.23) |
| 227 | m/z = 600.71 (C43H28N4 = 600.23) | 228 | m/z = 676.81 (C49H32N4 = 676.26) |

TABLE 4-continued

| Compound | FD-MS | Compound | FD-MS |
|---|---|---|---|
| 229 | m/z = 524.61 (C37H24N4 = 524.20) | 230 | m/z = 600.71 (C43H28N4 = 600.23) |
| 231 | m/z = 600.71 (C43H28N4 = 600.23) | 232 | m/z = 676.81 (C49H32N4 = 676.26) |
| 233 | m/z = 588.70 (C42H28N4 = 588.23) | 234 | m/z = 529.65 (C36H23N3S = 529.16) |
| 235 | m/z = 804.93 (C59H36N2O2 = 804.28) | 236 | m/z = 837.06 (C59H36N2S2 = 836.23) |
| 237 | m/z = 600.71 (C43H28N4 = 600.23) | 238 | m/z = 676.81 (C49H32N4 = 676.26) |
| 239 | m/z = 676.81 (C49H32N4 = 676.26) | 240 | m/z = 752.90 (C55H36N4 = 752.29) |
| 241 | m/z = 600.71 (C43H28N4 = 600.23) | 242 | m/z = 676.81 (C49H32N4 = 676.26) |
| 243 | m/z = 676.81 (C49H32N4 = 676.26) | 244 | m/z = 752.90 (C55H36N4 = 752.29) |
| 245 | m/z = 664.79 (C48H32N4 = 664.26) | 246 | m/z = 605.75 (C42H27N3S = 605.19) |
| 247 | m/z = 881.03 (C65H40N2O2 = 880.31) | 248 | m/z = 913.16 (C65H40N2S2 = 912.26) |
| 249 | m/z = 779.93 (C56H37N5 = 779.30) | 250 | m/z = 778.94 (C57H38N4 = 778.31) |
| 251 | m/z = 778.94 (C57H38N4 = 778.31) | 252 | m/z = 752.90 (C55H36N4 = 752.29) |
| 253 | m/z = 779.93 (C56H37N5 = 779.30) | 254 | m/z = 778.94 (C57H38N4 = 778.31) |
| 255 | m/z = 778.94 (C57H38N4 = 778.31) | 256 | m/z = 752.90 (C55H36N4 = 752.29) |
| 257 | m/z = 726.86 (C54H34N2O = 726.27) | 258 | m/z = 726.86 (C54H34N2O = 726.27) |
| 259 | m/z = 726.86 (C54H34N2O = 726.27) | 260 | m/z = 725.88 (C54H35N3 = 725.28) |
| 261 | m/z = 856.02 (C62H41N5 = 855.34) | 262 | m/z = 855.03 (C63H42N4 = 854.34) |
| 263 | m/z = 855.03 (C63H42N4 = 854.34) | 264 | m/z = 829.00 (C61H40N4 = 828.33) |
| 265 | m/z = 856.02 (C62H41N5 = 855.34) | 266 | m/z = 855.03 (C63H42N4 = 854.34) |
| 267 | m/z = 855.03 (C63H42N4 = 854.34) | 268 | m/z = 829.00 (C61H40N4 = 828.33) |
| 269 | m/z = 802.96 (C60H38N2O = 802.30) | 270 | m/z = 802.96 (C60H38N2O = 802.30) |
| 271 | m/z = 802.96 (C60H38N2O = 802.30) | 272 | m/z = 801.97 (C60H39N3 = 801.31) |
| 273 | m/z = 779.93 (C56H37N5 = 779.30) | 274 | m/z = 778.94 (C57H38N4 = 778.31) |
| 275 | m/z = 778.94 (C57H38N4 = 778.31) | 276 | m/z = 778.94 (C57H38N4 = 778.31) |
| 277 | m/z = 779.93 (C56H37N5 = 779.30) | 278 | m/z = 778.94 (C57H38N4 = 778.31) |
| 279 | m/z = 778.94 (C57H38N4 = 778.31) | 280 | m/z = 778.94 (C57H38N4 = 778.31) |
| 281 | m/z = 752.90 (C55H36N4 = 752.29) | 282 | m/z = 752.90 (C55H36N4 = 752.29) |
| 283 | m/z = 752.90 (C55H36N4 = 752.29) | 284 | m/z = 752.90 (C55H36N4 = 752.29) |
| 285 | m/z = 743.89 (C53H37N5 = 743.30) | 286 | m/z = 742.91 (C54H38N4 = 742.31) |
| 287 | m/z = 742.91 (C54H38N4 = 742.31) | 288 | m/z = 742.91 (C54H38N4 = 742.31) |
| 289 | m/z = 886.02 (C63H39N5 = 865.32) | 290 | m/z = 865.03 (C64H40N4 = 864.33) |
| 291 | m/z = 865.03 (C64H40N4 = 864.33) | 292 | m/z = 865.03 (C64H40N4 = 864.33) |
| 293 | m/z = 777.91 (C56H35N5 = 777.29) | 294 | m/z = 776.92 (C57H36N4 = 776.29) |
| 295 | m/z = 776.92 (C57H36N4 = 776.29) | 296 | m/z = 776.92 (C57H36N4 = 776.29) |
| 297 | m/z = 856.02 (C62H41N5 = 855.34) | 298 | m/z = 855.03 (C63H42N4 = 854.34) |
| 299 | m/z = 855.03 (C63H42N4 = 854.34) | 300 | m/z = 855.03 (C63H42N4 = 854.34) |
| 301 | m/z = 856.02 (C62H41N5 = 855.34) | 302 | m/z = 855.03 (C63H42N4 = 854.34) |
| 303 | m/z = 855.03 (C63H42N4 = 854.34) | 304 | m/z = 855.03 (C63H42N4 = 854.34) |
| 305 | m/z = 779.93 (C56H37N5 = 779.30) | 306 | m/z = 778.94 (C57H38N4 = 778.31) |
| 307 | m/z = 778.94 (C57H38N4 = 778.31) | 308 | m/z = 752.90 (C55H36N4 = 752.29) |
| 309 | m/z = 779.93 (C56H37N5 = 779.30) | 310 | m/z = 778.94 (C57H38N4 = 778.31) |
| 311 | m/z = 778.94 (C57H38N4 = 778.31) | 312 | m/z = 752.90 (C55H36N4 = 752.29) |
| 313 | m/z = 753.89 (C54H35N5 = 753.29) | 314 | m/z = 752.90 (C55H36N4 = 752.29) |
| 315 | m/z = 752.90 (C55H36N4 = 752.29) | 316 | m/z = 726.89 (C53H34N4 = 726.28) |
| 317 | m/z = 753.89 (C54H35N5 = 753.29) | 318 | m/z = 752.90 (C55H36N4 = 752.29) |
| 319 | m/z = 752.90 (C55H36N4 = 752.29) | 320 | m/z = 726.89 (C53H34N4 = 726.28) |
| 321 | m/z = 803.95 (C58H37N5 = 803.30) | 322 | m/z = 802.96 (C59H38N4 = 802.31) |
| 323 | m/z = 802.96 (C59H38N4 = 802.31) | 324 | m/z = 776.92 (C57H36N4 = 776.29) |
| 325 | m/z = 804.01 (C62H39N5 = 853.32) | 326 | m/z = 853.02 (C63H40N4 = 852.33) |
| 327 | m/z = 853.02 (C63H40N4 = 852.33) | 328 | m/z = 826.98 (C61H38N4 = 826.31) |

EXPERIMENTAL EXAMPLE

Experimental Example 1

(1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used. Next, an ITO substrate was installed in a substrate folder of a vacuum depositor, and the following 4,4',4"-tris(N,N-(2-naphthyl)-phenylamino)triphenylamine (2-TNATA) was introduced to a cell in the vacuum depositor.

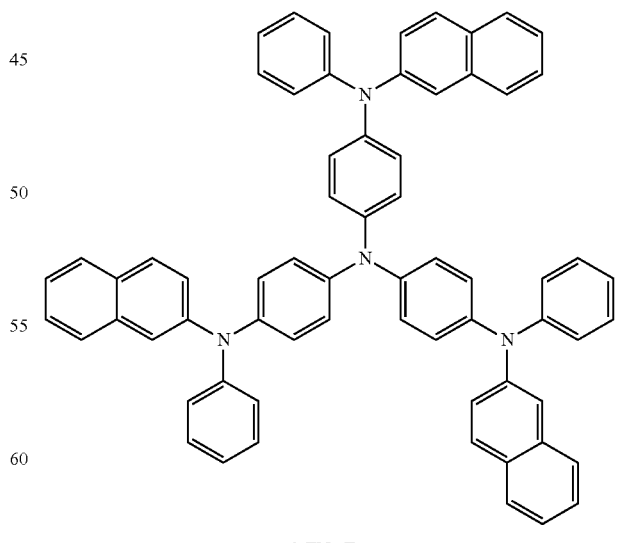

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell of the vacuum depositor, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

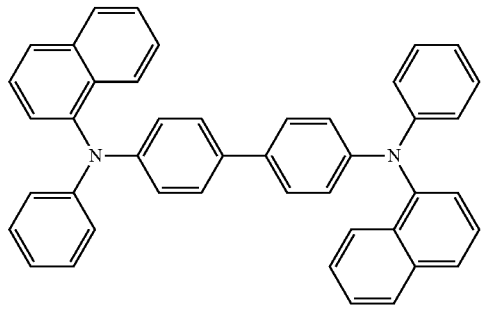

NPB

After forming the hole injection layer and the hole transfer layer as above, a blue light emitting material having a structure as below was deposited thereon as a light emitting layer. Specifically, in one side cell in the vacuum depositor, H1, a blue light emitting host material, was vacuum deposited to a thickness of 200 Å, and D1, a blue light emitting dopant material, was vacuum deposited thereon by 5% with respect to the host material.

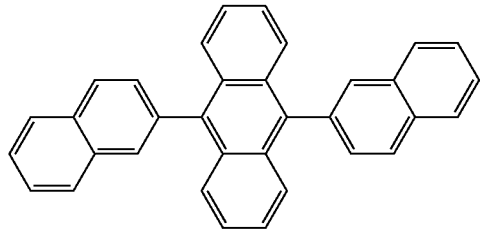

H1

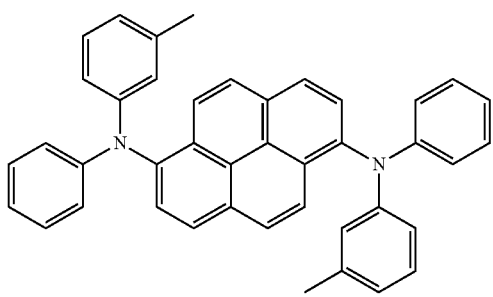

D1

Subsequently, a compound of the following structural formula E1 was deposited to a thickness of 300 Å as an electron transfer layer.

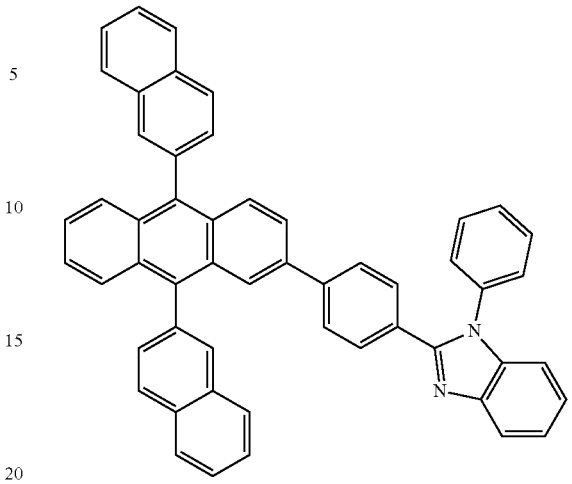

E1

As an electron injection layer, lithium fluoride (LiF) was deposited to a thickness of 10 Å, and an Al cathode was employed to have a thickness of 1,000 Å to manufacture an OLED. Meanwhile, all the organic compounds required to manufacture the OLED were vacuum sublimation purified under $10^{-6}$ torr to $10^{-8}$ torr by each material to be used in the OLED manufacture.

An electroluminescent device was manufactured in the same manner as in Experimental Example 1 except that a compound presented in the following Table 5 was used instead of Compound E1 when forming the electron transfer layer. Results of measuring a driving voltage, light emission efficiency, a color coordinate (CIE) and a lifetime of the blue organic light emitting device manufactured according to the present disclosure are as shown in the following Table 5.

(2) Driving Voltage and Light Emission Efficiency of Organic Light Emitting Device For the organic light emitting devices manufactured as above, electroluminescent light emission (EL) properties were measured using M7000 manufactured by McScience Inc., and with the measurement results, $T_{95}$ when standard luminance was 3,500 cd/m$^2$ was measured using a lifetime measurement system (M6000) manufactured by McScience Inc. Results of measuring a driving voltage, light emission efficiency, external quantum efficiency and a color coordinate (CIE) of the blue organic light emitting device manufactured according to the present disclosure are as shown in the following Table 5.

TABLE 5

| | Compound | Driving Voltage (V) | Light Emission Efficiency (cd/A) | CIE (x, y) | Lifetime (T95) |
|---|---|---|---|---|---|
| Example 1 | E1 | 5.70 | 6.00 | (0.134, 0.102) | 20 |
| Example 2 | 3 | 5.32 | 6.22 | (0.134, 0.102) | 32 |
| Example 3 | 5 | 5.36 | 6.30 | (0.134, 0.100) | 34 |
| Example 4 | 9 | 4.72 | 6.98 | (0.134, 0.100) | 51 |
| Example 5 | 13 | 4.80 | 6.89 | (0.134, 0.102) | 58 |
| Example 6 | 17 | 4.76 | 6.95 | (0.134, 0.102) | 50 |
| Example 7 | 37 | 4.68 | 6.93 | (0.134, 0.100) | 50 |
| Example 8 | 41 | 4.88 | 6.84 | (0.134, 0.102) | 57 |
| Example 9 | 45 | 4.77 | 6.90 | (0.134, 0.102) | 51 |
| Example 10 | 96 | 4.98 | 6.05 | (0.134, 0.101) | 34 |

TABLE 5-continued

| Compound | Driving Voltage (V) | Light Emission Efficiency (cd/A) | CIE (x, y) | Lifetime (T95) |
|---|---|---|---|---|
| Example 11 | 110 | 5.11 | 6.12 | (0.134, 0.102) | 48 |
| Example 12 | 112 | 4.96 | 6.10 | (0.134, 0.100) | 36 |
| Example 13 | 115 | 5.30 | 6.20 | (0.134, 0.101) | 40 |
| Example 14 | 117 | 5.22 | 6.03 | (0.134, 0.101) | 43 |
| Example 15 | 121 | 4.82 | 6.84 | (0.134, 0.101) | 52 |
| Example 16 | 125 | 4.84 | 6.97 | (0.134, 0.102) | 51 |
| Example 17 | 129 | 4.90 | 6.81 | (0.134, 0.101) | 56 |
| Example 18 | 149 | 4.88 | 6.82 | (0.134, 0.102) | 57 |
| Example 19 | 153 | 4.74 | 6.75 | (0.134, 0.101) | 51 |
| Example 20 | 157 | 4.81 | 6.82 | (0.134, 0.102) | 53 |
| Example 21 | 208 | 5.26 | 6.44 | (0.134, 0.102) | 32 |
| Example 22 | 222 | 5.21 | 6.38 | (0.134, 0.101) | 41 |
| Example 23 | 224 | 5.16 | 6.20 | (0.134, 0.101) | 38 |
| Example 24 | 227 | 5.15 | 6.42 | (0.134, 0.102) | 39 |
| Example 25 | 233 | 5.31 | 6.30 | (0.134, 0.103) | 37 |
| Example 26 | 239 | 5.33 | 6.22 | (0.134, 0.102) | 40 |
| Example 27 | 245 | 5.32 | 5.95 | (0.134, 0.101) | 41 |
| Example 28 | 273 | 4.82 | 6.35 | (0.134, 0.100) | 50 |
| Example 29 | 274 | 4.84 | 6.60 | (0.134, 0.100) | 49 |
| Example 30 | 285 | 4.94 | 6.68 | (0.134, 0.101) | 52 |
| Example 31 | 286 | 4.96 | 6.70 | (0.134, 0.101) | 47 |
| Example 32 | 293 | 4.91 | 6.69 | (0.134, 0.102) | 51 |
| Example 33 | 294 | 4.90 | 6.71 | (0.134, 0.102) | 50 |
| Comparative Example 3-1 | E2 | 5.57 | 6.12 | (0.134, 0.100) | 28 |
| Comparative Example 3-2 | E3 | 5.56 | 6.02 | (0.134, 0.101) | 29 |
| Comparative Example 3-3 | E4 | 5.60 | 6.09 | (0.134, 0.101) | 21 |

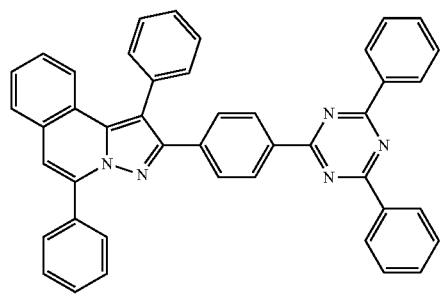

E2

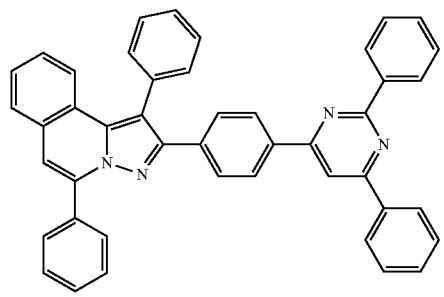

E3

E4

As seen from the results of Table 5, the organic light emitting device using the electron transfer layer material of the blue organic light emitting device of the present disclosure had a lower driving voltage, and significantly improved light emission efficiency and lifetime compared to Comparative Examples 1, 3-1, 3-2 and 3-3. Particularly, it was identified that Compounds 9, 13, 17, 37, 41, 45, 121, 125, 129, 149, 153 and 157 were superior in all aspects of driving, efficiency and lifetime. Such a result is considered to be due to the fact that, when using the disclosed compound having proper length, strength and flat properties as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transfer electrons without the compound being decomposed or destroyed.

For reference, those that are stable when excited are considered to be aryl or acene compounds, or polycyclic hetero-compounds. Accordingly, it is considered that excellent results in all aspects of driving, efficiency and lifetime are obtained by the compound of the present disclosure enhancing enhanced electron-transfer properties or improved stability.

Experimental Example 2

(1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used. Next, an ITO substrate was installed in a substrate folder of a vacuum depositor, and the following 4,4',4"-tris(N,N-(2-naphthyl)-phenylamino)triphenylamine (2-TNATA) was introduced to a cell in the vacuum depositor.

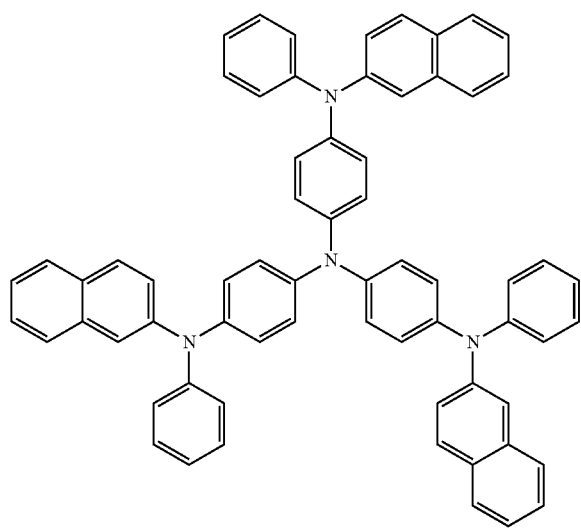

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell of the vacuum depositor, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

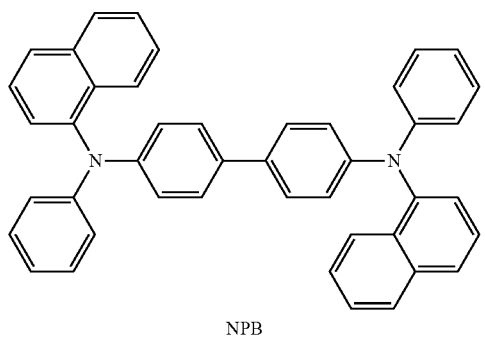

NPB

After forming the hole injection layer and the hole transfer layer as above, a blue light emitting material having a structure as below was deposited thereon as a light emitting layer. Specifically, in one side cell in the vacuum depositor, H1, a blue light emitting host material, was vacuum deposited to a thickness of 200 Å, and D1, a blue light emitting dopant material, was vacuum deposited thereon to 5% with respect to the host material.

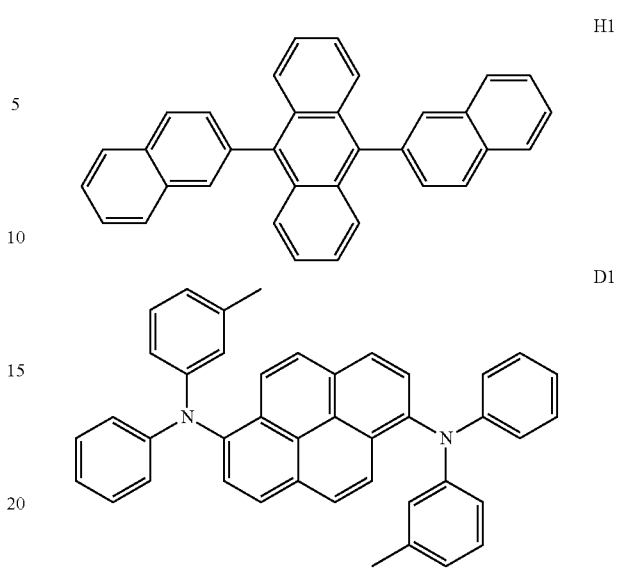

Subsequently, a compound of the following structural formula E1 was deposited to a thickness of 300 Å as an electron transfer layer.

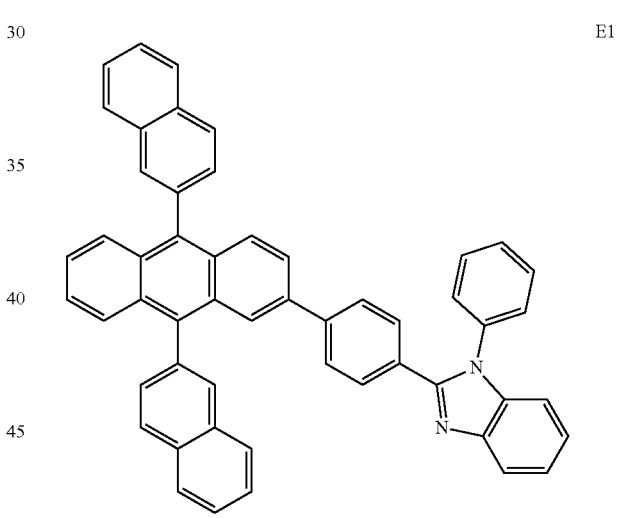

As an electron injection layer, lithium fluoride (LiF) was deposited to a thickness of 10 Å, and an Al cathode was employed to have a thickness of 1,000 Å to manufacture an OLED. Meanwhile, all the organic compounds required to manufacture the OLED were vacuum sublimation purified under $10^{-6}$ torr to $10^{-8}$ torr by each material to be used in the OLED manufacture.

An electroluminescent device was manufactured in the same manner as in Experimental Example 2 except that, after forming the electron transfer layer E1 to a thickness of 250 Å, a hole blocking layer was formed on the electron transfer layer to a thickness of 50 Å using a compound presented in the following Table 6. Results of measuring a driving voltage, light emission efficiency, a color coordinate (CIE) and a lifetime of the blue organic light emitting device manufactured according to the present disclosure are as shown in the following Table 6.

TABLE 6

| Compound | Driving Voltage (V) | Light Emission Efficiency (cd/A) | CIE (x, y) | Lifetime (T95) |
|---|---|---|---|---|
| Example 34 | 3 | 5.67 | 5.94 | (0.134, 0.100) | 31 |
| Example 35 | 5 | 5.65 | 5.97 | (0.134, 0.101) | 32 |
| Example 36 | 9 | 4.54 | 6.81 | (0.134, 0.100) | 54 |
| Example 37 | 13 | 4.53 | 6.88 | (0.134, 0.101) | 64 |
| Example 38 | 17 | 4.58 | 6.91 | (0.134, 0.101) | 57 |
| Example 39 | 37 | 4.51 | 6.95 | (0.134, 0.102) | 66 |
| Example 40 | 41 | 4.47 | 6.81 | (0.134, 0.102) | 51 |
| Example 41 | 45 | 4.53 | 6.83 | (0.134, 0.102) | 57 |
| Example 42 | 96 | 5.45 | 6.05 | (0.134, 0.101) | 40 |
| Example 43 | 110 | 5.42 | 6.03 | (0.134, 0.101) | 41 |
| Example 44 | 112 | 5.43 | 5.94 | (0.134, 0.101) | 42 |
| Example 45 | 115 | 5.37 | 6.08 | (0.134, 0.102) | 41 |
| Example 46 | 117 | 5.42 | 6.05 | (0.134, 0.102) | 45 |
| Example 47 | 121 | 4.54 | 6.46 | (0.134, 0.100) | 59 |
| Example 48 | 125 | 4.64 | 6.62 | (0.134, 0.101) | 55 |
| Example 49 | 129 | 4.62 | 6.53 | (0.134, 0.101) | 62 |
| Example 50 | 149 | 4.63 | 6.49 | (0.134, 0.101) | 58 |
| Example 51 | 153 | 4.73 | 6.47 | (0.134, 0.101) | 56 |
| Example 52 | 157 | 4.51 | 6.69 | (0.134, 0.100) | 61 |
| Example 53 | 208 | 5.33 | 5.86 | (0.134, 0.101) | 42 |
| Example 54 | 222 | 5.31 | 5.89 | (0.134, 0.101) | 44 |
| Example 55 | 224 | 5.43 | 5.85 | (0.134, 0.102) | 44 |
| Example 56 | 227 | 5.43 | 5.75 | (0.134, 0.100) | 41 |
| Example 57 | 233 | 5.31 | 5.95 | (0.134, 0.102) | 43 |
| Example 58 | 239 | 5.54 | 5.82 | (0.134, 0.101) | 45 |
| Example 59 | 245 | 5.51 | 5.93 | (0.134, 0.101) | 45 |
| Example 60 | 273 | 5.01 | 6.31 | (0.134, 0.101) | 56 |
| Example 61 | 274 | 5.00 | 6.30 | (0.134, 0.101) | 57 |
| Example 62 | 285 | 4.99 | 6.33 | (0.134, 0.101) | 55 |
| Example 63 | 286 | 4.97 | 6.30 | (0.134, 0.102) | 58 |
| Example 64 | 293 | 4.95 | 6.32 | (0.134, 0.102) | 56 |
| Example 65 | 294 | 4.97 | 6.34 | (0.134, 0.101) | 54 |
| Comparative Example 3-4 | E2 | 5.55 | 6.06 | (0.134, 0.101) | 44 |
| Comparative Example 3-5 | E3 | 5.52 | 6.13 | (0.134, 0.101) | 41 |
| Comparative Example 3-6 | E4 | 5.54 | 5.94 | (0.134, 0.101) | 40 |

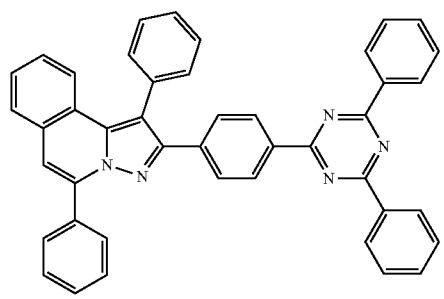

E2

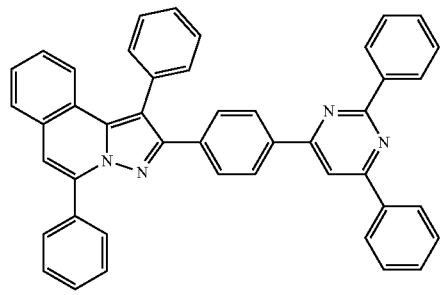

E3

E4

As seen from the results of Table 6, the organic light emitting device using the hole blocking layer material of the blue organic light emitting device of the present disclosure had a lower driving voltage, and significantly improved light emission efficiency and lifetime compared to Comparative Examples 3-4, 3-5 and 3-6. Such a reason is due to the fact that a bipolar type having both a p-type and an n-type blocks hole leakage and effectively traps excitons in the light emitting layer.

Experimental Example 3

(1) Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for ITO work function and remaining film removal, and the substrate was transferred to a thermal deposition apparatus for organic deposition.

On the transparent ITO electrode (anode), an organic material was formed in a 2 stack white organic light emitting device (WOLED) structure. As for the first stack, TAPC was thermal vacuum deposited to a thickness of 300 Å first to form a hole transfer layer. After forming the hole transfer layer, a light emitting layer was thermal vacuum deposited thereon as follows. The light emitting layer was deposited to 300 Å by doping FIrpic to TCz1, a host, by 8% as a blue phosphorescent dopant. After forming an electron transfer layer to 400 Å using TmPyPB, a charge generation layer was formed to 100 Å by doping $Cs_2CO_3$ to the compound described in the following Table 7 by 20%.

As for the second stack, $MoO_3$ was thermal vacuum deposited to a thickness of 50 Å first to form a hole injection layer. A hole transfer layer, a common layer, was formed by doping $MoO_3$ to TAPC by 20% to 100 Å and depositing TAPC to 300 Å. A light emitting layer was deposited thereon to 300 Å by doping $Ir(ppy)_3$, a green phosphorescent dopant, to TCz1, a host, by 8%, and an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic light emitting device.

Meanwhile, all the organic compounds required to manufacture the OLED were vacuum sublimation purified under $10^{-6}$ torr to $10^{-8}$ torr by each material to be used in the OLED manufacture.

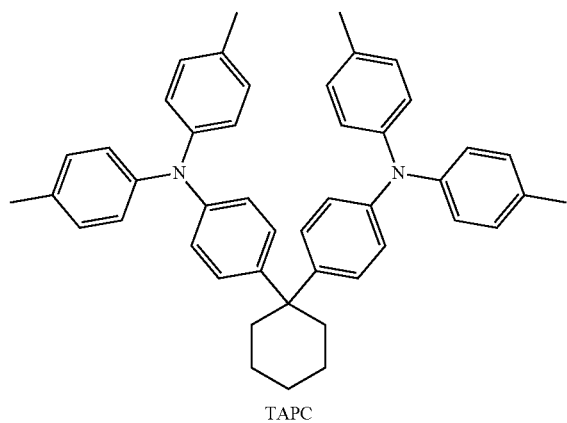

TAPC

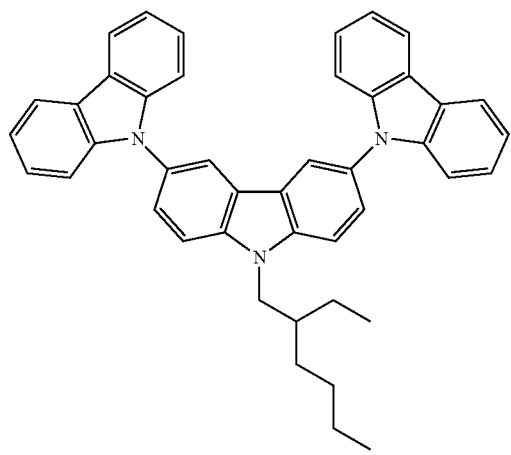

TCz1

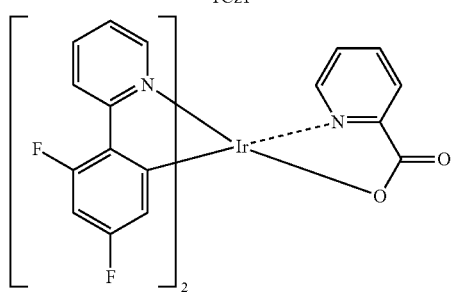

FIrpic

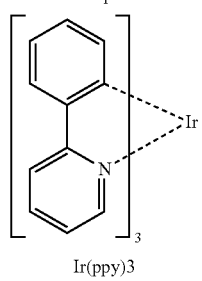

Ir(ppy)3

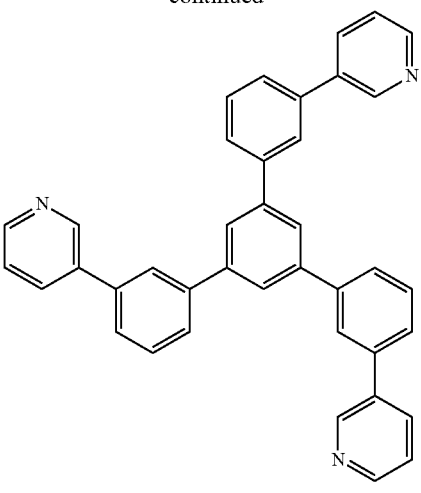

TmPyPB

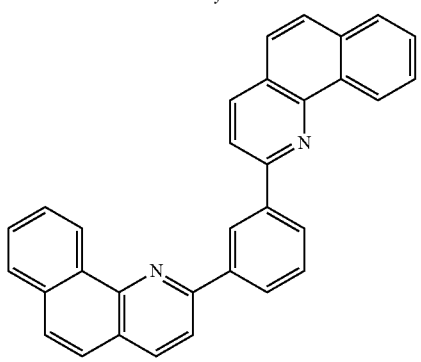

BBQB

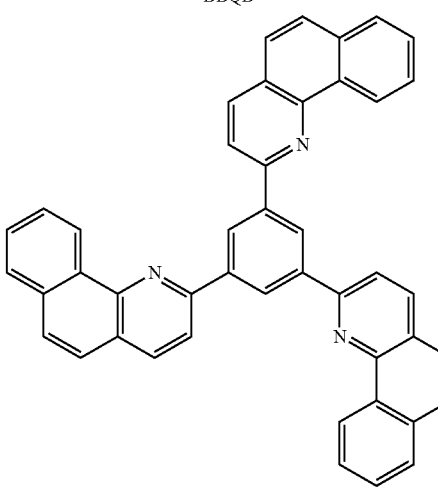

TBQB

2) Driving Voltage and Light Emission Efficiency of Organic Light Emitting Device For the organic light emitting devices manufactured as above, electroluminescent light emission (EL) properties were measured using M7000 manufactured by McScience Inc., and with the measurement results, $T_{95}$ when standard luminance was 3,500 cd/m² was measured using a lifetime measurement system (M6000) manufactured by McScience Inc. Results of measuring a driving voltage, light emission efficiency, external quantum efficiency and a color coordinate (CIE) of the white organic light emitting device manufactured according to the present disclosure are as shown in Table 7.

TABLE 7

| Com- pound | Driving Voltage (V) | Light Emission Efficiency (cd/A) | CIE (x, y) | Life- time (T95) |
|---|---|---|---|---|
| Example 66 | 1 | 7.22 | 69.21 | (0.222, 0.423) | 45 |
| Example 67 | 2 | 7.02 | 69.82 | (0.221, 0.422) | 46 |
| Example 68 | 3 | 7.00 | 69.45 | (0.219, 0.420) | 48 |
| Example 69 | 4 | 6.92 | 70.25 | (0.218, 0.419) | 50 |
| Example 70 | 5 | 7.24 | 68.45 | (0.221, 0.420) | 44 |
| Example 71 | 6 | 7.27 | 67.88 | (0.210, 0.422) | 45 |
| Example 72 | 7 | 7.16 | 66.23 | (0.215, 0.421) | 42 |
| Example 73 | 8 | 7.18 | 67.89 | (0.221, 0.423) | 43 |
| Example 74 | 9 | 7.75 | 60.77 | (0.212, 0.421) | 38 |
| Example 75 | 37 | 7.78 | 60.70 | (0.218, 0.420) | 35 |
| Example 76 | 111 | 7.66 | 59.22 | (0.211, 0.428) | 30 |
| Example 77 | 112 | 7.64 | 59.50 | (0.220, 0.425) | 31 |
| Example 78 | 113 | 7.14 | 68.84 | (0.219, 0.420) | 34 |
| Example 79 | 114 | 7.02 | 69.08 | (0.212, 0.429) | 40 |
| Example 80 | 115 | 6.95 | 71.00 | (0.213, 0.421) | 49 |
| Example 81 | 116 | 6.90 | 70.75 | (0.220, 0.423) | 51 |
| Example 82 | 117 | 7.09 | 68.68 | (0.219, 0.421) | 45 |
| Example 83 | 118 | 7.10 | 67.17 | (0.210, 0.422) | 45 |
| Example 84 | 119 | 7.20 | 67.58 | (0.211, 0.425) | 47 |
| Example 85 | 120 | 7.22 | 68.24 | (0.214, 0.420) | 43 |
| Example 86 | 121 | 7.70 | 59.22 | (0.215, 0.421) | 36 |
| Example 87 | 149 | 7.79 | 60.94 | (0.211, 0.429) | 37 |
| Example 88 | 223 | 7.76 | 60.26 | (0.212, 0.429) | 33 |
| Example 89 | 224 | 7.78 | 61.15 | (0.213, 0.429) | 39 |
| Comparative Example 3-7 | TmPyPB | 8.44 | 57.99 | (0.212, 0.429) | 29 |
| Comparative Example 3-8 | BBQB | 8.46 | 58.23 | (0.217, 0.426) | 28 |
| Comparative Example 3-9 | TBQB | 8.39 | 58.68 | (0.220, 0.428) | 26 |

As seen from the results of Table 7, the organic light emitting device using the charge generation layer material of the 2-stack white organic light emitting device of the present disclosure had a lower driving voltage and improved light emission efficiency compared to Comparative Example 1. Particularly, it was identified that Compounds 2, 3, 4, 114, 115 and 116 were significantly superior in all aspects of driving, efficiency and lifetime.

Such a result is considered to be due to the fact that the compound of the present disclosure used as the N-type charge generation layer formed with the disclosed skeleton having proper length, strength and flat properties and a proper hetero-compound capable of binding with a metal forms a gap state in the N-type charge generation layer by doping an alkali metal or an alkaline earth metal, and electrons produced from the P-type charge generation layer are readily injected to the electron transfer layer through the gap state produced in the N-type charge generation layer. Accordingly, it is considered that the P-type charge generation layer favorably injects and transfers electrons to the N-type charge generation layer, and as a result, a driving voltage was lowered, and efficiency and lifetime were improved in the organic light emitting device.

The invention claimed is:

1. A heterocyclic compound represented by the following Chemical Formula 1:

[Chemical Formula 1]

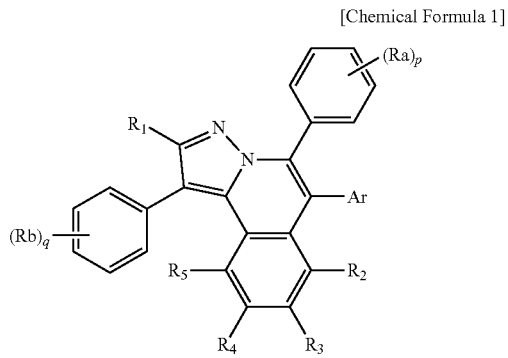

wherein, in Chemical Formula 1, $R_1$ is hydrogen; a C1 to C60 alkyl group; a C6 to C60 aryl group; a C2 to C60 heteroaryl group; P(=O)RR'; or SiRR'R";

Ar is selected from the group consisting of deuterium; a halogen group; —CN; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group;

$R_2$ to $R_5$, $R_a$ and $R_b$ are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group; or a substituted or unsubstituted heteroaryl group, or two or more groups adjacent to each other bond to each other to form a substituted or unsubstituted aliphatic or aromatic hydrocarbon ring;

wherein R, R' and R" are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group; and p and q are an integer of 0 to 5.

2. The heterocyclic compound of claim 1, wherein the "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine;

and C2 to C60 monocyclic or polycyclic heteroarylamine, or being unsubstituted, or being substituted with a substituent linking two or more substituents selected from among the substituents illustrated above, or being unsubstituted; and wherein R, R' and R" have the same definitions as in Chemical Formula 1.

3. The heterocyclic compound of claim 1, wherein Ar may be represented by -(L)m-(Z)n;

L is a direct bond; a substituted or unsubstituted arylene group; or a substituted or unsubstituted heteroarylene group;

Z is deuterium; a substituted or unsubstituted alkyl group; a halogen group; —CN; a substituted or unsubstituted alkyl group; a substituted or unsubstituted aryl group; a substituted or unsubstituted heteroaryl group; —SiRR'R"; or —P(=O)RR';

m is an integer of 0 to 4;

n is an integer of 1 to 5; and r, R' and R" have the same definitions as in Chemical Formula 1.

4. The heterocyclic compound of claim 3, wherein L is a direct bond; a substituted or unsubstituted C6 to C40 arylene group; or a substituted or unsubstituted C2 to C40 heteroarylene group;

wherein Z is a substituted or unsubstituted C6 to C40 aryl group; a substituted or unsubstituted C2 to C40 heteroaryl group; or —P(=O)RR'; and R, R' and R" have the same definitions as in claim 3.

5. The heterocyclic compound of claim 1, wherein $R_2$ to $R_5$, $R_a$ and $R_b$ are hydrogen.

6. The heterocyclic compound of claim 1, wherein $R_1$ of Chemical Formula 1 is hydrogen; or a C6 to C40 aryl group.

7. The heterocyclic compound of claim 1, wherein Chemical Formula 1 is represented by any one of the following compounds:

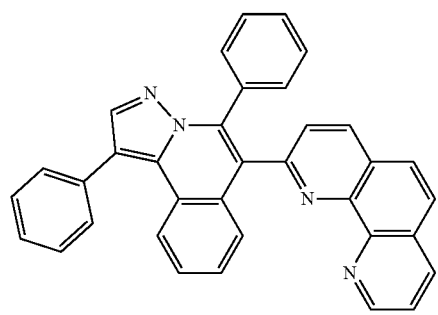

1

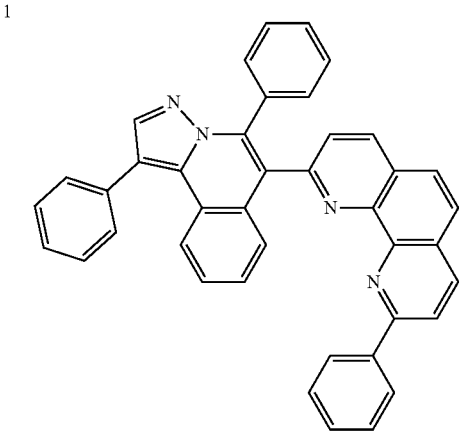

2

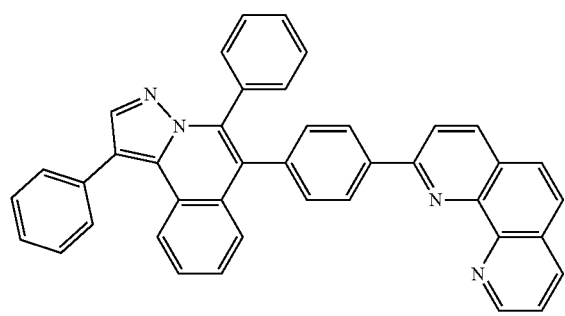

3

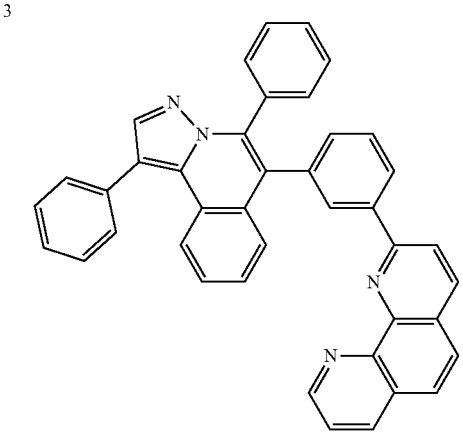

4

-continued
5
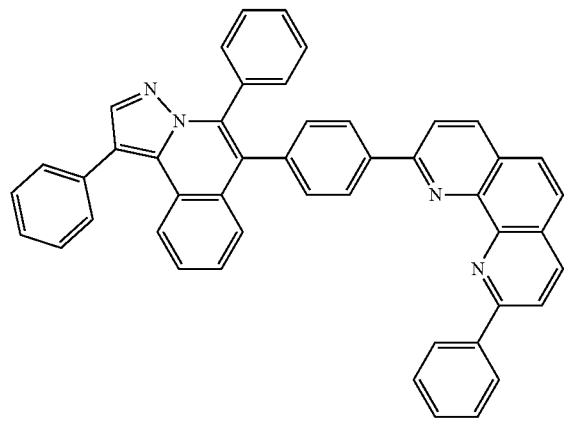
6
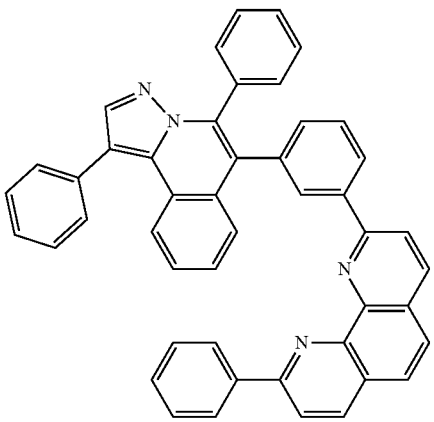
7
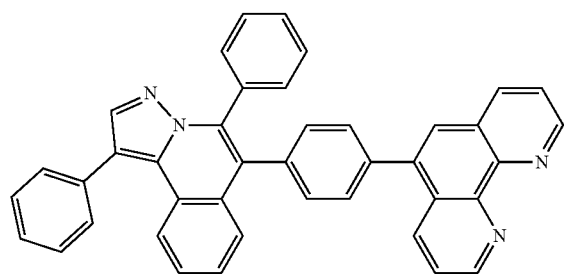
8
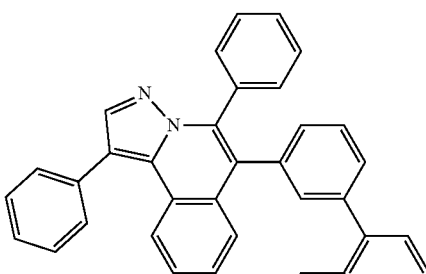
9
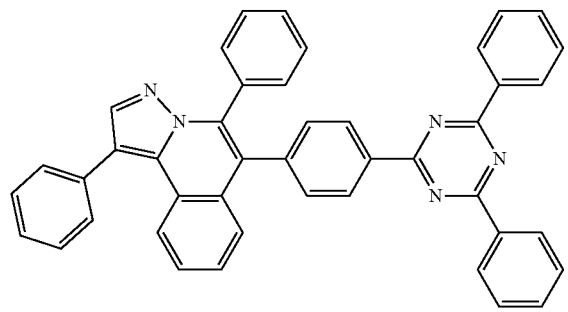
10
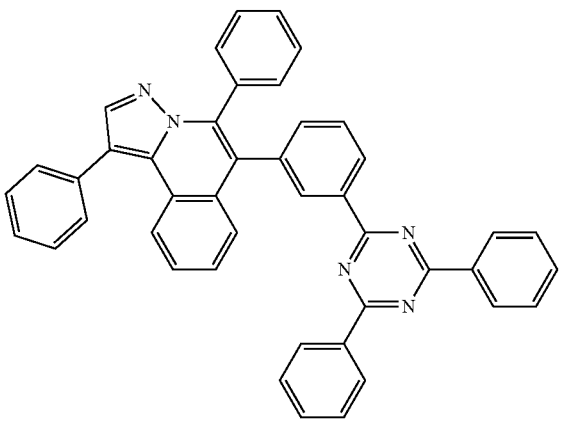
11
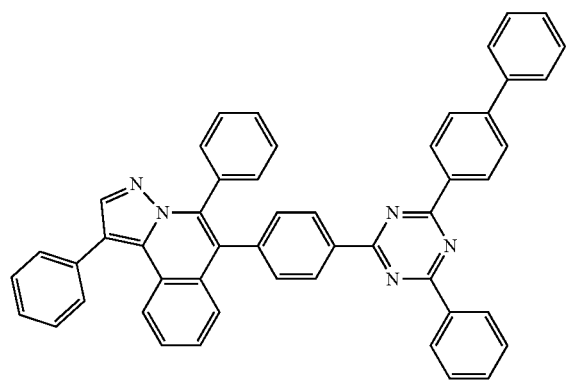
12
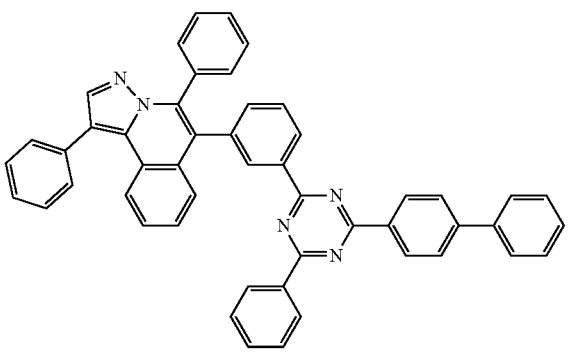

-continued
13
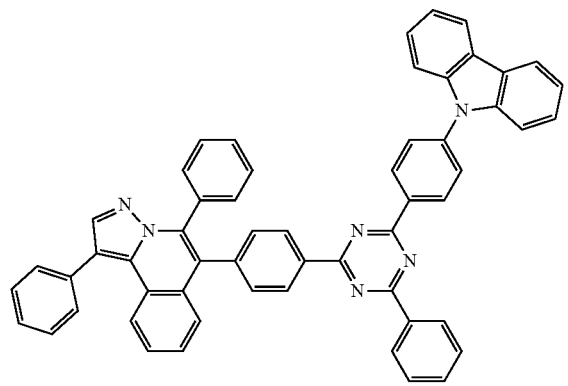
14
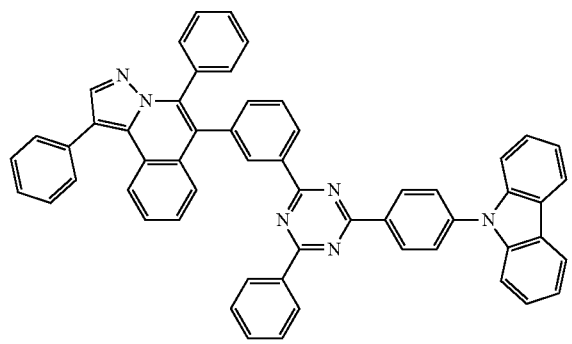
15
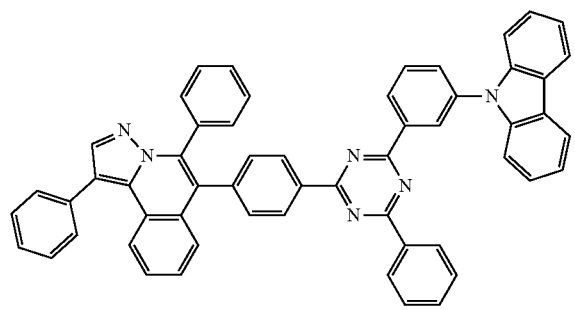
16
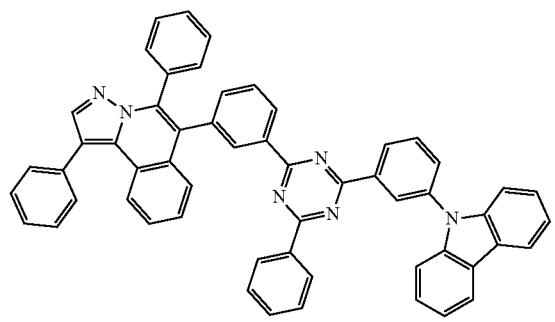
17
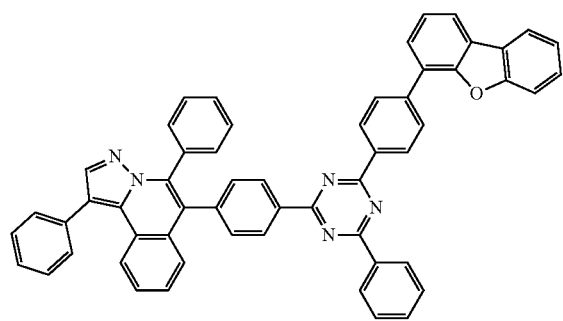
18
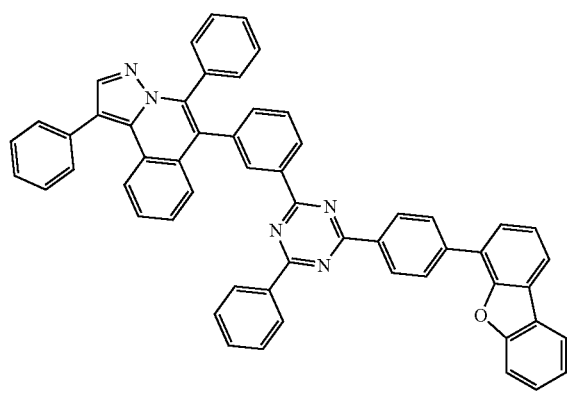
19
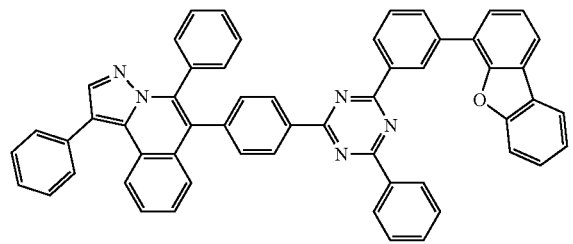
20
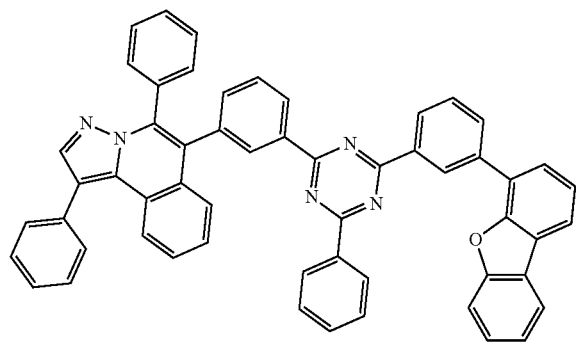

-continued
21
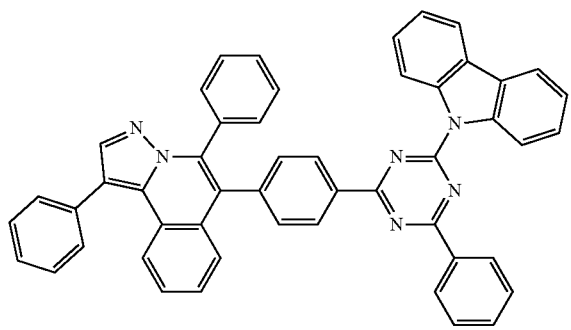
22
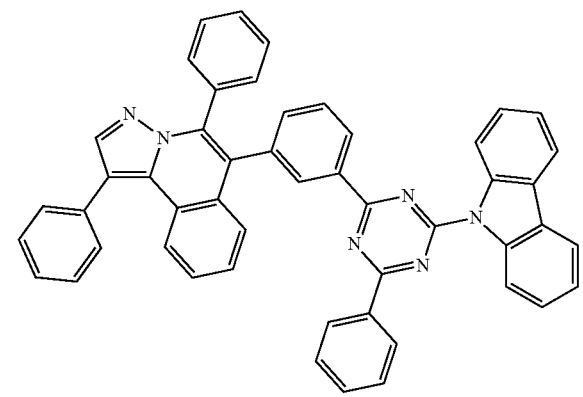
23
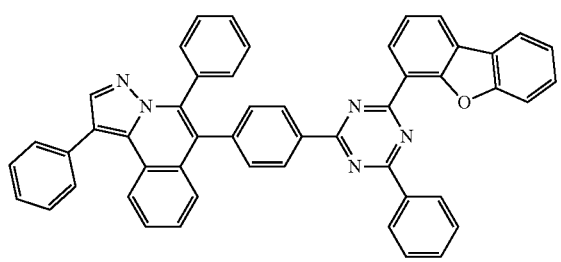
24
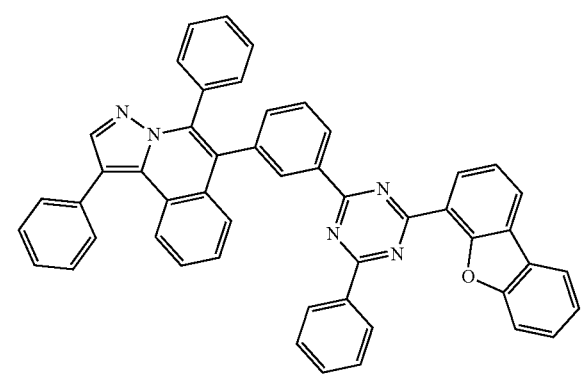
25
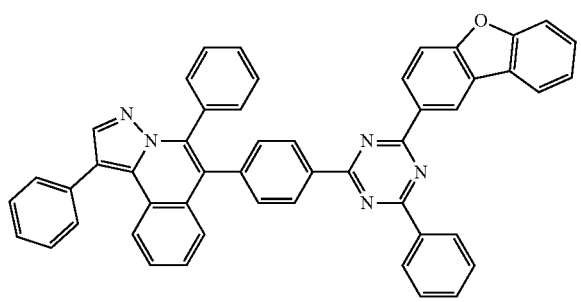
26
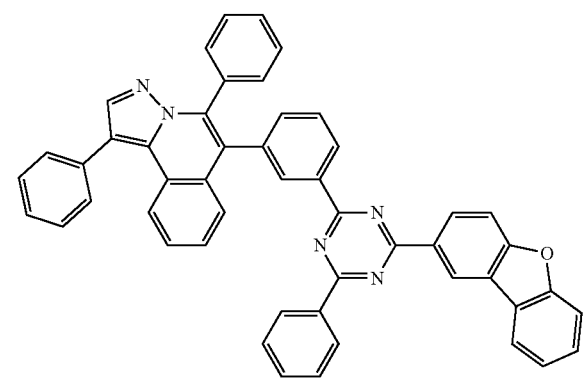
27
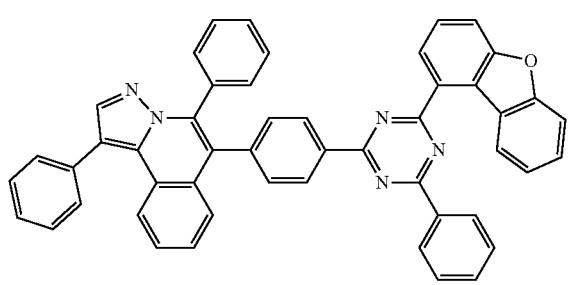
28
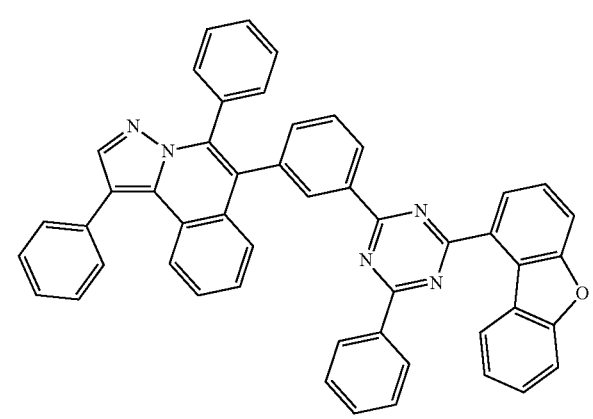

-continued
29
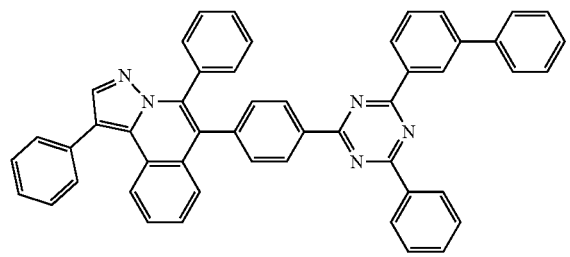
30
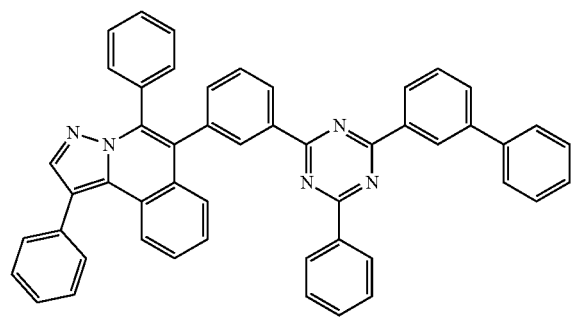
31
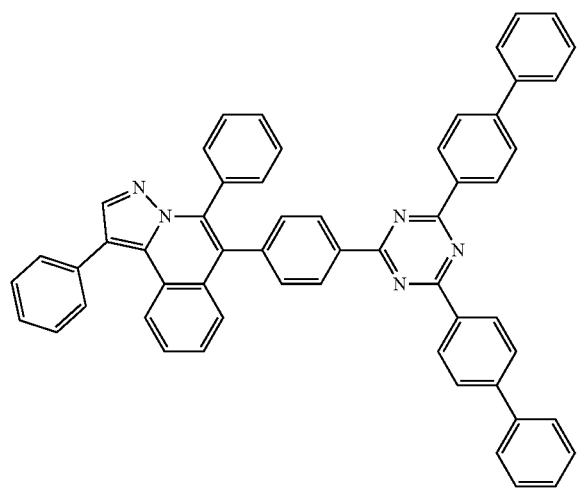
32
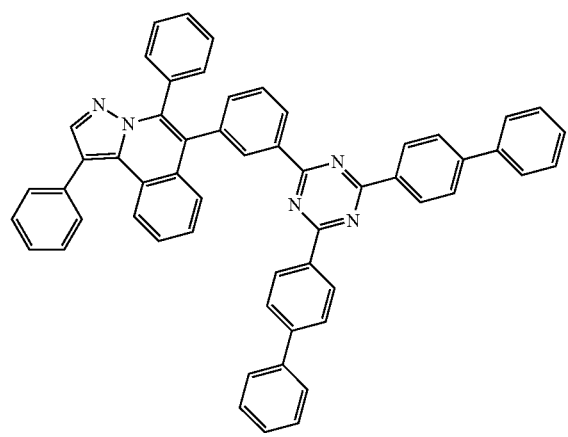
33
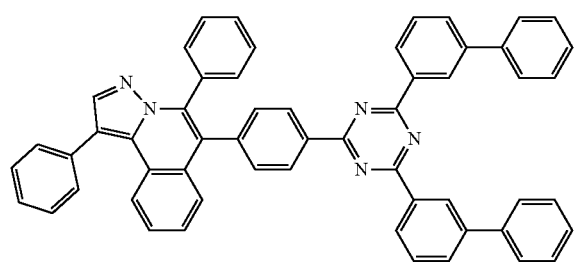
34
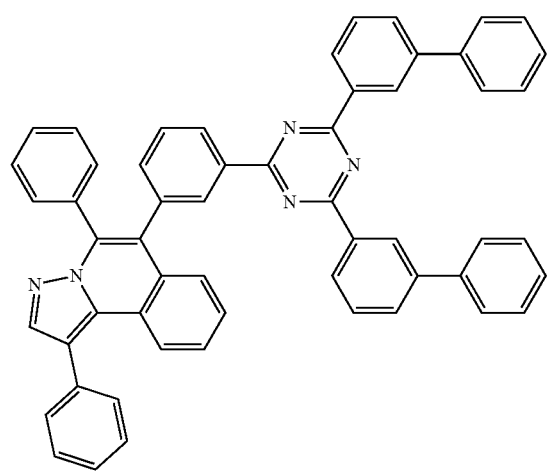

-continued
35
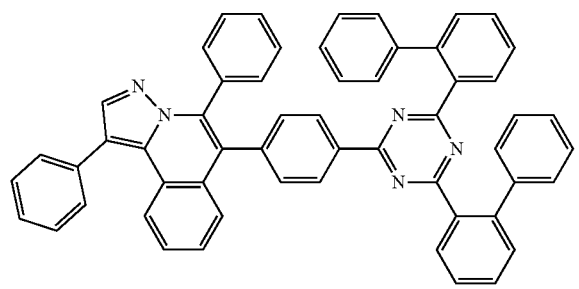
36
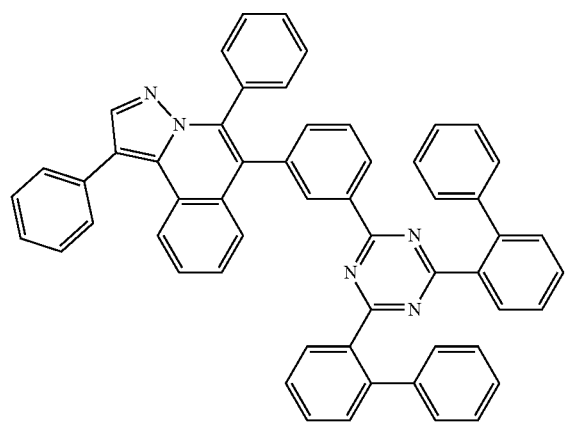
37
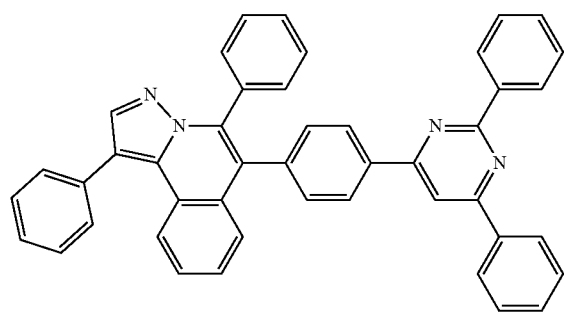
38
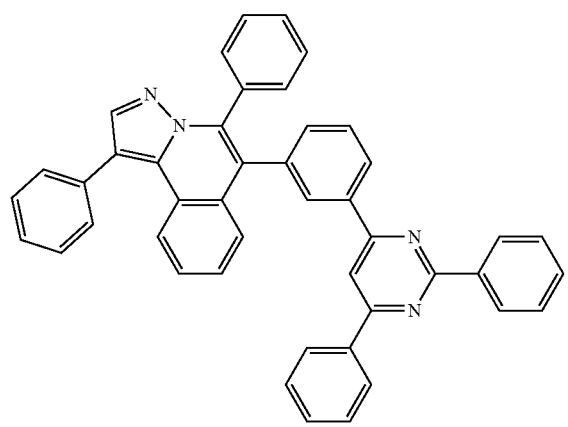
39
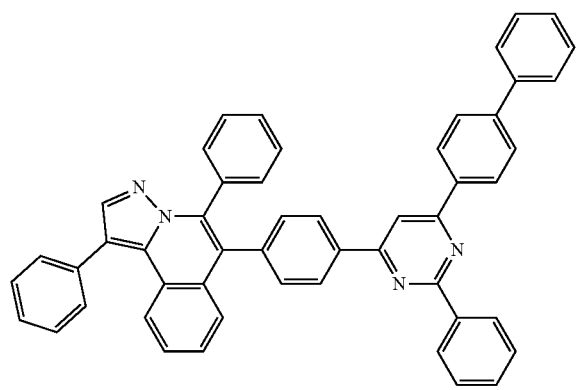
40
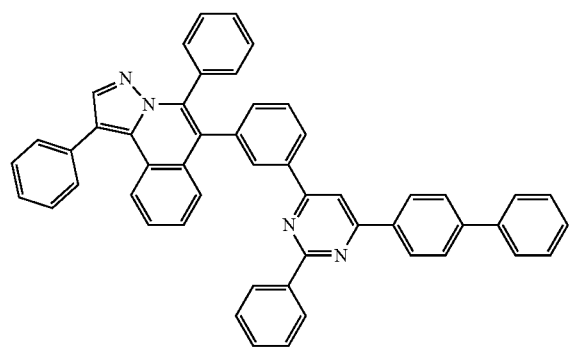

-continued
41
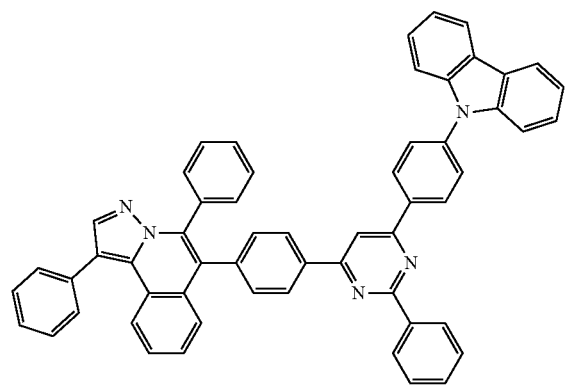
42
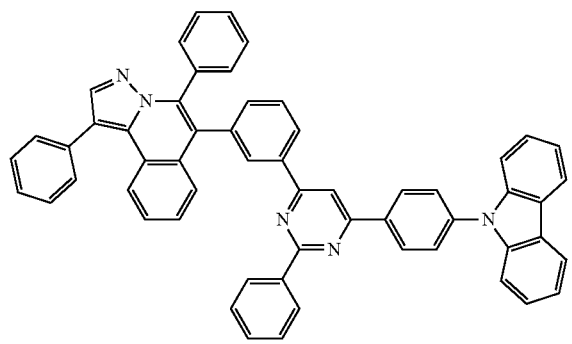
43
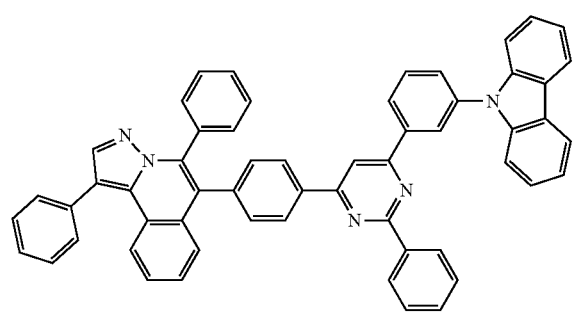
44
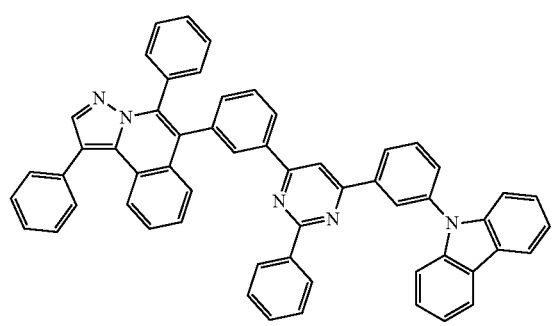
45
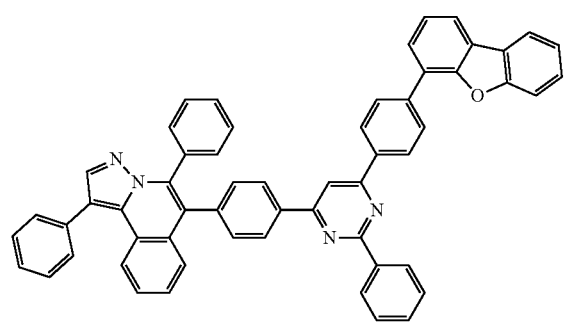
46
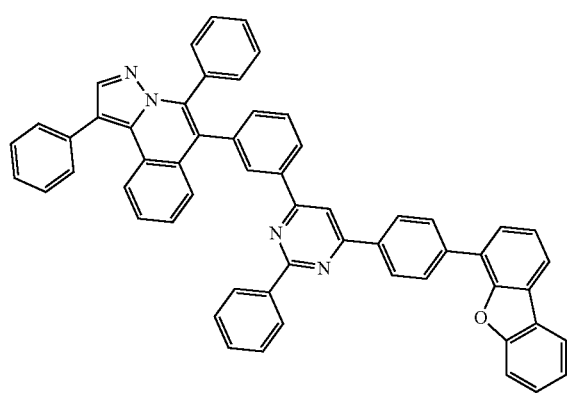
47
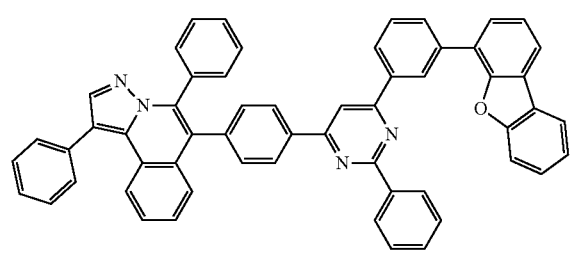
48
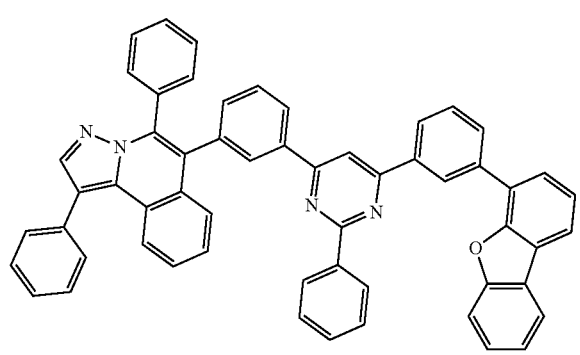

-continued
49
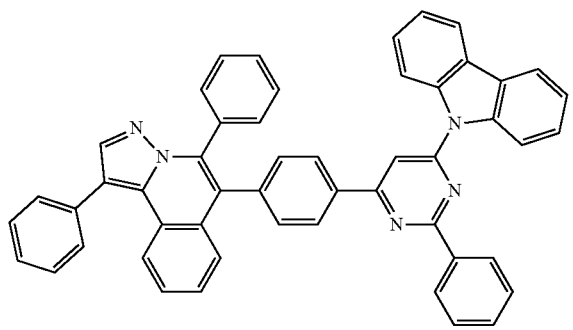
50
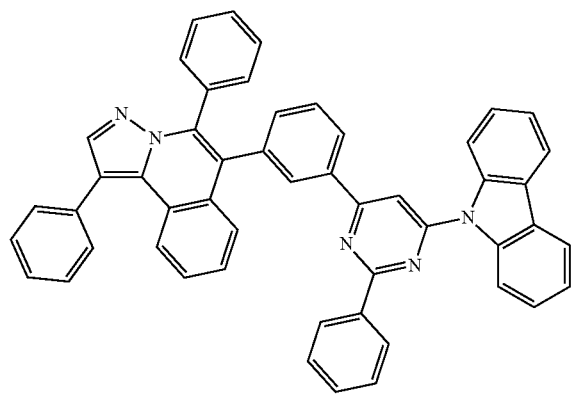
51
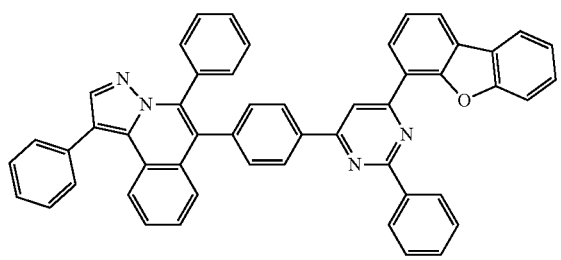
52
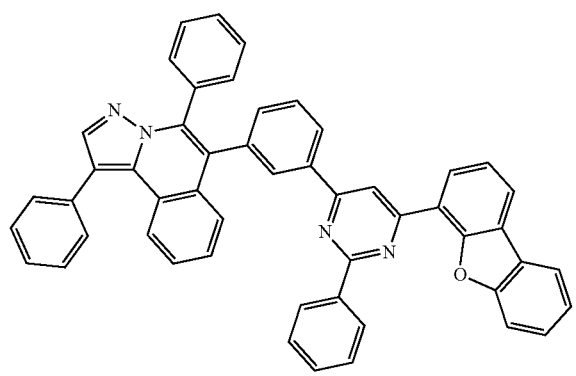
53
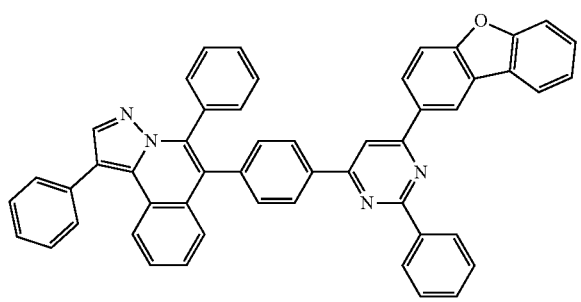
54
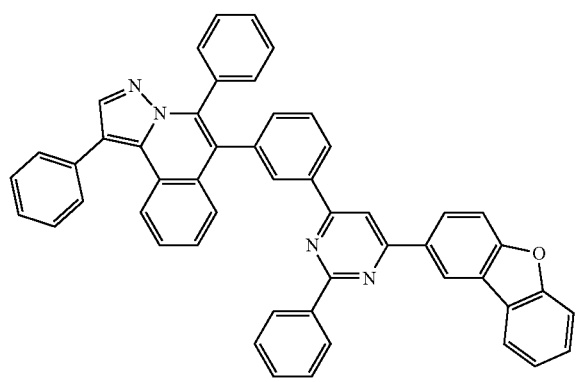
55
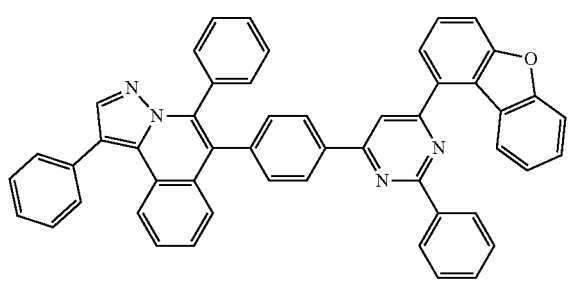
56
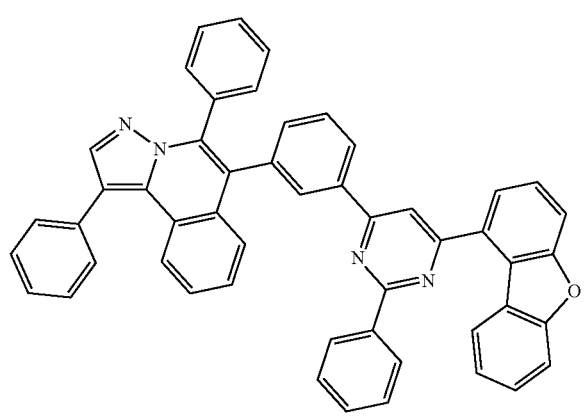

57
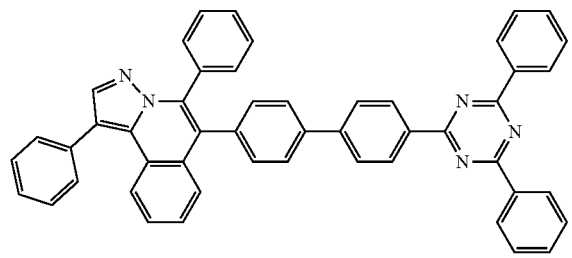
58
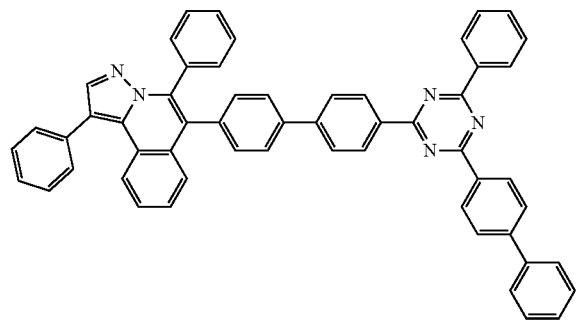
59
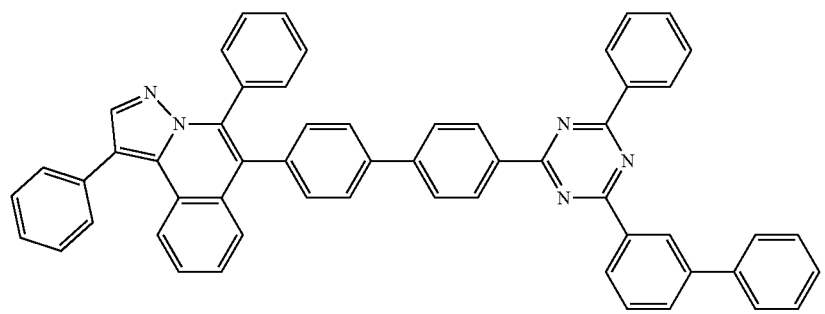
60
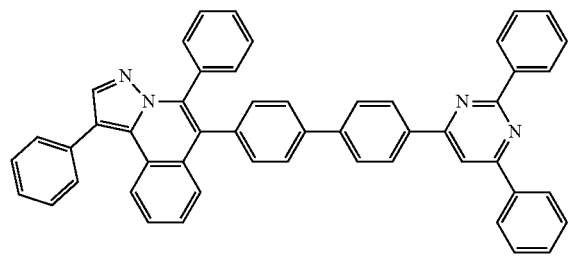
61
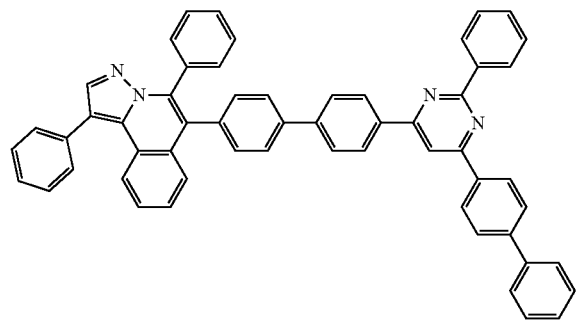
62
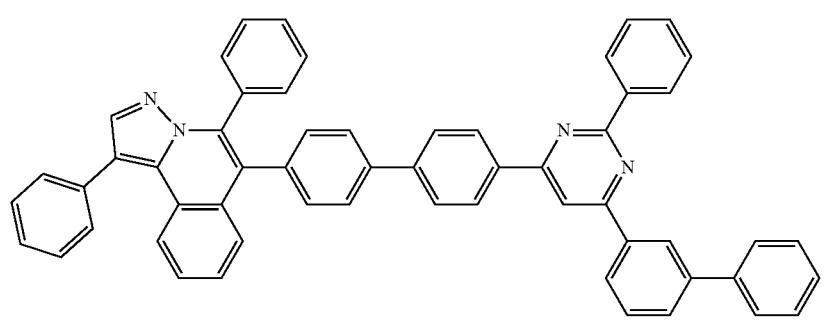
63
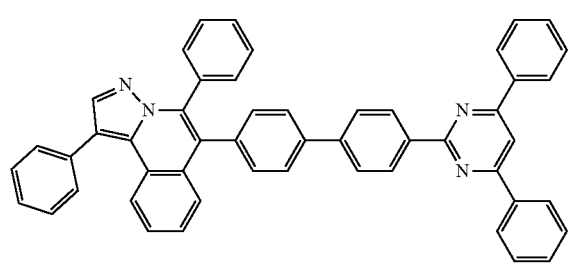
64
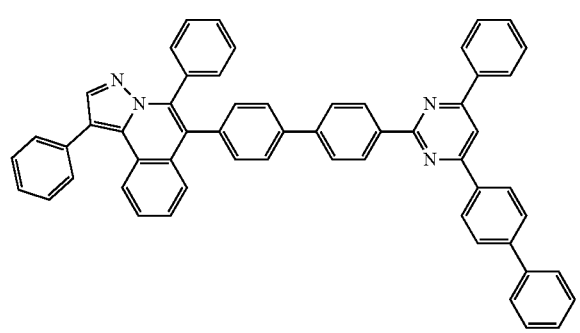

65
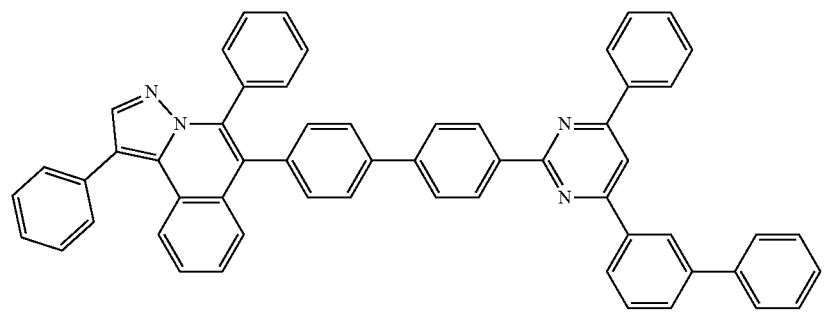
66
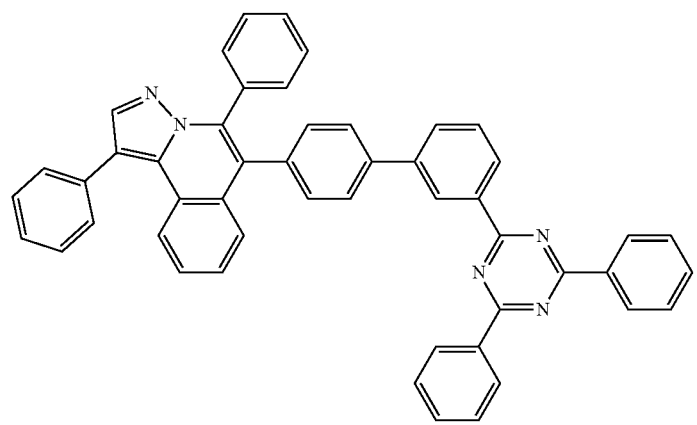
67
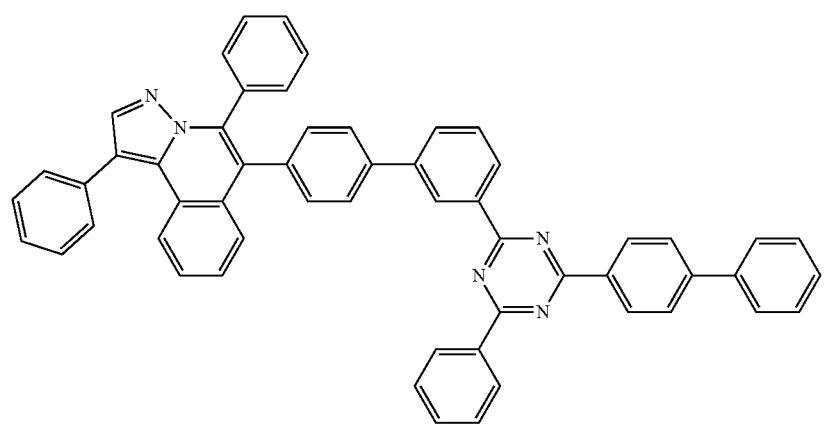
68
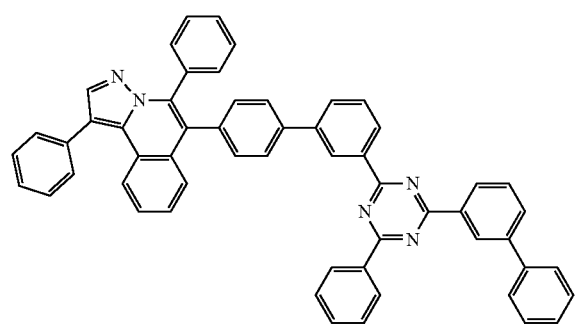
69
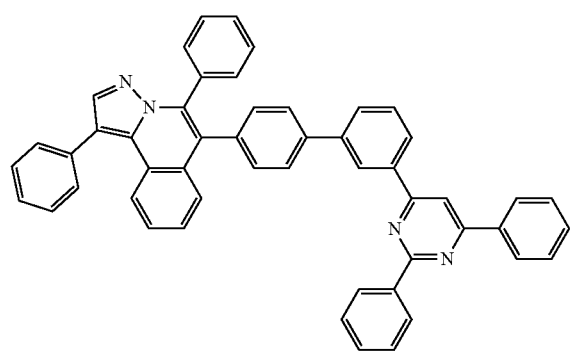

70
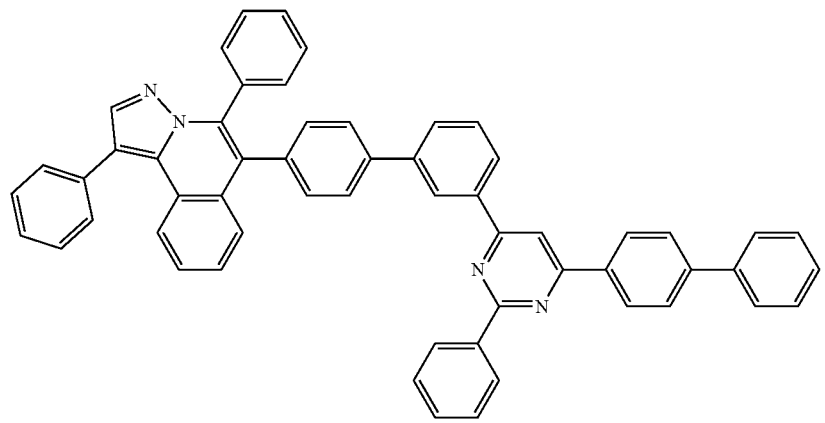
71
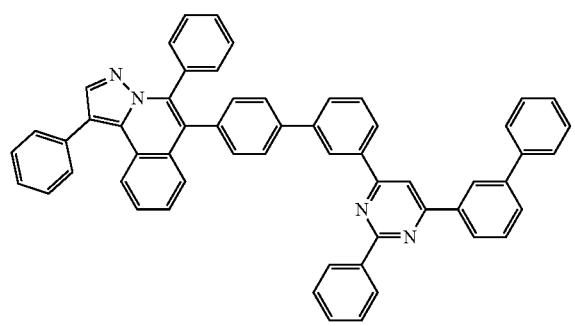
72
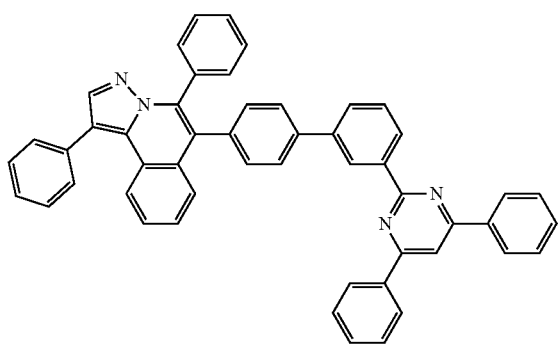
73
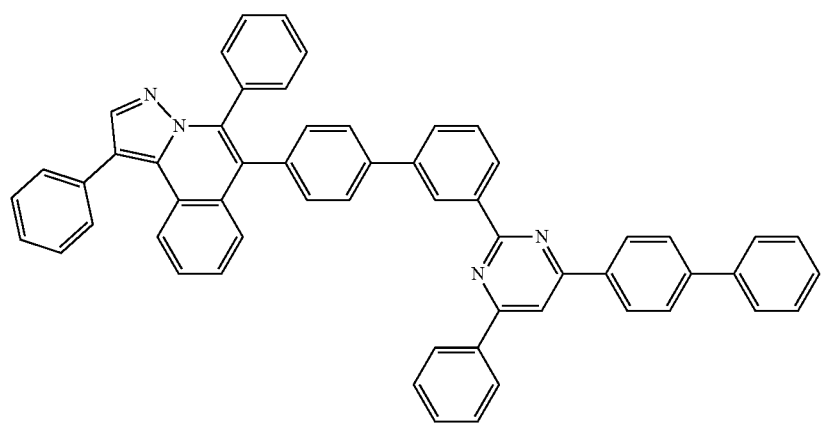
74
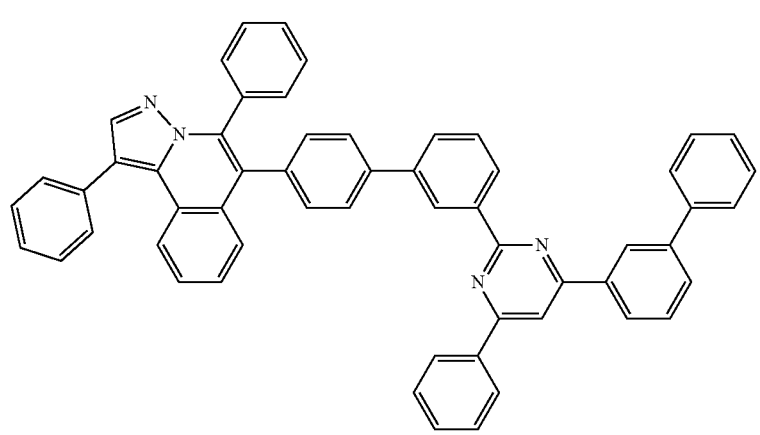

75
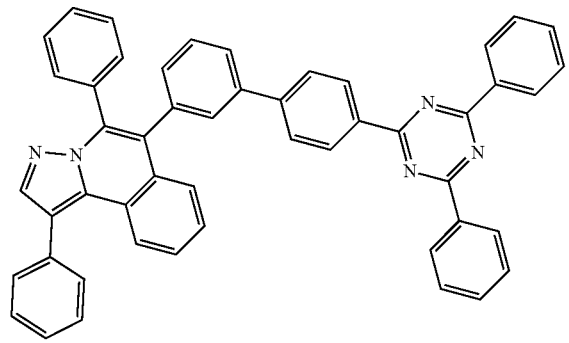
76
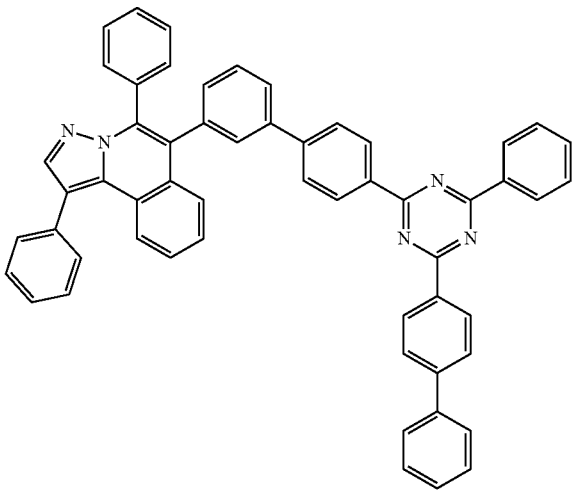
77
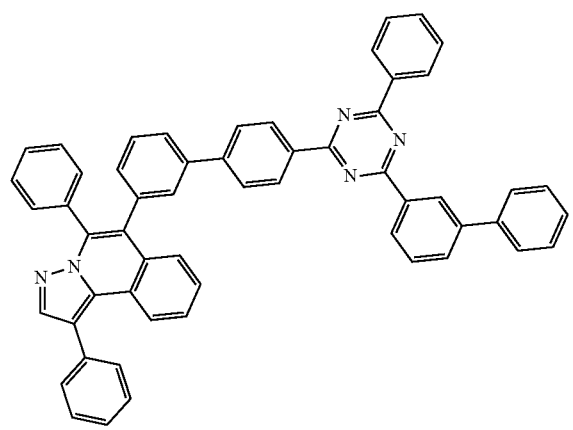
78
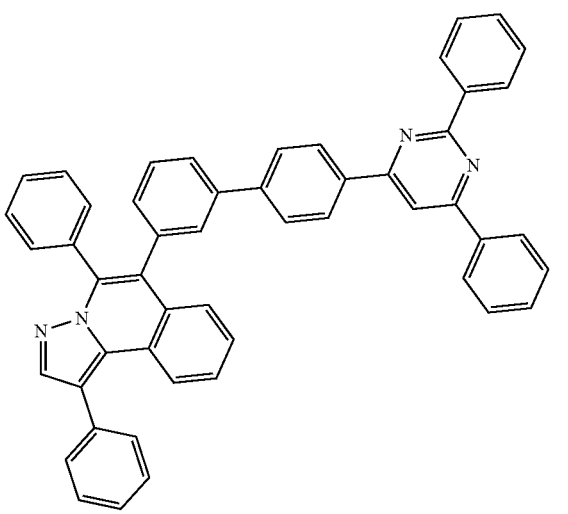
79
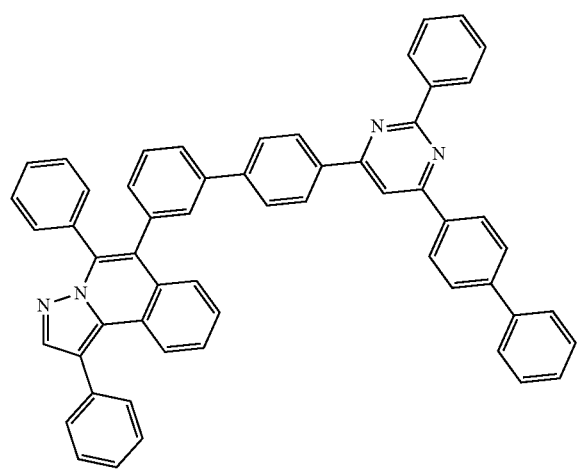
80
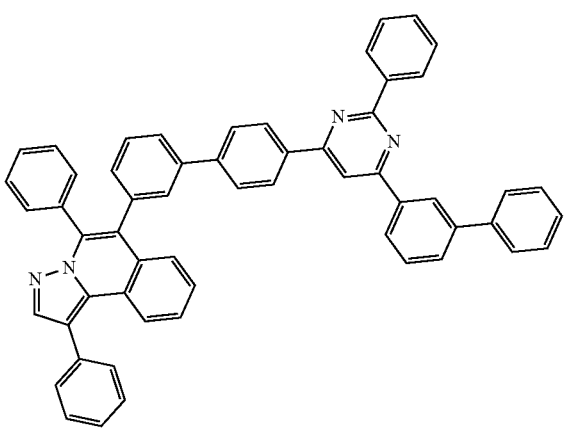

-continued
81
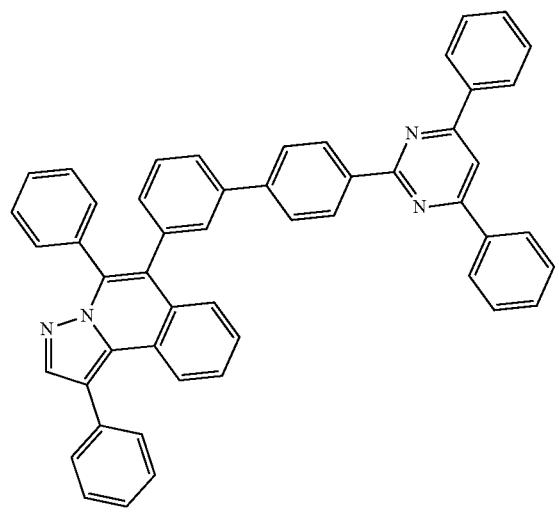
82
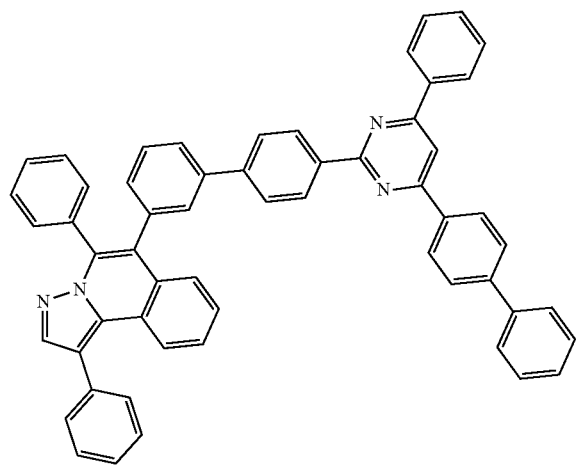
83
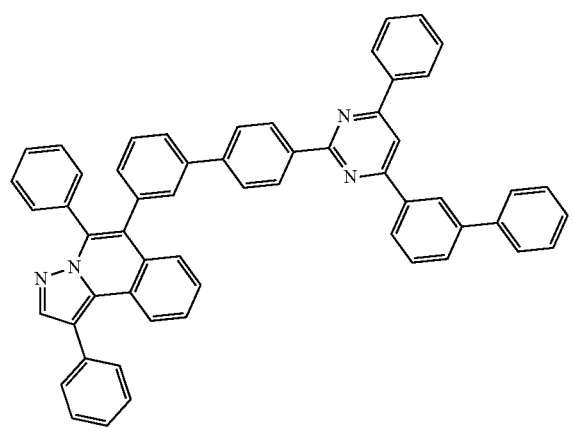
84
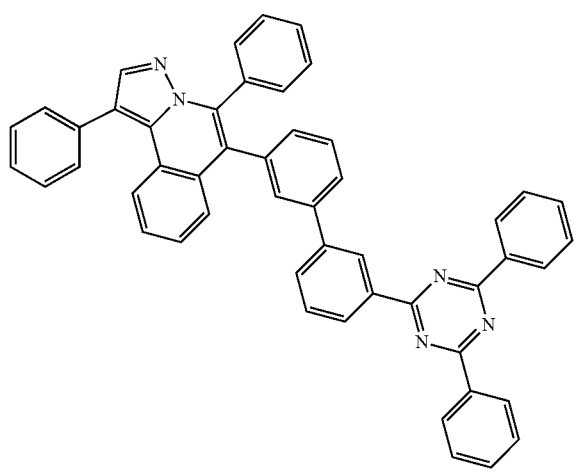
85
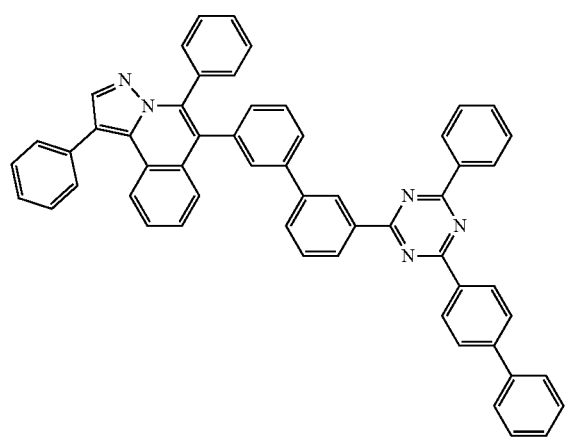
86
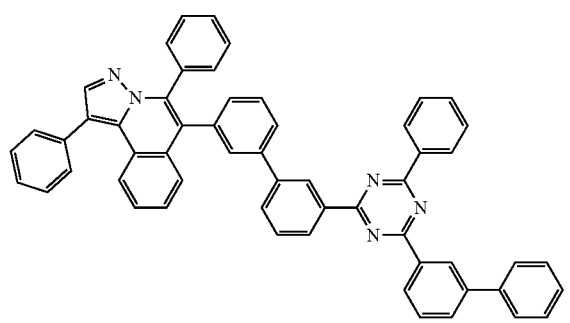

-continued
87
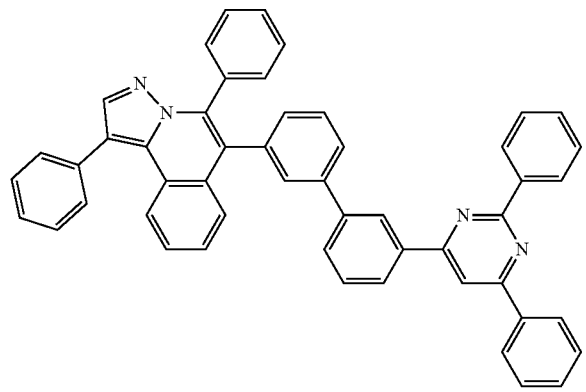
88
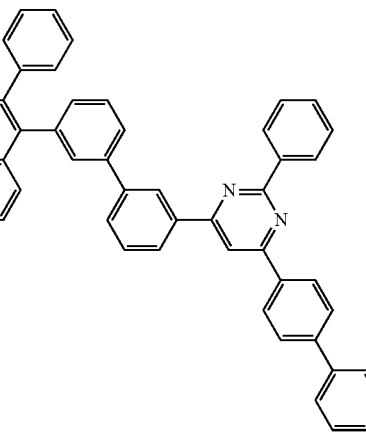
89
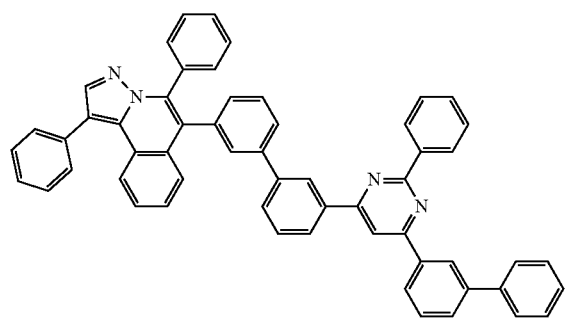
90
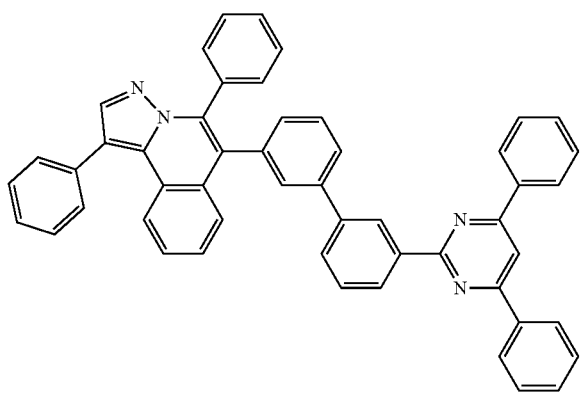
91
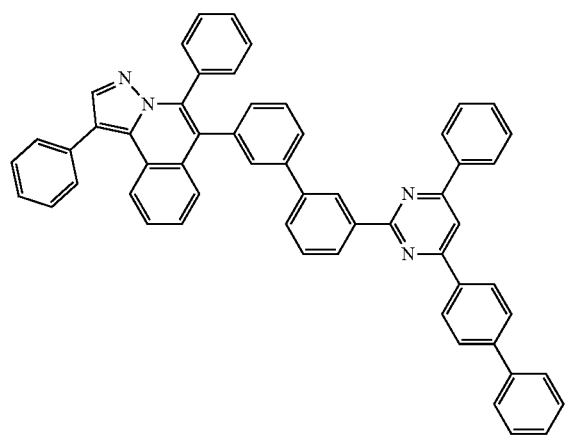
92
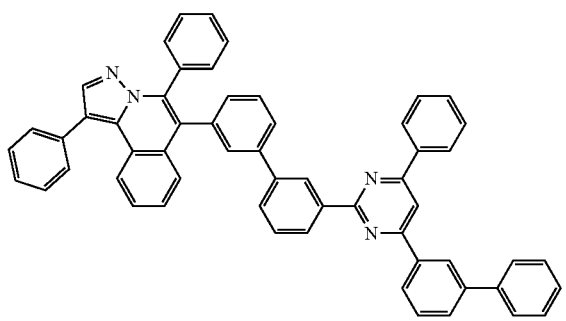
93
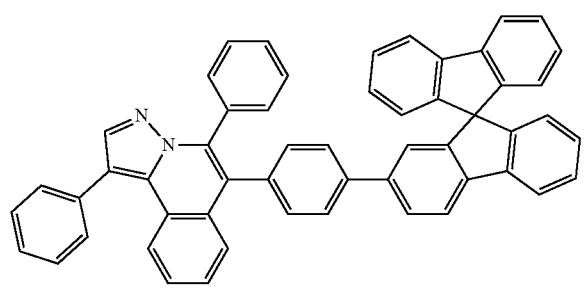
94
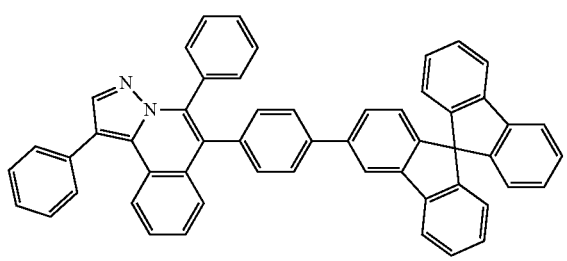

-continued
95
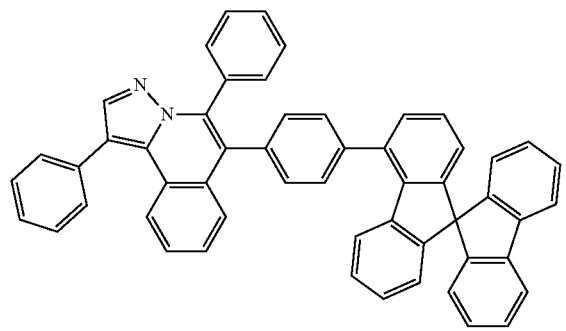
96
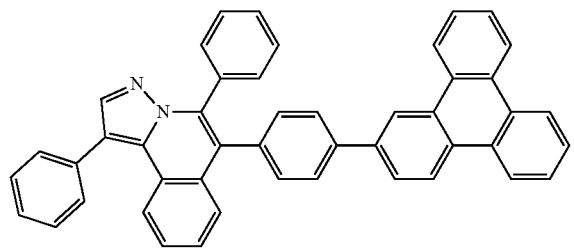
97
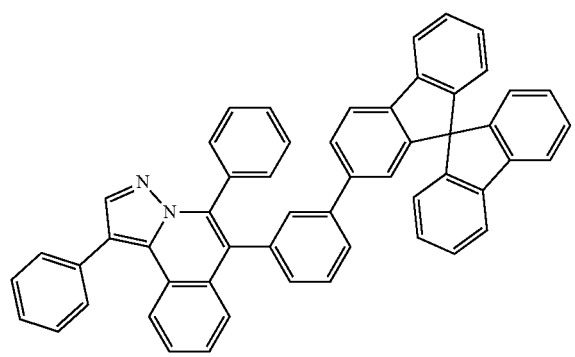
98
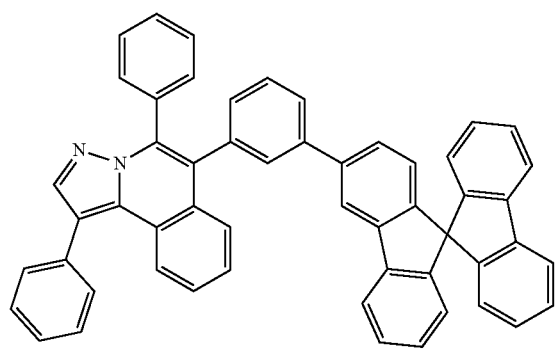
99
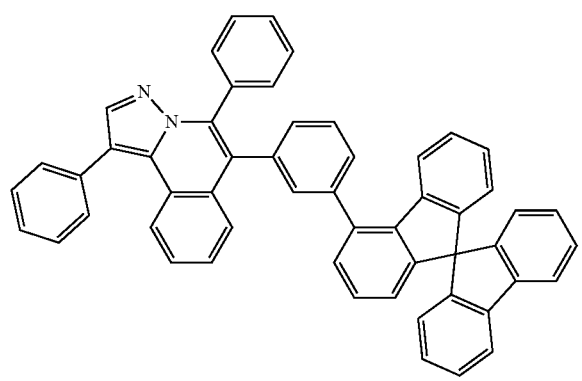
100
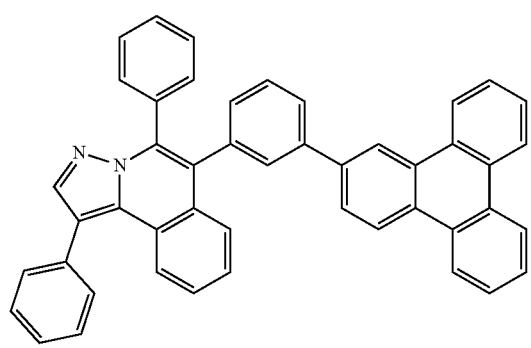
101
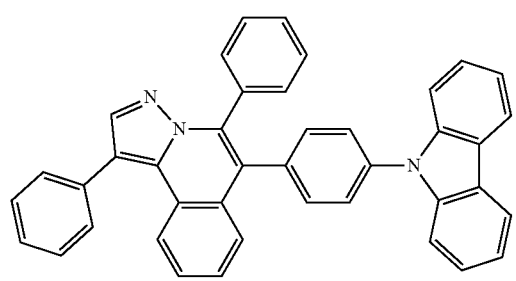
102
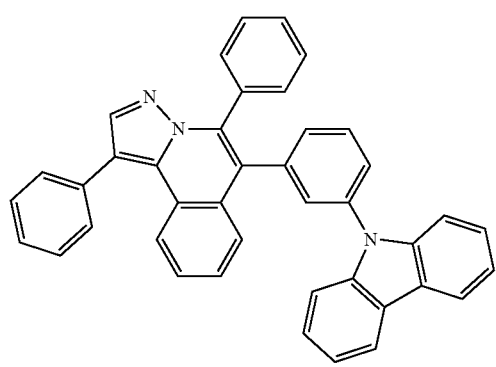

-continued
103
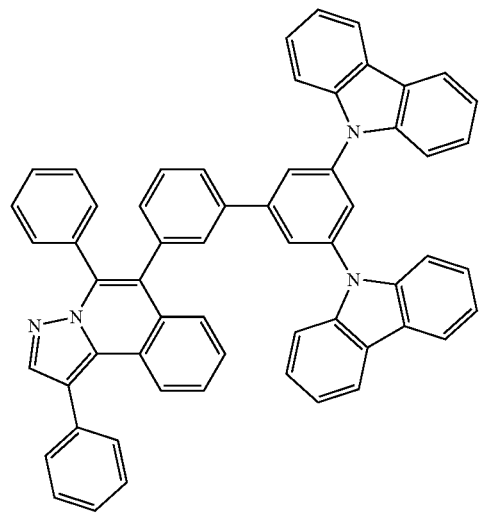
104
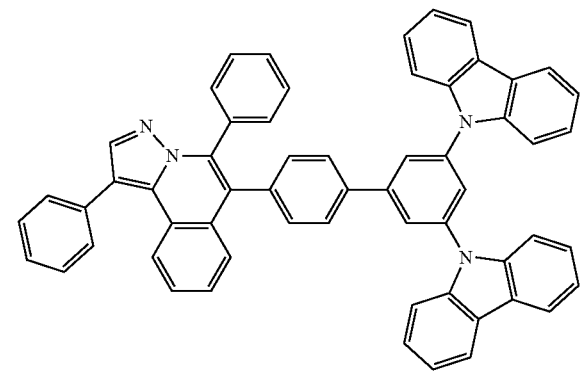
105
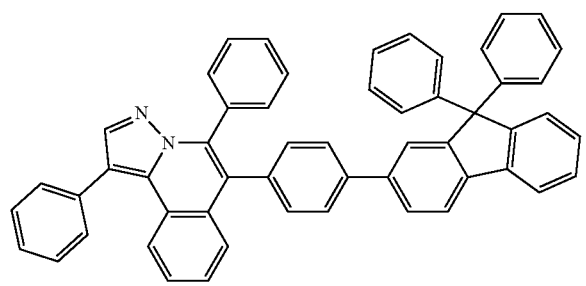
106
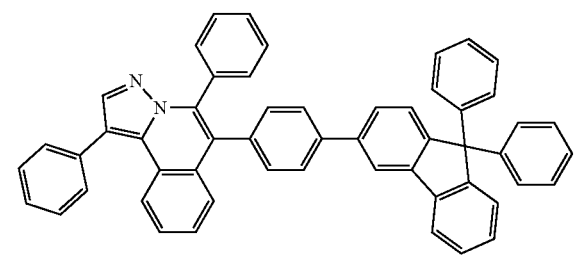
107
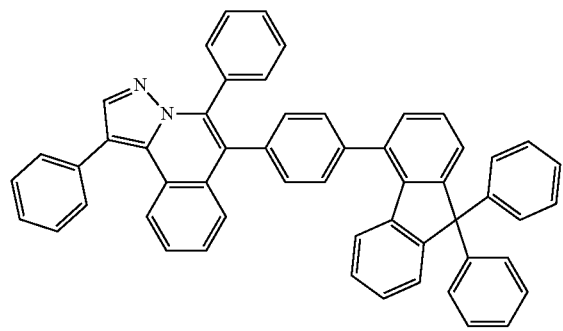
108
109
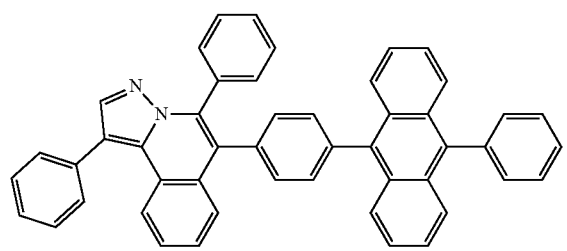
110
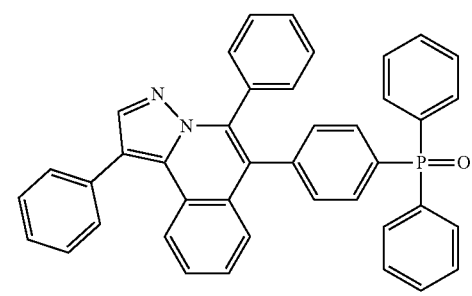

-continued
111
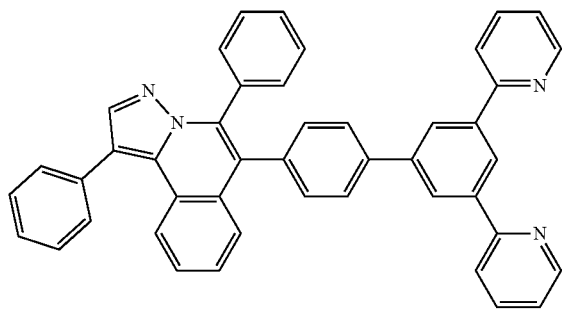
112
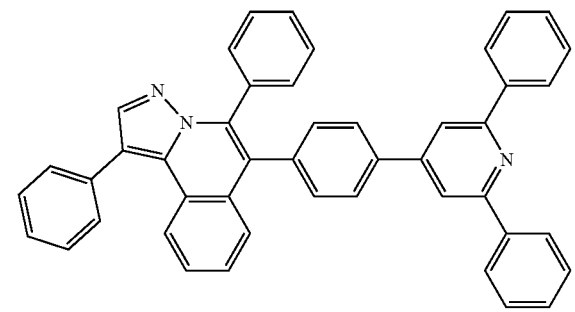
113
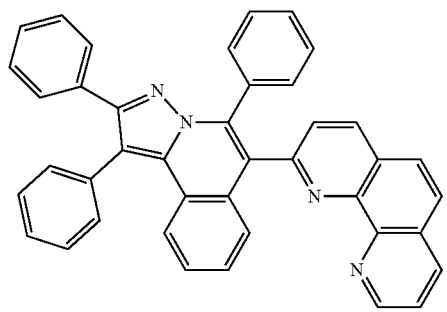
114
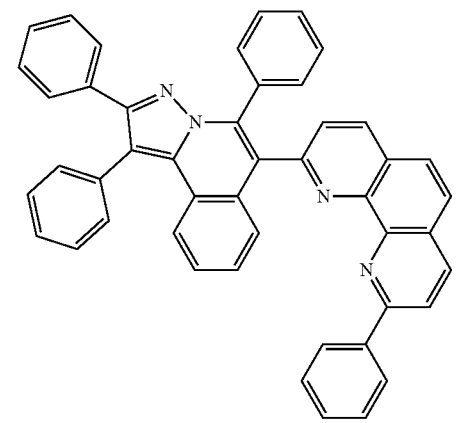
115
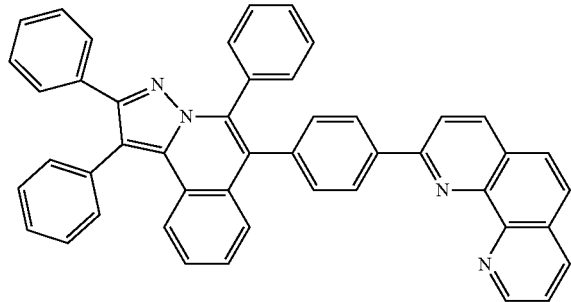
116
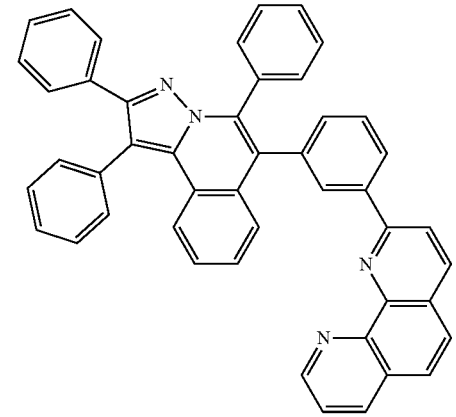
117
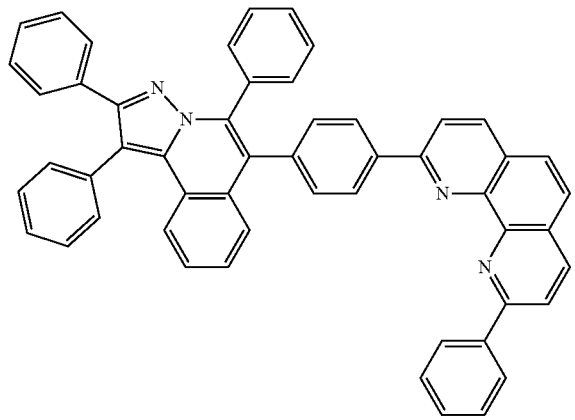
118
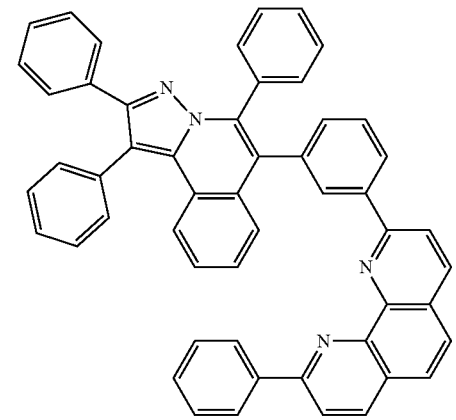

-continued
119
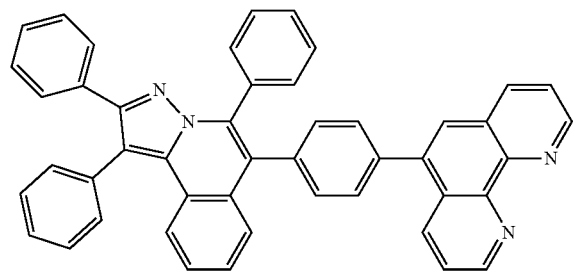
120
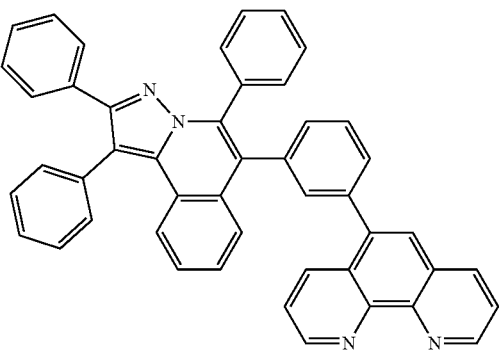
121
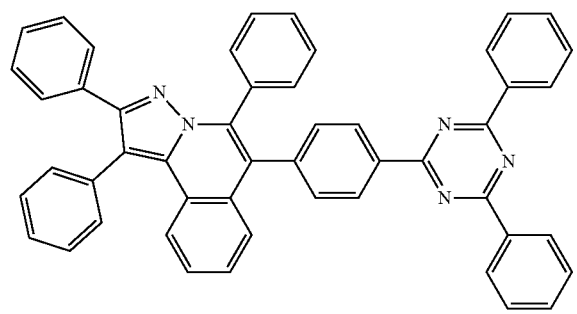
122
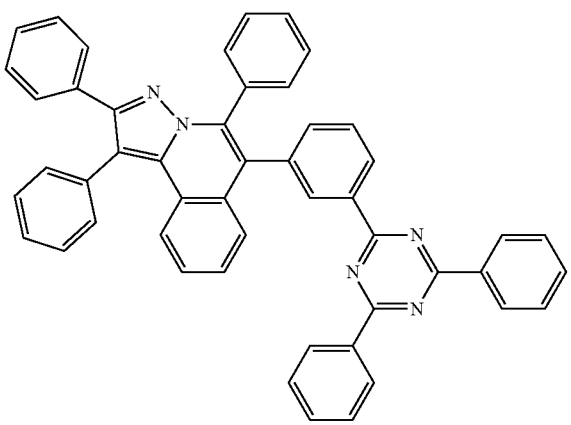
123
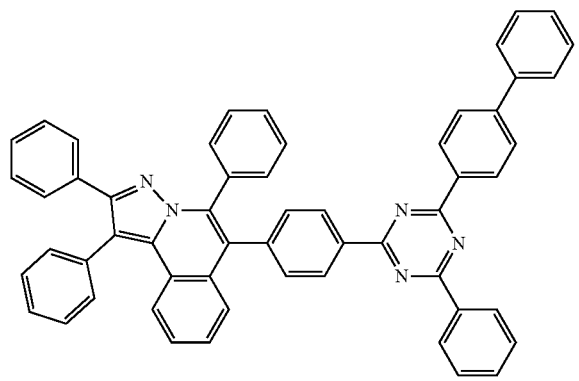
124
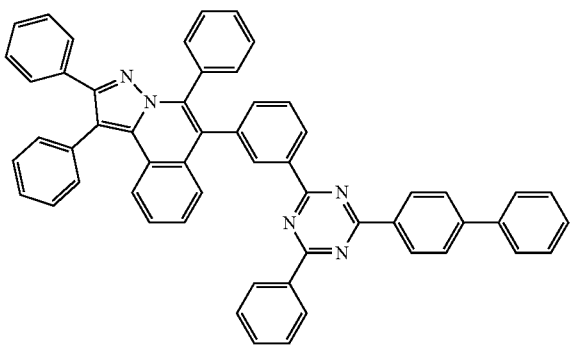
125
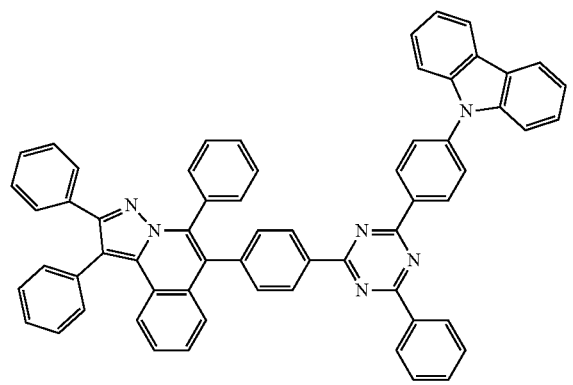
126
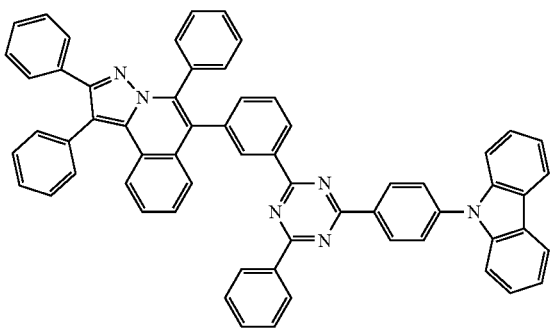

127
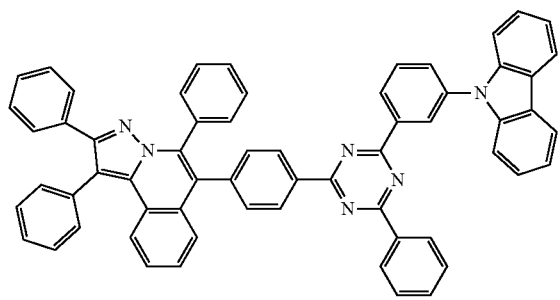
128
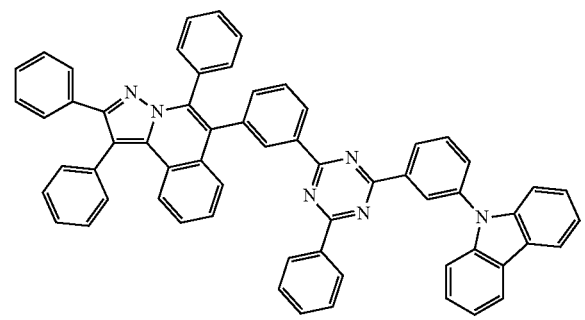
129
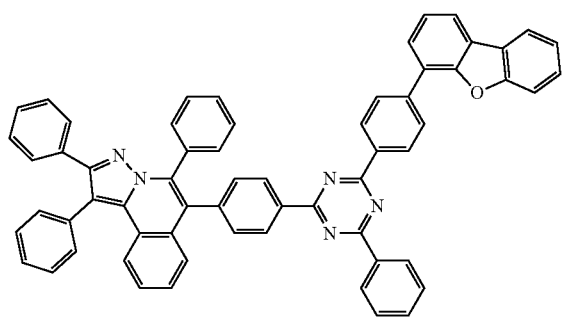
130
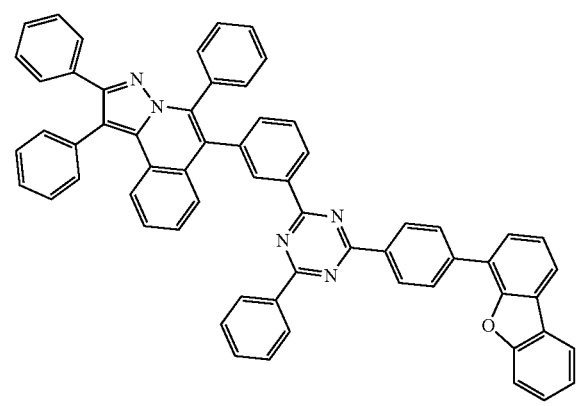
131
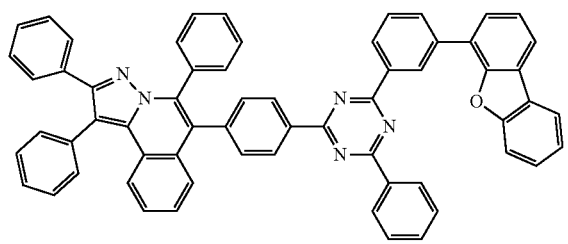
132
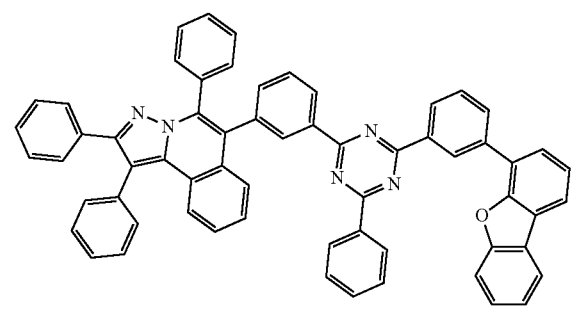
133
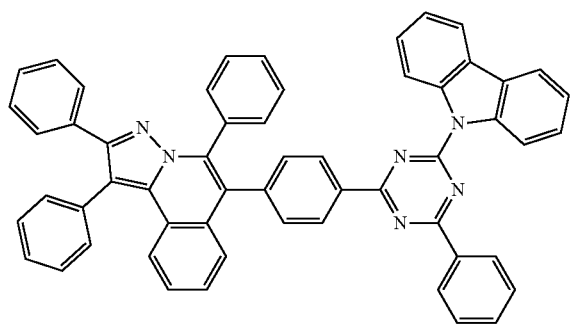
134
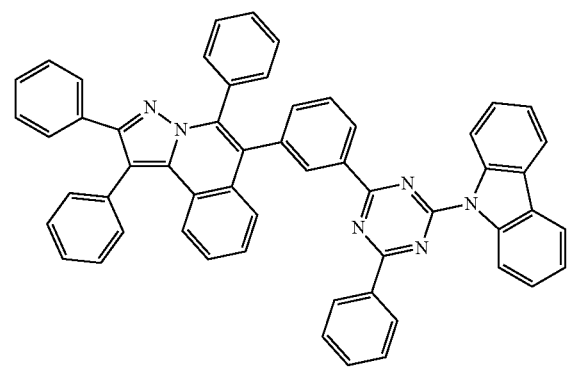

-continued
| 135 | 136 |
|---|---|
| 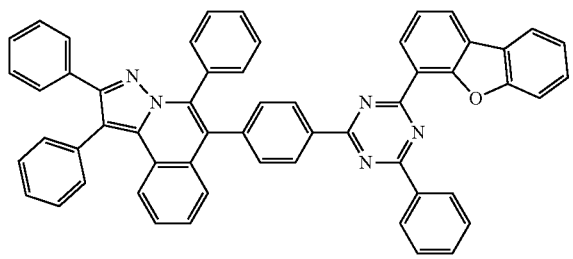 | 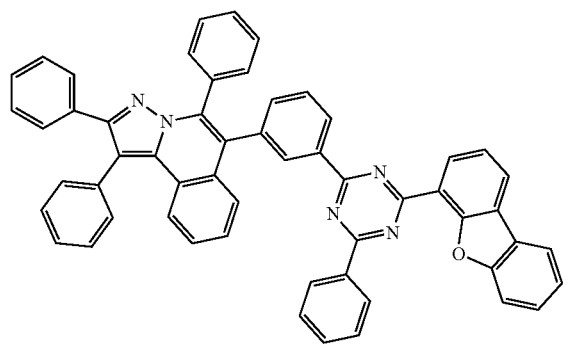 |
| 137 | 138 |
| 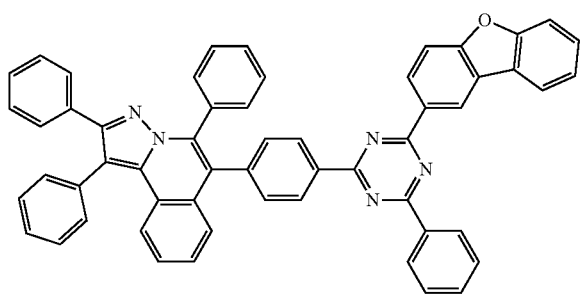 | 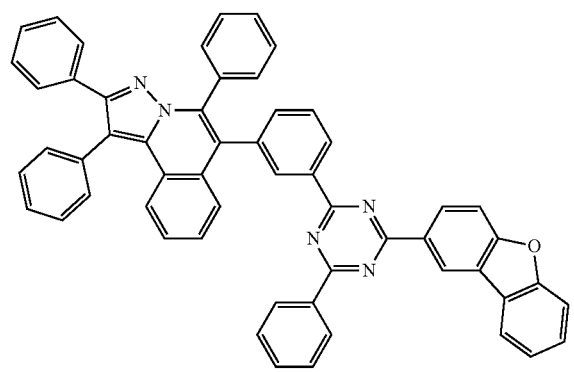 |
| 139 | 140 |
| 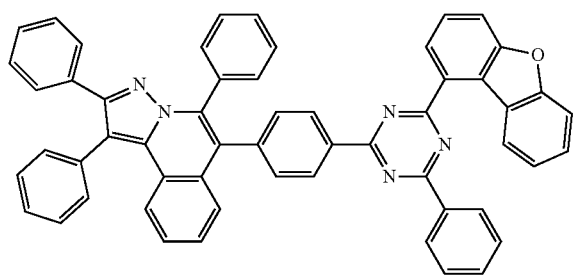 | 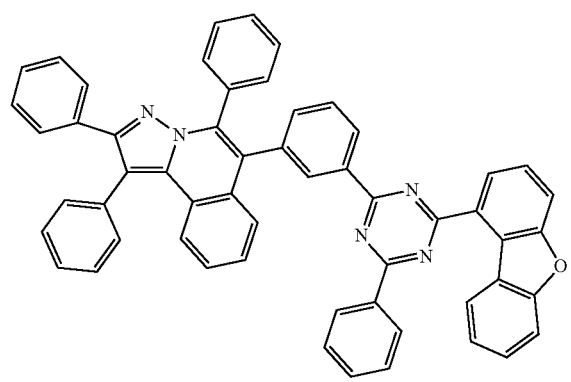 |
| 141 | 142 |
| 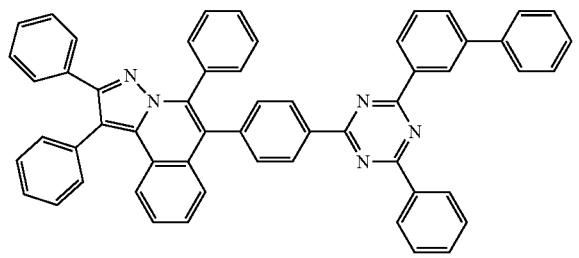 | 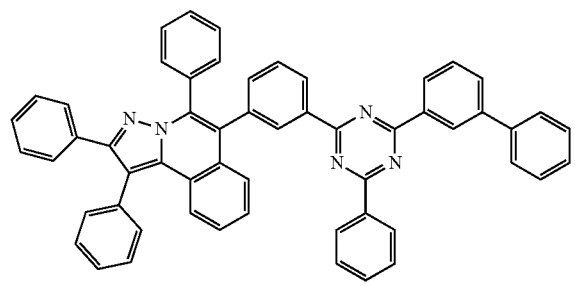 |

-continued
143
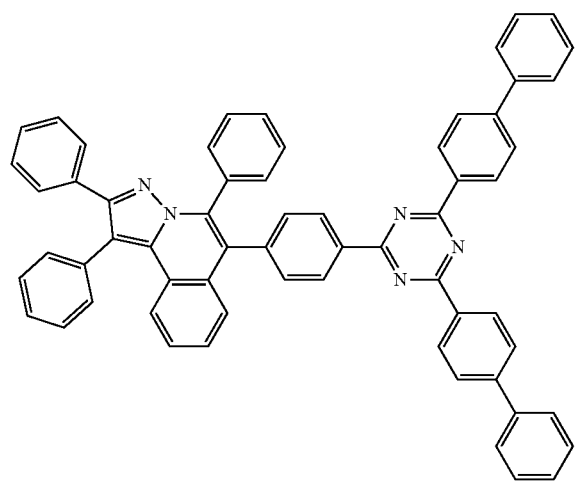
144
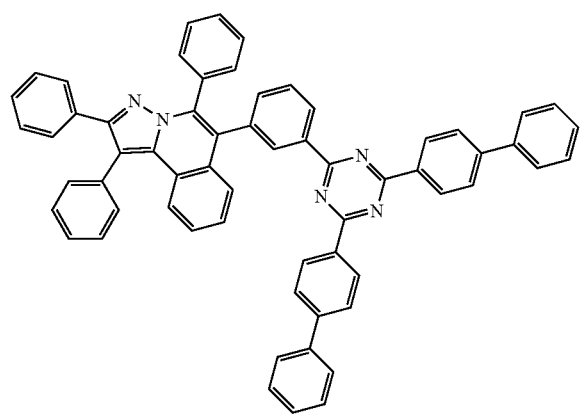
145
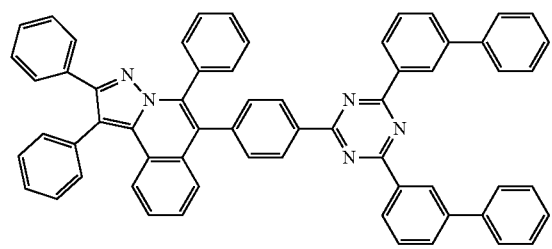
146
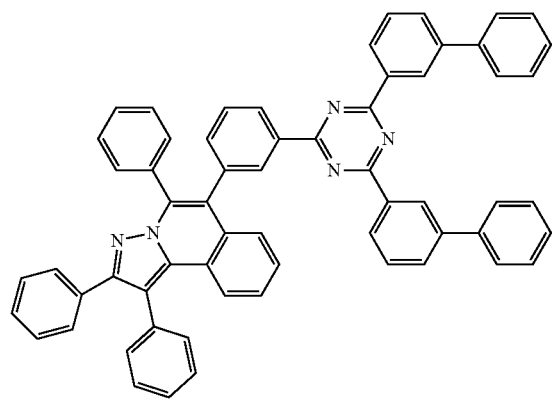
147
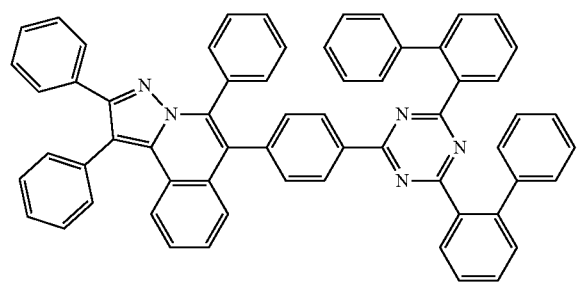
148
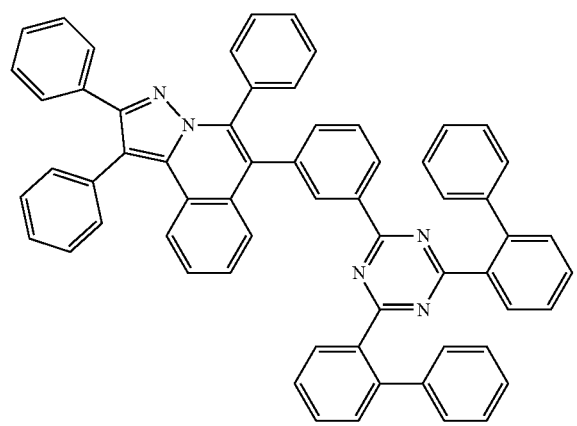

-continued
149
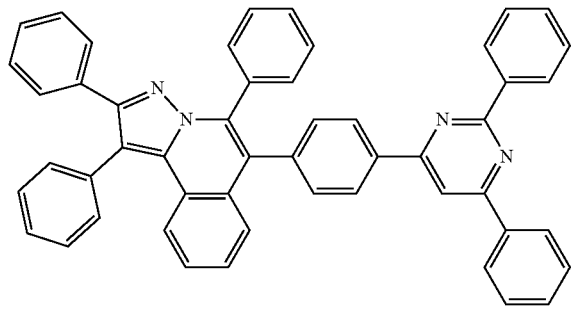
150
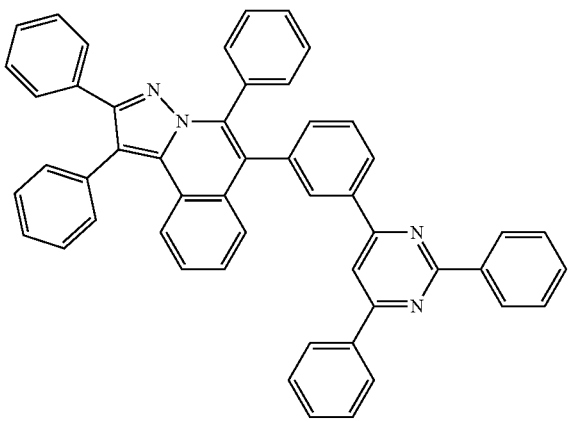
151
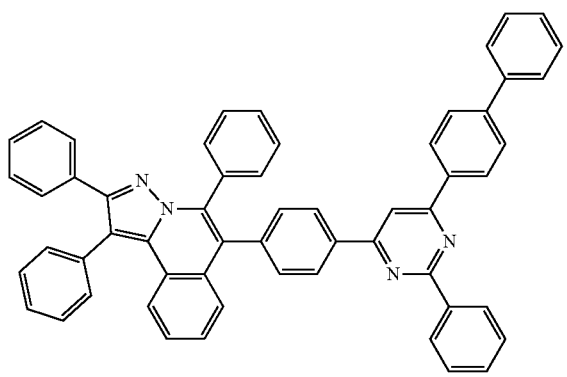
152
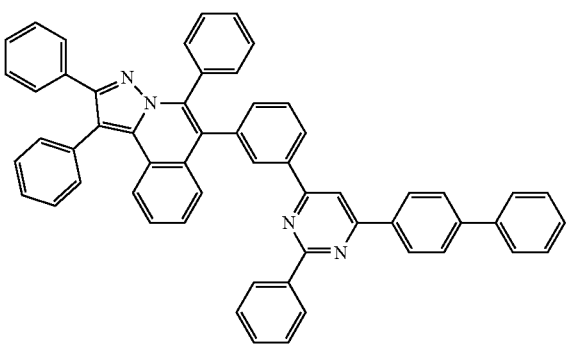
153
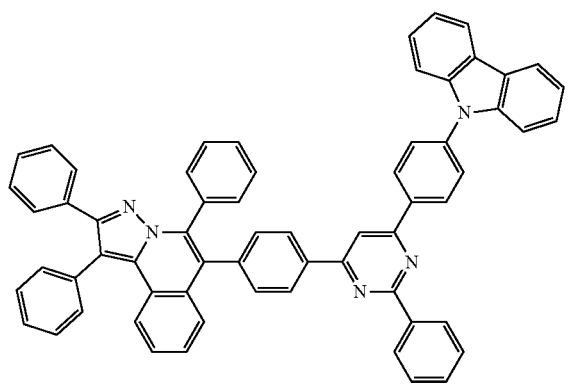
154
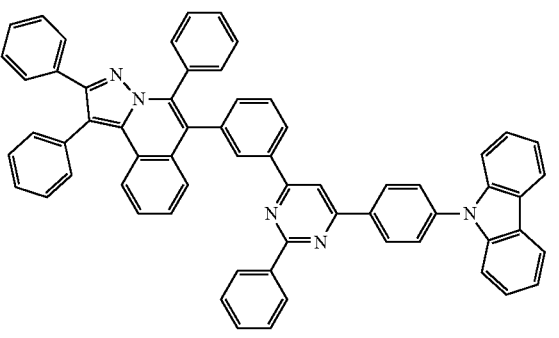
155
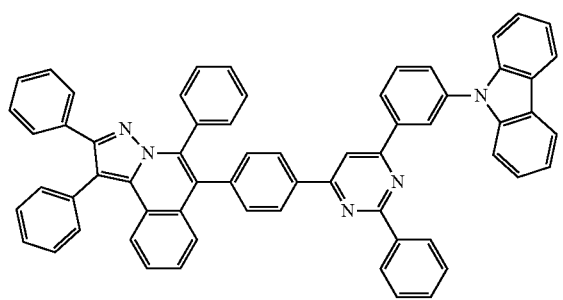
156
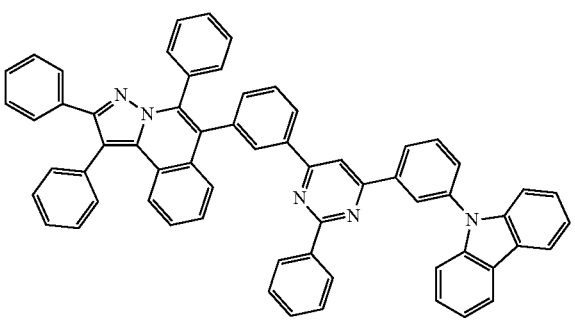

157
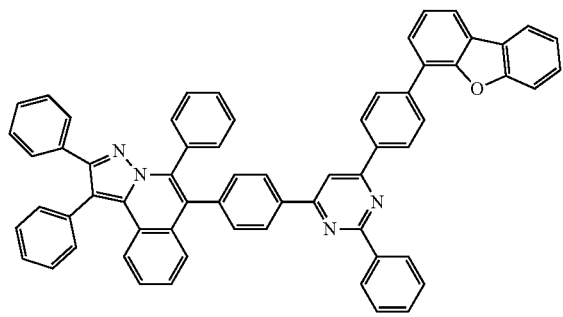
158
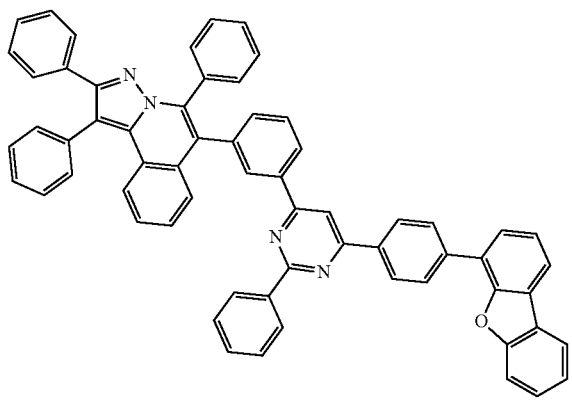
159
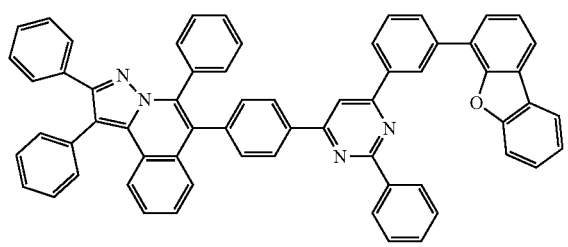
160
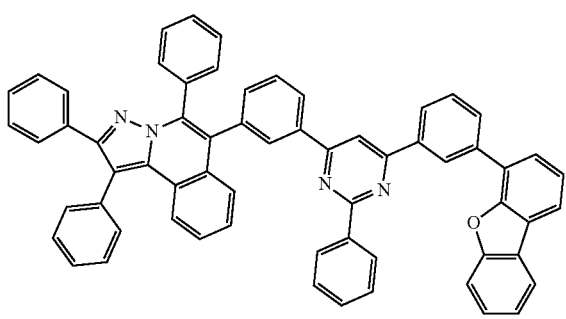
161
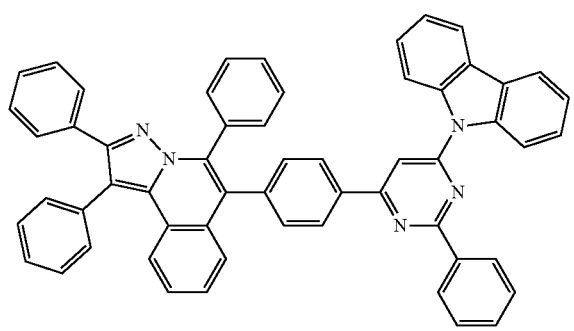
162
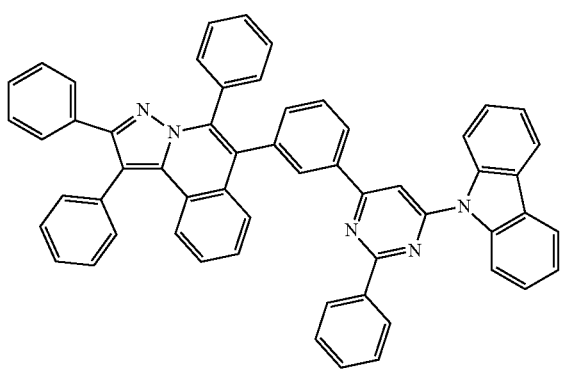
163
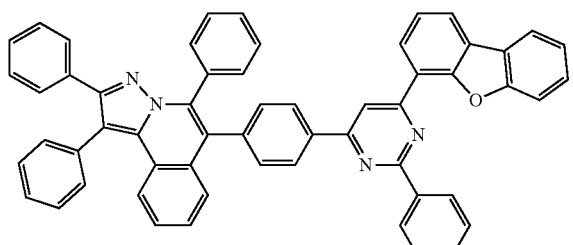
164
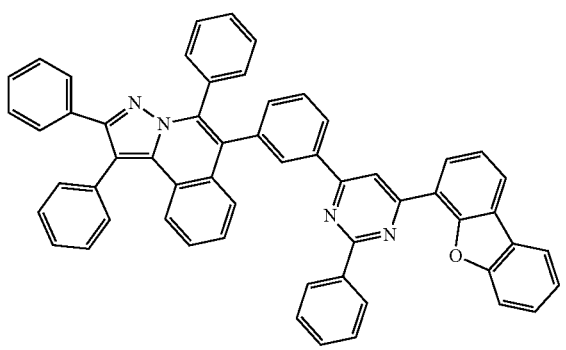

-continued
165
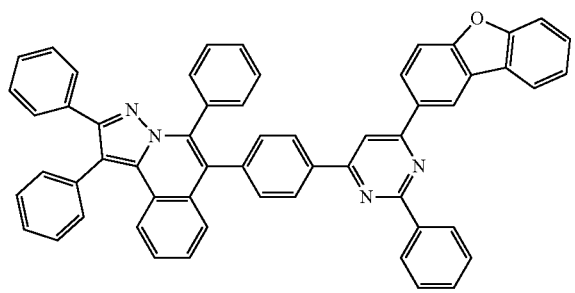
166
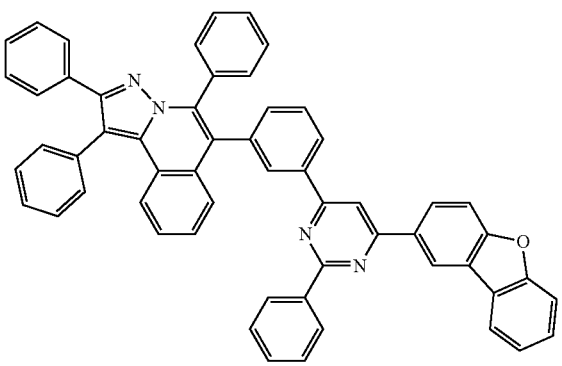
167
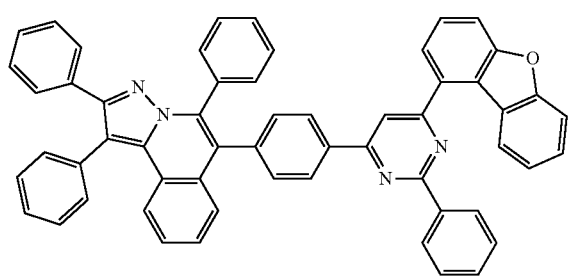
168
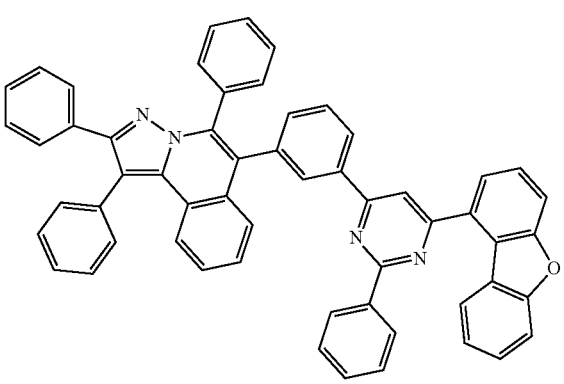
169
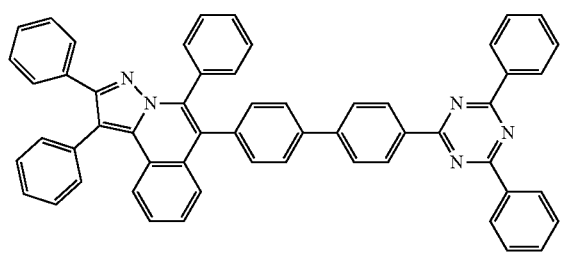
170
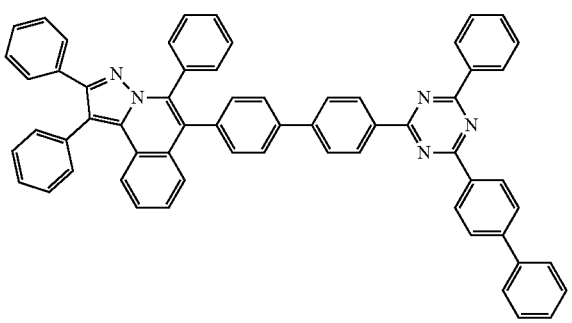
171
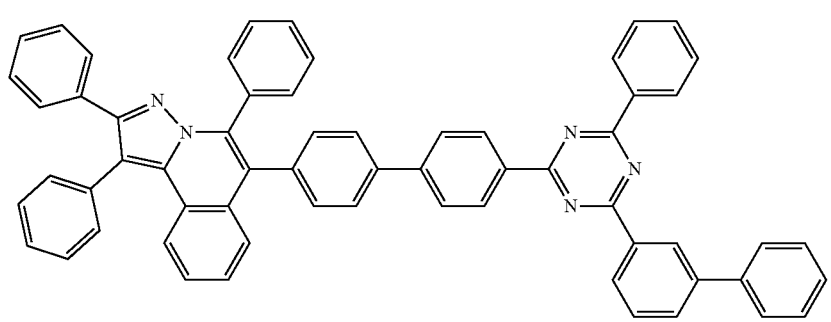

172
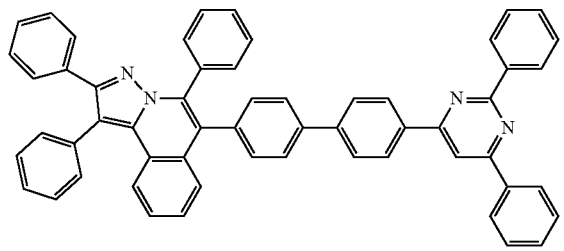
173
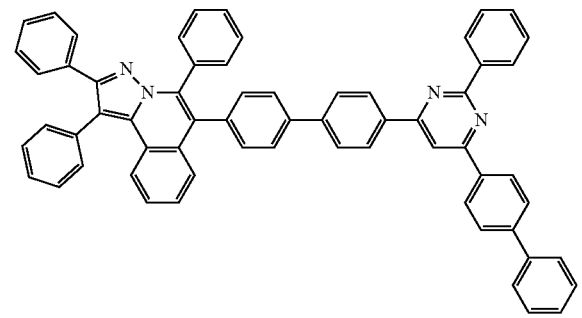
174
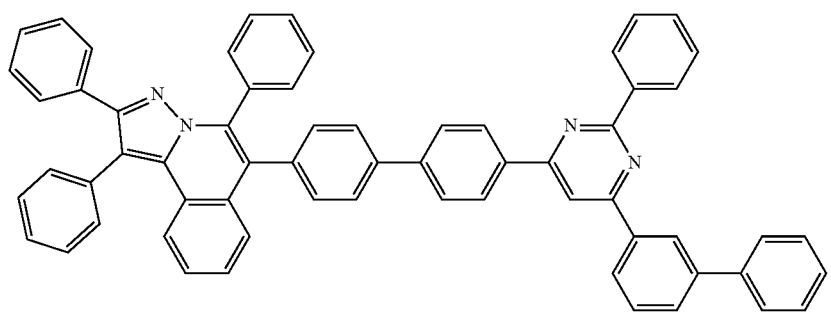
175
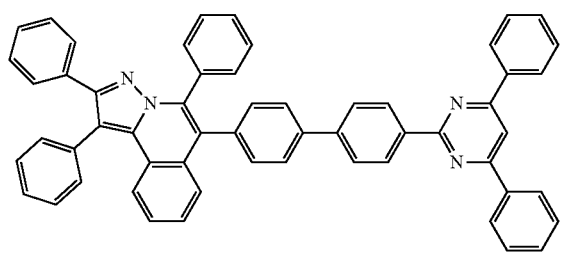
176
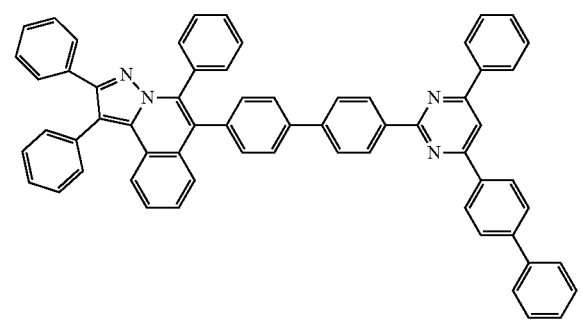
177
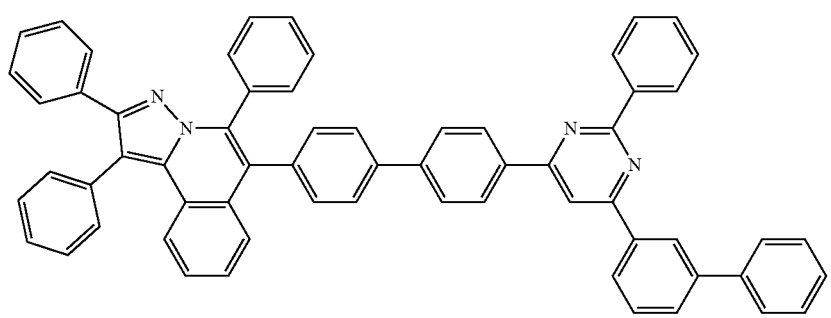

-continued
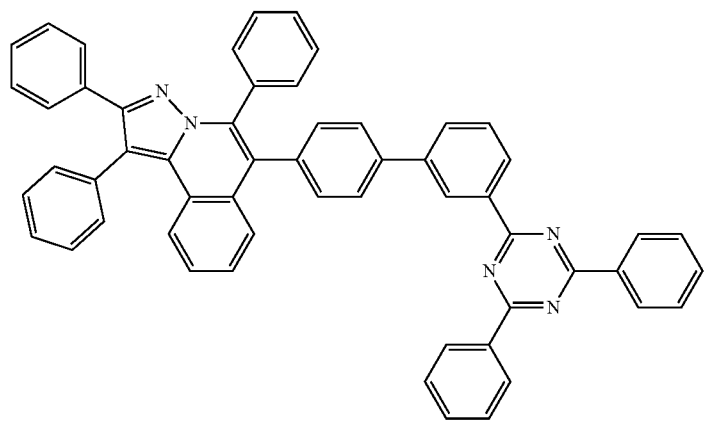
178
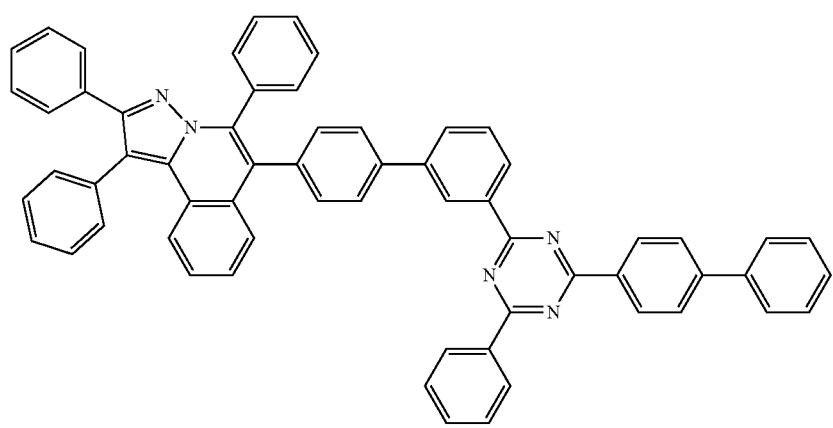
179
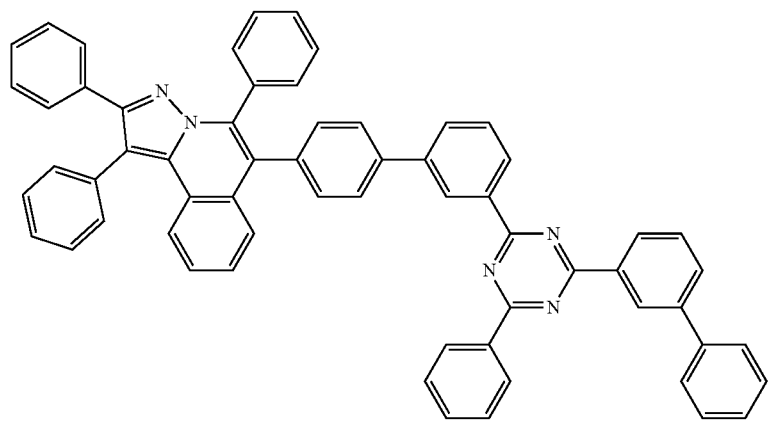
180

181
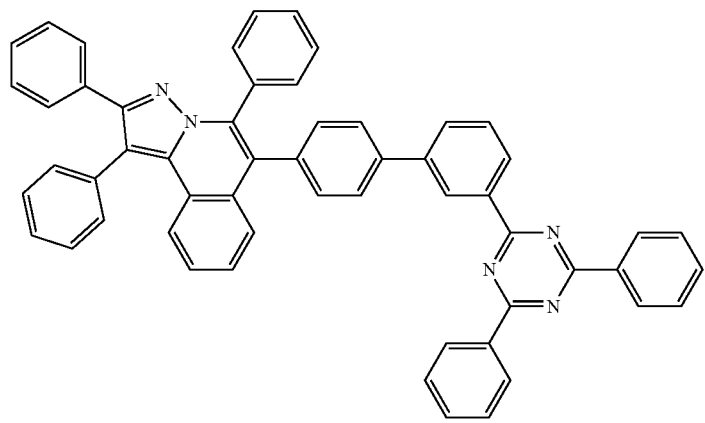
182
183

-continued
184
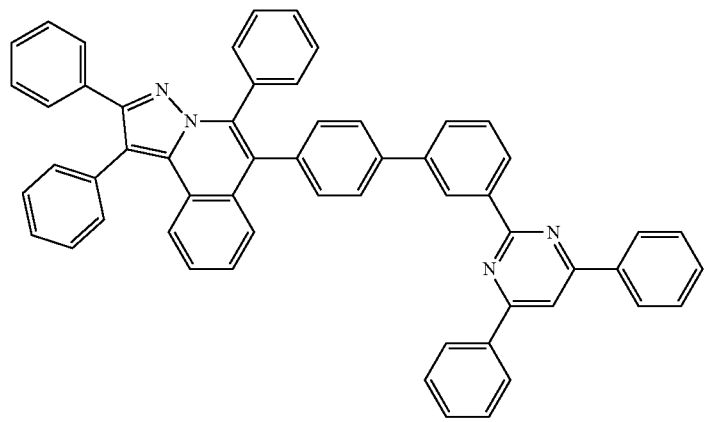
185
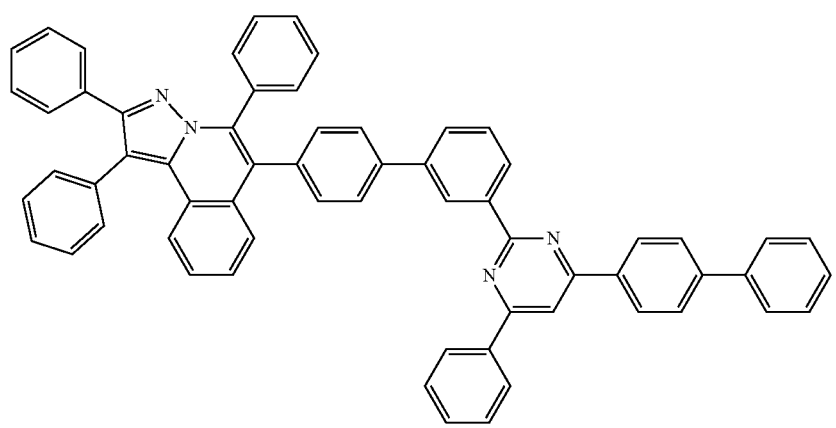
186
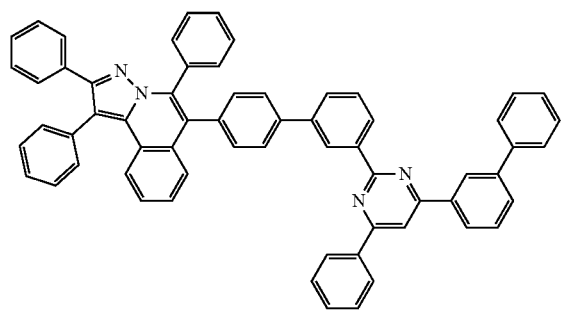
187
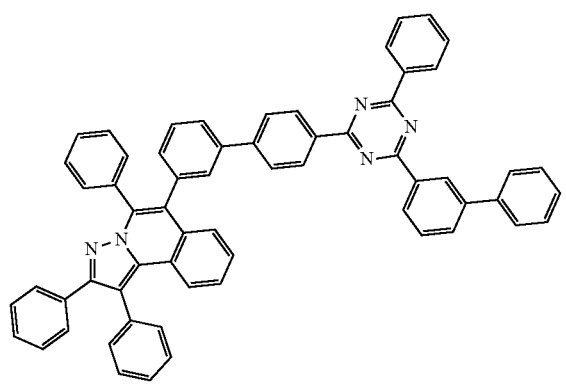
188
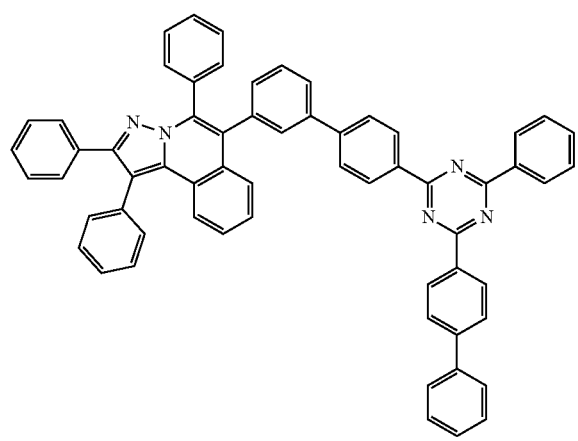
189

-continued
190
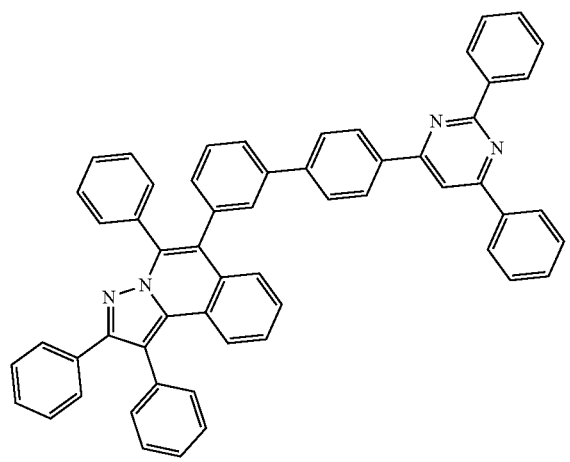
191
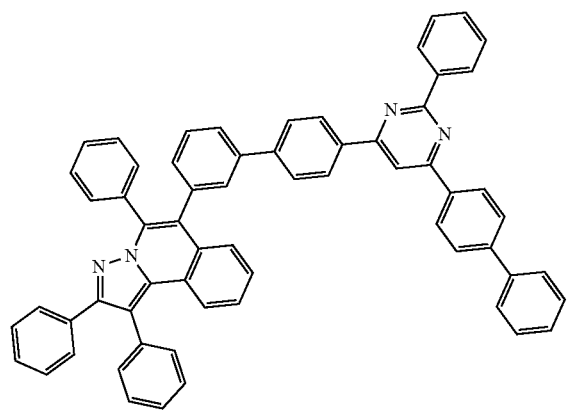
192
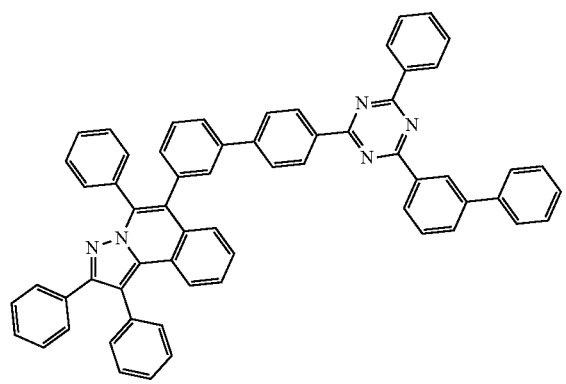
193
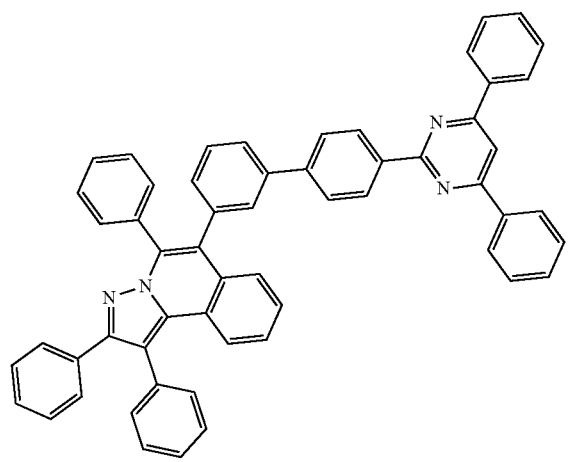
194
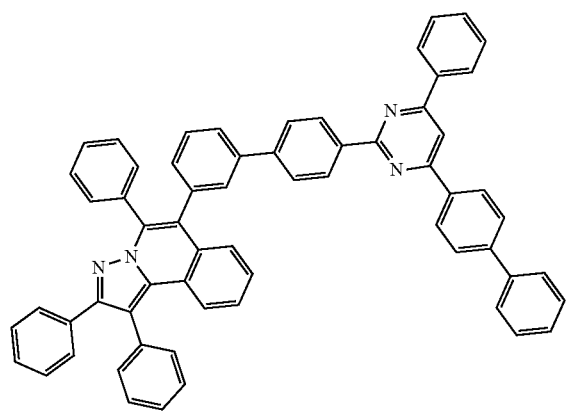
195
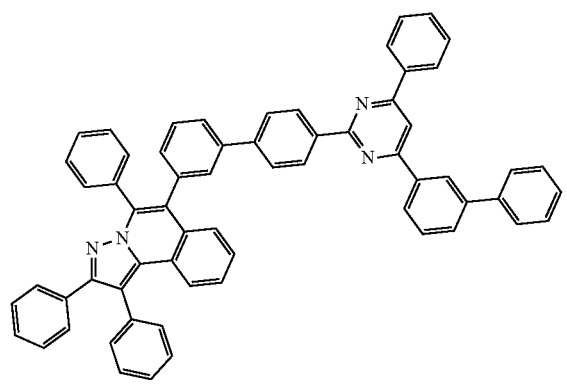

-continued
196
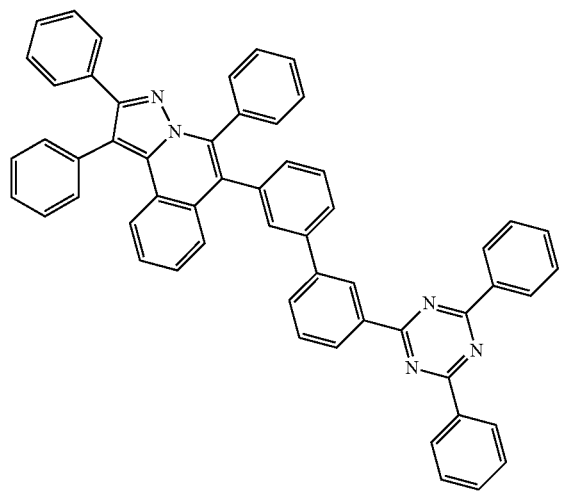
197
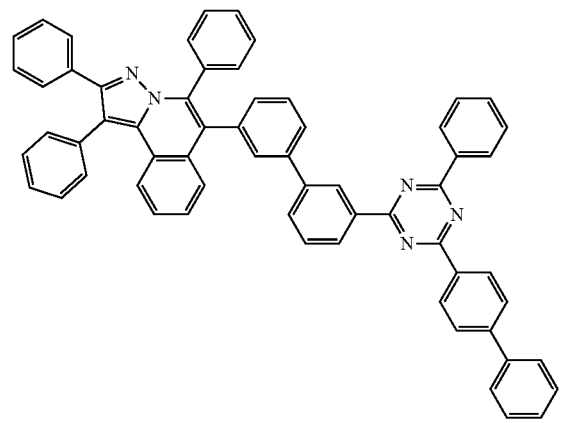
198
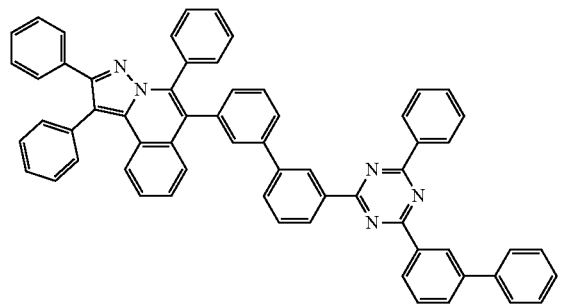
199
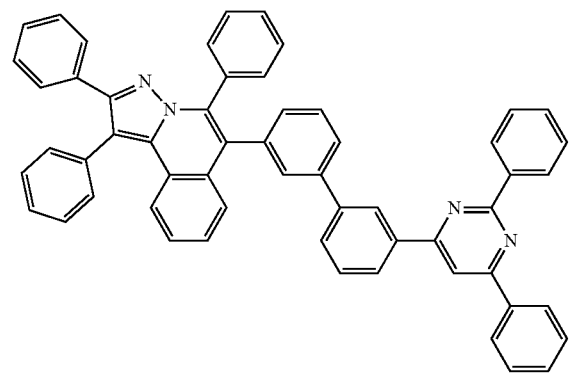
200
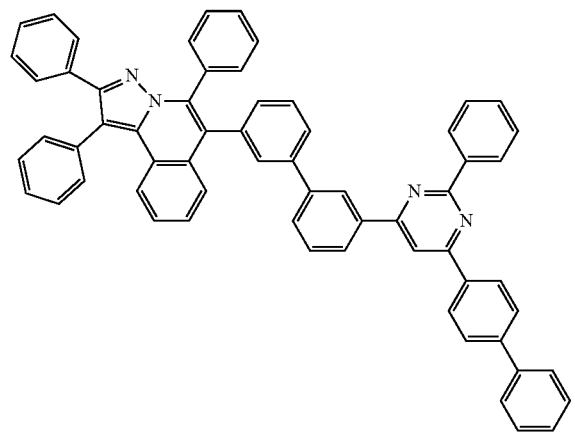
201
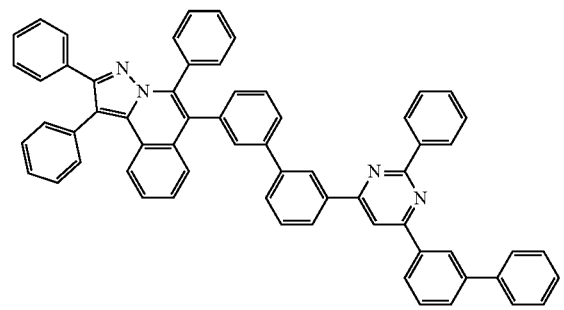

-continued
202
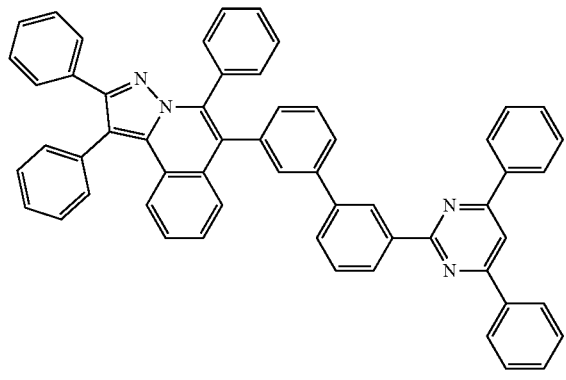
203
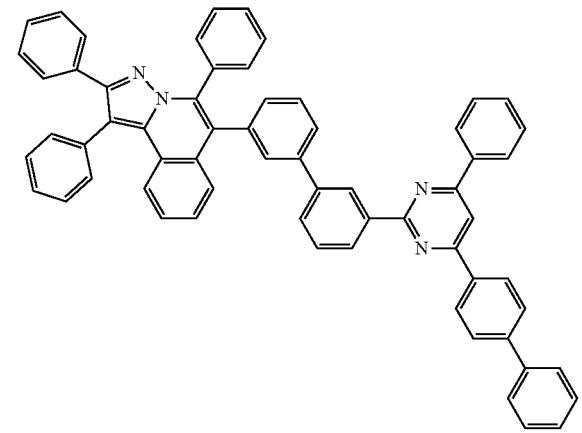
204
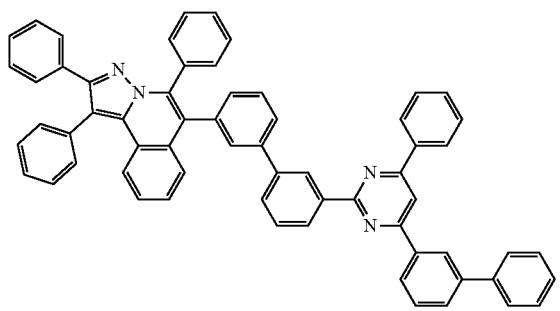
205
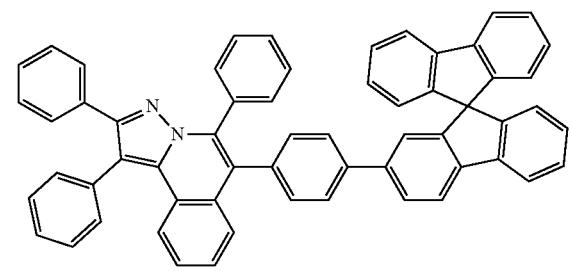
206
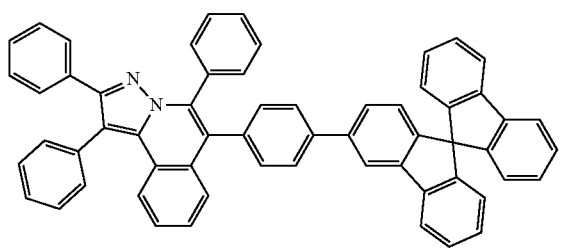
207
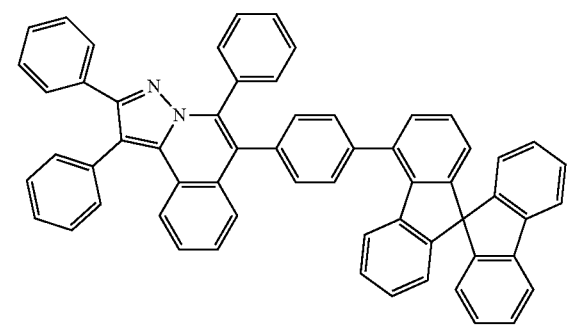
208
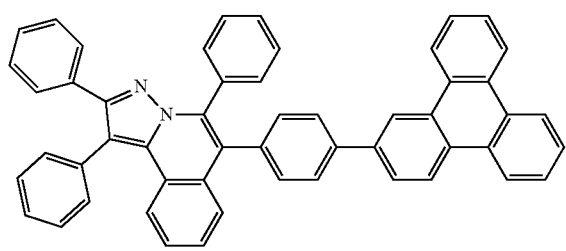
209
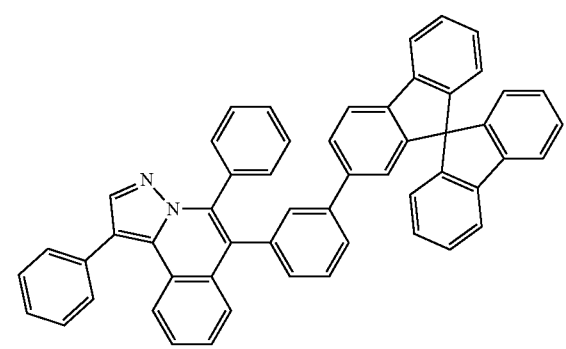

-continued
210
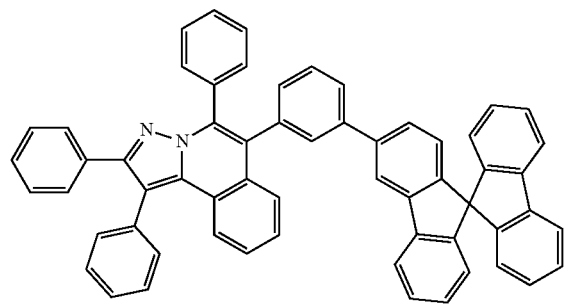
211
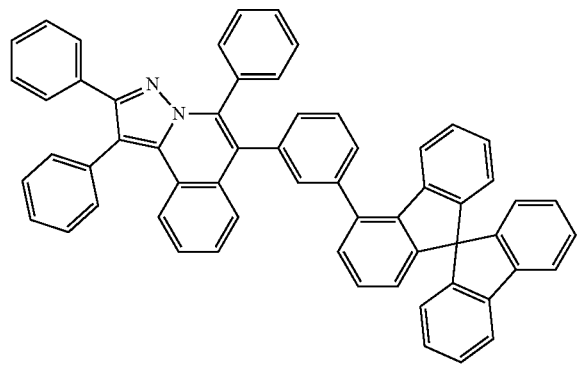
212
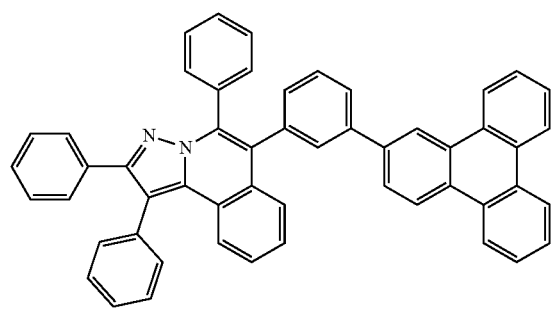
213
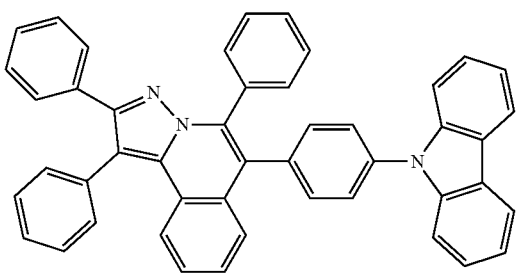
214
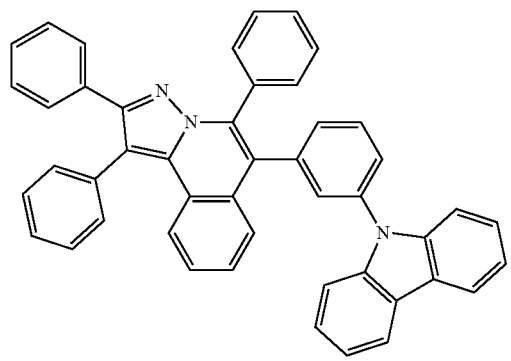
215
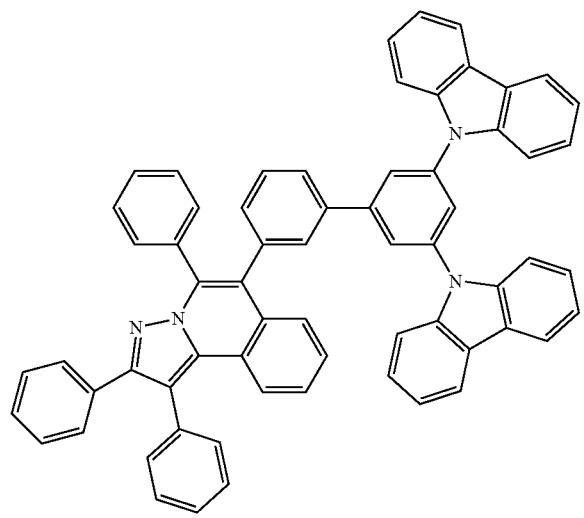
216
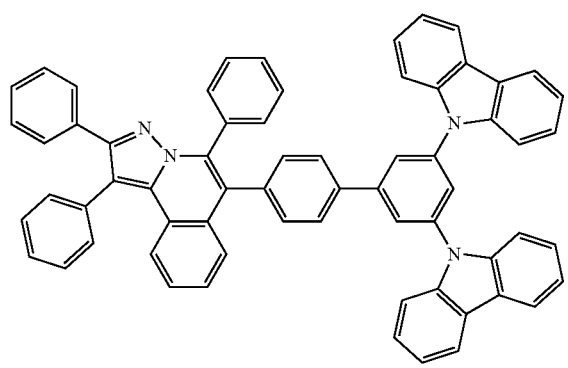
217
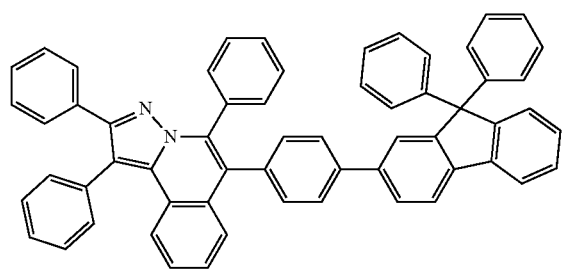

-continued
218
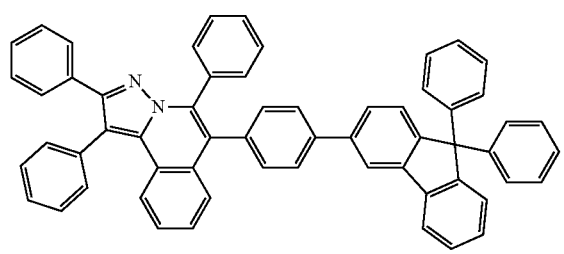
219
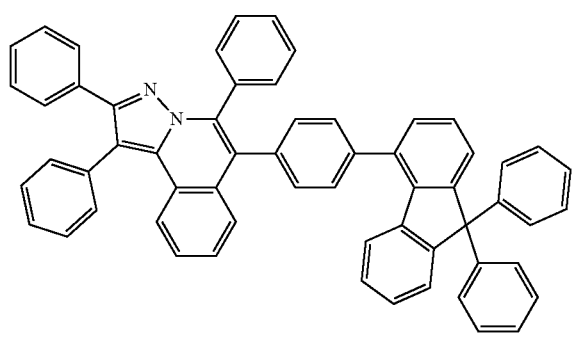
220
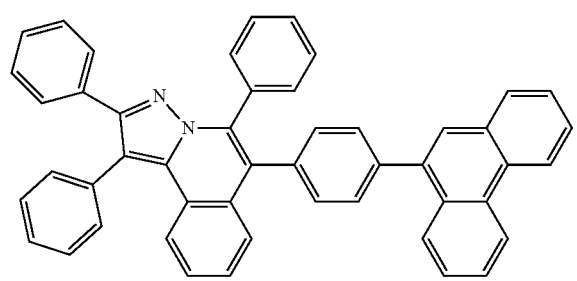
221
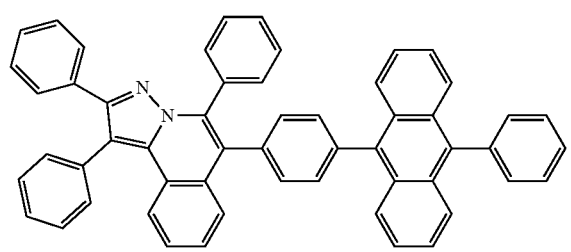
222
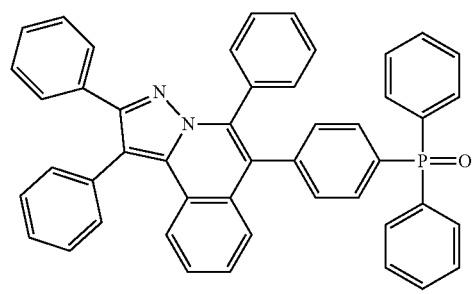
223
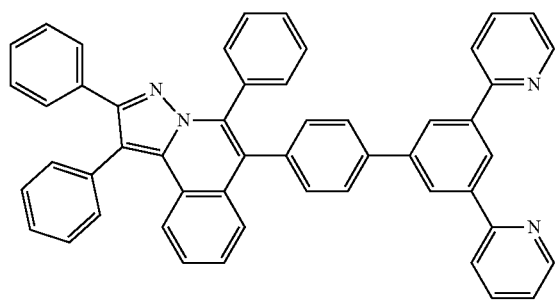 [SMILES: c1ccc(-c2cc(-c3ccc(-c4c(-c5ccccc5)n5nc(-c6ccccc6)c(-c6ccccc6)c5c5ccccc45)cc3)cc(-c3ccccc3)n2)cc1]
224
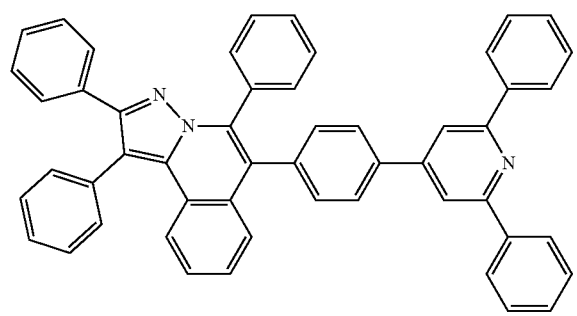
225
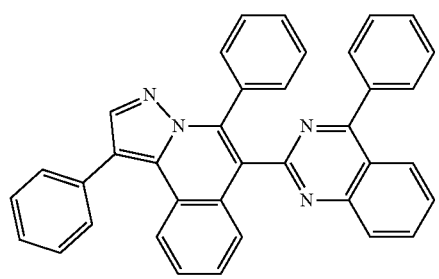

-continued
226
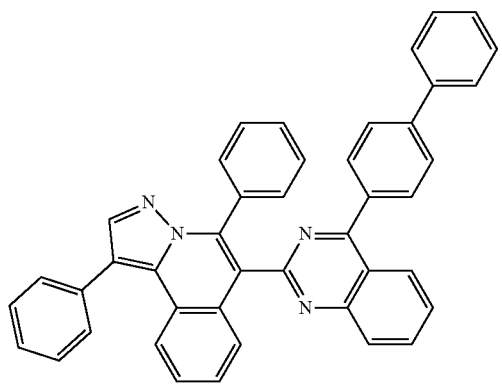
227
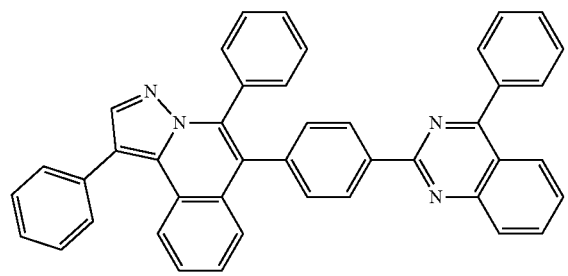
228
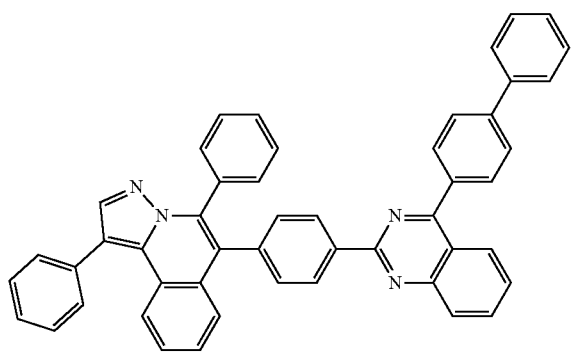
229
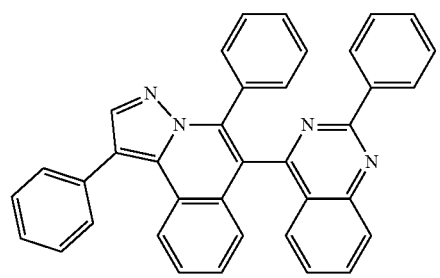
230
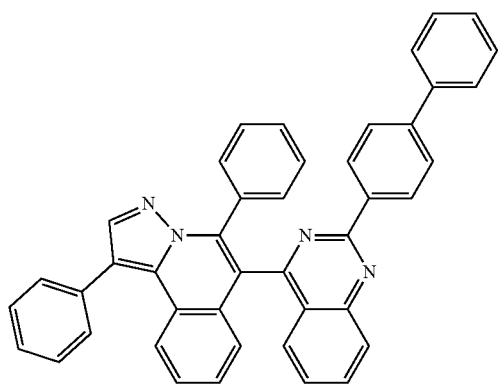
231
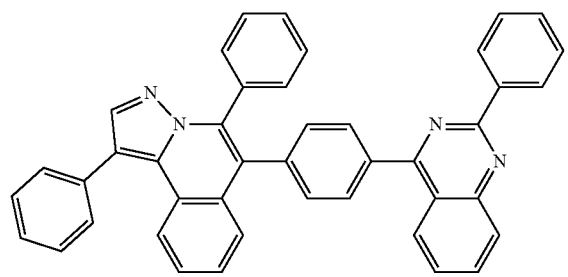
232
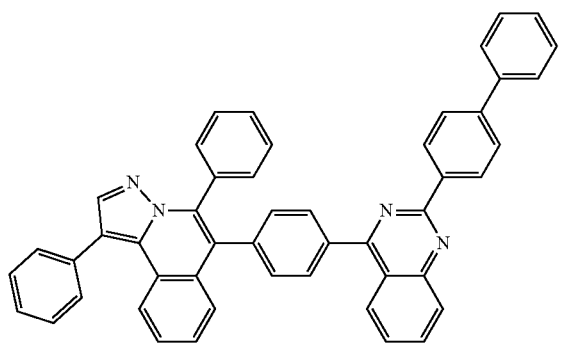
233
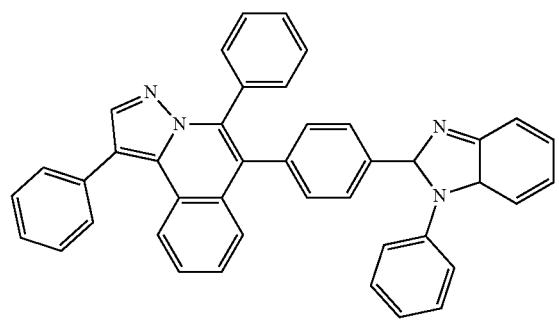

-continued
234
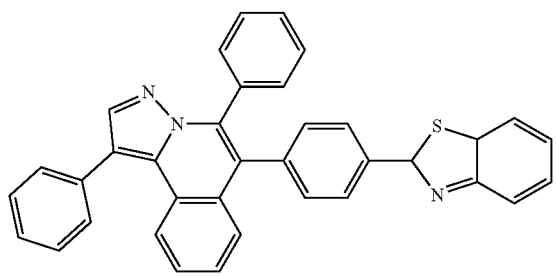
235
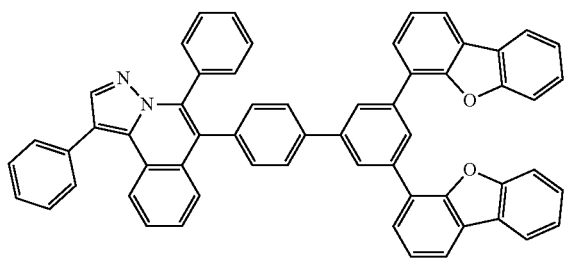
236
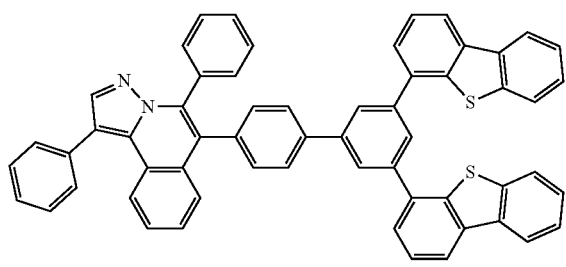
237
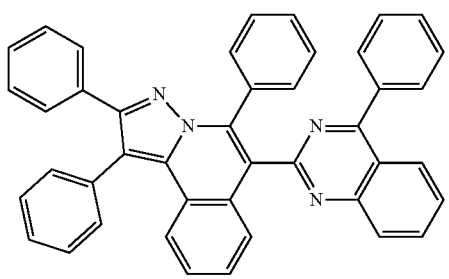
238
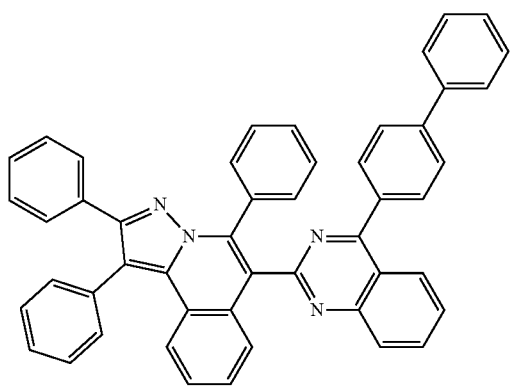
239
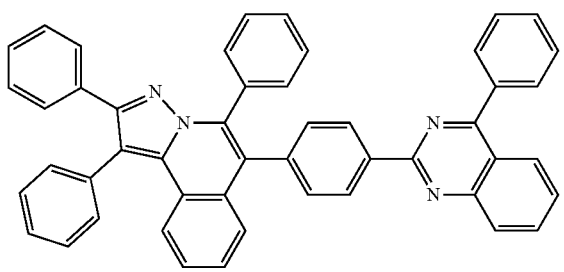 [SMILES: c1ccc(-c2nn3c(-c4ccccc4)c(-c4ccc(-c5nc(-c6ccccc6)c6ccccc6n5)cc4)c4ccccc4c3c2-c2ccccc2)cc1]
240
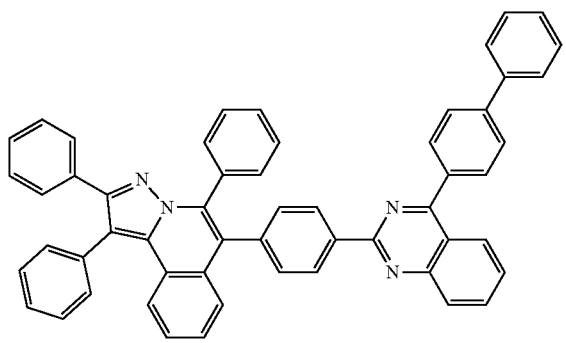
241
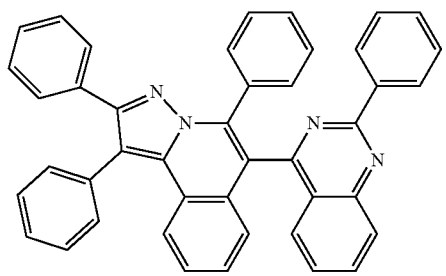

-continued
242
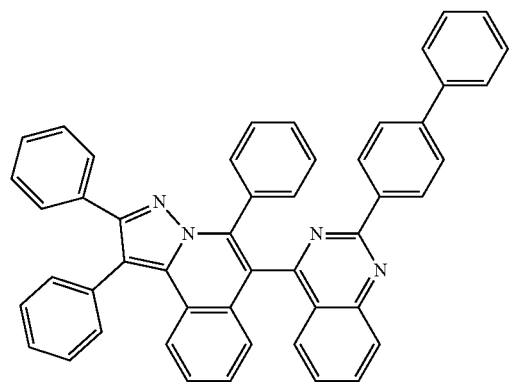
243
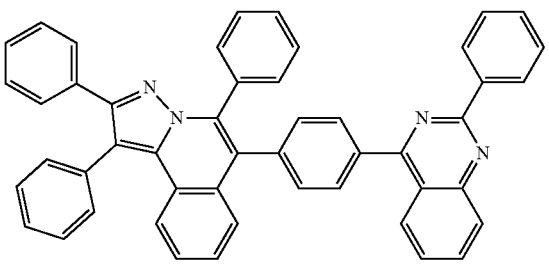
244
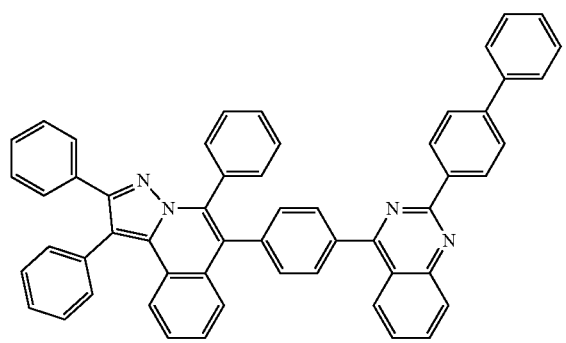
245
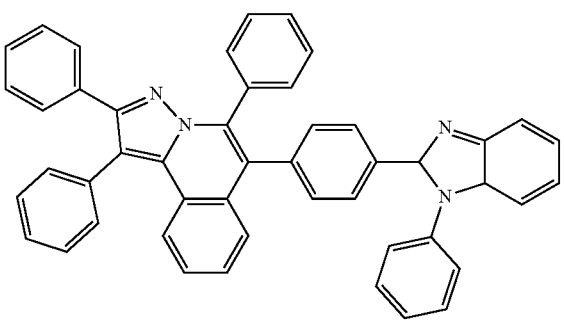 [SMILES: c1ccc(-c2nn3c(-c4ccccc4)c(-c4ccc(-c5nc6ccccc6n5-c5ccccc5)cc4)c4ccccc4c3c2-c2ccccc2)cc1]
246
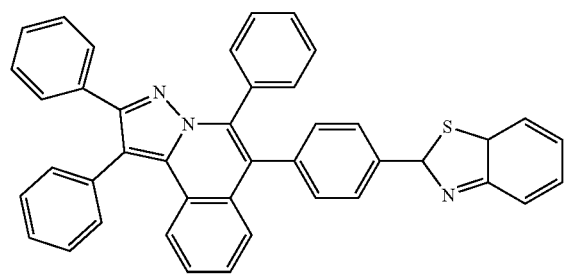
247
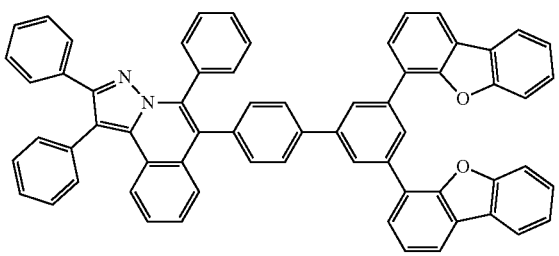
248
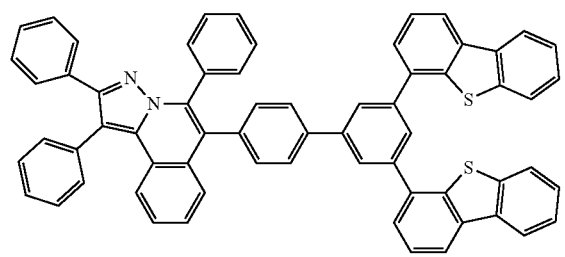
249
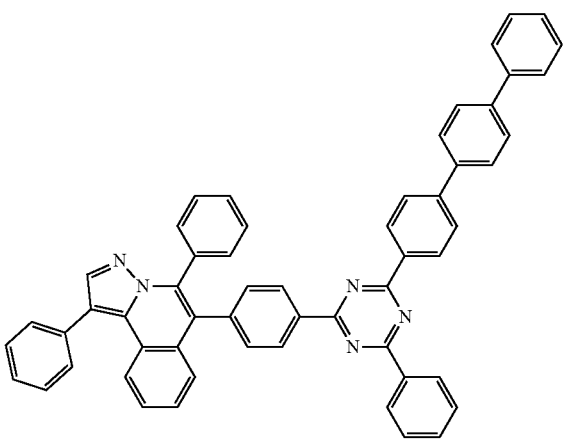

-continued
250
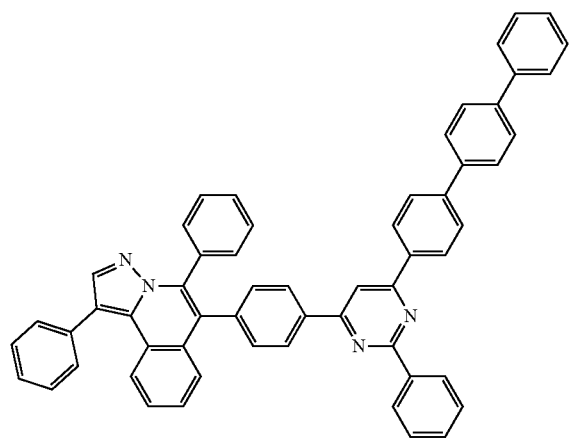
251
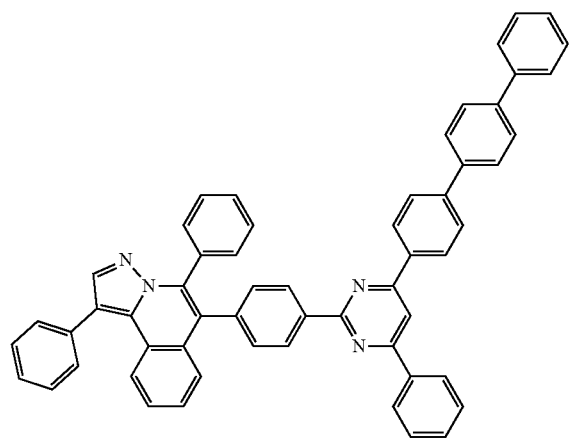
252
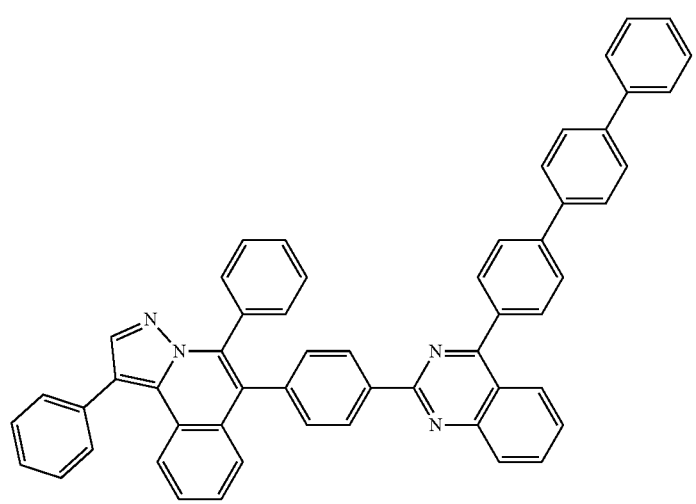
253
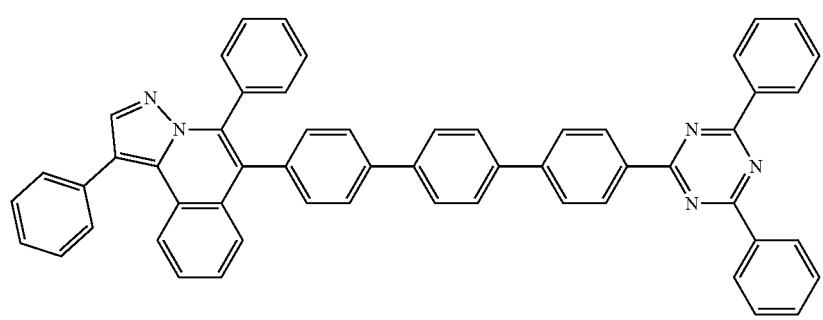
254
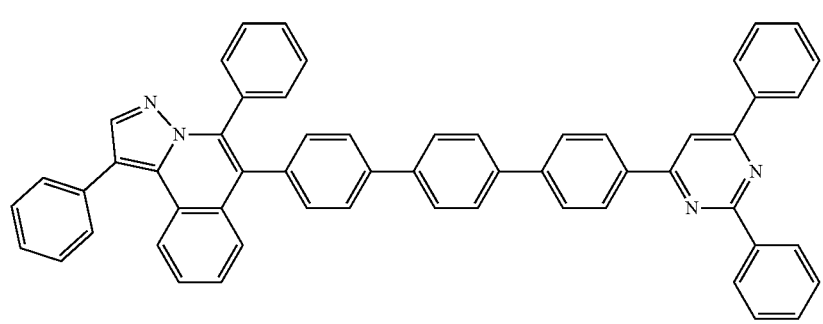

-continued
255
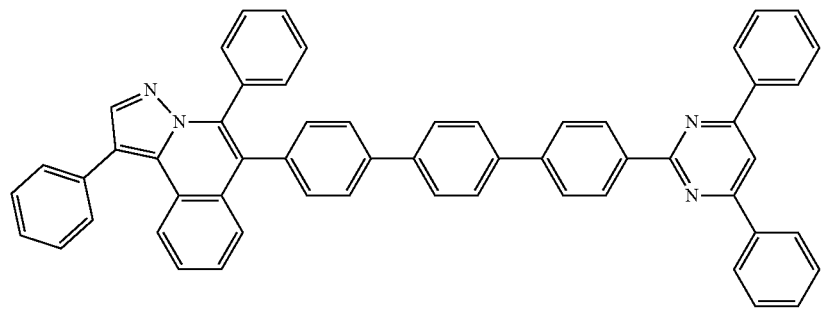
256
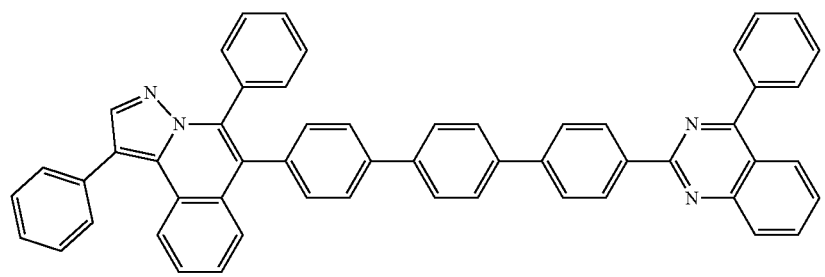
257
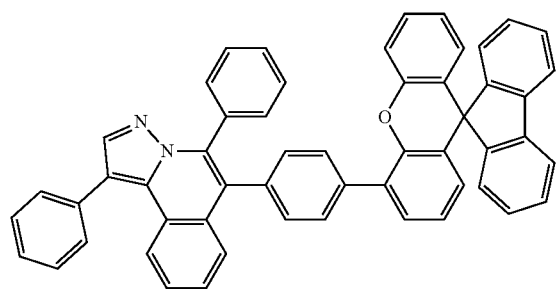
258
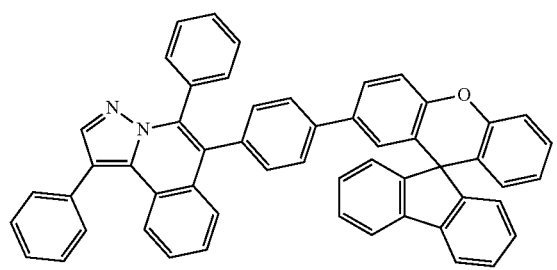
259
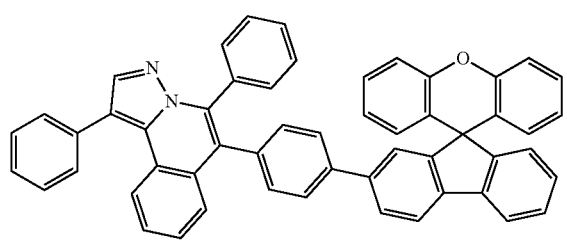
260
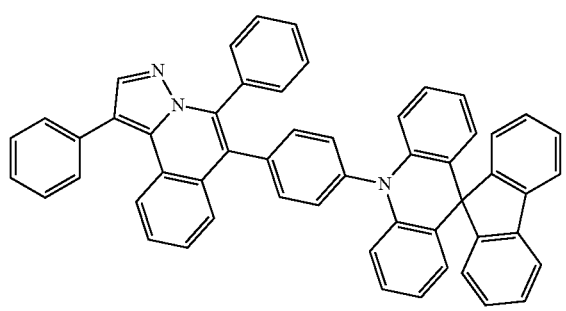

261
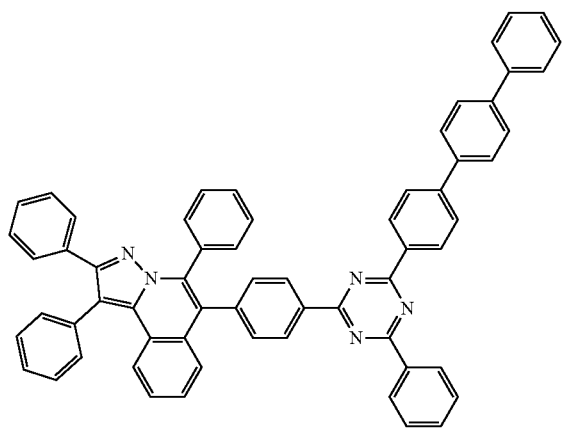
262
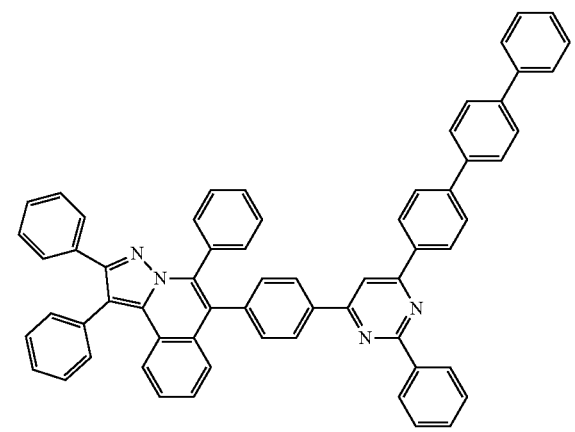
263
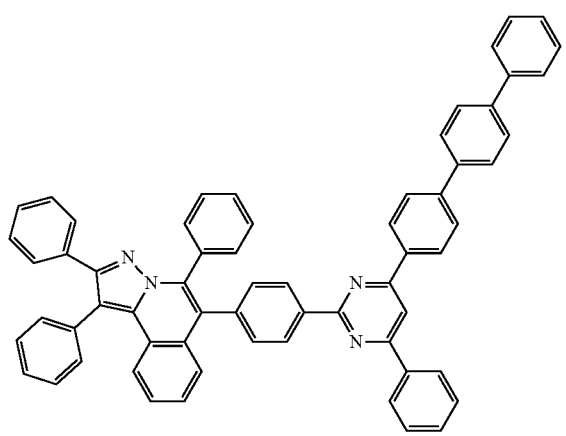
264
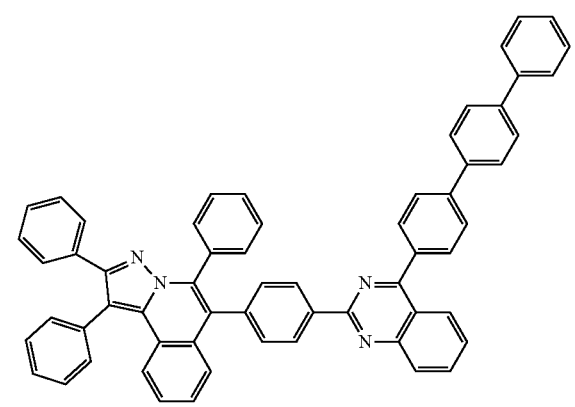
265
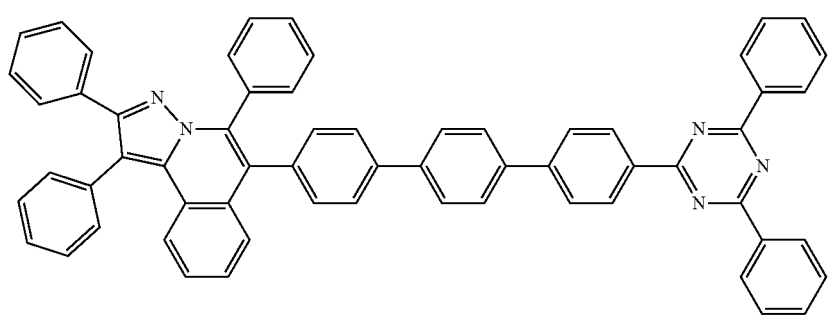
266
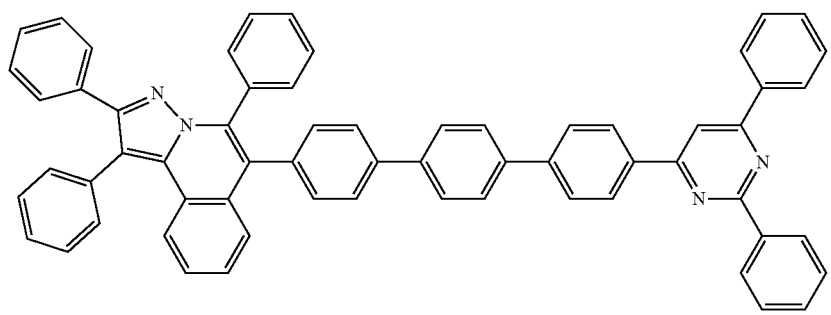

267
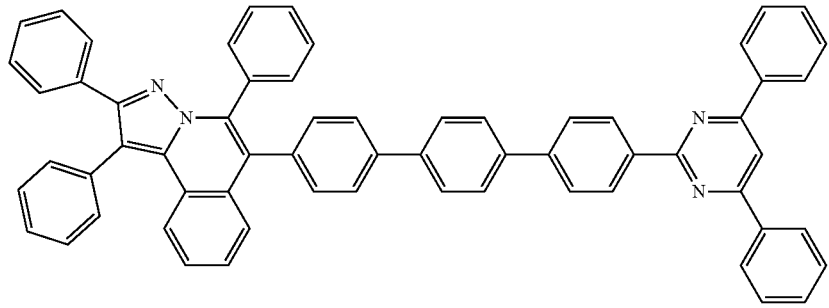
268
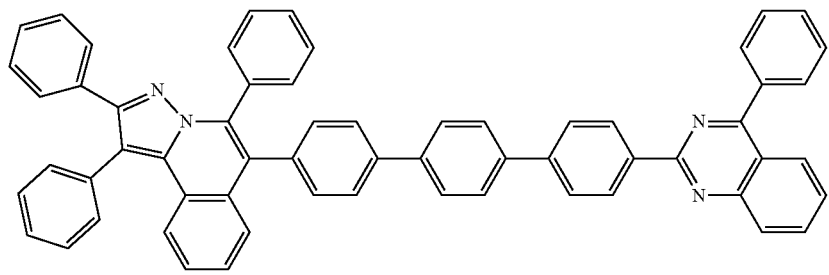
269 270
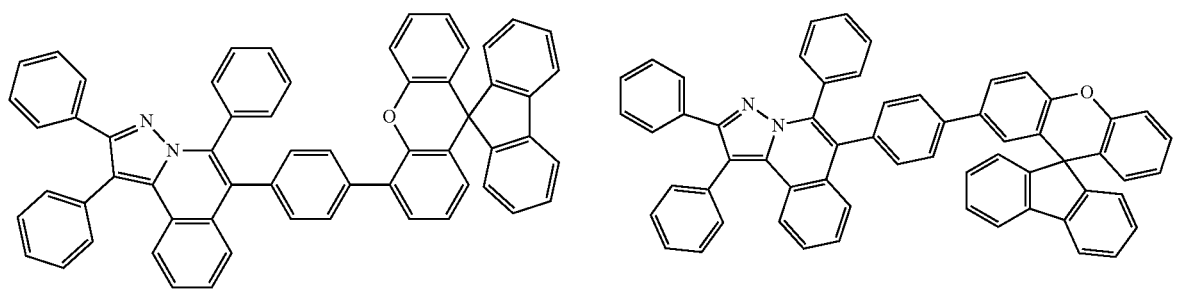
271 272
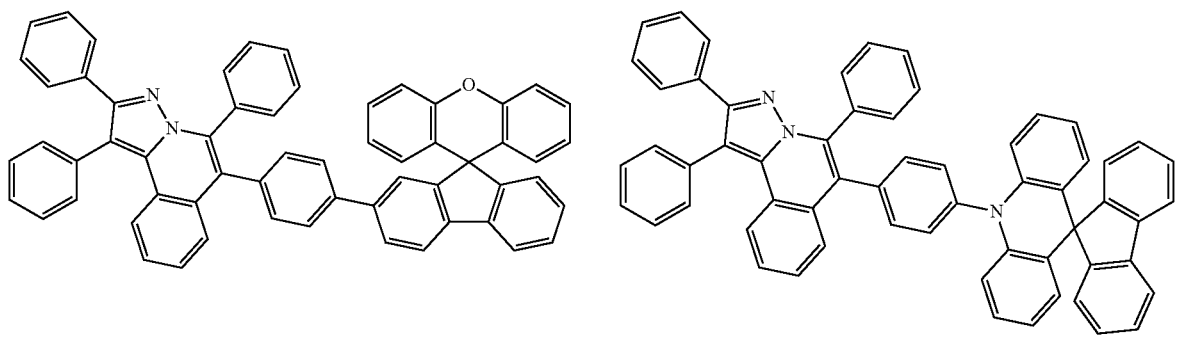
273 274
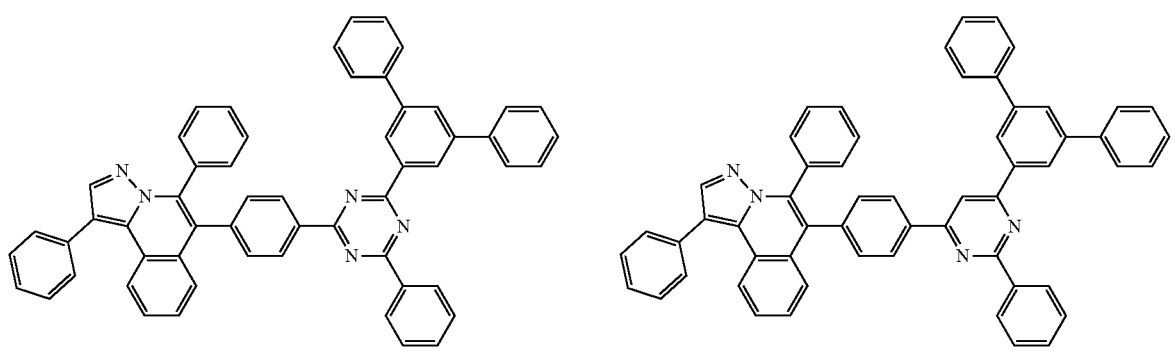

275
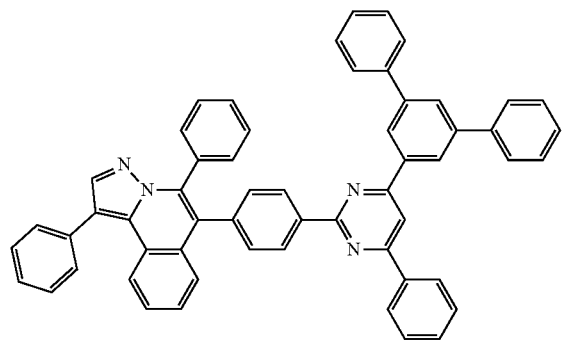
276
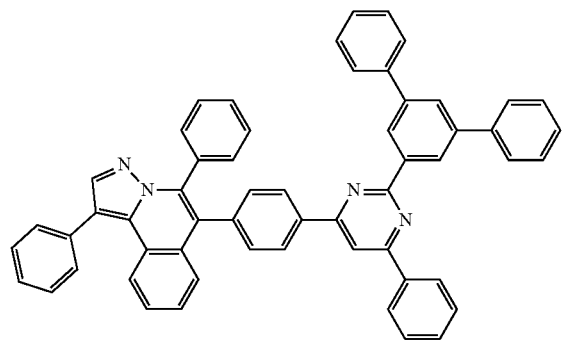
277
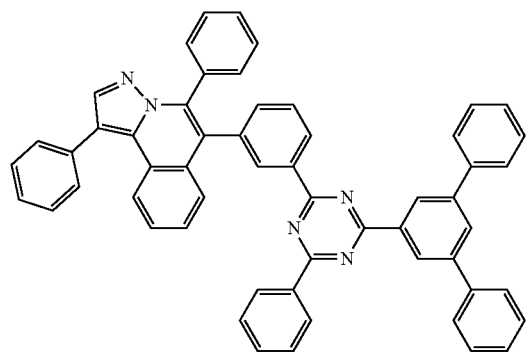
278
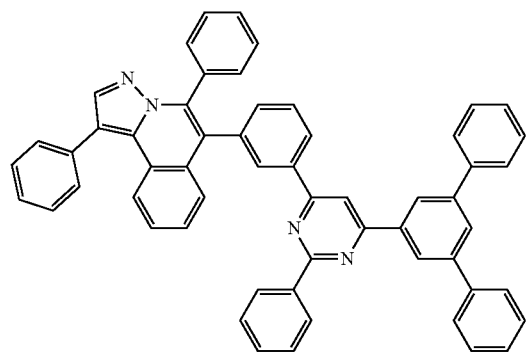
279
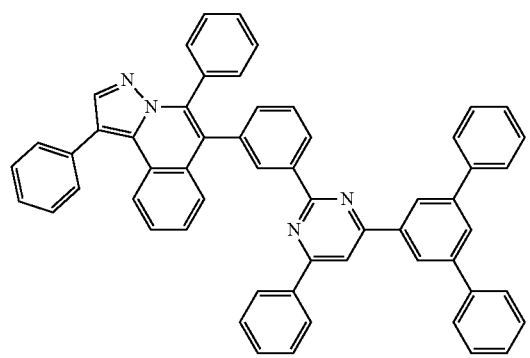
280
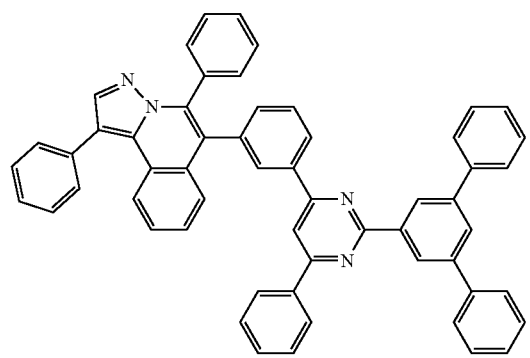
281
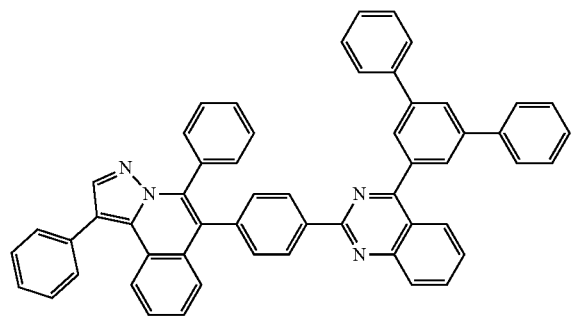
282
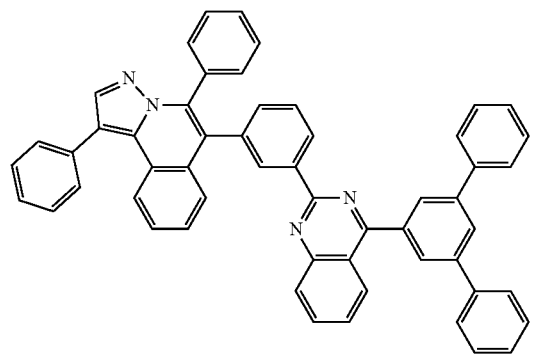

283
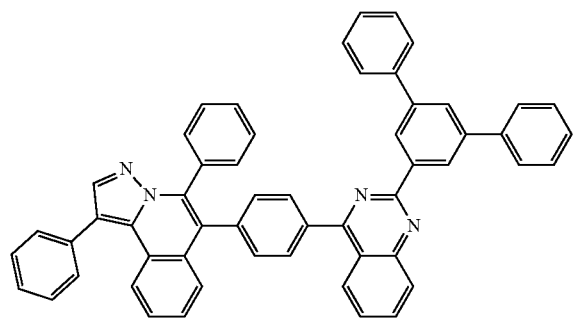
284
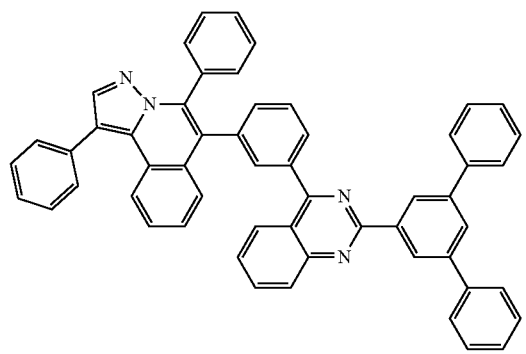
285
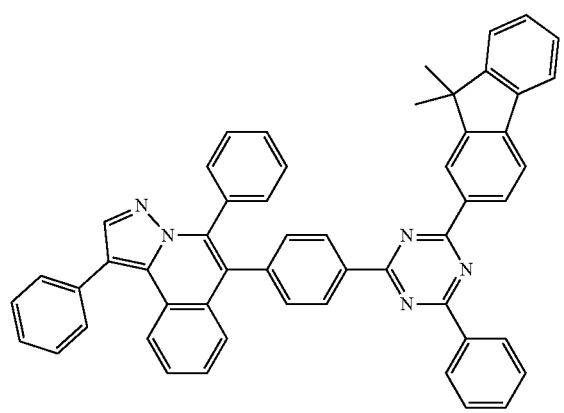
286
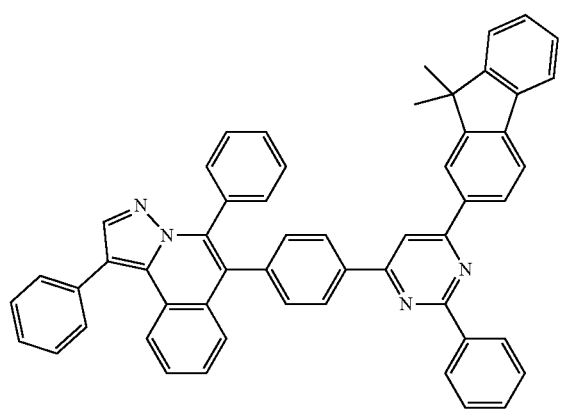
287
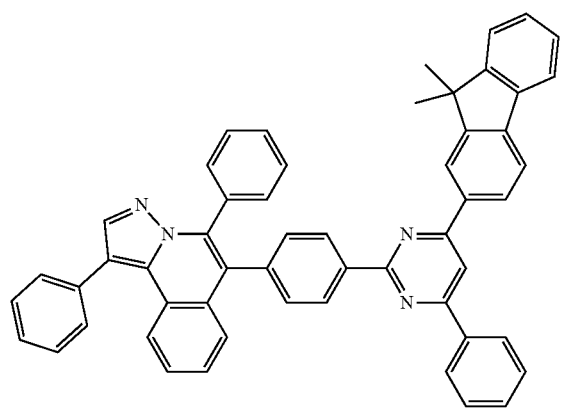
288
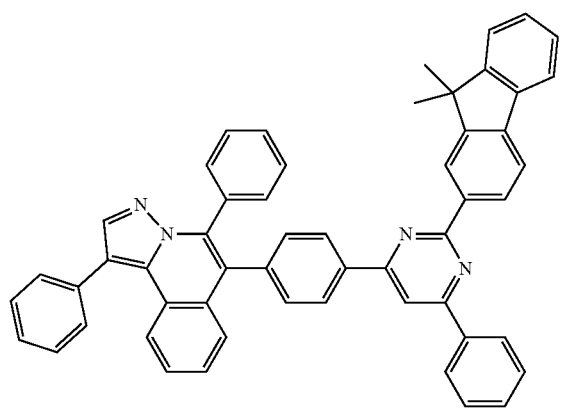

-continued
289
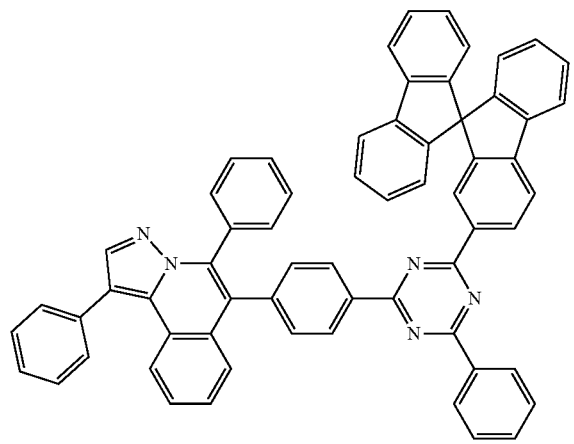
290
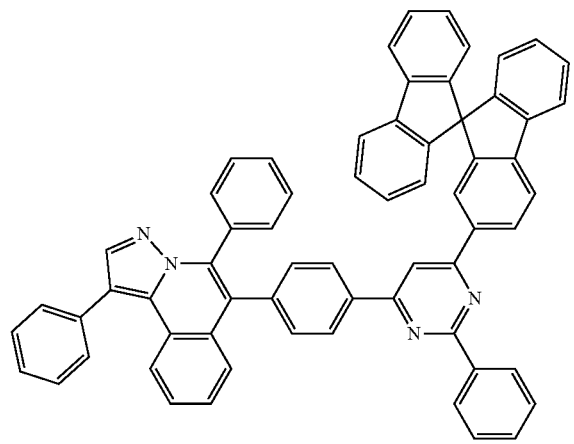
291
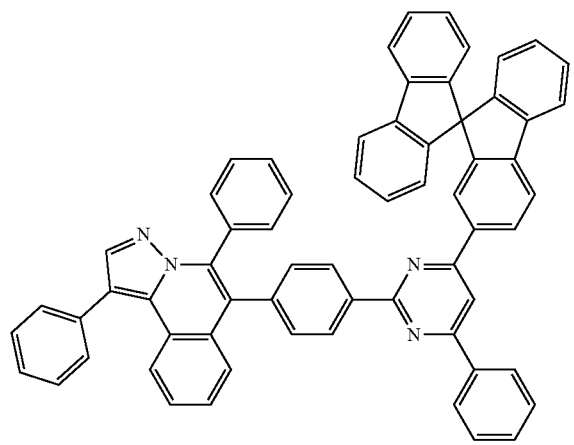
292
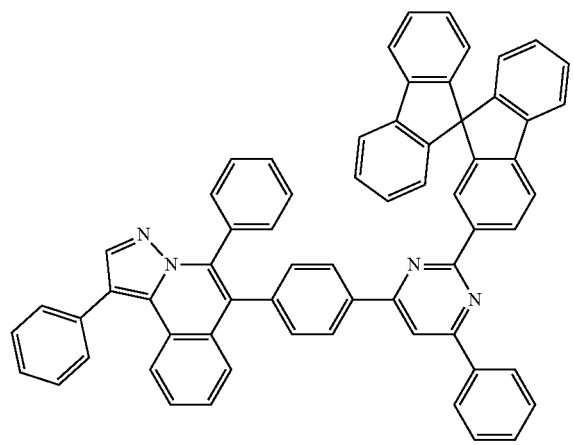
293
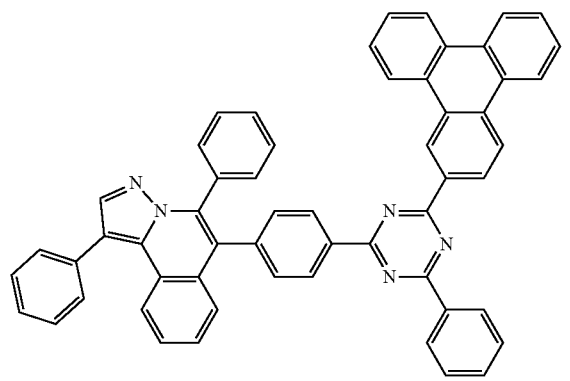
294
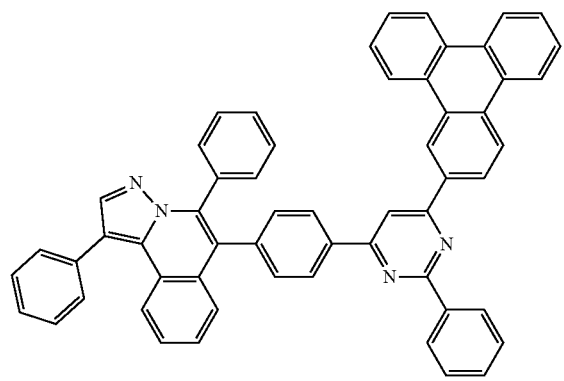

-continued
295
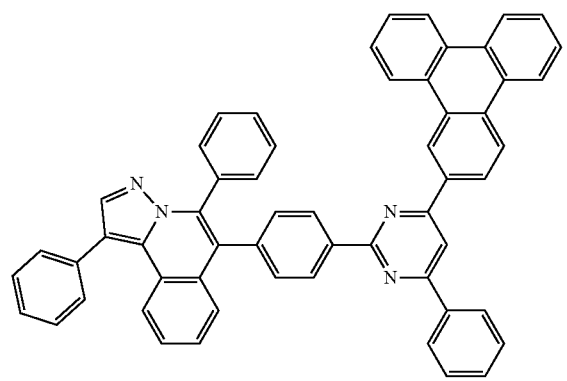
296
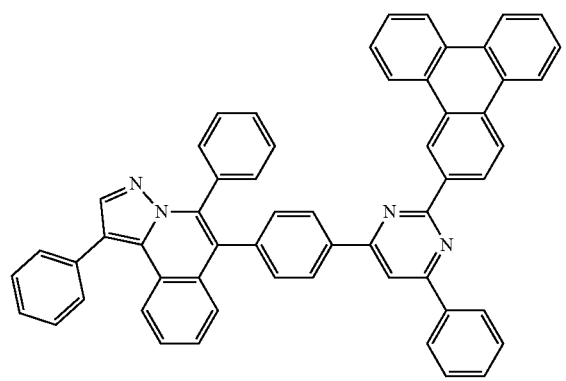
297
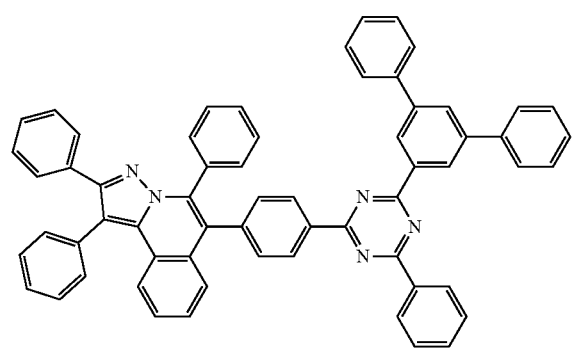
298
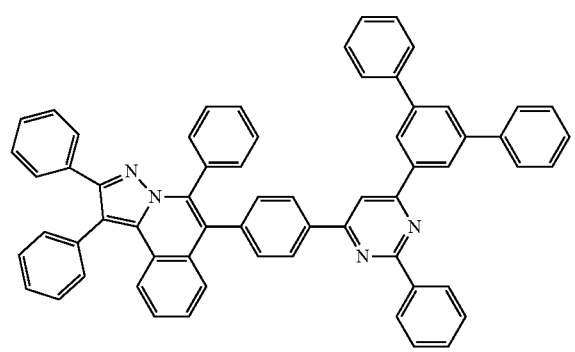
299
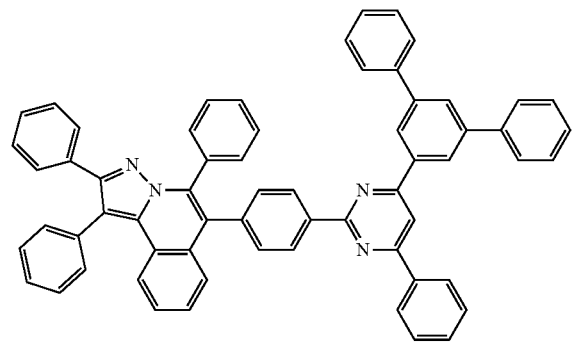
300
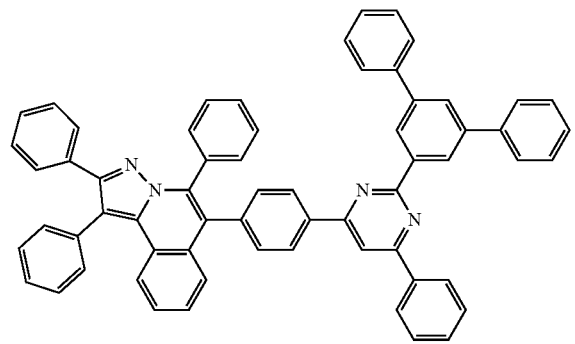
301
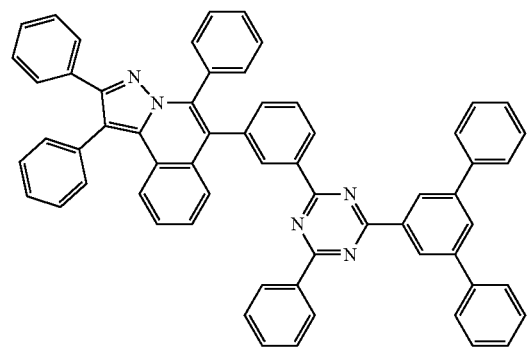
302
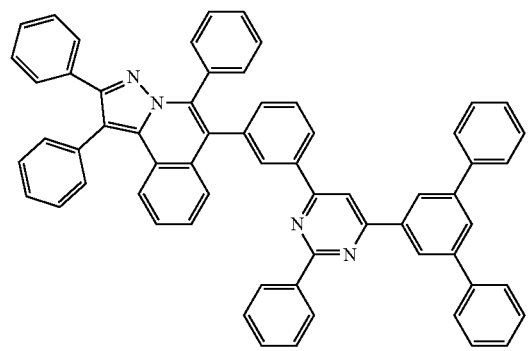

-continued
303
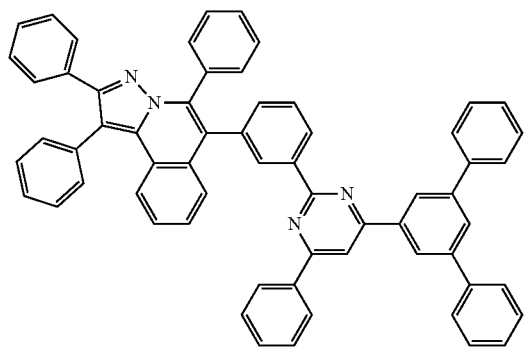
304
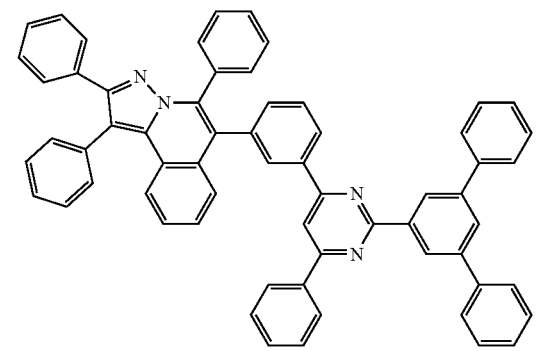
305
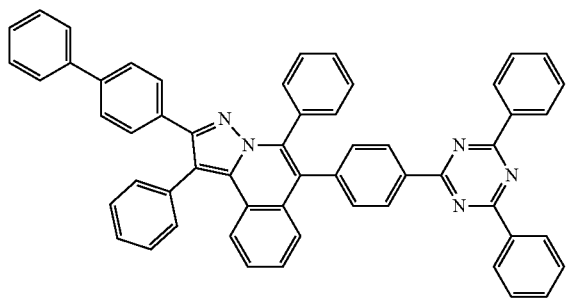
306
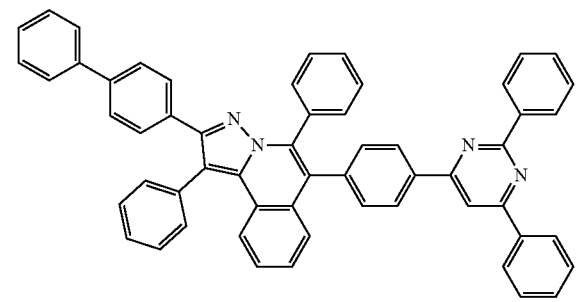
307
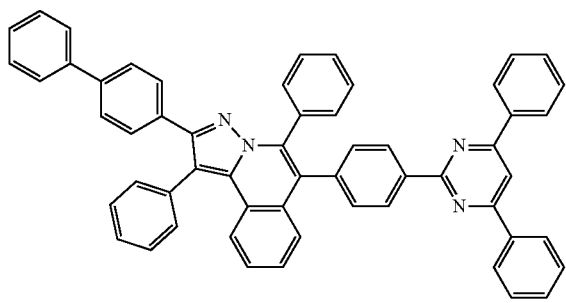
308
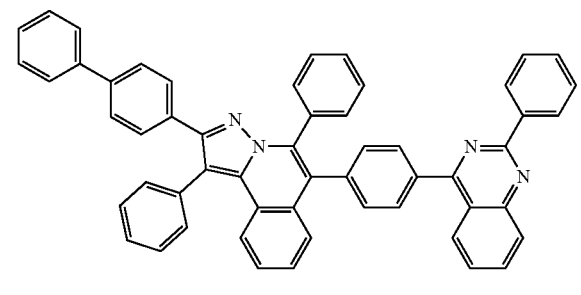
309
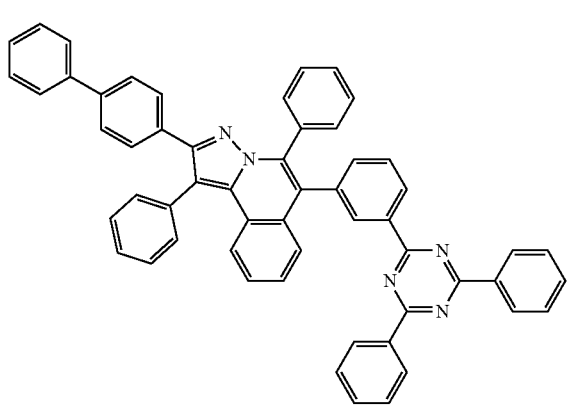
310
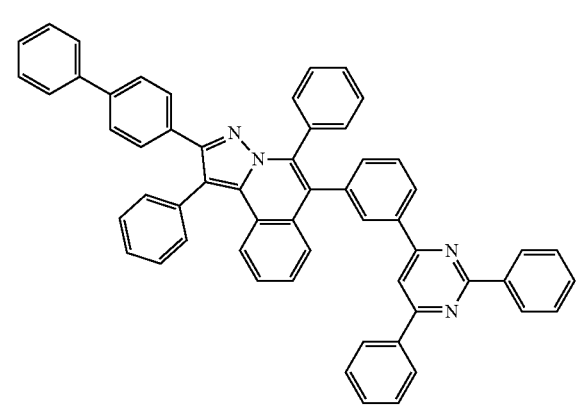

-continued
311
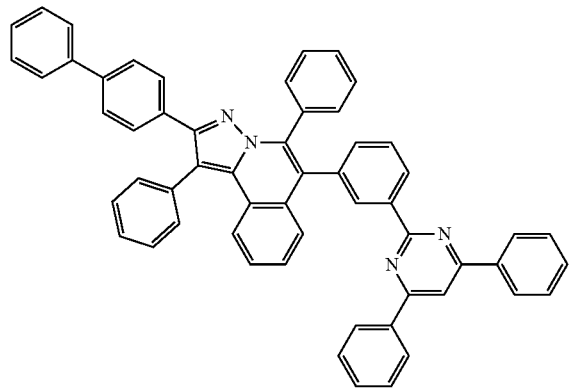
312
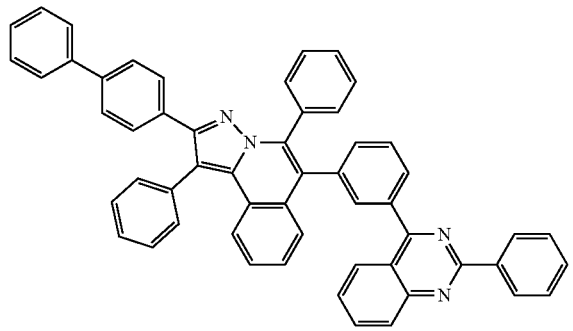
313
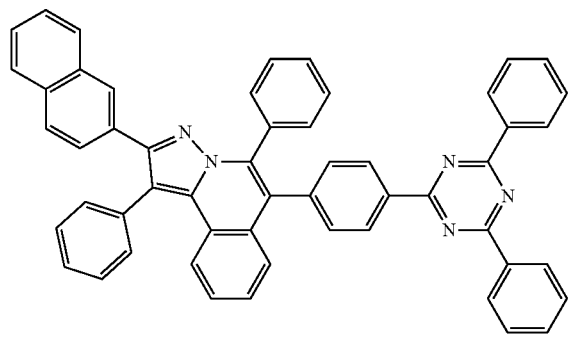
314
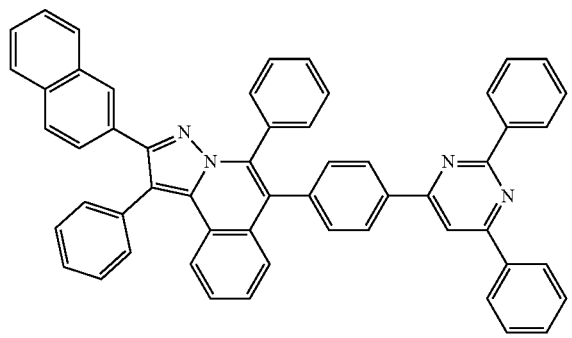
315
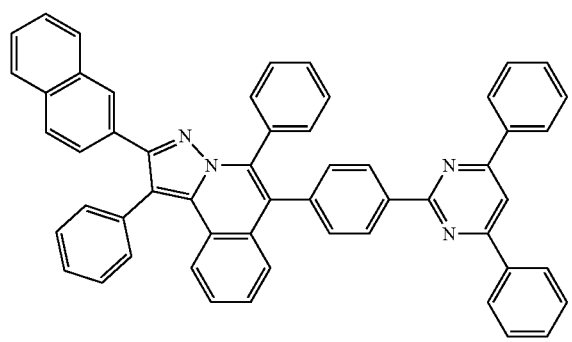
316
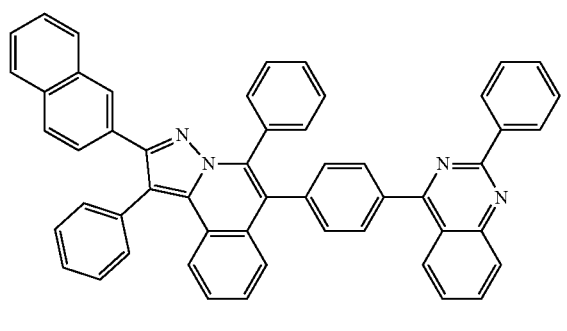
317
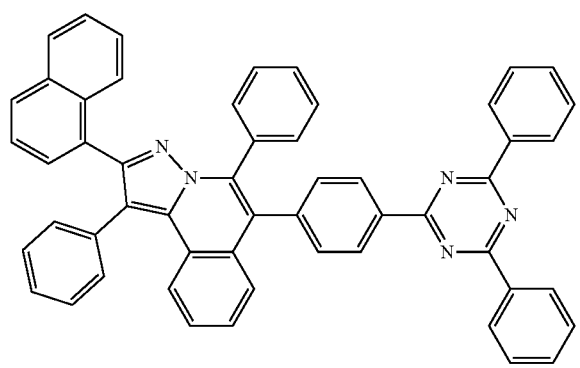
318
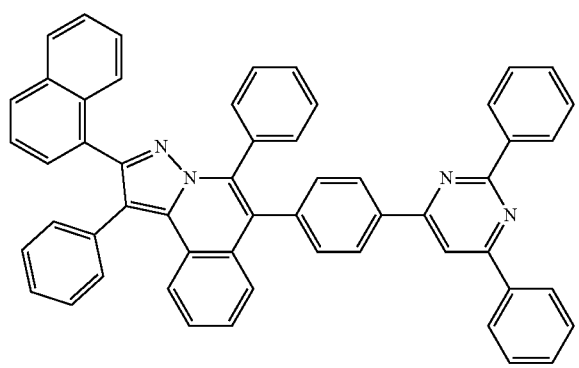

-continued
319
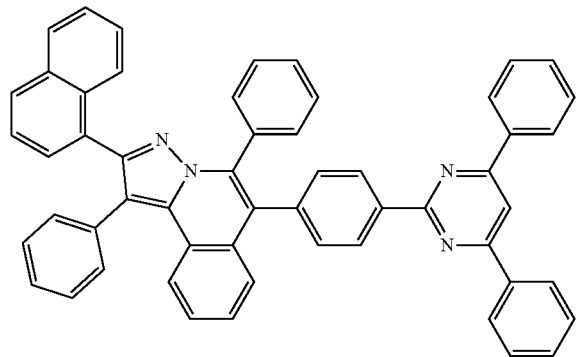
320
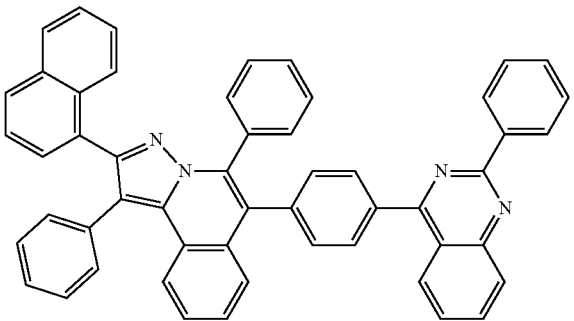
321
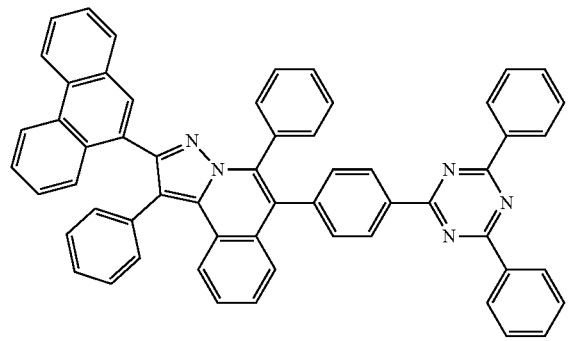
322
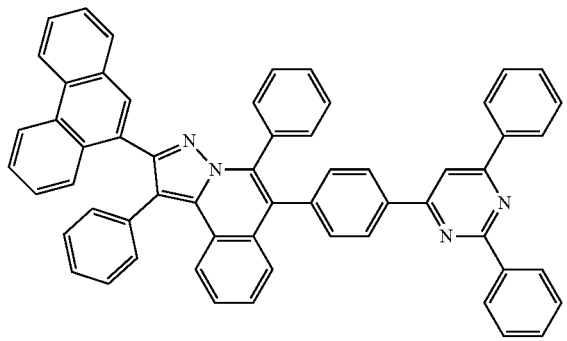
323
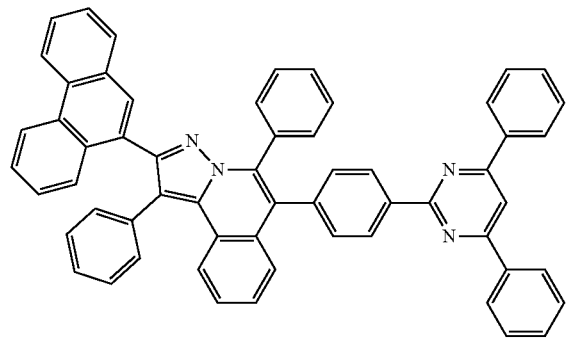
324
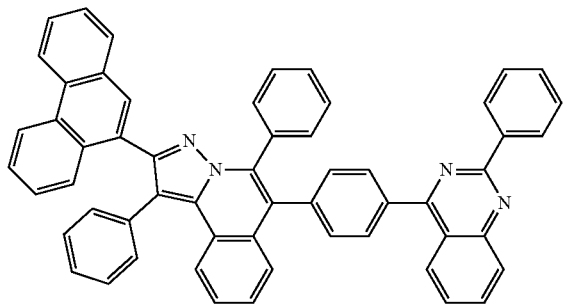
325
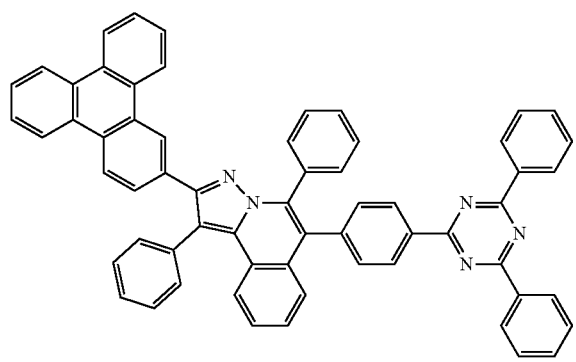
326
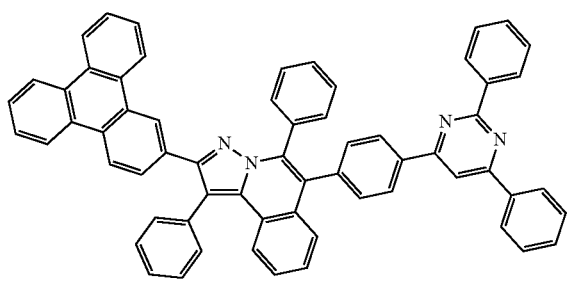

-continued

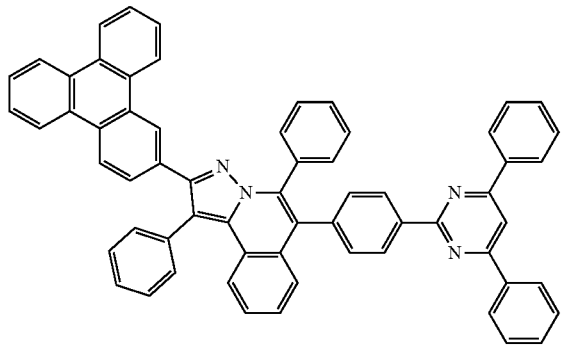
327

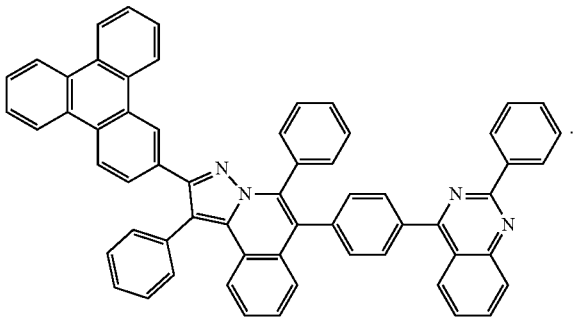
328

8. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound of claim 1.

9. The organic light emitting device of claim 8, wherein the organic material layer comprises an electron transfer layer, and the electron transfer layer comprises the heterocyclic compound.

10. The organic light emitting device of claim 8, wherein the organic material layer comprises an electron injection layer or an electron transfer layer, and the electron injection layer or the electron transfer layer comprises the heterocyclic compound.

11. The organic light emitting device of claim 8, wherein the organic material layer comprises an electron blocking layer or a hole blocking layer, and the electron blocking layer or the hole blocking layer comprises the heterocyclic compound.

12. The organic light emitting device of claim 8, comprising:
a first electrode;
a first stack provided on the first electrode and comprising a first light emitting layer;
a charge generation layer provided on the first stack;
a second stack provided on the charge generation layer and comprising a second light emitting layer; and
a second electrode provided on the second stack.

13. The organic light emitting device of claim 12, wherein the charge generation layer comprises the heterocyclic compound represented by Chemical Formula 1.

14. The organic light emitting device of claim 13, wherein the charge generation layer is an N-type charge generation layer, and the charge generation layer further comprises a dopant in addition to the heterocyclic compound represented by Chemical Formula 1.

* * * * *